(12) United States Patent
Protzko

(10) Patent No.: US 11,136,293 B2
(45) Date of Patent: Oct. 5, 2021

(54) PROCESSES FOR THE PRODUCTION OF TRYPTAMINES

(71) Applicant: New Atlas Biotechnologies LLC, Berkeley, CA (US)

(72) Inventor: Ryan Protzko, Berkeley, CA (US)

(73) Assignee: New Atlas Biotechnologies LLC, Berkeley, CA (US)

( * ) Notice: Subject to any disclaimer, the term of this patent is extended or adjusted under 35 U.S.C. 154(b) by 0 days.

(21) Appl. No.: 17/192,863

(22) Filed: Mar. 4, 2021

(65) Prior Publication Data

US 2021/0277433 A1 Sep. 9, 2021

Related U.S. Application Data

(63) Continuation of application No. 17/012,737, filed on Sep. 4, 2020, which is a continuation of application No. PCT/US2019/021489, filed on Mar. 8, 2019.

(60) Provisional application No. 62/640,443, filed on Mar. 8, 2018.

(51) Int. Cl.
| | |
|---|---|
| *C07D 209/16* | (2006.01) |
| *C12N 9/02* | (2006.01) |
| *C12N 9/12* | (2006.01) |
| *C12N 9/88* | (2006.01) |
| *A61K 31/4045* | (2006.01) |
| *C12P 17/10* | (2006.01) |

(52) U.S. Cl.
CPC ........ *C07D 209/16* (2013.01); *A61K 31/4045* (2013.01); *C12N 9/0042* (2013.01); *C12N 9/0071* (2013.01); *C12N 9/0083* (2013.01); *C12N 9/1205* (2013.01); *C12N 9/88* (2013.01); *C12Y 106/02004* (2013.01); *C12Y 114/16004* (2013.01); *C12Y 114/99* (2013.01); *C12Y 207/01* (2013.01); *C12Y 401/01* (2013.01); *C12P 17/10* (2013.01)

(58) Field of Classification Search
CPC .................................................. C07D 209/16
See application file for complete search history.

(56) References Cited

U.S. PATENT DOCUMENTS

| 3,075,992 A | 1/1963 | Hofmann et al. |
| 6,447,784 B1 | 9/2002 | Bermudes et al. |
| 2021/0147888 A1 | 5/2021 | Vogan et al. |

FOREIGN PATENT DOCUMENTS

| WO | WO-9534657 A2 | 12/1995 |
| WO | WO-02079153 A1 | 10/2002 |
| WO | WO-2013085922 A1 | 6/2013 |
| WO | WO-2013127915 A1 | 9/2013 |
| WO | WO-2017123418 A1 | 7/2017 |
| WO | WO-2019173797 A1 | 9/2019 |
| WO | WO-2019180309 A1 | 9/2019 |
| WO | WO-2021086513 A1 | 5/2021 |

OTHER PUBLICATIONS

Adams et al. In vivo production of psilocybin in *E. coli*. Metabolic Engineering 56:111-119 (2019). Available online Sep. 21, 2019.
Blaschko et al. A comparative study of hydroxyindole oxidases. Br J Pharmacol Chemother. Dec. 1960; 15(4): 625-633.
Carbonaro et al. Neuropharmacology of N,N-Dimethyltryptamine. Brain Res Bull. Sep. 2016; 126(Pt 1): 74-88. Published online Apr. 25, 2016. doi: 10.1016/j.brainresbull.2016.04.016.
Carrier, M.I., et al., Expression of Human IL-1B in *Salmonella typhimurium* A Model System for the Delivery of Recombinant Therapeutic Proteins in Vivo, The Journal of Immunology, 1992, pp. 1176-1181, vol. 148, No. 4, The American Association of Immunologists.
CAS Registry No. 1373882-09-7; entered STN database on May 16, 2012.
CB Therapeutics Achieves Major Breakthrough in the Biosynthesis of Psilocybin, Psilocin and Related Tryptamine-based Compounds. Business Wire (Dec. 4, 2019). 2 pages.
Co-pending U.S. Appl. No. 17/012,737, inventor PROTZKO; Ryan, filed Sep. 4, 2020.
Datsenko et al. One-step inactivation of chromosomal genes in *Escherichia coli* K-12 using PCR products. Proc Natl Acad Sci U S A. Jun. 6, 2000; 97(12): 6640-6645. Published online May 30, 2000. doi: 10.1073/pnas.120163297.
Deloache et al. An enzyme-coupled biosensor enables (S)-reticuline production in yeast from glucose. Nat Chem Biol. Jul. 2015;11(7):465-71.doi: 10.1038/nchembio.1816. Epub May 18, 2015.
Derry et al. Sumatriptan (all routes of administration) for acute migraine attacks in adults—overview of Cochrane reviews. Cochrane Database Syst Rev. May 2014; 2014(5): CD009108. Published online May 27, 2014. doi: 10.1002/14651858.CD009108.pub2.
Fricke et al. Enzymatic Route toward 6-Methylated Baeocystin and Psilocybin. Chembiochem. Nov. 18, 2019;20(22):2824-2829.doi: 10.1002/cbic.201900358. Epub Oct. 17, 2019.

(Continued)

*Primary Examiner* — Shawquia Jackson
(74) *Attorney, Agent, or Firm* — Wilson Sonsini Goodrich & Rosati

(57) ABSTRACT

Disclosed herein are prokaryotic and eukaryotic microbes, including *E. coli* and *S. cerevisiae*, genetically altered to biosynthesize tryptamine and tryptamine derivatives. The microbes of the disclosure may be engineered to contain plasmids and stable gene integrations containing sufficient genetic information for conversion of an anthranilate or an indole to a tryptamine. The fermentative production of substituted tryptamines in a whole-cell biocatalyst may be useful for cost effective production of these compounds for therapeutic use.

25 Claims, 19 Drawing Sheets
Specification includes a Sequence Listing.

(56) References Cited

OTHER PUBLICATIONS

Fricke et al. Enzymatic Synthesis of Psilocybin. Angew Chem Int Ed Engl. Sep. 25, 2017;56(40):12352-12355.doi: 10.1002/anie.201705489. Epub Aug. 25, 2017.
Fricke et al. Production Options for Psilocybin: Making of the Magic. Chem. Eur. J. 2019, 25, 897-903. First published: Jul. 16, 2018. DOI: https://doi.org/10.1002/chem.201802758.
Gartz et al. Ethnomycology, biochemistry, and cultivation of Psilocybe samuiensis Guzmán, Bandala and Allen, a new psychoactive fungus from Koh Samui, Thailand. J Ethnopharmacol. Jul. 8, 1994;43(2):73-80. doi: 10.1016/0378-8741 (94)90006-x.
Gartz, J. Extraction and analysis of indole derivatives from fungal biomass. J Basic Microbiol. 1994;34(1):17-22.doi: 10.1002/jobm.3620340104.
Griffiths et al. Psilocybin can occasion mystical-type experiences having substantial and sustained personal meaning and spiritual significance. Psychopharmacology (Berl). Aug. 2006;187(3):268-83.doi: 10.1007/s00213-006-0457-5. Epub Jul. 7, 2006.
Hanson et al. Codon optimality, bias and usage in translation and mRNA decay. Nat Rev Mol Cell Biol. Jan. 2018; 19(1): 20-30. Published online Oct. 11, 2017. doi: 10.1038/nrm.2017.91.
Hasler et al. Acute psychological and physiological effects of psilocybin in healthy humans: a double-blind, placebo-controlled dose-effect study. Psychopharmacology (Berl). Mar. 2004;172(2):145-56.doi: 10.1007/s00213-003-1640-6. Epub Nov. 13, 2003.
Hoefgen et al. Facile assembly and fluorescence-based screening method for heterologous expression of biosynthetic pathways in fungi. Metabolic Engineering 48(2018):44-51 (May 26, 2018).
Hofmann et al. Konstitutionsaufklärung und Synthese von Psilocybin. Experientia 14, 397-399 (1958). DOI: https://doi.org/10.1007/BF02160424.
Hofmann et al. Psilocybin und Psilocin, zwei psychotrope Wirkstoffe aus mexikanischen Rauschpilzen. Helvetica Chimica Acta, vol. 42, Issue 5 (1959). DOI: https://doi.org/10.1002/hlca.19590420518.
Kelly et al. Measuring the activity of BioBrick promoters using an in vivo reference standard. J Biol Eng. 2009; 3: 4. Published online Mar. 20, 2009. doi: 10.1186/1754-1611-3-4.13 pages.
Lenz et al. Identification of •-N-Methyl-4-hydroxytryptamine (Norpsilocin) as a Psilocybe Natural Product. J Nat Prod. Oct. 27, 2017;80(10):2835-2838.doi: 10.1021/acs.jnatprod.7b00407. Epub Sep. 20, 2017.
Milne et al. Metabolic engineering of *Saccharomyces cerevisiae* for the de novo production of psilocybin and related tryptamine derivatives. Metabolic Engineering 60:25-36 (2020). Available online Mar. 26, 2020.
Moreno et al. Safety, tolerability, and efficacy of psilocybin in 9 patients with obsessive-compulsive disorder. J Clin Psychiatry. Nov. 2006;67(11):1735-40.doi: 10.4088/jcp.v67n1110.
Nichols, David E. The Heffter Research Institute: past and hopeful future. J Psychoactive Drugs. Jan.-Mar. 2014;46(1):20-6.doi: 10.1080/02791072.2014.873688.
Park et al. Production of serotonin by dual expression of tryptophan decarboxylase and tryptamine 5-hydroxylase in *Escherichia coli*. Appl Microbiol Biotechnol. Mar. 2011;89(5):1387-94. doi: 10.1007/s00253-010-2994-4. Epub Nov. 16, 2010.
PCT/US2019/021489 International Search Report and Written Opinion dated May 24, 2019.
Quax et al. Codon Bias as a Means to Fine-Tune Gene Expression. Mol Cell. Jul. 16, 2015; 59(2): 149-161. doi: 10.1016/j.molcel.2015.05.035.
Sizemore, et al. Attenuated Shigella as a DNA delivery vehicle for DNA-mediated immunization. Science. Oct. 13, 1995;270(5234):299-302.

SEQUENCE LISTING

<160> NUMBER OF SEQ ID NOS: 49

<210> SEQ ID NO 1
<211> LENGTH: 4969
<212> TYPE: DNA
<213> ORGANISM: Escherichia coli

<400> SEQUENCE: 1

```
atggctgaca ttctgctgct cgataatatc gactctttta cgtacaacct ggcagatcag      60
ttgcgcagca atgggcataa cgtggtgatt taccgcaacc atattccggc gcaaacctta     120
attgaacgcc tggcgaccat gagcaatccg gtgctgatgc tttctcctgg ccccggtgtg     180
ccgagcgaag ccggttgtat gccggaactc ctcacccgct gcgtggcaa gctgcccatt     240 attggcattt gcctcggaca tcaggcgatt gtcgaagctt acggggcta tgtcggtcag     300 gcgggcgaaa ttctccacgg taaagcctcc agcattgaac atgacggtca ggcgatgttt     360
gccggattaa caaacccgct gccggtggcg cgttatcact cgctggttgg cagtaacatt     420
ccggccggtt taaccatcaa cgcccatttt aatggcatgg tgatggcagt acgtcacgat     480
gcggatcgcg tttgtggatt ccagttccat ccggaatcca ttctcaccac ccagggcgct     540
cgcctgctgg aacaaacgct ggcctgggcg cagcagaaac tagagccagc caacacgctg     600
caaccgattc tggaaaaact gtatcaggcg cagacgctta gccaacaaga aagccaccag     660 ctgtttttcag cggtggtgcg tggcgagctg aagccggaac aactggcggc ggcgctggtg     720
agcatgaaaa ttcgcggtga gcacccgaac gagatcgccg gggcagcaac cgcgctactg     780
gaaaacgcag cgccgttccc gcgcccggat tatctgtttg ctgatatcgt cggtactggc     840
ggtgacggca gcaacagtat caatatttct accgccagtg cgtttgtcgc cgcggcctgt     900
gggctgaaag tggcgaaaca cggcaaccgt agcgtctcca gtaaatctgg ttcgtccgat     960
ctgctggcgg cgttcggtat taatcttgat atgaacgccg ataaatcgcg ccaggcgctg    1020
gatgagttag gtgtatgttt cctctttgcg ccgaagtatc acaccggatt ccgccacgcg    1080
atgccggttc gccagcaact gaaaacccgc accctgttca atgtgctggg gccattgatt    1140
aacccggcgc atccgccgct ggcgttaatt ggtgtttata gtccggaact ggtgctgccg    1200
attgccgaaa ccttgcgcgt gctggggtat caacgcgcgg cggtggtgca cagcggcggg    1260
atggatgaag tttcattaca cgcgccgaca atcgttgccg aactgcatga cggcgaaatt    1320
```

```
aaaagctatc agctcaccgc agaagacttt ggcctgacac cctaccacca ggagcaactg    1380
gcaggcggaa caccggaaga aaaccgtgac attttaacac gtttgttaca aggtaaaggc    1440
gacgccgccc atgaagcagc cgtcgctgcg aacgtcgcca tgttaatgcg cctgcatggc    1500
catgaagatc tgcaagccaa tgcgcaaacc gttcttgagg tactgcgcag tggttccgct    1560
tacgacagag tcaccgcact ggcggcacga gggtaaatga tgcaaaccgt tttagcgaaa    1620
atcgtcgcag acaaggcgat ttgggtagaa gcccgcaaac agcagcaacc gctggccagt    1680
tttcagaatg aggttcagcc gagcacgcga cattttatg atgcgctaca gggtgcgcgc    1740
acggcgttta ttctggagtg caagaaagcg tcgccgtcaa aaggcgtgat ccgtgatgat    1800
ttcgatccag cacgcattgc cgccatttat aaacattacg cttcggcaat tcggtgctg    1860 actgatgaga aatattttca ggggagcttt aatttcctcc ccatcgtcag ccaaatcgcc    1920
ccgcagccga ttttatgtaa agacttcatt atcgacccct accagatcta tctggcgcgc    1980
tattaccagg ccgatgcctg cttattaatg cttttcagtac tggatgacga ccaatatcgc    2040
cagcttgccg ccgtcgctca cagtctggag atggggggtgc tgaccgaagt cagtaatgaa    2100
gaggaacagg agcgcgccat tgcattggga gcaaaggtcg ttggcatcaa caaccgcgat    2160
ctgcgtgatt tgtcgattga tctcaaccgt acccgcgagc ttgcgccgaa actggggcac    2220
aacgtgacgg taatcagcga atccggcatc aatacttacg ctcaggtgcg cgagttaagc    2280
cacttcgcta acgttttct gattggttcg gcgttgatgg cccatgacga tttgcacgcc    2340
gccgtgcgcc gggtgttgct gggtgagaat aaagtatgtg gcctgacgcg tgggcaagat    2400
gctaaagcag cttatgacgc gggcgcgatt tacgtgggt tgattttgt tgcgacatca    2460 ccgcgttgcg tcaacgttga acaggcgcag gaagtgatgg ctgcggcacc gttgcagtat    2520
gttggcgtgt tccgcaatca cgatattgcc gatgtggtgg acaaagctaa ggtgttatcg    2580
ctggcggcag tgcaactgca tggtaatgaa gaacagctgt atatcgatac gctgcgtgaa    2640
gctctgccag cacatgttgc catctggaaa gcattaagcg tcggtgaaac cctgcccgcc    2700
cgcgagtttc agcacgttga taaatatgtt ttagacaacg ccagggtgg aagcgggcaa    2760 cgttttgact ggtcactatt aaatggtcaa tcgcttggca acgttctgct ggcggggggc    2820
ttaggcgcag ataactgcgt ggaagcggca caaaccggct gcgccggact tgatttttaat    2880 tctgctgtag agtcgcaacc gggcatcaaa acgcacgtc ttttggcctc ggttttccag    2940
acgctgcgcg catattaagg aaaggaacaa tgacaacatt acttaacccc tattttggtg    3000
agtttggcgg catgtacgtg ccacaaatcc tgatgcctgc tctgcgccag ctggaagaag    3060
cttttgtcag tgcgcaaaaa gatcctgaat ttcaggctca gttcaacgac ctgctgaaaa    3120
actatgccgg gcgtccaacc gcgctgacca aatgccagaa cattacagcc gggacgaaca    3180
ccacgctgta tctcaagcgt gaagatttgc tgcacggcgg cgcgcataaa actaaccagg    3240
tgctggggca ggcgttgctg gcgaagcgga tgggtaaaac cgaaatcatc gccgaaaccg    3300
gtgccggtca gcatggcgtg gcgtcggccc ttgccagcgc cctgctcggc ctgaaatgcc    3360
gtatttatat gggtgccaaa gacgttgaac gccagtcgcc taacgttttt cgtatgcgct    3420
taatgggtgc ggaagtgatc ccggtgcata gcggttccgc gacgctgaaa gatgcctgta    3480
acgaggcgct gcgcgactgg tccggtagtt acgaaaccgc gcactatatg ctgggcaccg    3540
cagctggccc gcatccttat ccgaccattg tgcgtgagtt tcagcggatg attggcgaag    3600
aaaccaaagc gcagattctg gaaagagaag gtcgcctgcc ggatgccgtt atcgcctgtg    3660
ttggcggcgg ttcgaatgcc atcggcatgt ttgctgattt catcaatgaa accaacgtcg    3720
```

-continued

```
gcctgattgg tgtggagcca ggtggtcacg gtatcgaaac tggcgagcac ggcgcaccgc      3780
taaaacatgg tcgcgtgggt atctatttcg gtatgaaagc gccgatgatg caaaccgaag      3840
acgggcagat tgaagaatct tactccatct ccgccggact ggatttcccg tctgtcggcc      3900
cacaacacgc gtatcttaac agcactggac gcgctgatta cgtgtctatt accgatgatg      3960
aagcccttga agccttcaaa cgctgtgcc tgcacgaagg gatcatcccg gcgctggaat       4020
cctcccacgc cctggcccat gcgttgaaaa tgatgcgcga aaacccggat aaagagcagc      4080
tactggtggt taacctttcc ggtcgcggcg ataaagacat cttcaccgtt cacgatattt      4140
tgaaagcacg aggggaaatc tgatggaacg ctacgaatct ctgtttgccc agttgaagga      4200
gcgcaaagaa ggcgcattcg ttcctttcgt cacgctcggt gatccgggca ttgagcagtc      4260
attgaaaatt atcgatacgc taattgaagc cggtgctgac gcgctggagt taggtatccc      4320
cttctccgac ccactggcgg atggcccgac gattcaaaac gccactctgc gcgcctttgc      4380
ggcaggtgtg actccggcac aatgttttga atgctggca ctgattcgcc agaaacaccc       4440
gaccattccc attggcctgt tgatgtatgc caatctggtg tttaacaaag gcattgatga      4500
gttttatgcc cagtgcgaaa aagtcggcgt cgattcggtg ctggttgccg atgtgccagt      4560
tgaagagtcc gcgcccttcc gccaggccgc gttgcgtcat aatgtcgcac ctatcttcat      4620
ctgcccgcca aatgccgatg acgacctgct gcgccagata gcctcttacg gtcgtggtta      4680
cacctatttg ctgtcacgag caggcgtgac cggcgcagaa aaccgcgccg cgttacccct      4740
caatcatctg gttgcgaagc tgaaagagta caacgctgca cctccattgc agggatttgg      4800
tatttccgcc ccggatcagg taaaagcagc gattgatgca ggagctgcgg gcgcgatttc      4860
tggttcggcc attgttaaaa tcatcgagca acatattaat gagccagaga aaatgctggc      4920
ggcactgaaa gtttttgtac aaccgatgaa agcggcgacg cgcagttaa                  4969
```

<210> SEQ ID NO 2
<211> LENGTH: 4390
<212> TYPE: DNA
<213> ORGANISM: Bacillus subtilis

<400> SEQUENCE: 2

```
atgaacagat ttctacaatt gtgcgttgac ggaaaaaccc ttactgccgg tgaggctgaa       60
acgctgatga atatgatgat ggcagcggaa atgactcctt ctgaaatggg ggggatattg      120
tcaattcttg ctcatcgggg ggagacgcca gaagagcttg cgggttttgt gaaggcaatg      180
cgggcacacg ctcttacagt cgatggactt cctgatattg ttgatacatg cggaacaggg      240
ggagacggta tttccacttt taatatctca acggcctcgg caattgttgc ctcggcagct      300
ggtgcgaaaa tcgctaagca tggcaatcgc tctgtctctt ctaaaagcgg aagcgctgat      360
gttttagagg agctagaggt ttctattcaa accactcccg aaaaggtcaa agcagcatt      420
gaaacaaaca catggggatt tcttttttgcg ccgcttacc attcgtctat gaaacatgta      480
gcaggtacta gaaaagagct aggtttcaga acggtattta atctgcttgg gccgctcagc      540
aatcctttac aggcgaagcg tcaggtgatt ggggtctatt ctgttgaaaa agctggactg      600
atggcaagcg cactggagac gtttcagccg aagcacgtta tgtttgtatc aagccgtgac      660
ggtttagatg agctttcaat tacagcaccg accgacgtga ttgaattaaa ggacggagag      720
cgccgggagt ataccgtttc acccgaagat ttcggtttca caaatggcag acttgaagat      780
ttacaggtgc agtctccgaa agagagcgct tatctcattc agaatatttt tgaaaataaa      840
```

```
agcagcagtt ccgctttatc tattacggct tttaatgcgg gtgctgcgat ttacacggcg      900
ggaattaccg cctcactgaa ggaaggaacg gagctggcgt tagagacgat tacaagcgga      960
ggcgctgccg cgcagcttga acgactaaag cagaagagg aagagatcta tgcttgaaaa     1020
aatcatcaaa caaagaaag aagaagtgaa acactggtt ctgccggtag agcagccttt      1080
cgagaaacgt tcatttaagg aggcgctggc aagcccgaat cggtttatcg ggttgattgc     1140
cgaagtgaag aaagcatcgc cgtcaaaagg gcttattaaa gaggattttg tacctgtgca     1200
gattgcaaaa gactatgagg ctgcgaaggc agatgcgatt ccgtttttaa cagacacccc     1260
gttttttcaa ggggaaaaca gctatttatc agacgtaaag cgtgctgttt cgattcctgt     1320
acttagaaaa gattttattg attctcttca gtagaggaa tcaagaagaa tcggagcgga     1380
tgccatattg ttaatcggcg aggtgcttga tcccttacac cttcatgaat tatatcttga     1440
agcaggtgaa aaggggatgg acgtgttagt ggaggttcat gatgcatcaa cgctagaaca     1500
aatattgaaa gtgttcacac ccgacattct cggcgtaaat aatcgaaacc taaaaacgtt     1560
tgaaacatct gtaaagcaga cagaacaaat cgcatctctc gttccgaaag aatccttgct     1620
tgtcagcgaa agcggaatcg gttctttaga acatttaaca tttgtcaatg aacatggggc     1680
gcgagctgta cttatcggtg aatcattgat gagacaaact tctcagcgta aagcaatcca     1740
tgctttgttt agggagtgag gttgtgaaga accggcatt aaaatattgc ggtattcggt     1800
cactaaagga tttgcagctt gcggcggaat cacaggctga ttacctagga tttatttttg     1860
ctgaaagcaa acgaaaagta tctccggaag atgtgaaaaa atggctgaac caagttcgtg     1920
tcgaaaaaca ggttgcaggt gtttttgtta atgaatcaat agagacgatg tcacgtattg     1980
ccaagagctt gaagctcgac gtcattcagc ttcacggtga tgaaaaaccg gcggatgctg     2040
ctgctcttcg caagctgaca ggctgtgaaa tatggaaggc gcttcaccat caagataaca     2100
caactcaaga aatagcccgc tttaaagata atgttgacgg cttttgtgatt gattcatctg     2160 taaaagggtc tagaggcgga actggtgttg cattttcttg ggaatgtgtg ccggaatatc     2220
agcaggcggc tattggtaaa cgctgcttta tcgctggcgg cgtgaatccg gatagcatca     2280
cacgcctatt gaaatggcag ccagaaggaa ttgaccttgc cagcggaatt gaaaaaaacg     2340
gacaaaaaga tcagaatctg atgaggcttt tagaagaaag gatgaaccga tatgtatcca     2400
tatccgaatg aaataggcag atacggtgat tttggcggaa agtttgttcc ggaaacactc     2460
atgcagccgt tagatgaaat acaaacagca tttaaacaaa tcaaggatga tcccgctttt     2520
cgtgaagagt attataagct gttaaaggac tattccggac gcccgactgc attaacatac     2580
gctgatcgag tcactgaata cttaggcggc gcgaaaatct atttgaaacg agaagattta     2640
aaccatacag gttctcataa aatcaataat gcgctaggtc aagcgctgct tgctaaaaaa     2700
atgggcaaaa cgaaaatcat tgctgaaacc ggtgccggcc agcatggtgt tgccgctgca     2760
acagttgcag ccaaattcgg cttttcctgt actgtgttta tgggtgaaga ggatgttgcc     2820
cgccagtctc tgaacgtttt ccgcatgaag cttcttggag cggaggtagt gcctgtaaca     2880
agcggaaacg gaacattgaa ggatgccaca atgaggcga tccggtactg ggttcagcat     2940
tgtgaggatc acttttatat gattggatca gttgtcggcc cgcatcctta tccgcaagtg     3000
gtccgtgaat tcaaaaaat gatcggagag gaagcgaagg atcagttgaa acgtattgaa     3060
ggcactatgc ctgataaagt agtggcatgt gtaggcggag gaagcaatgc gatgggtatg     3120
tttcaggcat ttttaaatga agatgttgaa ctgatcggcg ctgaagcagc aggaaaagga     3180
attgatacac ctcttcatgc cgccactatt tcgaaaggaa ccgtagggt tattcacggt     3240
```

| | | |
|---|---|---|
| tcattgactt atctcattca ggatgagttc gggcaaatta ttgagcccta ctctatttca | 3300 | |
| gccggtctcg actatcctgg aatcggtccg gagcatgcat atttgcataa aagcggccgt | 3360 | |
| gtcacttatg acagtataac cgatgaagaa gcggtggatg cattaaagct tttgtcagaa | 3420 | |
| aaagagggga ttttgccggc aatcgaatct gcccatgcgt tagcgaaagc attcaaactc | 3480 | |
| gccaaaggaa tggatcgcgg tcaactcatt ctcgtctgtt tatcaggccg gggagacaag | 3540 | |
| gatgtcaaca cattaatgaa tgtattggaa gaagaggtga agcccatgt ttaaattgga | 3600 | |
| tcttcaacca tcagaaaaat tgtttatccc gtttattacg gcgggcgatc cagttcctga | 3660 | |
| ggtttcgatt gaactggcga agtcactcca aaaagcaggc gccacagcat ggagcttgg | 3720 | |
| tgttgcatac tctgacccgc ttgcagacgg tccggtgatc cagcgggctt caaagcgggc | 3780 | |
| gcttgatcaa ggaatgaata tcgtaaaggc aatcgaatta ggcggagaaa tgaaaaaaaa | 3840 | |
| cggagtgaat attccgatta tcctctttac gtattataat cctgtgttac aattgaacaa | 3900 | |
| agaatacttt ttcgctttac tgcgggaaaa tcatattgac ggtctgcttg ttccggatct | 3960 | |
| gccattagaa gaaagcaaca gccttcaaga ggaatgtaaa agccatgagg tgacgtatat | 4020 | |
| ttctttagtt gcgccgacaa gcgaaagccg tttgaaaacc attattgaac aagccgaggg | 4080 | |
| gttcgtctac tgtgtatctt ctctgggtgt gaccggtgtc cgcaatgagt tcaattcatc | 4140 | |
| cgtgtacccg ttcattcgta ctgtgaagaa tctcagcact gttccggttg ctgtagggtt | 4200 | |
| cggtatatca aaccgtgaac aggtcataaa gatgaatgaa attagtgacg tgtcgtagt | 4260 | |
| gggaagtgcg ctcgtcagaa aaatagaaga attaaaggac cggctcatca gcgctgaaac | 4320 | |
| gagaaatcag gcgctgcagg agtttgagga ttatgcaatg gcgtttagcg gcttgtacag | 4380 | |
| tttaaaatga | 4390 | |

<210> SEQ ID NO 3
<211> LENGTH: 5467
<212> TYPE: DNA
<213> ORGANISM: Lactococcus lactis
<400> SEQUENCE: 3

| | | |
|---|---|---|
| atgaaaacaa ggagtcatca aatgaaaaat gaacttgaaa aagtgatgtc aggtcgtgac | 60 | |
| atgaccgaaa atgaaatgaa tatgcttgct aattcaatta ccaaggtga attaagcgag | 120 | |
| gtccaaattg ccagcttttt agtagcatta aaatgaaag gtgaagcagc aagcgaattg | 180 | |
| actggtttgg ctcgagcttt acaaaaagca gcgattccca ttccaacaaa tttgacaaat | 240 | |
| gcgatggaca ttgtggaac aggaggcgac cgctcattca gttttaatat ttcaaccaca | 300 | |
| gccgcttttg ttttagcagc tggtggagtc aatatggcaa acacggaaa tcgctccatt | 360 | |
| accagtaaat ctggctcggc agacgttctt gaggccttag gaatcaatct ttatttacca | 420 | |
| gcagaaaagt tagctcaagt ttttgacaaa gttggtttag ttttcctttt tgctcaaaat | 480 | |
| ctccacccag cgatgaaata cttcacgcca gtccgcagac aactcgaaat tccaacaatt | 540 | |
| atgaacttga ctgggccact aatcaatcca attccacttg atacgcaact tcttggtacc | 600 | |
| tcacgtccag atttacttga attaacagca aatgttttga aaggcttggg ccgtaagcga | 660 | |
| gcattagtca tcacaggtga aggcggaatg gacgaagcaa ctccctttgg acttaatcat | 720 | |
| tacgcacttt tagaaaatga caaagtgact ttgcatgaat ttagagcctc agaagttggt | 780 | |
| atttcagaag ttcaactcaa tgatattcgt ggaggtgaag ccccagaaaa tgctgaaatt | 840 | |
| ttaaaaaatg tccttgaaaa tcaaccgtca gccttttag aaacgaccgt tttaaatgcc | 900 | |

```
ggacttggat tttatgccaa tggaaaagtt gattccatca aatccggagt tgaccttgca    960
agagaagtaa ttagtacagg agcagctctt accaagttgc atgaattaca agcagaacaa   1020
attggttaaa aatcttgatg gcaaattttg aaatagcaga aaatgagaga aaaatatgaa   1080
cataaaaaaa ggaaaattte tagaaacaat cctagcagaa aaacgacttg aaattgctaa   1140
aatgccagaa gaacaagtag gaaaagttcg tcaaacatac aattttatg attacttaaa    1200 agaacattcc gaccagcttc aagtgattgc cgaagtcaaa aaagcttcgc ccagtctagg   1260
tgatattaac ttagaagtgg atatcgttga ccaagccaaa aattacgaac aagccggtgc   1320
cgctatgatt tccgtcttaa ctgaccctgt attttttaaa ggaaatattg aatatctctg   1380
tgaaatttca gaaaatgtcc aaatccccac cttgaacaag gattttatca tcgataaaaa   1440
acaaatcaat cgggcagtta atgcgggagc aacagttatt ttactcattg tcgcagtttt   1500
tgaaaatcaa taccccaaac tccaaaacct ctacaactac gcactttcac taggacttga   1560
agttcttgtt gaaacacata taaagcaga acttgagatt gctcatcagc ttggagctaa   1620
aattattgga gttaataatc gtaatttaaa aacctttgaa gtgatcttac aaaattcagt   1680
agatttgaca ccctacttta agaagacag tatctacatt tccgaatcag gcattttag    1740 cgcaaacgaa gcccaaaaag tttccgatac tttcaatgaa atattggttg aacagcact    1800 catgcaatca gaaaatctag aaaaatcttt gaaagattta aaagtcaaga ggaaaacgaa   1860
tgaaaattaa aatctgtggc ttatctacaa aagaagctgt tgatacagct gtagaatctg   1920
gtgtcacaca tctcggtttt attcttagtc cctcaaaacg ccaagttgca ccagaaaaaa   1980
ttcttcaaat cacaaacgat gtcccaaaaa cagtcaaaaa agtaggagtt tttgttgatg   2040
aacctattga ttttgtaaaa aaagccattc aagttgctca actcgatctg gttcagcttc   2100
acggaaatga agatatgaat tacattaatc aactagatat ttcggttatt aaagcaataa   2160
gaccagacca agaattaaa gaatacgaag atgtaatttt attatttgat agtccacaag   2220
ctggaagtgg tcaagcattt gattgggact cttttggtgac cagcggtctg aaaaataaat   2280 tttcatcgc tggtggactt aatccagaaa atgtagcagc tgctattcaa cattttccaa   2340
atgcctacgg tgtggatgtt tcttctggag tagaaactga cggaattaaa aaccttacaa   2400 aaataaaaa ctttgttcaa aatgcaagcc ttgcctcatc aaagcaatta tttatagaat   2460
ttttaagaat cacaaaaaag ctaaatgaaa ataagattat cccttattta atgggaagtt   2520
tagcagttga gcaaataatc aattttccaa caaatcctga tgacattgat attcaactca   2580
aaacgtctga ttttgaaaat tttgagcaat taacaagttt aatggaaaaa ttaggttatc   2640
agcttattga cttacatgag cataaatttg aaaaagctag tattcatgtt ggctttgcaa   2700
gtgtggagac ccttaaaaac tatgccgggg ttgactattt gaccattcaa caagaaagaa   2760
tggaaaatgg cgaaaaatat catcttccaa atgttgaaca atcccttaaa atctatgagg   2820
cagcaaaacg agatgagtgg cgaggaggga agcaaaaaga ttcctttatt ttcgatgagt   2880
taataaagga acagaagagg aatgacaatg aatgataatc ttattgaaga gggtgtagag   2940
attcgaaatg gtctcattat taagtcaatt caaaagaag atatattaga gctttggcaa   3000
attagttatg gacctaaatc tgatttacat tggatgtctt tcaacgctcc ctattttgag   3060
gagccaatcc tgagttggga agaattttca agaaaaatat ctcttaaaat aaattaacca   3120
aatgttgcac ttattatctt tcaaaatcga atcattggaa tgctgtcagc ttattggaa    3180 gacggtaaat tacaaaaatg gcttgagttt ggtatagtga tttatgatag taaattgtgg   3240
ggacgtggaa ttggacagga tgccttatct ttttggttga agcacctttt tgaaacttat   3300
```

```
ccgaagattc agcacatagg atttacaact tggtcaggaa atcaaggaat gatgagacta    3360
ggagaaaaaa gtggtctaaa acttgaaggg caaatcagaa aagttagata ttggcaagaa    3420
acttggtatg attcaataaa atatggaatt ttaagagaag aactaaaaaa ataaataaaa    3480
aaaatcaaag gagcaacaac atgacctaca accaacctaa caacaaagga ttttacggcc    3540
aattcggggg ccaattcgta cctgagacac taatgacagc agtaaaacaa ttagaagaag    3600
cctacgtaga tagtaaaaaa gaccctctct ttcaagcaga acttaaagaa ttacttaaag    3660
actatgttgg acgagaaaac ccactctatt atgcaaaacg cttaacagaa tatgcgggcg    3720
gagcaaaaat ttatcttaaa agagaagacc taaaccatac aggagcacac aaaattaaca    3780
atgccctcgg acaagtcctc cttgccaaaa aatgggaaa aataaagtc attgctgaaa     3840
caggtgcagg ccaacacggt gtcgcaagcg caaccgcggc tgccctcttt ggcatggaat    3900
gtacgattta tatgggtgaa gaagacgtta aaagacaatc tctcaatgtc tttcgcatgg    3960
aattactcgg ggcaaaagtt cattcagtaa ctgatggttc acgcgtactt aaagatgcgg    4020
ttaatgcagc acttagagca tgggttgctc aagttgaaga tacgcattat gtaatgggct    4080
cagttcttgg accacatcca tttccacaaa ttgtgcgtga ttatcaagct gttattggac    4140
aggaagcgcg tgcccaattt ttagaaaaag aaaataaact tccagatgct ttagtagctt    4200
gtgtcggtgg aggttcaaat tctatgggac tttttatcc cttcgttaat gatgaatcag    4260
ttgccatgta tggtgttgaa gccgctggcc ttgggattga tacaccacat catgcggcaa    4320
caattactaa aggccgcccc ggtgttcttc acggaacact catggatgtc cttcaagatg    4380
aaaatggtca aatgttagaa gcctttagta tttcagccgg tttagactat ccaggaatcg    4440
gaccagaaca ctcttatttc aatgctgttg gacgagcaaa atatgttgat attacagatg    4500
aagaagcact tgaaggtttt aaaatcttat ctagaactga aggaattatc ccagcactag    4560
aaagttctca tgctatcgcc tatgcagtca aattagcaaa agaattagga gcagataaat    4620
caatgattgt ttgtctttca ggacgtggag ataaggatgt ggttcaagtt aaagaacgac    4680
ttgaagcaga aaaagaggtg aaaaaatgaa aactttacaa atgactttaa gcaataaaaa    4740
aaataatttt attccttata tcatggctgg cgaccatgaa aaaggcttag aaggtcttaa    4800
agaaaccatt caactgcttg agcaagctgg gagttccgct attgaaattg gcgttccatt    4860
ttcagatccg gttgctgatg gtccagtcat cgaacaagcg ggtttgcgtg cgttagcaag    4920
aaatgtatca ctttcaagta ttcttgaaac cttaaaaaca attgatacaa aagttcctct    4980
agtaattatg acctatttca atcccgttta tcagtttgga attgaaaagt tgttgcagc    5040
tcttgaaaaa acaccagtta aaggccttat cattcctgat ttgcctaaag aacatgagga    5100
ctatatcaaa ccatttatca atgataaaga tatctgtttta gttcctctgg tctcattaac    5160
cacgccactt tctcggcaaa aagaacttgt agccgatgct gaaggattta tctatgccgt    5220
tgcaataaat ggagtaactg ggaaagaaaa tgcttatagt aaccagcttg accaacattt    5280
aaaagcgtta tcttcattaa cggatgttcc tgttttgaca ggatttggaa tttctacatt    5340
atctgatgtg gaccgtttta ataaagtgtc ctcaggagtt attgttggtt caaaaattgt    5400
tcgtgattta catgaaggta agaaaacga agttattaaa tttattgaaa acgcaatcaa    5460
ttttttaa                                                             5467
```

<210> SEQ ID NO 4
<211> LENGTH: 4573
<212> TYPE: DNA

<213> ORGANISM: Corynebacterium glutamicum

<400> SEQUENCE: 4

```
atgacttctc cagcaacact gaaagttctc aacgcctact tggataaccc cactccaacc    60
ctggaggagg caattgaggt gttcaccccg ctgaccgtgg gtgaatacga tgacgtgcac   120
atcgcagcgc tgcttgccac catccgtact cgcggtgagc agttcgctga tattgccggc   180
gctgccaagg cgttcctcgc ggcggctcgt ccgttcccga ttactggcgc aggtttgcta   240
gattccgctg gtactggtgg cgacggtgcc aacaccatca acatcaccac cggcgcatcc   300
ctgatcgcag catccggtgg agtgaagctg gttaagcacg gcaaccgttc ggtgagctcc   360
aagtccggct ccgccgatgt gctggaagcg ctgaatattc ctttgggcct tgatgtggat   420
cgtgctgtga agtggttcga agcgtccaac ttcaccttcc tgttcgcacc tgcgtacaac   480
cctgcgattg cgcatgtgca gccggttcgc caggcgctga aattccccac catcttcaac   540
acgcttggac cattgctgtc cccggcgcgc ccggagcgtc agatcatggg cgtggccaat   600
gccaatcatg gacagctcat cgccgaggtc ttccgcgagt tgggccgtac acgcgcgctt   660
gttgtgcatg gcgcaggcac cgatgagatc gcagtccacg gcaccacctt ggtgtgggag   720
cttaaagaag acggcaccat cgagcattac accatcgagc tgaggaccct tggccttggc   780
cgctacaccc ttgaggatct cgtaggtggc ctcggcactg agaacgccga agctatgcgc   840
gctactttcg cgggcaccgg ccctgatgca caccgtgatg cgttggctgc gtccgcaggt   900
gcgatgttct acctcaacgg cgatgtcgac tccttgaaag atggtgcaca aaaggcgctt   960
tccttgcttg ccgacggcac cacccaggca tggttggcca agcacgaaga gatcgattac  1020
tcagaaaagg agtcttccaa tgactagtaa taatctgccc acagtgttgg aaagcatcgt  1080
cgagggtcgt cgcggacacc tggaggaaat tcgcgctcgc atcgctcacg tggatgtgga  1140
tgcgcttcca aaatccaccc gttctctgtt tgattccctc aaccagggta ggggaggggc  1200
gcgtttcatc atggagtgca agtccgcatc gccttctttg gaatgattc gtgagcacta  1260
ccagccgggt gaaatcgctc gcgtgtactc tcgctacgcc agcggcattt ccgtgctgtg  1320
cgagccggat cgttttggtg gcgattacga tcacctcgct accgttgccg ctacctctca  1380
tcttccggtg ctgtgcaaag acttcatcat tgatcctgtc caggtacacg cggcgcgtta  1440
ctttggtgct gatgccatcc tgctcatgct ctctgtgctt gatgatgaag agtacgcagc  1500
actcgctgcc gaggctgcgc gttttgatct ggatatcctc accgaggtta ttgatgagga  1560
ggaagtcgcc cgcgccatca gctgggtgc gaagatcttt ggcgtcaacc accgcaacct  1620
gcatgatctg tccattgatt tggatcgttc acgtcgcctg tccaagctca ttccagcaga  1680
tgccgtgctc gtgtctgagt ctggcgtgcg cgataccgaa accgtccgcc agctaggtgg  1740
gcactccaat gcattcctcg ttggctccca gctgaccagc caggaaaacg tcgatctggc  1800
agcccgcgaa ttagtctacg gccccaacaa agtctgcgga ctcacctcac caagtgcagc  1860
acaaaccgct cgcgcagcgg gtgcggtcta cggcgggctc atcttcgaag aggcatcgcc  1920
acgcaatgtt tcacgtgaaa cattgcaaaa aatcatcgcc gcagagccca acctgcgcta  1980
cgtcgcggtc agccgtcgca cctccgggta caaggatttg cttgtcgacg gcatcttcgc  2040
cgtacaaatc cacgccccac tgcaggacag cgtcgaagca gaaaaggcat tgatcgccgc  2100
cgttcgtgaa gaggttggac gcaggttcca ggtctggcgc gcgatctcga tgtccagccc  2160
cttgggggct gaagtggcag ctgccggtgga gggtgacgtc gataagctaa ttcttgatgc  2220
ccatgaaggt ggcagcgggg aagtattcga ctgggctacg gtgccggccg ctgtgaaggc  2280
```

```
aaagtctttg ctcgcgggag gcatctctcc ggacaacgct gcgcaggcac tcgctgtggg    2340
ctgcgcaggt ttggacatca actctggcgt ggaataccccc gccggtgcag gcacgtgggc   2400
tggggcgaaa gacgccggcg cgctgctgaa aattttcgcg accatctcca cattccatta   2460
ctaaaggttt aaataggatc atgactgaaa agaaaacttt gggcggctcc acgctgctgc   2520
ctgcatactt cggtgaattc ggcggccagt tcgtcgcgga atccctcctg cctgctctcg   2580
accagctgga gaaggccttc gttgacgcga ccaacagccc agagttccgc gaagaactcg   2640
gcggctacct ccgcgattac ctcggccgcc caaccccgct gaccgaatgc tccaacctgc   2700
cactcgcagg cgaaggcaaa ggctttgcgc ggatcttcct caagcgcgaa gacctcgtcc   2760
acggcggtgc acacaaaact aaccaggtga tcggccaggt gctgcttgcc aagcgcatgg   2820
gcaaaacccg catcatcgca gagaccggcg caggccagca cggcaccgcc accgctctcg   2880
catgtgcgct catgggcctc gagtgcgttg tctacatggg cgccaaggac gttgcccgcc   2940
agcagcccaa cgtctaccgc atgcagctgc acggcgcgaa ggtcatcccc gtggaatctg   3000
gttccggcac cctgaaggac gccgtgaatg aagcgctgcg cgattggacc gcaaccttcc   3060
acgagtccca ctaccttctc ggcaccgccg ccggcccgca cccattccca accatcgtgc   3120
gtgaattcca caaggtgatc tctgaggaag ccaaggcaca gatgctagag cgcaccggca   3180
agcttcccga cgttgtggtc gcctgtgtcg gtggtggctc caacgccatc ggcatgttcg   3240
cagacttcat tgacgatgaa ggtgtagagc tcgtcggcgc tgagccagcc ggtgaaggcc   3300
tcgactccgg caagcacggc gcaaccatca ccaacggtca gatcggcatc ctgcacggca   3360
cccgttccta cctgatgcgc aactccgacg gccaagtgga agagtcctac tccatctccg   3420
ccggacttga ttacccaggc gtcggcccac agcacgcaca cctgcacgcc accgccgcg    3480 ccacctacgt tggtatcacc gacgccgaag ccctccaagc attccagtac ctcgcccgct   3540
acgaaggcat catccccgca ctggaatcct cacacgcgtt cgcctacgca ctcaagcgcg   3600
ccaagaccgc cgaagaggaa ggccagaact taaccatcct cgtctcccta tccggccgtg   3660
gcgacaagga cgttgaccac gtgcgccgca ccctcgaaga aaatccagaa ctgatcctga   3720
aggacaaccg atgagccgtt acgacgatct ttttgcacgc ctcgacacgg caggggaggg   3780
cgcctttgtt cccttcatca tgctgagcga cccttcacca gaggaggctt ccagatcat   3840 ctccacagca atcgaagctg gcgcagatgc actggaactt ggcgtacctt tctccgaccc   3900
agttgccgat ggccccaccg tcgcggaatc ccacctccgc gcactcgacg gcggcgccac   3960
cgtagacagc gcactcgagc agatcaagcg cgtgcgcgca gcctacccag aggttcccat   4020
cggaatgctc atctacggca acgttccttt cacccgtggc ttggatcgct tctaccaaga   4080
gttcgctgaa gctggcgcag actccatcct cctgccagac gtcccagtcc gcgaaggcgc   4140
accgttttct gcagcagctg cagcagccgg aattgatccc atttacatcg ctccggccaa   4200
cgccagcgag aaaaccctcg agggtgtctc cgccgcatca aagggctaca tctacgccat   4260
ctcccgcgac ggcgtcaccg gcaccgaacg tgaatcatcc accgacggcc tgtccgcagt   4320
ggtggacaac atcaagaaat ttgatggcgc acccatcctc ttgggcttcg gcatctcatc   4380
ccctcagcac gtggcagacg cgattgcagc gggtgcttcc ggtgcgatca cgggttccgc   4440
gatcaccaag atcattgctt cccactgcga aggtgagcac ccgaacccgt ccaccattcg   4500
agatatggac ggtttgaaga aggatctcac tgagttcatc tctgcgatga aggcagcgac   4560
caagaaggtt tag                                                       4573
```

<210> SEQ ID NO 5
<211> LENGTH: 531
<212> TYPE: PRT
<213> ORGANISM: Escherichia coli

<400> SEQUENCE: 5

```
Met Ala Asp Ile Leu Leu Asp Asn Ile Asp Ser Phe Thr Tyr Asn
1               5                   10                  15

Leu Ala Asp Gln Leu Arg Ser Asn Gly His Asn Val Val Ile Tyr Arg
            20                  25                  30

Asn His Ile Pro Ala Gln Thr Leu Ile Glu Arg Leu Ala Thr Met Ser
                35                  40                  45

Asn Pro Val Leu Met Leu Ser Pro Gly Pro Gly Val Pro Ser Glu Ala
    50                  55                  60

Gly Cys Met Pro Glu Leu Leu Thr Arg Leu Arg Gly Lys Leu Pro Ile
65                  70                  75                  80

Ile Gly Ile Cys Leu Gly His Gln Ala Ile Val Glu Ala Tyr Gly Gly
                85                  90                  95

Tyr Val Gly Gln Ala Gly Glu Ile Leu His Gly Lys Ala Ser Ser Ile
            100                 105                 110

Glu His Asp Gly Gln Ala Met Phe Ala Gly Leu Thr Asn Pro Leu Pro
        115                 120                 125

Val Ala Arg Tyr His Ser Leu Val Gly Ser Asn Ile Pro Ala Gly Leu
    130                 135                 140

Thr Ile Asn Ala His Phe Asn Gly Met Val Met Ala Val Arg His Asp
145                 150                 155                 160

Ala Asp Arg Val Cys Gly Phe Gln Phe His Pro Glu Ser Ile Leu Thr
                165                 170                 175

Thr Gln Gly Ala Arg Leu Leu Glu Gln Thr Leu Ala Trp Ala Gln Gln
            180                 185                 190

Lys Leu Glu Pro Ala Asn Thr Leu Gln Pro Ile Leu Glu Lys Leu Tyr
        195                 200                 205

Gln Ala Gln Thr Leu Ser Gln Gln Glu Ser His Gln Leu Phe Ser Ala
    210                 215                 220

Val Val Arg Gly Glu Leu Lys Pro Glu Gln Leu Ala Ala Ala Leu Val
225                 230                 235                 240

Ser Met Lys Ile Arg Gly Glu His Pro Asn Glu Ile Ala Gly Ala Ala
                245                 250                 255

Thr Ala Leu Leu Glu Asn Ala Ala Pro Phe Pro Arg Pro Asp Tyr Leu
            260                 265                 270

Phe Ala Asp Ile Val Gly Thr Gly Gly Asp Gly Ser Asn Ser Ile Asn
        275                 280                 285

Ile Ser Thr Ala Ser Ala Phe Val Ala Ala Ala Cys Gly Leu Lys Val
    290                 295                 300

Ala Lys His Gly Asn Arg Ser Val Ser Ser Lys Ser Gly Ser Ser Asp
305                 310                 315                 320

Leu Leu Ala Ala Phe Gly Ile Asn Leu Asp Met Asn Ala Asp Lys Ser
                325                 330                 335

Arg Gln Ala Leu Asp Glu Leu Gly Val Cys Phe Leu Phe Ala Pro Lys
            340                 345                 350

Tyr His Thr Gly Phe Arg His Ala Met Pro Val Arg Gln Gln Leu Lys
        355                 360                 365

Thr Arg Thr Leu Phe Asn Val Leu Gly Pro Leu Ile Asn Pro Ala His
    370                 375                 380
```

Pro Pro Leu Ala Leu Ile Gly Val Tyr Ser Pro Glu Leu Val Leu Pro
385                 390                 395                 400

Ile Ala Glu Thr Leu Arg Val Leu Gly Tyr Gln Arg Ala Ala Val Val
            405                 410                 415

His Ser Gly Gly Met Asp Glu Val Ser Leu His Ala Pro Thr Ile Val
        420                 425                 430

Ala Glu Leu His Asp Gly Glu Ile Lys Ser Tyr Gln Leu Thr Ala Glu
    435                 440                 445

Asp Phe Gly Leu Thr Pro Tyr His Gln Glu Gln Leu Ala Gly Gly Thr
450                 455                 460

Pro Glu Glu Asn Arg Asp Ile Leu Thr Arg Leu Leu Gln Gly Lys Gly
465                 470                 475                 480

Asp Ala Ala His Glu Ala Ala Val Ala Ala Asn Val Ala Met Leu Met
                485                 490                 495

Arg Leu His Gly His Glu Asp Leu Gln Ala Asn Ala Gln Thr Val Leu
            500                 505                 510

Glu Val Leu Arg Ser Gly Ser Ala Tyr Asp Arg Val Thr Ala Leu Ala
        515                 520                 525

Ala Arg Gly
    530

<210> SEQ ID NO 6
<211> LENGTH: 348
<212> TYPE: PRT
<213> ORGANISM: Corynebacterium glutamicum

<400> SEQUENCE: 6

Met Thr Ser Pro Ala Thr Leu Lys Val Leu Asn Ala Tyr Leu Asp Asn
1               5                   10                  15

Pro Thr Pro Thr Leu Glu Glu Ala Ile Glu Val Phe Thr Pro Leu Thr
            20                  25                  30

Val Gly Glu Tyr Asp Asp Val His Ile Ala Ala Leu Leu Ala Thr Ile
        35                  40                  45

Arg Thr Arg Gly Glu Gln Phe Ala Asp Ile Ala Gly Ala Ala Lys Ala
    50                  55                  60

Phe Leu Ala Ala Arg Pro Phe Pro Ile Thr Gly Ala Gly Leu Leu
65                  70                  75                  80

Asp Ser Ala Gly Thr Gly Gly Asp Gly Ala Asn Thr Ile Asn Ile Thr
                85                  90                  95

Thr Gly Ala Ser Leu Ile Ala Ala Ser Gly Gly Val Lys Leu Val Lys
            100                 105                 110

His Gly Asn Arg Ser Val Ser Ser Lys Ser Gly Ser Ala Asp Val Leu
        115                 120                 125

Glu Ala Leu Asn Ile Pro Leu Gly Leu Asp Val Asp Arg Ala Val Lys
    130                 135                 140

Trp Phe Glu Ala Ser Asn Phe Thr Phe Leu Phe Ala Pro Ala Tyr Asn
145                 150                 155                 160

Pro Ala Ile Ala His Val Gln Pro Val Arg Gln Ala Leu Lys Phe Pro
                165                 170                 175

Thr Ile Phe Asn Thr Leu Gly Pro Leu Leu Ser Pro Ala Arg Pro Glu
            180                 185                 190

Arg Gln Ile Met Gly Val Ala Asn Ala Asn His Gly Gln Leu Ile Ala
        195                 200                 205

Glu Val Phe Arg Glu Leu Gly Arg Thr Arg Ala Leu Val Val His Gly

Ala Gly Thr Asp Glu Ile Ala Val His Gly Thr Thr Leu Val Trp Glu
225                 230                 235                 240

Leu Lys Glu Asp Gly Thr Ile Glu His Tyr Thr Ile Glu Pro Glu Asp
                245                 250                 255

Leu Gly Leu Gly Arg Tyr Thr Leu Glu Asp Leu Val Gly Leu Gly
            260                 265                 270

Thr Glu Asn Ala Glu Ala Met Arg Ala Thr Phe Ala Gly Thr Gly Pro
                275                 280                 285

Asp Ala His Arg Asp Ala Leu Ala Ala Ser Ala Gly Ala Met Phe Tyr
            290                 295                 300

Leu Asn Gly Asp Val Asp Ser Leu Lys Asp Gly Ala Gln Lys Ala Leu
305                 310                 315                 320

Ser Leu Leu Ala Asp Gly Thr Thr Gln Ala Trp Leu Ala Lys His Glu
                325                 330                 335

Glu Ile Asp Tyr Ser Glu Lys Glu Ser Ser Asn Asp
                340                 345

<210> SEQ ID NO 7
<211> LENGTH: 348
<212> TYPE: PRT
<213> ORGANISM: Corynebacterium glutamicum

<400> SEQUENCE: 7

Met Thr Ser Pro Ala Thr Leu Lys Val Leu Asn Ala Tyr Leu Asp Asn
1               5                   10                  15

Pro Thr Pro Thr Leu Glu Glu Ala Ile Glu Val Phe Thr Pro Leu Thr
            20                  25                  30

Val Gly Glu Tyr Asp Asp Val His Ile Ala Ala Leu Leu Ala Thr Ile
        35                  40                  45

Arg Thr Arg Gly Glu Gln Phe Ala Asp Ile Ala Gly Ala Ala Lys Ala
    50                  55                  60

Phe Leu Ala Ala Ala Arg Pro Phe Pro Ile Thr Gly Ala Gly Leu Leu
65                  70                  75                  80

Asp Ser Ala Gly Thr Gly Gly Asp Gly Ala Asn Thr Ile Asn Ile Thr
                85                  90                  95

Thr Gly Ala Ser Leu Ile Ala Ala Ser Gly Gly Val Lys Leu Val Lys
            100                 105                 110

His Gly Asn Arg Ser Val Ser Ser Lys Ser Gly Ser Ala Asp Val Leu
        115                 120                 125

Glu Ala Leu Asn Ile Pro Leu Gly Leu Asp Val Asp Arg Ala Val Lys
    130                 135                 140

Trp Phe Glu Ala Phe Asn Phe Thr Phe Leu Phe Ala Pro Ala Tyr Asn
145                 150                 155                 160

Pro Glu Ile Ala His Val Gln Pro Val Arg Gln Ala Leu Lys Phe Pro
                165                 170                 175

Thr Ile Phe Asn Thr Leu Gly Pro Leu Leu Ser Pro Ala Arg Pro Glu
            180                 185                 190

Arg Gln Ile Met Gly Val Ala Asn Ala Asn His Gly Gln Leu Ile Ala
        195                 200                 205

Glu Val Phe Arg Glu Leu Gly Arg Thr Arg Ala Leu Val Val His Gly
    210                 215                 220

Ala Gly Thr Asp Glu Ile Ala Val His Gly Thr Thr Leu Val Trp Glu
225                 230                 235                 240

```
Leu Lys Glu Asp Gly Thr Ile Glu His Tyr Thr Ile Glu Pro Glu Asp
            245                 250                 255

Leu Gly Leu Gly Arg Tyr Thr Leu Glu Asp Leu Val Gly Gly Leu Gly
        260                 265                 270

Thr Glu Asn Ala Glu Ala Met Arg Ala Thr Phe Ala Gly Thr Gly Pro
            275                 280                 285

Asp Ala His Arg Asp Ala Leu Ala Ala Ser Ala Gly Ala Met Phe Tyr
        290                 295                 300

Leu Asn Gly Asp Val Asp Ser Leu Lys Asp Gly Ala Gln Lys Ala Leu
305                 310                 315                 320

Ser Leu Leu Ala Asp Gly Thr Thr Gln Ala Trp Leu Ala Lys His Glu
            325                 330                 335

Glu Ile Asp Tyr Ser Glu Lys Glu Ser Ser Asn Asp
            340                 345
```

<210> SEQ ID NO 8
<211> LENGTH: 452
<212> TYPE: PRT
<213> ORGANISM: Escherichia coli

<400> SEQUENCE: 8

```
Met Gln Thr Val Leu Ala Lys Ile Val Ala Asp Lys Ala Ile Trp Val
1               5                   10                  15

Glu Thr Arg Lys Glu Gln Gln Pro Leu Ala Ser Phe Gln Asn Glu Val
            20                  25                  30

Gln Pro Ser Thr Arg His Phe Tyr Asp Ala Leu Gln Gly Ala Arg Thr
        35                  40                  45

Ala Phe Ile Leu Glu Cys Lys Lys Ala Ser Pro Ser Lys Gly Val Ile
    50                  55                  60

Arg Asp Asp Phe Asp Pro Ala Arg Ile Ala Ile Tyr Lys His Tyr
65                  70                  75                  80

Ala Ser Ala Ile Ser Val Leu Thr Asp Glu Lys Tyr Phe Gln Gly Ser
                85                  90                  95

Phe Asp Phe Leu Pro Ile Val Ser Gln Ile Ala Pro Gln Pro Ile Leu
            100                 105                 110

Cys Lys Asp Phe Ile Ile Asp Pro Tyr Gln Ile Tyr Leu Ala Arg Tyr
        115                 120                 125

Tyr Gln Ala Asp Ala Cys Leu Leu Met Leu Ser Val Leu Asp Asp Glu
    130                 135                 140

Gln Tyr Arg Gln Leu Ala Ala Val Ala His Ser Leu Glu Met Gly Val
145                 150                 155                 160

Leu Thr Glu Val Ser Asn Glu Glu Glu Leu Glu Arg Ala Ile Ala Leu
                165                 170                 175

Gly Ala Lys Val Val Gly Ile Asn Asn Arg Asp Leu Arg Asp Leu Ser
            180                 185                 190

Ile Asp Leu Asn Arg Thr Arg Glu Leu Ala Pro Lys Leu Gly His Asn
        195                 200                 205

Val Thr Val Ile Ser Glu Ser Gly Ile Asn Thr Tyr Ala Gln Val Arg
    210                 215                 220

Glu Leu Ser His Phe Ala Asn Gly Phe Leu Ile Gly Ser Ala Leu Met
225                 230                 235                 240

Ala His Asp Asp Leu Asn Ala Ala Val Arg Arg Val Leu Leu Gly Glu
                245                 250                 255

Asn Lys Val Cys Gly Leu Thr Arg Gly Gln Asp Ala Lys Ala Ala Tyr
            260                 265                 270
```

```
Asp Ala Gly Ala Ile Tyr Gly Gly Leu Ile Phe Val Ala Thr Ser Pro
        275                 280                 285

Arg Cys Val Asn Val Glu Gln Ala Gln Glu Val Met Ala Ala Ala Pro
    290                 295                 300

Leu Gln Tyr Val Gly Val Phe Arg Asn His Asp Ile Ala Asp Val Ala
305                 310                 315                 320

Asp Lys Ala Lys Val Leu Ser Leu Ala Ala Val Gln Leu His Gly Asn
                325                 330                 335

Glu Asp Gln Leu Tyr Ile Asp Asn Leu Arg Glu Ala Leu Pro Ala His
                340                 345                 350

Val Ala Ile Trp Lys Ala Leu Ser Val Gly Thr Leu Pro Ala Arg
                355                 360                 365

Asp Phe Gln His Ile Asp Lys Tyr Val Phe Asp Asn Gly Gln Gly Gly
                370                 375                 380

Ser Gly Gln Arg Phe Asp Trp Ser Leu Leu Asn Gly Gln Thr Leu Gly
385                 390                 395                 400

Asn Val Leu Leu Ala Gly Gly Leu Gly Ala Asp Asn Cys Val Glu Ala
                405                 410                 415

Ala Gln Thr Gly Cys Ala Gly Leu Asp Phe Asn Ser Ala Val Glu Ser
                420                 425                 430

Gln Pro Gly Ile Lys Asp Ala Arg Leu Leu Ala Ser Val Phe Gln Thr
                435                 440                 445

Leu Arg Ala Tyr
        450

<210> SEQ ID NO 9
<211> LENGTH: 474
<212> TYPE: PRT
<213> ORGANISM: Corynebacterium glutamicum

<400> SEQUENCE: 9

Met Thr Ser Asn Asn Leu Pro Thr Val Leu Glu Ser Ile Val Glu Gly
1               5                   10                  15

Arg Arg Gly His Leu Glu Glu Ile Arg Ala Arg Ile Ala His Val Asp
                20                  25                  30

Val Asp Ala Leu Pro Lys Ser Thr Arg Ser Leu Phe Asp Ser Leu Asn
            35                  40                  45

Gln Gly Arg Gly Gly Ala Arg Phe Ile Met Glu Cys Lys Ser Ala Ser
        50                  55                  60

Pro Ser Leu Gly Met Ile Arg Glu His Tyr Gln Pro Gly Glu Ile Ala
65                  70                  75                  80

Arg Val Tyr Ser Arg Tyr Ala Ser Gly Ile Ser Val Leu Cys Glu Pro
                85                  90                  95

Asp Arg Phe Gly Gly Asp Tyr Asp His Leu Ala Thr Val Ala Ala Thr
                100                 105                 110

Ser His Leu Pro Val Leu Cys Lys Asp Phe Ile Ile Asp Pro Val Gln
        115                 120                 125

Val His Ala Ala Arg Tyr Phe Gly Ala Asp Ala Ile Leu Leu Met Leu
    130                 135                 140

Ser Val Leu Asp Asp Glu Glu Tyr Ala Ala Leu Ala Glu Ala Ala
145                 150                 155                 160

Arg Phe Asp Leu Asp Ile Leu Thr Glu Val Ile Asp Glu Glu Val
                165                 170                 175

Ala Arg Ala Ile Lys Leu Gly Ala Lys Ile Phe Gly Val Asn His Arg
```

```
            180                 185                 190
Asn Leu His Asp Leu Ser Ile Asp Leu Asp Arg Ser Arg Arg Leu Ser
                195                 200                 205

Lys Leu Ile Pro Ala Asp Ala Val Leu Val Ser Glu Ser Gly Val Arg
    210                 215                 220

Asp Thr Glu Thr Val Arg Gln Leu Gly Gly His Ser Asn Ala Phe Leu
225                 230                 235                 240

Val Gly Ser Gln Leu Thr Ser Gln Glu Asn Val Asp Leu Ala Ala Arg
                245                 250                 255

Glu Leu Val Tyr Gly Pro Asn Lys Val Cys Gly Leu Thr Ser Pro Ser
        260                 265                 270

Ala Ala Gln Thr Ala Arg Ala Ala Gly Ala Val Tyr Gly Gly Leu Ile
            275                 280                 285

Phe Glu Glu Ala Ser Pro Arg Asn Val Ser Arg Glu Thr Leu Gln Lys
290                 295                 300

Ile Ile Ala Ala Glu Pro Asn Leu Arg Tyr Val Ala Val Ser Arg Arg
305                 310                 315                 320

Thr Ser Gly Tyr Lys Asp Leu Leu Val Asp Gly Ile Phe Ala Val Gln
                325                 330                 335

Ile His Ala Pro Leu Gln Asp Ser Val Glu Ala Glu Lys Ala Leu Ile
            340                 345                 350

Ala Ala Val Arg Glu Glu Val Gly Pro Gln Val Gln Val Trp Arg Ala
        355                 360                 365

Ile Ser Met Ser Ser Pro Leu Gly Ala Glu Val Ala Ala Val Glu
370                 375                 380

Gly Asp Val Asp Lys Leu Ile Leu Asp Ala His Glu Gly Gly Ser Gly
385                 390                 395                 400

Glu Val Phe Asp Trp Ala Thr Val Pro Ala Ala Val Lys Ala Lys Ser
                405                 410                 415

Leu Leu Ala Gly Gly Ile Ser Pro Asp Asn Ala Ala Gln Ala Leu Ala
            420                 425                 430

Val Gly Cys Ala Gly Leu Asp Ile Asn Ser Gly Val Glu Tyr Pro Ala
        435                 440                 445

Gly Ala Gly Thr Trp Ala Gly Ala Lys Asp Ala Gly Ala Leu Leu Lys
    450                 455                 460

Ile Phe Ala Thr Ile Ser Thr Phe His Tyr
465                 470

<210> SEQ ID NO 10
<211> LENGTH: 397
<212> TYPE: PRT
<213> ORGANISM: Escherichia coli

<400> SEQUENCE: 10

Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80
```

```
Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Glu Asp Gly Gln Ile Glu Glu Ser Tyr Ser Ile Ser Ala Gly Leu
    290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
        355                 360                 365

Glu Gln Leu Leu Val Val Asn Leu Ser Gly Arg Gly Asp Lys Asp Ile
    370                 375                 380

Phe Thr Val His Asp Ile Leu Lys Ala Arg Gly Glu Ile
385                 390                 395

<210> SEQ ID NO 11
<211> LENGTH: 417
<212> TYPE: PRT
<213> ORGANISM: Corynebacterium glutamicum

<400> SEQUENCE: 11

Met Thr Glu Lys Glu Asn Leu Gly Gly Ser Thr Leu Leu Pro Ala Tyr
1               5                   10                  15

Phe Gly Glu Phe Gly Gly Gln Phe Val Ala Glu Ser Leu Leu Pro Ala
            20                  25                  30

Leu Asp Gln Leu Glu Lys Ala Phe Val Asp Ala Thr Asn Ser Pro Glu
        35                  40                  45

Phe Arg Glu Glu Leu Gly Gly Tyr Leu Arg Asp Tyr Leu Gly Arg Pro
    50                  55                  60
```

```
Thr Pro Leu Thr Glu Cys Ser Asn Leu Pro Leu Ala Gly Glu Gly Lys
 65                  70                  75                  80

Gly Phe Ala Arg Ile Phe Leu Lys Arg Glu Asp Leu Val His Gly Gly
                 85                  90                  95

Ala His Lys Thr Asn Gln Val Ile Gly Gln Val Leu Leu Ala Lys Arg
            100                 105                 110

Met Gly Lys Thr Arg Ile Ile Ala Glu Thr Gly Ala Gly Gln His Gly
        115                 120                 125

Thr Ala Thr Ala Leu Ala Cys Ala Leu Met Gly Leu Glu Cys Val Val
130                 135                 140

Tyr Met Gly Ala Lys Asp Val Ala Arg Gln Gln Pro Asn Val Tyr Arg
145                 150                 155                 160

Met Gln Leu His Gly Ala Lys Val Ile Pro Val Glu Ser Gly Ser Gly
                165                 170                 175

Thr Leu Lys Asp Ala Val Asn Glu Ala Leu Arg Asp Trp Thr Ala Thr
            180                 185                 190

Phe His Glu Ser His Tyr Leu Leu Gly Thr Ala Ala Gly Pro His Pro
        195                 200                 205

Phe Pro Thr Ile Val Arg Glu Phe His Lys Val Ile Ser Glu Glu Ala
210                 215                 220

Lys Ala Gln Met Leu Glu Arg Thr Gly Lys Leu Pro Asp Val Val Val
225                 230                 235                 240

Ala Cys Val Gly Gly Gly Ser Asn Ala Ile Gly Met Phe Ala Asp Phe
                245                 250                 255

Ile Asp Asp Glu Gly Val Glu Leu Val Gly Ala Glu Pro Ala Gly Glu
            260                 265                 270

Gly Leu Asp Ser Gly Lys His Gly Ala Thr Ile Thr Asn Gly Gln Ile
        275                 280                 285

Gly Ile Leu His Gly Thr Arg Ser Tyr Leu Met Arg Asn Ser Asp Gly
290                 295                 300

Gln Val Glu Glu Ser Tyr Ser Ile Ser Ala Gly Leu Asp Tyr Pro Gly
305                 310                 315                 320

Val Gly Pro Gln His Ala His Leu His Ala Thr Gly Arg Ala Thr Tyr
                325                 330                 335

Val Gly Ile Thr Asp Ala Glu Ala Leu Gln Ala Phe Gln Tyr Leu Ala
            340                 345                 350

Arg Tyr Glu Gly Ile Ile Pro Ala Leu Glu Ser Ser His Ala Phe Ala
        355                 360                 365

Tyr Ala Leu Lys Arg Ala Lys Thr Ala Glu Glu Gly Gln Asn Leu
370                 375                 380

Thr Ile Leu Val Ser Leu Ser Gly Arg Gly Asp Lys Asp Val Asp His
385                 390                 395                 400

Val Arg Arg Thr Leu Glu Glu Asn Pro Glu Leu Ile Leu Lys Asp Asn
                405                 410                 415

Arg

<210> SEQ ID NO 12
<211> LENGTH: 520
<212> TYPE: PRT
<213> ORGANISM: Escherichia coli

<400> SEQUENCE: 12

Met Gln Thr Gln Lys Pro Thr Leu Glu Leu Leu Thr Cys Glu Gly Ala
 1                   5                  10                  15
```

Tyr Arg Asp Asn Pro Thr Ala Leu Phe His Gln Leu Cys Gly Asp Arg
                20                  25                  30

Pro Ala Thr Leu Leu Glu Ser Ala Asp Ile Asp Ser Lys Asp Asp
            35                  40                  45

Leu Lys Ser Leu Leu Val Asp Ser Ala Leu Arg Ile Thr Ala Leu
 50                  55                  60

Gly Asp Thr Val Thr Ile Gln Ala Leu Ser Gly Asn Gly Glu Ala Leu
 65                  70                  75                  80

Leu Ala Leu Leu Asp Asn Ala Leu Pro Ala Gly Val Glu Ser Glu Gln
                 85                  90                  95

Ser Pro Asn Cys Arg Val Leu Arg Phe Pro Pro Val Ser Pro Leu Leu
                100                 105                 110

Asp Glu Asp Ala Arg Leu Cys Ser Leu Ser Val Phe Asp Ala Phe Arg
                115                 120                 125

Leu Leu Gln Asn Leu Leu Asn Val Pro Lys Glu Glu Arg Glu Ala Met
130                 135                 140

Phe Phe Gly Gly Leu Phe Ser Tyr Asp Leu Val Ala Gly Phe Glu Asp
145                 150                 155                 160

Leu Pro Gln Leu Ser Ala Glu Asn Asn Cys Pro Asp Phe Cys Phe Tyr
                165                 170                 175

Leu Ala Glu Thr Leu Met Val Ile Asp His Gln Lys Lys Ser Thr Arg
                180                 185                 190

Ile Gln Ala Ser Leu Phe Ala Pro Asn Glu Glu Lys Gln Arg Leu
                195                 200                 205

Thr Ala Arg Leu Asn Glu Leu Arg Gln Gln Leu Thr Glu Ala Ala Pro
        210                 215                 220

Pro Leu Pro Val Val Ser Val Pro His Met Arg Cys Glu Cys Asn Gln
225                 230                 235                 240

Ser Asp Glu Glu Phe Gly Gly Val Val Arg Leu Leu Gln Lys Ala Ile
                245                 250                 255

Arg Ala Gly Glu Ile Phe Gln Val Val Pro Ser Arg Arg Phe Ser Leu
                260                 265                 270

Pro Cys Pro Ser Pro Leu Ala Ala Tyr Tyr Val Leu Lys Lys Ser Asn
            275                 280                 285

Pro Ser Pro Tyr Met Phe Phe Met Gln Asp Asn Asp Phe Thr Leu Phe
            290                 295                 300

Gly Ala Ser Pro Glu Ser Ser Leu Lys Tyr Asp Ala Thr Ser Arg Gln
305                 310                 315                 320

Ile Glu Ile Tyr Pro Ile Ala Gly Thr Arg Pro Arg Gly Arg Arg Ala
                325                 330                 335

Asp Gly Ser Leu Asp Arg Asp Leu Asp Ser Arg Ile Glu Leu Glu Met
            340                 345                 350

Arg Thr Asp His Lys Glu Leu Ser Glu His Leu Met Leu Val Asp Leu
        355                 360                 365

Ala Arg Asn Asp Leu Ala Arg Ile Cys Thr Pro Gly Ser Arg Tyr Val
        370                 375                 380

Ala Asp Leu Thr Lys Val Asp Arg Tyr Ser Tyr Val Met His Leu Val
385                 390                 395                 400

Ser Arg Val Val Gly Glu Leu Arg His Asp Leu Asp Ala Leu His Ala
                405                 410                 415

Tyr Arg Ala Cys Met Asn Met Gly Thr Leu Ser Gly Ala Pro Lys Val
            420                 425                 430

```
Arg Ala Met Gln Leu Ile Ala Glu Ala Glu Gly Arg Arg Gly Ser
            435                 440                 445

Tyr Gly Gly Ala Val Gly Tyr Phe Thr Ala His Gly Asp Leu Asp Thr
450                 455                 460

Cys Ile Val Ile Arg Ser Ala Leu Val Glu Asn Gly Ile Ala Thr Val
465                 470                 475                 480

Gln Ala Gly Ala Gly Val Val Leu Asp Ser Val Pro Gln Ser Glu Ala
                485                 490                 495

Asp Glu Thr Arg Asn Lys Ala Arg Ala Val Leu Arg Ala Ile Ala Thr
            500                 505                 510

Ala His His Ala Gln Glu Thr Phe
            515                 520

<210> SEQ ID NO 13
<211> LENGTH: 280
<212> TYPE: PRT
<213> ORGANISM: Corynebacterium glutamicum

<400> SEQUENCE: 13

Met Ser Arg Tyr Asp Asp Leu Phe Ala Arg Leu Asp Thr Ala Gly Glu
1               5                   10                  15

Gly Ala Phe Val Pro Phe Ile Met Leu Ser Asp Pro Ser Pro Glu Glu
                20                  25                  30

Ala Phe Gln Ile Ile Ser Thr Ala Ile Glu Ala Gly Ala Asp Ala Leu
            35                  40                  45

Glu Leu Gly Val Pro Phe Ser Asp Pro Val Ala Asp Gly Pro Thr Val
50                  55                  60

Ala Glu Ser His Leu Arg Ala Leu Asp Gly Gly Ala Thr Val Asp Ser
65                  70                  75                  80

Ala Leu Glu Gln Ile Lys Arg Val Arg Ala Ala Tyr Pro Glu Val Pro
                85                  90                  95

Ile Gly Met Leu Ile Tyr Gly Asn Val Pro Phe Thr Arg Gly Leu Asp
            100                 105                 110

Arg Phe Tyr Gln Glu Phe Ala Glu Ala Gly Ala Asp Ser Ile Leu Leu
        115                 120                 125

Pro Asp Val Pro Val Arg Glu Gly Ala Pro Phe Ser Ala Ala Ala Ala
130                 135                 140

Ala Ala Gly Ile Asp Pro Ile Tyr Ile Ala Pro Ala Asn Ala Ser Glu
145                 150                 155                 160

Lys Thr Leu Glu Gly Val Ser Ala Ala Ser Lys Gly Tyr Ile Tyr Ala
                165                 170                 175

Ile Ser Arg Asp Gly Val Thr Gly Thr Glu Arg Glu Ser Ser Thr Asp
            180                 185                 190

Gly Leu Ser Ala Val Val Asp Asn Ile Lys Lys Phe Asp Gly Ala Pro
        195                 200                 205

Ile Leu Leu Gly Phe Gly Ile Ser Ser Pro Gln His Val Ala Asp Ala
210                 215                 220

Ile Ala Ala Gly Ala Ser Gly Ala Ile Thr Gly Ser Ala Ile Thr Lys
225                 230                 235                 240

Ile Ile Ala Ser His Cys Glu Gly Glu His Pro Asn Pro Ser Thr Ile
                245                 250                 255

Arg Asp Met Asp Gly Leu Lys Lys Asp Leu Thr Glu Phe Ile Ser Ala
            260                 265                 270

Met Lys Ala Ala Thr Lys Lys Val
        275                 280
```

<210> SEQ ID NO 14
<211> LENGTH: 439
<212> TYPE: PRT
<213> ORGANISM: Psilocybe cubensis

<400> SEQUENCE: 14

Met Gln Val Ile Pro Ala Cys Asn Ser Ala Ala Ile Arg Ser Leu Cys
1               5                   10                  15

Pro Thr Pro Glu Ser Phe Arg Asn Met Gly Trp Leu Ser Val Ser Asp
            20                  25                  30

Ala Val Tyr Ser Glu Phe Ile Gly Glu Leu Ala Thr Arg Ala Ser Asn
        35                  40                  45

Arg Asn Tyr Ser Asn Glu Phe Gly Leu Met Gln Pro Ile Gln Glu Phe
    50                  55                  60

Lys Ala Phe Ile Glu Ser Asp Pro Val Val His Gln Glu Phe Ile Asp
65                  70                  75                  80

Met Phe Glu Gly Ile Gln Asp Ser Pro Arg Asn Tyr Gln Glu Leu Cys
                85                  90                  95

Asn Met Phe Asn Asp Ile Phe Arg Lys Ala Pro Val Tyr Gly Asp Leu
            100                 105                 110

Gly Pro Pro Val Tyr Met Ile Met Ala Lys Leu Met Asn Thr Arg Ala
        115                 120                 125

Gly Phe Ser Ala Phe Thr Arg Gln Arg Leu Asn Leu His Phe Lys Lys
    130                 135                 140

Leu Phe Asp Thr Trp Gly Leu Phe Leu Ser Ser Lys Asp Ser Arg Asn
145                 150                 155                 160

Val Leu Val Ala Asp Gln Phe Asp Asp Arg His Cys Gly Trp Leu Asn
                165                 170                 175

Glu Arg Ala Leu Ser Ala Met Val Lys His Tyr Asn Gly Arg Ala Phe
            180                 185                 190

Asp Glu Val Phe Leu Cys Asp Lys Asn Ala Pro Tyr Tyr Gly Phe Asn
        195                 200                 205

Ser Tyr Asp Asp Phe Phe Asn Arg Arg Phe Arg Asn Arg Asp Ile Asp
    210                 215                 220

Arg Pro Val Val Gly Gly Val Asn Asn Thr Thr Leu Ile Ser Ala Ala
225                 230                 235                 240

Cys Glu Ser Leu Ser Tyr Asn Val Ser Tyr Asp Val Gln Ser Leu Asp
                245                 250                 255

Thr Leu Val Phe Lys Gly Glu Thr Tyr Ser Leu Lys His Leu Leu Asn
            260                 265                 270

Asn Asp Pro Phe Thr Pro Gln Phe Glu His Gly Ser Ile Leu Gln Gly
        275                 280                 285

Phe Leu Asn Val Thr Ala Tyr His Arg Trp His Ala Pro Val Asn Gly
    290                 295                 300

Thr Ile Val Lys Ile Ile Asn Val Pro Gly Thr Tyr Phe Ala Gln Ala
305                 310                 315                 320

Pro Ser Thr Ile Gly Asp Pro Ile Pro Asp Asn Asp Tyr Asp Pro Pro
                325                 330                 335

Pro Tyr Leu Lys Ser Leu Val Tyr Phe Ser Asn Ile Ala Ala Arg Gln
            340                 345                 350

Ile Met Phe Ile Glu Ala Asp Asn Lys Glu Ile Gly Leu Ile Phe Leu
        355                 360                 365

Val Phe Ile Gly Met Thr Glu Ile Ser Thr Cys Glu Ala Thr Val Ser

```
                370                 375                 380
Glu Gly Gln His Val Asn Arg Gly Asp Asp Leu Gly Met Phe His Phe
385                 390                 395                 400

Gly Gly Ser Ser Phe Ala Leu Gly Leu Arg Lys Asp Cys Arg Ala Glu
                405                 410                 415

Ile Val Glu Lys Phe Thr Glu Pro Gly Thr Val Ile Arg Ile Asn Glu
                420                 425                 430

Val Val Ala Ala Leu Lys Ala
            435

<210> SEQ ID NO 15
<211> LENGTH: 439
<212> TYPE: PRT
<213> ORGANISM: Psilocybe cyanescens

<400> SEQUENCE: 15

Met Gln Val Leu Pro Ala Cys Gln Ser Ser Ala Leu Lys Thr Leu Cys
1               5                   10                  15

Pro Ser Pro Glu Ala Phe Arg Lys Leu Gly Trp Leu Pro Thr Ser Asp
                20                  25                  30

Glu Val Tyr Asn Glu Phe Ile Asp Asp Leu Thr Gly Arg Thr Cys Asn
                35                  40                  45

Glu Lys Tyr Ser Ser Gln Val Thr Leu Leu Lys Pro Ile Gln Asp Phe
50                  55                  60

Lys Thr Phe Ile Glu Asn Asp Pro Ile Val Tyr Gln Glu Phe Ile Ser
65                  70                  75                  80

Met Phe Glu Gly Ile Glu Gln Ser Pro Thr Asn Tyr His Glu Leu Cys
                85                  90                  95

Asn Met Phe Asn Asp Ile Phe Arg Lys Ala Pro Leu Tyr Gly Asp Leu
                100                 105                 110

Gly Pro Pro Val Tyr Met Ile Met Ala Arg Ile Met Asn Thr Gln Ala
                115                 120                 125

Gly Phe Ser Ala Phe Thr Lys Glu Ser Leu Asn Phe His Phe Lys Lys
            130                 135                 140

Leu Phe Asp Thr Trp Gly Leu Phe Leu Ser Ser Lys Asn Ser Arg Asn
145                 150                 155                 160

Val Leu Val Ala Asp Gln Phe Asp Asp Lys His Tyr Gly Trp Phe Ser
                165                 170                 175

Glu Arg Ala Lys Thr Ala Met Met Ile Asn Tyr Pro Gly Arg Thr Phe
                180                 185                 190

Glu Lys Val Phe Ile Cys Asp Glu His Val Pro Tyr His Gly Phe Thr
                195                 200                 205

Ser Tyr Asp Asp Phe Phe Asn Arg Arg Phe Arg Asp Lys Asp Thr Asp
            210                 215                 220

Arg Pro Val Val Gly Gly Val Thr Asp Thr Thr Leu Ile Gly Ala Ala
225                 230                 235                 240

Cys Glu Ser Leu Ser Tyr Asn Val Ser His Asn Val Gln Ser Leu Asp
                245                 250                 255

Thr Leu Val Ile Lys Gly Glu Ala Tyr Ser Leu Lys His Leu Leu His
                260                 265                 270

Asn Asp Pro Phe Thr Pro Gln Phe Glu His Gly Ser Ile Ile Gln Gly
            275                 280                 285

Phe Leu Asn Val Thr Ala Tyr His Arg Trp His Ser Pro Val Asn Gly
        290                 295                 300
```

```
Thr Ile Val Lys Ile Val Asn Val Pro Gly Thr Tyr Phe Ala Gln Ala
305                 310                 315                 320

Pro Tyr Thr Ile Gly Ser Pro Ile Pro Asp Asn Asp Arg Asp Pro Pro
                325                 330                 335

Pro Tyr Leu Lys Ser Leu Val Tyr Phe Ser Asn Ile Ala Ala Arg Gln
                340                 345                 350

Ile Met Phe Ile Glu Ala Asp Asn Lys Asp Ile Gly Leu Ile Phe Leu
                355                 360                 365

Val Phe Ile Gly Met Thr Glu Ile Ser Thr Cys Glu Ala Thr Val Cys
370                 375                 380

Glu Gly Gln His Val Asn Arg Gly Asp Asp Leu Gly Met Phe His Phe
385                 390                 395                 400

Gly Gly Ser Ser Phe Ala Leu Gly Leu Arg Lys Asp Ser Lys Ala Lys
                405                 410                 415

Ile Leu Glu Lys Phe Ala Lys Pro Gly Thr Val Ile Arg Ile Asn Glu
                420                 425                 430

Leu Val Ala Ser Val Arg Lys
                435

<210> SEQ ID NO 16
<211> LENGTH: 436
<212> TYPE: PRT
<213> ORGANISM: Psilocybe cyanescens

<400> SEQUENCE: 16

Met Gln Val Leu Thr Ala Cys Tyr Thr Ser Thr Leu Lys Ser Leu Leu
1               5                   10                  15

Pro Ser Phe Asp Ala Phe Arg Ser Met Gly Trp Leu Pro Val Ser Asp
                20                  25                  30

Lys Thr Tyr Asn Glu Trp Ile Gly Asp Leu Arg Ser Arg Ala Ser Asp
                35                  40                  45

Lys Asn Tyr Thr Ser Gln Val Gly Leu Ile Gln Pro Ile Lys Asp Phe
            50                  55                  60

Lys Ala Phe Ile Glu Ser Asp Pro Val Val His Gln Glu Phe Ile Thr
65              70                  75                  80

Met Phe Glu Gly Ile Glu Glu Ser Pro Arg Asn Tyr Glu Glu Leu Cys
                85                  90                  95

His Met Phe Asn Asp Ile Phe Arg Lys Ala Pro Val Tyr Gly Asp Leu
                100                 105                 110

Gly Pro Pro Val Tyr Met Val Met Ala Arg Ile Met Asn Thr Gln Ala
                115                 120                 125

Gly Phe Ser Ala Phe Thr Lys Gln Ser Leu Asn Ser His Phe Lys Arg
                130                 135                 140

Leu Phe Asp Thr Trp Gly Val Phe Leu Ser Ser Lys Glu Ser Arg Tyr
145                 150                 155                 160

Val Leu Val Thr Asp Gln Phe Asp Asp Asn His Tyr Gly Trp Leu Ser
                165                 170                 175

Asp Arg Ala Lys Ser Ala Met Val Lys His Tyr Tyr Gly Arg Thr Phe
                180                 185                 190

Glu Gln Val Phe Ile Cys Asp Glu His Ala Pro Tyr His Gly Phe Gln
                195                 200                 205

Ser Tyr Asp Asp Phe Phe Asn Arg Arg Phe Asp Arg Asp Ile Asp
                210                 215                 220

Arg Pro Val Val Gly Gly Ile Glu Asn Thr Thr Leu Ile Ser Ala Ala
225                 230                 235                 240
```

-continued

```
Cys Glu Ser Leu Ser Tyr Asn Val Cys His Asp Leu Gln Ser Leu Asp
                245                 250                 255

Thr Leu Phe Val Lys Gly Glu Ser Tyr Ser Leu Lys His Leu Leu Asn
            260                 265                 270

Asp Asp Pro Phe Ala Arg Gln Phe Glu His Gly Ser Ile Leu Gln Gly
        275                 280                 285

Phe Leu Asn Val Thr Ala Tyr His Arg Trp His Ala Pro Val Asn Gly
    290                 295                 300

Thr Ile Leu Lys Ile Ile Asn Val Pro Gly Thr Tyr Phe Ala Gln Ala
305                 310                 315                 320

Pro His Thr Ile Gly Asp Ser Leu Asp Ser Asp His Pro Pro Tyr Leu
                325                 330                 335

Lys Ser Leu Ala Tyr Phe Ser Asn Ile Ala Ala Arg Gln Ile Met Phe
            340                 345                 350

Ile Glu Ala Asp Asn Lys Asp Ile Gly Leu Ile Phe Leu Val Phe Ile
        355                 360                 365

Gly Met Thr Glu Ile Ser Thr Cys Glu Ala Thr Val Ser Glu Gly Gln
    370                 375                 380

His Val Asn Arg Gly Asp Asp Leu Gly Met Phe His Phe Gly Gly Ser
385                 390                 395                 400

Ser Phe Ala Leu Gly Leu Arg Lys Asp Cys Lys Ala Glu Ile Phe Glu
                405                 410                 415

Arg Phe Ala Glu Gln Gly Thr Val Ile Lys Ile Asn Glu Val Val Ala
            420                 425                 430

Ala Val Lys Asp
            435

<210> SEQ ID NO 17
<211> LENGTH: 430
<212> TYPE: PRT
<213> ORGANISM: Gymnopilus dilepis

<400> SEQUENCE: 17

Met Ala Lys Thr Leu Arg Pro Thr Ala Gln Ala Phe Arg Glu Leu Gly
1               5                   10                  15

Trp Leu Pro Ala Ser Asp Gly Val Tyr Asn Lys Phe Met Lys Asp Leu
            20                  25                  30

Thr Asn Arg Ala Ser Asn Glu Asn His Leu Cys His Val Ala Leu Leu
        35                  40                  45

Gln Pro Ile Gln Asp Phe Lys Thr Phe Ile Glu Asn Asp Pro Val Val
    50                  55                  60

Tyr Gln Glu Phe Val Cys Met Phe Glu Gly Ile Glu Glu Ser Pro Arg
65                  70                  75                  80

Asn Tyr His Glu Leu Cys Asn Met Phe Asn Glu Ile Phe Arg Arg Ala
                85                  90                  95

Pro Tyr Tyr Gly Asp Leu Gly Pro Val Tyr Met Ala Met Ala Lys
            100                 105                 110

Ile Met Asn Thr Arg Ala Gly Phe Ser Ala Phe Thr Arg Glu Ser Leu
        115                 120                 125

Asn Phe His Phe Lys Arg Leu Phe Asp Thr Trp Gly Leu Phe Leu Ser
    130                 135                 140

Ser Pro Ala Ser Arg Asp Val Leu Val Ala Asp Lys Phe Asp Ser Lys
145                 150                 155                 160

His Tyr Gly Trp Phe Ser Glu Pro Ala Lys Ala Ala Met Met Ala Gln
```

```
              165                 170                 175
Tyr Asp Gly Arg Thr Phe Glu Gln Val Phe Ile Cys Asp Glu Thr Ala
            180                 185                 190

Pro Tyr His Gly Phe Lys Ser Tyr Asp Asp Phe Phe Asn Arg Lys Phe
            195                 200                 205

Arg Ala Met Asp Ile Asp Arg Pro Val Gly Gly Ile Ala Asn Thr
210                 215                 220

Thr Leu Ile Gly Ser Pro Cys Glu Ala Leu Ser Tyr Asn Val Ser Asp
225                 230                 235                 240

Asp Val His Ser Leu Glu Thr Leu Tyr Phe Lys Gly Glu Gly Tyr Ser
                245                 250                 255

Leu Arg His Leu Leu His Asp Asp Pro Ser Thr Glu Gln Phe Glu His
            260                 265                 270

Gly Ser Ile Ile Gln Gly Phe Leu Asn Ile Thr Gly Tyr His Arg Trp
            275                 280                 285

His Ala Pro Val Ser Gly Thr Ile Met Lys Ile Val Asp Val Pro Gly
            290                 295                 300

Thr Tyr Phe Ala Gln Ala Pro Ser Thr Ile Gly Asp Pro Phe Pro Val
305                 310                 315                 320

Asn Asp Tyr Asp Pro Gln Ala Pro Tyr Leu Arg Ser Leu Ala Tyr Phe
                325                 330                 335

Ser Asn Ile Ala Ala Arg Gln Ile Ile Phe Ile Gln Ala Asp Asn Glu
            340                 345                 350

Asp Ile Gly Leu Ile Tyr Leu Ile Leu Ile Gly Met Thr Glu Val Ser
            355                 360                 365

Thr Cys Glu Ala Leu Val Cys Pro Gly Gln His Val Glu Arg Gly Asp
370                 375                 380

Asp Leu Gly Met Phe His Phe Gly Gly Ser Ser Phe Ala Leu Gly Leu
385                 390                 395                 400

Arg Lys Asn Ser Lys Ala Ala Ile Leu Glu Glu Leu Lys Thr Gln Gly
                405                 410                 415

Thr Val Ile Lys Val Asn Asp Val Ile Ala Ala Val Gln Ala
            420                 425                 430

<210> SEQ ID NO 18
<211> LENGTH: 480
<212> TYPE: PRT
<213> ORGANISM: Homo sapiens

<400> SEQUENCE: 18

Met Asn Ala Ser Glu Phe Arg Arg Gly Lys Glu Met Val Asp Tyr
1               5                   10                  15

Met Ala Asn Tyr Met Glu Gly Ile Glu Gly Arg Gln Val Tyr Pro Asp
                20                  25                  30

Val Glu Pro Gly Tyr Leu Arg Pro Leu Ile Pro Ala Ala Ala Pro Gln
            35                  40                  45

Glu Pro Asp Thr Phe Glu Asp Ile Ile Asn Asp Val Glu Lys Ile Ile
50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110
```

```
Glu Leu Glu Thr Val Met Met Asp Trp Leu Gly Lys Met Leu Glu Leu
            115                 120                 125

Pro Lys Ala Phe Leu Asn Glu Lys Ala Gly Glu Gly Gly Gly Val Ile
130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
            420                 425                 430

Ile His Leu Val Pro Cys His Leu Arg Asp Lys Phe Val Leu Arg Phe
        435                 440                 445

Ala Ile Cys Ser Arg Thr Val Glu Ser Ala His Val Gln Arg Ala Trp
    450                 455                 460

Glu His Ile Lys Glu Leu Ala Ala Asp Val Leu Arg Ala Glu Arg Glu
465                 470                 475                 480

<210> SEQ ID NO 19
<211> LENGTH: 480
<212> TYPE: PRT
<213> ORGANISM: Bacillus atrophaeus

<400> SEQUENCE: 19

Met Ser Glu Asn Leu Gln Leu Ser Ala Glu Glu Met Arg Gln Leu Gly
1               5                   10                  15
```

```
Tyr Gln Ala Val Asp Leu Ile Ile Asp His Met Asn His Leu Lys Ser
         20                  25                  30

Lys Pro Val Ser Glu Thr Ile Asp Ser Asp Ile Leu Arg Asn Lys Leu
         35                  40                  45

Thr Glu Ser Ile Pro Glu Asn Gly Ser Asp Pro Lys Glu Leu Leu His
 50                  55                  60

Phe Leu Asn Arg Asn Val Phe Asn Gln Ile Thr His Val Asp His Pro
 65                  70                  75                  80

His Phe Leu Ala Phe Val Pro Gly Pro Asn Asn Tyr Val Gly Val Val
                 85                  90                  95

Ala Asp Phe Leu Ala Ser Gly Phe Asn Val Phe Pro Thr Ala Trp Ile
             100                 105                 110

Ala Gly Ala Gly Ala Glu Gln Ile Glu Leu Thr Thr Ile Asn Trp Leu
         115                 120                 125

Lys Ser Met Leu Gly Phe Pro Asp Ser Ala Glu Gly Leu Phe Val Ser
130                 135                 140

Gly Gly Ser Met Ala Asn Leu Thr Ala Leu Thr Val Ala Arg Gln Ala
145                 150                 155                 160

Lys Leu Asn Asn Asp Ile Glu Asn Ala Val Val Tyr Phe Ser Asp Gln
                 165                 170                 175

Thr His Phe Ser Val Asp Arg Ala Leu Lys Val Leu Gly Phe Lys His
             180                 185                 190

His Gln Ile Cys Arg Ile Glu Thr Asp Glu His Leu Arg Ile Ser Val
         195                 200                 205

Ser Ala Leu Lys Lys Gln Ile Lys Glu Asp Arg Thr Lys Gly Lys Lys
         210                 215                 220

Pro Phe Cys Val Ile Ala Asn Ala Gly Thr Thr Asn Cys Gly Ala Val
225                 230                 235                 240

Asp Ser Leu Asn Glu Leu Ala Asp Leu Cys Asn Asp Glu Asp Val Trp
                 245                 250                 255

Leu His Ala Asp Gly Ser Tyr Gly Ala Pro Ala Ile Leu Ser Glu Lys
             260                 265                 270

Gly Ser Ala Met Leu Gln Gly Ile His Arg Ala Asp Ser Leu Thr Leu
         275                 280                 285

Asp Pro His Lys Trp Leu Phe Gln Pro Tyr Asp Val Gly Cys Val Leu
290                 295                 300

Ile Arg Asn Ser Gln Tyr Leu Ser Lys Thr Phe Arg Met Met Pro Glu
305                 310                 315                 320

Tyr Ile Lys Asp Ser Glu Thr Asn Val Glu Gly Ile Asn Phe Gly
                 325                 330                 335

Glu Cys Gly Ile Glu Leu Ser Arg Arg Phe Arg Ala Leu Lys Val Trp
             340                 345                 350

Leu Ser Phe Lys Val Phe Gly Val Ala Ala Phe Arg Gln Ala Ile Asp
         355                 360                 365

His Gly Ile Met Leu Ala Glu Gln Val Glu Ala Phe Leu Gly Lys Ala
         370                 375                 380

Lys Asp Trp Glu Val Val Thr Pro Ala Gln Leu Gly Ile Val Thr Phe
385                 390                 395                 400

Arg Tyr Ile Pro Ser Glu Leu Ala Ser Thr Asp Thr Ile Asn Glu Ile
                 405                 410                 415

Asn Lys Lys Leu Val Lys Glu Ile Thr His Arg Gly Phe Ala Met Leu
             420                 425                 430
```

```
Ser Thr Thr Glu Leu Lys Glu Lys Val Val Ile Arg Leu Cys Ser Ile
            435                 440                 445

Asn Pro Arg Thr Thr Thr Glu Glu Met Leu Gln Ile Met Met Lys Ile
450                 455                 460

Lys Ala Leu Ala Glu Glu Val Ser Ile Ser Tyr Pro Cys Val Ala Glu
465                 470                 475                 480

<210> SEQ ID NO 20
<211> LENGTH: 500
<212> TYPE: PRT
<213> ORGANISM: Catharanthus roseus

<400> SEQUENCE: 20

Met Gly Ser Ile Asp Ser Thr Asn Val Ala Met Ser Asn Ser Pro Val
1               5                   10                  15

Gly Glu Phe Lys Pro Leu Glu Ala Glu Phe Arg Lys Gln Ala His
            20                  25                  30

Arg Met Val Asp Phe Ile Ala Asp Tyr Tyr Lys Asn Val Glu Thr Tyr
                35                  40                  45

Pro Val Leu Ser Glu Val Glu Pro Gly Tyr Leu Arg Lys Arg Ile Pro
50                  55                  60

Glu Thr Ala Pro Tyr Leu Pro Glu Pro Leu Asp Asp Ile Met Lys Asp
65                  70                  75                  80

Ile Gln Lys Asp Ile Ile Pro Gly Met Thr Asn Trp Met Ser Pro Asn
                85                  90                  95

Phe Tyr Ala Phe Phe Pro Ala Thr Val Ser Ser Ala Ala Phe Leu Gly
            100                 105                 110

Glu Met Leu Ser Thr Ala Leu Asn Ser Val Gly Phe Thr Trp Val Ser
            115                 120                 125

Ser Pro Ala Ala Thr Glu Leu Glu Met Ile Val Met Asp Trp Leu Ala
        130                 135                 140

Gln Ile Leu Lys Leu Pro Lys Ser Phe Met Phe Ser Gly Thr Gly Gly
145                 150                 155                 160

Gly Val Ile Gln Asn Thr Thr Ser Glu Ser Ile Leu Cys Thr Ile Ile
                165                 170                 175

Ala Ala Arg Glu Arg Ala Leu Glu Lys Leu Gly Pro Asp Ser Ile Gly
            180                 185                 190

Lys Leu Val Cys Tyr Gly Ser Asp Gln Thr His Thr Met Phe Pro Lys
        195                 200                 205

Thr Cys Lys Leu Ala Gly Ile Tyr Pro Asn Asn Ile Arg Leu Ile Pro
210                 215                 220

Thr Thr Val Glu Thr Asp Phe Gly Ile Ser Pro Gln Val Leu Arg Lys
225                 230                 235                 240

Met Val Glu Asp Asp Val Ala Ala Gly Tyr Val Pro Leu Phe Leu Cys
                245                 250                 255

Ala Thr Leu Gly Thr Thr Ser Thr Thr Ala Thr Asp Pro Val Asp Ser
            260                 265                 270

Leu Ser Glu Ile Ala Asn Glu Phe Gly Ile Trp Ile His Val Asp Ala
        275                 280                 285

Ala Tyr Ala Gly Ser Ala Cys Ile Cys Pro Glu Phe Arg His Tyr Leu
290                 295                 300

Asp Gly Ile Glu Arg Val Asp Ser Leu Ser Leu Ser Pro His Lys Trp
305                 310                 315                 320

Leu Leu Ala Tyr Leu Asp Cys Thr Cys Leu Trp Val Lys Gln Pro His
                325                 330                 335
```

```
Leu Leu Leu Arg Ala Leu Thr Thr Asn Pro Glu Tyr Leu Lys Asn Lys
            340                 345                 350

Gln Ser Asp Leu Asp Lys Val Val Asp Phe Lys Asn Trp Gln Ile Ala
            355                 360                 365

Thr Gly Arg Lys Phe Arg Ser Leu Lys Leu Trp Leu Ile Leu Arg Ser
        370                 375                 380

Tyr Gly Val Val Asn Leu Gln Ser His Ile Arg Ser Asp Val Ala Met
385                 390                 395                 400

Gly Lys Met Phe Glu Glu Trp Val Arg Ser Asp Ser Arg Phe Glu Ile
                405                 410                 415

Val Val Pro Arg Asn Phe Ser Leu Val Cys Phe Arg Leu Lys Pro Asp
            420                 425                 430

Val Ser Ser Leu His Val Glu Glu Val Asn Lys Lys Leu Leu Asp Met
            435                 440                 445

Leu Asn Ser Thr Gly Arg Val Tyr Met Thr His Thr Ile Val Gly Gly
            450                 455                 460

Ile Tyr Met Leu Arg Leu Ala Val Gly Ser Ser Leu Thr Glu Glu His
465                 470                 475                 480

His Val Arg Arg Val Trp Asp Leu Ile Gln Lys Leu Thr Asp Asp Leu
                485                 490                 495

Leu Lys Glu Ala
            500

<210> SEQ ID NO 21
<211> LENGTH: 309
<212> TYPE: PRT
<213> ORGANISM: Psilocybe cubensis

<400> SEQUENCE: 21

Met His Ile Arg Asn Pro Tyr Arg Thr Pro Ile Asp Tyr Gln Ala Leu
1               5                   10                  15

Ser Glu Ala Phe Pro Pro Leu Lys Pro Phe Val Ser Val Asn Ala Asp
            20                  25                  30

Gly Thr Ser Ser Val Asp Leu Thr Ile Pro Glu Ala Gln Arg Ala Phe
        35                  40                  45

Thr Ala Ala Leu Leu His Arg Asp Phe Gly Leu Thr Met Thr Ile Pro
    50                  55                  60

Glu Asp Arg Leu Cys Pro Thr Val Pro Asn Arg Leu Asn Tyr Val Leu
65                  70                  75                  80

Trp Ile Glu Asp Ile Phe Asn Tyr Thr Asn Lys Thr Leu Gly Leu Ser
                85                  90                  95

Asp Asp Arg Pro Ile Lys Gly Val Asp Ile Gly Thr Gly Ala Ser Ala
            100                 105                 110

Ile Tyr Pro Met Leu Ala Cys Ala Arg Phe Lys Ala Trp Ser Met Val
        115                 120                 125

Gly Thr Glu Val Glu Arg Lys Cys Ile Asp Thr Ala Arg Leu Asn Val
    130                 135                 140

Val Ala Asn Asn Leu Gln Asp Arg Leu Ser Ile Leu Glu Thr Ser Ile
145                 150                 155                 160

Asp Gly Pro Ile Leu Val Pro Ile Phe Glu Ala Thr Glu Glu Tyr Glu
                165                 170                 175

Tyr Glu Phe Thr Met Cys Asn Pro Pro Phe Tyr Asp Gly Ala Ala Asp
            180                 185                 190

Met Gln Thr Ser Asp Ala Ala Lys Gly Phe Gly Phe Gly Val Gly Ala
```

```
            195                 200                 205
Pro His Ser Gly Thr Val Ile Glu Met Ser Thr Glu Gly Gly Glu Ser
    210                 215                 220

Ala Phe Val Ala Gln Met Val Arg Glu Ser Leu Lys Leu Arg Thr Arg
225                 230                 235                 240

Cys Arg Trp Tyr Thr Ser Asn Leu Gly Lys Leu Lys Ser Leu Lys Glu
                245                 250                 255

Ile Val Gly Leu Leu Lys Glu Leu Glu Ile Ser Asn Tyr Ala Ile Asn
                260                 265                 270

Glu Tyr Val Gln Gly Ser Thr Arg Arg Tyr Ala Val Ala Trp Ser Phe
            275                 280                 285

Thr Asp Ile Gln Leu Pro Glu Glu Leu Ser Arg Pro Ser Asn Pro Glu
        290                 295                 300

Leu Ser Ser Leu Phe
305

<210> SEQ ID NO 22
<211> LENGTH: 312
<212> TYPE: PRT
<213> ORGANISM: Psilocybe cyanescens

<400> SEQUENCE: 22

Met His Ile Arg Asn Pro Tyr Arg Ser Pro Ile Asp Tyr Gln Ala Leu
1               5                   10                  15

Val Glu Ala Phe Pro Pro Leu Arg Pro Tyr Val Thr Val Asn Gln Asp
                20                  25                  30

Asn Thr Thr Ser Ile Asp Leu Thr Val Pro Glu Val Gln Arg Leu Tyr
            35                  40                  45

Thr Ala Ala Leu Leu His Arg Asp Phe Gly Leu Val Ile Asp Leu Pro
        50                  55                  60

Glu Asp Arg Leu Cys Pro Thr Leu Leu Thr Arg Thr Pro Arg Leu Asn
65                  70                  75                  80

Tyr Val Leu Trp Val Glu Asp Ile Leu Lys Val Thr Asn Thr Ala Leu
                85                  90                  95

Gly Leu Ser Glu Asp Arg Pro Val Lys Gly Ile Asp Ile Gly Thr Gly
            100                 105                 110

Ala Ala Ala Ile Tyr Pro Met Leu Ala Cys Ala Arg Phe Lys Thr Trp
        115                 120                 125

Ser Met Ile Gly Thr Glu Ile Asp Arg Lys Cys Ile Asp Thr Ala Arg
130                 135                 140

Val Asn Val Leu Thr Asn Asn Leu Gln Asp Arg Leu Ser Ile Ile Glu
145                 150                 155                 160

Thr Ser Ile Asp Gly Pro Ile Leu Val Pro Ile Phe Glu Ala Thr Thr
                165                 170                 175

Asp Tyr Glu Tyr Asp Phe Thr Met Cys Asn Pro Pro Phe Tyr Asp Gly
            180                 185                 190

Ala Ala Asp Met Gln Thr Ser Asp Ala Ala Lys Gly Phe Gly Phe Gly
        195                 200                 205

Val Asn Ala Pro His Ser Gly Thr Val Ile Glu Met Ser Thr Glu Gly
    210                 215                 220

Gly Glu Ser Ala Phe Val Ala Gln Met Val Arg Glu Ser Leu Asp His
225                 230                 235                 240

Arg Thr Arg Cys Arg Trp Phe Ser Asn Leu Gly Lys Leu Lys Ser
                245                 250                 255
```

```
Leu His Glu Ile Val Gly Leu Leu Arg Glu His Gln Ile Ser Asn Tyr
        260                 265                 270

Ala Ile Asn Glu Tyr Val Gln Gly Thr Thr Arg Arg Tyr Ala Ile Ala
        275                 280                 285

Trp Ser Phe Thr Asn Ile Arg Leu Pro Glu Asp Leu Thr Arg Pro Ser
        290                 295                 300

Asn Pro Glu Leu Ser Ser Leu Phe
305                 310

<210> SEQ ID NO 23
<211> LENGTH: 317
<212> TYPE: PRT
<213> ORGANISM: Psilocybe cyanescens

<400> SEQUENCE: 23

Met His Asn Arg Asn Pro Tyr Arg Asp Val Ile Asp Tyr Gln Ala Leu
1               5                   10                  15

Ala Glu Ala Tyr Pro Pro Leu Lys Pro His Val Thr Val Asn Ala Asp
                20                  25                  30

Asn Thr Ala Ser Ile Asp Leu Thr Ile Pro Glu Val Gln Arg Gln Tyr
            35                  40                  45

Thr Ala Ala Leu Leu His Arg Asp Phe Gly Leu Thr Ile Thr Leu Pro
        50                  55                  60

Glu Asp Arg Leu Cys Pro Thr Val Pro Asn Arg Leu Asn Tyr Val Leu
65                  70                  75                  80

Trp Ile Glu Asp Ile Phe Gln Cys Thr Asn Lys Ala Leu Gly Leu Ser
                85                  90                  95

Asp Asp Arg Pro Val Lys Gly Val Asp Ile Gly Thr Gly Ala Ser Ala
                100                 105                 110

Ile Tyr Pro Met Leu Ala Cys Ala Arg Phe Lys Gln Trp Ser Met Ile
            115                 120                 125

Ala Thr Glu Val Glu Arg Lys Cys Ile Asp Thr Ala Arg Leu Asn Val
        130                 135                 140

Leu Ala Asn Asn Leu Gln Asp Arg Leu Ser Ile Leu Glu Val Ser Val
145                 150                 155                 160

Asp Gly Pro Ile Leu Val Pro Ile Phe Asp Thr Phe Glu Arg Ala Thr
                165                 170                 175

Ser Asp Tyr Glu Phe Glu Phe Thr Met Cys Asn Pro Pro Phe Tyr Asp
            180                 185                 190

Gly Ala Ala Asp Met Gln Thr Ser Asp Ala Ala Lys Gly Phe Gly Phe
        195                 200                 205

Gly Val Asn Ala Pro His Ser Gly Thr Val Ile Glu Met Ala Thr Glu
210                 215                 220

Gly Gly Glu Ala Ala Phe Val Ala Gln Met Val Arg Glu Ser Met Lys
225                 230                 235                 240

Leu Gln Thr Arg Cys Arg Trp Phe Thr Ser Asn Leu Gly Lys Leu Lys
                245                 250                 255

Ser Leu His Glu Ile Val Ala Leu Leu Arg Glu Ser Gln Ile Thr Asn
            260                 265                 270

Tyr Ala Ile Asn Glu Tyr Val Gln Gly Thr Thr Arg Arg Tyr Ala Leu
        275                 280                 285

Ala Trp Ser Phe Thr Asp Ile Lys Leu Thr Glu Glu Leu Tyr Arg Pro
        290                 295                 300

Ser Asn Pro Glu Leu Gly Pro Leu Cys Ser Thr Phe Val
305                 310                 315
```

<210> SEQ ID NO 24
<211> LENGTH: 309
<212> TYPE: PRT
<213> ORGANISM: Gymnopilus dilepis

<400> SEQUENCE: 24

Met His Ile Arg Asn Pro Tyr Leu Thr Pro Pro Asp Tyr Glu Ala Leu
1               5                   10                  15

Ala Glu Ala Phe Pro Ala Leu Lys Pro Tyr Val Thr Val Asn Pro Asp
            20                  25                  30

Lys Thr Thr Thr Ile Asp Phe Ala Ile Pro Glu Ala Gln Arg Leu Tyr
        35                  40                  45

Thr Ala Ala Leu Leu Tyr Arg Asp Phe Gly Leu Thr Ile Thr Leu Pro
    50                  55                  60

Pro Asp Arg Leu Cys Pro Thr Val Pro Asn Arg Leu Asn Tyr Val Leu
65                  70                  75                  80

Trp Ile Gln Asp Ile Leu Gln Ile Thr Ser Ala Ala Leu Gly Leu Pro
                85                  90                  95

Glu Ala Arg Gln Val Lys Gly Val Asp Ile Gly Thr Gly Ala Ala Ala
            100                 105                 110

Ile Tyr Pro Ile Leu Gly Cys Ser Leu Ala Lys Asn Trp Ser Met Val
        115                 120                 125

Gly Thr Glu Val Glu Gln Lys Cys Ile Asp Ile Ala Arg Gln Asn Val
    130                 135                 140

Ile Ser Asn Gly Leu Gln Asp Arg Ile Thr Ile Thr Ala Asn Thr Ile
145                 150                 155                 160

Asp Ala Pro Ile Leu Leu Pro Leu Phe Glu Gly Asp Ser Asn Phe Glu
                165                 170                 175

Trp Glu Phe Thr Met Cys Asn Pro Pro Phe Tyr Asp Gly Ala Ala Asp
            180                 185                 190

Met Glu Thr Ser Gln Asp Ala Lys Gly Phe Gly Phe Gly Val Asn Ala
        195                 200                 205

Pro His Thr Gly Thr Val Val Glu Met Ala Thr Asp Gly Gly Glu Ala
    210                 215                 220

Ala Phe Val Ser Gln Met Val Arg Glu Ser Leu His Leu Lys Thr Arg
225                 230                 235                 240

Cys Arg Trp Phe Thr Ser Asn Leu Gly Lys Leu Lys Ser Leu His Glu
                245                 250                 255

Ile Val Gly Leu Leu Arg Glu His Gln Ile Thr Asn Tyr Ala Ile Asn
            260                 265                 270

Glu Tyr Val Gln Gly Thr Thr Arg Arg Tyr Ala Ile Ala Trp Ser Phe
        275                 280                 285

Thr Asp Leu Arg Leu Ser Asp His Leu Pro Arg Pro Pro Asn Pro Asp
    290                 295                 300

Leu Ser Ala Leu Phe
305

<210> SEQ ID NO 25
<211> LENGTH: 263
<212> TYPE: PRT
<213> ORGANISM: Homo sapiens

<400> SEQUENCE: 25

Met Lys Gly Gly Phe Thr Gly Gly Asp Glu Tyr Gln Lys His Phe Leu
1               5                   10                  15

```
Pro Arg Asp Tyr Leu Ala Thr Tyr Tyr Ser Phe Asp Gly Ser Pro Ser
                20                  25                  30

Pro Glu Ala Glu Met Leu Lys Phe Asn Leu Glu Cys Leu His Lys Thr
            35                  40                  45

Phe Gly Pro Gly Gly Leu Gln Gly Asp Thr Leu Ile Asp Ile Gly Ser
 50                  55                  60

Gly Pro Thr Ile Tyr Gln Val Leu Ala Ala Cys Asp Ser Phe Gln Asp
 65                  70                  75                  80

Ile Thr Leu Ser Asp Phe Thr Asp Arg Asn Arg Glu Glu Leu Glu Lys
                85                  90                  95

Trp Leu Lys Lys Glu Pro Gly Ala Tyr Asp Trp Thr Pro Ala Val Lys
            100                 105                 110

Phe Ala Cys Glu Leu Glu Gly Asn Ser Gly Arg Trp Glu Glu Lys Glu
        115                 120                 125

Glu Lys Leu Arg Ala Ala Val Lys Arg Val Leu Lys Cys Asp Val His
    130                 135                 140

Leu Gly Asn Pro Leu Ala Pro Ala Val Leu Pro Leu Ala Asp Cys Val
145                 150                 155                 160

Leu Thr Leu Leu Ala Met Glu Cys Ala Cys Cys Ser Leu Asp Ala Tyr
                165                 170                 175

Arg Ala Ala Leu Cys Asn Leu Ala Ser Leu Leu Lys Pro Gly Gly His
            180                 185                 190

Leu Val Thr Thr Val Thr Leu Arg Leu Pro Ser Tyr Met Val Gly Lys
        195                 200                 205

Arg Glu Phe Ser Cys Val Ala Leu Glu Lys Glu Val Glu Gln Ala
    210                 215                 220

Val Leu Asp Ala Gly Phe Asp Ile Glu Gln Leu Leu His Ser Pro Gln
225                 230                 235                 240

Ser Tyr Ser Val Thr Asn Ala Ala Asn Asn Gly Val Cys Phe Ile Val
                245                 250                 255

Ala Arg Lys Lys Pro Gly Pro
            260

<210> SEQ ID NO 26
<211> LENGTH: 209
<212> TYPE: PRT
<213> ORGANISM: Acinetobacter sp.

<400> SEQUENCE: 26

Met Ile Tyr Lys Phe Tyr Gln Gln His Ile Phe Pro His Leu Leu Asn
1               5                   10                  15

Gln Val Met Gln Thr Pro Ser Leu Met Asp Gln Arg Gln Leu Leu
            20                  25                  30

Leu Pro Ile Ala Gly Asp Val Leu Glu Ile Gly Phe Gly Thr Gly Val
            35                  40                  45

Asn Leu Pro Phe Tyr Gln Asn Val Glu Thr Leu Tyr Ala Leu Glu Pro
         50                  55                  60

Asn Ala Asp Leu Tyr Gln Leu Ala Ala Lys Arg Ile His Glu Ser Thr
65                  70                  75                  80

Ile His Val Gln His Ile Gln Ala Tyr Ala Glu Lys Leu Pro Phe Ala
                85                  90                  95

Asp Ala Ser Leu Asp His Ile Val Ser Thr Trp Thr Leu Cys Ser Ile
            100                 105                 110

Glu Asn Leu Ala Gln Ala Leu Ile Glu Met Tyr Arg Val Leu Lys Pro
```

```
            115                 120                 125
Asn Gly Thr Leu His Leu Val Glu His Val Gln Tyr Gln Asp Asn Ala
    130                 135                 140

Lys Leu Gln His Leu Gln Asn Leu Leu Thr Pro Ile Gln Lys Arg Leu
145                 150                 155                 160

Ala Asp Gly Cys His Leu Asn Arg Asn Ile Glu Gln Ala Leu Arg Asp
                165                 170                 175

Ala His Phe Asp Phe Thr Glu Gln His Tyr Phe Ala Ala Gln Gly Ile
            180                 185                 190

Pro Lys Leu Ala Gln Arg Met Phe Phe Ala Arg Ala Gln Lys Gln Pro
        195                 200                 205

Glu

<210> SEQ ID NO 27
<211> LENGTH: 445
<212> TYPE: PRT
<213> ORGANISM: Oryza sativa

<400> SEQUENCE: 27

Met Glu Ile Thr Ser Ser Ala Met Leu Lys Thr Thr Thr Pro Pro
1               5                   10                  15

His Pro Leu Ala Gly Glu Lys Val Pro Leu Ser Ala Phe Asp Arg Ala
            20                  25                  30

Ala Phe Asp Val Phe Val Pro Leu Val Phe Ala Tyr Arg Ala Pro Ala
        35                  40                  45

Pro Ser Ser Glu Ala Val Lys Glu Gly Leu Arg Val Ala Val Ala Ala
    50                  55                  60

Tyr Pro Leu Val Ser Gly Arg Ile Ala Val Asp Gly Gln Gly Arg Arg
65                  70                  75                  80

Arg Arg Arg Arg Val Leu His Val Asn Asn Glu Gly Val Leu Val Leu
                85                  90                  95

Asp Ala Thr Val Glu Val Asp Leu Asp Ala Val Leu Ala Ala Asn Val
            100                 105                 110

Ala Thr Asp Leu Tyr Pro Ala Leu Pro Glu His Ser Phe Gly Ala Ala
        115                 120                 125

Leu Leu Gln Val Gln Leu Thr Arg Phe Gly Cys Gly Gly Leu Val Val
    130                 135                 140

Gly Leu Ile Gly His His His Val Phe Asp Gly His Ser Met Ser Thr
145                 150                 155                 160

Phe Cys Ala Thr Trp Ala Arg Ala Val Arg Asp Ser Glu Ala Phe Ile
                165                 170                 175

Val Pro Ser Pro Ser Leu Asp Arg Ala Ile Thr Gly Val Pro Arg Ser
            180                 185                 190

Pro Pro Ala Pro Val Phe Asp His Arg Ser Ile Glu Phe Lys Val Gly
        195                 200                 205

Asn Lys Ser Ser Asp Ser Ser Gly Ala Ala Ala Ala Ala Val Glu
    210                 215                 220

Lys Ile Ala Asn Ile Gly Val Arg Phe Thr Ala Lys Phe Val Ala Glu
225                 230                 235                 240

Leu Lys Ala Arg Val Gly Gly Arg Cys Ser Thr Phe Glu Cys Val Leu
                245                 250                 255

Ala His Ala Trp Lys Lys Ile Thr Ala Ala Arg Gly Leu Lys Pro Glu
            260                 265                 270

Glu Phe Thr Arg Val Arg Val Ala Val Asn Cys Arg Arg Arg Ala Asn
```

```
            275                 280                 285
Pro Pro Ala Pro Ala Asp Leu Phe Gly Asn Met Val Leu Trp Ala Phe
290                 295                 300
Pro Arg Leu Gln Val Arg Arg Leu Leu Ser Ser Ser Tyr Arg Asp Val
305                 310                 315                 320
Val Gly Ala Ile Arg Ala Ala Val Ala Arg Val Asp Ala Glu Tyr Ile
                    325                 330                 335
Gln Ser Phe Val Asp Tyr Val Glu Val Ala Asp Ala Arg Gly Glu Glu
                340                 345                 350
Leu Ala Ala Thr Ala Ala Glu Pro Gly Glu Thr Leu Cys Pro Asp Leu
                355                 360                 365
Glu Val Asp Ser Trp Leu Gly Phe Arg Phe His Glu Met Asp Leu Gly
370                 375                 380
Thr Gly Pro Pro Ala Ala Val Leu Ser Pro Asp Leu Pro Ile Glu Gly
385                 390                 395                 400
Leu Met Ile Leu Val Pro Val Gly Gly Asp Gly Gly Val Asp Leu
                405                 410                 415
Phe Val Ala Leu Ala Asp Asp His Ala Gln Ala Phe Glu Gln Ile Cys
                420                 425                 430
Tyr Ser Leu Glu Glu His Ala Met Ile His Ser His Leu
                435                 440                 445

<210> SEQ ID NO 28
<211> LENGTH: 207
<212> TYPE: PRT
<213> ORGANISM: Homo sapiens

<400> SEQUENCE: 28

Met Ser Thr Gln Ser Thr His Pro Leu Lys Pro Glu Ala Pro Arg Leu
1               5                   10                  15
Pro Pro Gly Ile Pro Glu Ser Pro Ser Cys Gln Arg Arg His Thr Leu
                20                  25                  30
Pro Ala Ser Glu Phe Arg Cys Leu Thr Pro Glu Asp Ala Val Ser Ala
                35                  40                  45
Phe Glu Ile Glu Arg Glu Ala Phe Ile Ser Val Leu Gly Val Cys Pro
            50                  55                  60
Leu Tyr Leu Asp Glu Ile Arg His Phe Leu Thr Leu Cys Pro Glu Leu
65                  70                  75                  80
Ser Leu Gly Trp Phe Glu Glu Gly Cys Leu Val Ala Phe Ile Ile Gly
                85                  90                  95
Ser Leu Trp Asp Lys Glu Arg Leu Met Gln Glu Ser Leu Thr Leu His
                100                 105                 110
Arg Ser Gly Gly His Ile Ala His Leu His Val Leu Ala Val His Arg
                115                 120                 125
Ala Phe Arg Gln Gln Gly Arg Gly Pro Ile Leu Leu Trp Arg Tyr Leu
130                 135                 140
His His Leu Gly Ser Gln Pro Ala Val Arg Arg Ala Ala Leu Met Cys
145                 150                 155                 160
Glu Asp Ala Leu Val Pro Phe Tyr Glu Arg Phe Ser Phe His Ala Val
                165                 170                 175
Gly Pro Cys Ala Ile Thr Val Gly Ser Leu Thr Phe Met Glu Leu His
                180                 185                 190
Cys Ser Leu Arg Gly His Pro Phe Leu Arg Arg Asn Ser Gly Cys
                195                 200                 205
```

<210> SEQ ID NO 29
<211> LENGTH: 275
<212> TYPE: PRT
<213> ORGANISM: Drosophila melanogaster

<400> SEQUENCE: 29

Met Glu Val Gln Lys Leu Pro Asp Gln Ser Leu Ile Ser Ser Met Met
1               5                   10                  15

Leu Asp Ser Arg Cys Gly Leu Asn Asp Leu Tyr Pro Ile Ala Arg Leu
            20                  25                  30

Thr Gln Lys Met Glu Asp Ala Leu Thr Val Ser Gly Lys Pro Ala Ala
        35                  40                  45

Cys Pro Val Asp Gln Asp Cys Pro Tyr Thr Ile Glu Leu Ile Gln Pro
    50                  55                  60

Glu Asp Gly Glu Ala Val Ile Ala Met Leu Lys Thr Phe Phe Phe Lys
65                  70                  75                  80

Asp Glu Pro Leu Asn Thr Phe Leu Asp Leu Gly Glu Cys Lys Glu Leu
                85                  90                  95

Glu Lys Tyr Ser Leu Lys Pro Leu Pro Asp Asn Cys Ser Tyr Lys Ala
            100                 105                 110

Val Asn Lys Lys Gly Glu Ile Ile Gly Val Phe Leu Asn Gly Leu Met
        115                 120                 125

Arg Arg Pro Ser Pro Asp Asp Val Pro Glu Lys Ala Ala Asp Ser Cys
130                 135                 140

Glu His Pro Lys Phe Lys Lys Ile Leu Ser Leu Met Asp His Val Glu
145                 150                 155                 160

Glu Gln Phe Asn Ile Phe Asp Val Tyr Pro Asp Glu Glu Leu Ile Leu
                165                 170                 175

Asp Gly Lys Ile Leu Ser Val Asp Thr Asn Tyr Arg Gly Leu Gly Ile
            180                 185                 190

Ala Gly Arg Leu Thr Glu Arg Ala Tyr Glu Tyr Met Arg Glu Asn Gly
        195                 200                 205

Ile Asn Val Tyr His Val Leu Cys Ser Ser His Tyr Ser Ala Arg Val
    210                 215                 220

Met Glu Lys Leu Gly Phe His Glu Val Phe Arg Met Gln Phe Ala Asp
225                 230                 235                 240

Tyr Lys Pro Gln Gly Glu Val Val Phe Lys Pro Ala Ala Pro His Val
                245                 250                 255

Gly Ile Gln Val Met Ala Lys Glu Val Gly Pro Ala Lys Ala Ala Gln
            260                 265                 270

Thr Lys Leu
        275

<210> SEQ ID NO 30
<211> LENGTH: 209
<212> TYPE: PRT
<213> ORGANISM: Danio rerio

<400> SEQUENCE: 30

Met Met Ala Pro Gln Val Val Ser Ser Pro Phe Leu Lys Pro Phe Phe
1               5                   10                  15

Leu Lys Thr Pro Ile Ser Val Ser Ser Pro Arg Arg Gln Arg Arg His
            20                  25                  30

Thr Leu Pro Ala Ser Glu Phe Arg Asn Leu Thr Pro Gln Asp Ala Ile
        35                  40                  45

```
Ser Val Phe Glu Ile Glu Arg Glu Ala Phe Ile Ser Val Ser Gly Glu
    50                  55                  60

Cys Pro Leu Thr Leu Asp Glu Val Leu Val Phe Leu Gly Gln Cys Pro
 65                  70                  75                  80

Glu Leu Ser Met Gly Trp Phe Glu Glu Gly Gln Leu Val Ala Phe Ile
                 85                  90                  95

Ile Gly Ser Gly Trp Asp Lys Glu Lys Leu Glu Gln Glu Ala Met Ser
                100                 105                 110

Thr His Val Pro Asp Ser Pro Thr Val His Ile His Val Leu Ser Val
                115                 120                 125

His Arg His Cys Arg Gln Gln Gly Lys Gly Ser Ile Leu Leu Trp Arg
130                 135                 140

Tyr Leu Gln Tyr Leu Arg Cys Leu Pro Gly Leu Arg Arg Ala Leu Leu
145                 150                 155                 160

Val Cys Glu Glu Phe Leu Val Pro Phe Tyr Gln Lys Ala Gly Phe Lys
                165                 170                 175

Glu Lys Gly Pro Ser Ala Ile Ser Val Ala Ala Leu Thr Phe Thr Glu
                180                 185                 190

Met Glu Tyr Gln Leu Gly Gly Leu Ala Tyr Ala Arg Arg Asn Ser Gly
                195                 200                 205

Cys

<210> SEQ ID NO 31
<211> LENGTH: 436
<212> TYPE: PRT
<213> ORGANISM: Oryza sativa

<400> SEQUENCE: 31

Met Ala Ala Val Thr Val Glu Ile Thr Arg Ser Glu Val Leu Arg Pro
  1               5                  10                  15

Ser Pro Ala Ser Ala Gly Gly Gly Glu Met Val Pro Leu Thr Val Phe
                 20                  25                  30

Asp Arg Ala Ala Thr Asp Gly Tyr Ile Pro Thr Met Phe Ala Trp Asp
                 35                  40                  45

Ala Ala Ala Ala Ala Ala Leu Ser Asn Asp Ala Ile Lys Asp Gly Leu
    50                  55                  60

Ala Ala Val Leu Ser Arg Phe Pro His Leu Ala Gly Arg Phe Ala Val
 65                  70                  75                  80

Asp Glu Arg Gly Arg Lys Cys Phe Arg Leu Asn Asn Ala Gly Ala Arg
                 85                  90                  95

Val Leu Glu Ala Ser Ala Ala Gly Asp Leu Ala Asp Ala Leu Ala His
                100                 105                 110

Asp Val Ala Ala His Val Asn Gln Leu Tyr Pro Gln Ala Asp Lys Asp
                115                 120                 125

Arg Val Asp Glu Pro Leu Leu Gln Val Gln Leu Thr Arg Tyr Thr Cys
130                 135                 140

Gly Gly Leu Val Ile Gly Ala Val Ser His Gln Val Ala Asp Gly
145                 150                 155                 160

Gln Ser Met Ser Val Phe Phe Thr Glu Trp Ala Ala Ala Val Arg Thr
                165                 170                 175

Ala Gly Ala Ala Leu Pro Thr Pro Phe Leu Asp Arg Ser Ala Val Ala
                180                 185                 190

Ala Pro Arg Ile Pro Pro Ala Pro Ala Phe Asp His Arg Asn Val Glu
                195                 200                 205
```

```
Phe Arg Gly Glu Gly Ser Arg Ser His Ser Tyr Gly Ala Leu Pro Leu
    210                 215                 220

Glu Arg Met Arg Asn Leu Ala Val His Phe Pro Pro Glu Phe Val Ala
225                 230                 235                 240

Gly Leu Lys Ala Arg Val Gly Ala Arg Cys Ser Thr Phe Gln Cys
                245                 250                 255

Leu Leu Ala His Ala Trp Lys Lys Ile Thr Ala Ala Arg Asp Leu Ser
            260                 265                 270

Pro Lys Glu Tyr Thr Gln Val Arg Val Ala Val Asn Cys Arg Gly Arg
        275                 280                 285

Ala Gly Pro Ala Val Pro Thr Asp Tyr Phe Gly Asn Met Val Leu Trp
290                 295                 300

Ala Phe Pro Arg Met Gln Val Arg Asp Leu Leu Ser Ala Ser Tyr Ala
305                 310                 315                 320

Ala Val Val Gly Val Ile Arg Asp Ala Val Ala Arg Val Asp Glu Arg
                325                 330                 335

Tyr Ile Gln Ser Phe Val Asp Phe Gly Glu Val Ala Ala Gly Asp Glu
            340                 345                 350

Leu Ala Pro Thr Ala Ala Glu Pro Gly Thr Ala Phe Cys Pro Asp Leu
        355                 360                 365

Glu Val Asp Ser Trp Ile Gly Phe Arg Phe His Asp Leu Asp Phe Gly
370                 375                 380

Gly Gly Pro Pro Cys Ala Phe Leu Pro Pro Asp Val Pro Ile Asp Gly
385                 390                 395                 400

Leu Leu Ile Phe Val Pro Ser Cys Ala Ala Lys Gly Gly Val Glu Met
                405                 410                 415

Phe Met Ala Leu Asp Asp Gln His Val Glu Ala Leu Arg Gln Ile Cys
            420                 425                 430

Tyr Ser Met Asp
            435

<210> SEQ ID NO 32
<211> LENGTH: 508
<212> TYPE: PRT
<213> ORGANISM: Psilocybe cubensis

<400> SEQUENCE: 32

Met Ile Ala Val Leu Phe Ser Phe Val Ile Ala Gly Cys Ile Tyr Tyr
1               5                   10                  15

Ile Val Ser Arg Arg Val Arg Arg Ser Arg Leu Pro Pro Gly Pro Pro
                20                  25                  30

Gly Ile Pro Ile Pro Phe Ile Gly Asn Met Phe Asp Met Pro Glu Glu
            35                  40                  45

Ser Pro Trp Leu Thr Phe Leu Gln Trp Gly Arg Asp Tyr Asn Thr Asp
        50                  55                  60

Ile Leu Tyr Val Asp Ala Gly Gly Thr Glu Met Val Ile Leu Asn Thr
65                  70                  75                  80

Leu Glu Thr Ile Thr Asp Leu Leu Glu Lys Arg Gly Ser Ile Tyr Ser
                85                  90                  95

Gly Arg Leu Glu Ser Thr Met Val Asn Glu Leu Met Gly Trp Glu Phe
            100                 105                 110

Asp Leu Gly Phe Ile Thr Tyr Gly Asp Arg Trp Arg Glu Glu Arg Arg
        115                 120                 125

Met Phe Ala Lys Glu Phe Ser Glu Lys Gly Ile Lys Gln Phe Arg His
    130                 135                 140
```

Ala Gln Val Lys Ala Ala His Gln Leu Val Gln Leu Thr Lys Thr
145                 150                 155                 160

Pro Asp Arg Trp Ala Gln His Ile Arg His Gln Ile Ala Ala Met Ser
            165                 170                 175

Leu Asp Ile Gly Tyr Gly Ile Asp Leu Ala Glu Asp Pro Trp Leu
        180                 185                 190

Glu Ala Thr His Leu Ala Asn Glu Gly Leu Ala Ile Ala Ser Val Pro
        195                 200                 205

Gly Lys Phe Trp Val Asp Ser Phe Pro Ser Leu Lys Tyr Leu Pro Ala
210                 215                 220

Trp Phe Pro Gly Ala Val Phe Lys Arg Lys Ala Lys Val Trp Arg Glu
225                 230                 235                 240

Ala Ala Asp His Met Val Asp Met Pro Tyr Glu Thr Met Arg Lys Leu
            245                 250                 255

Ala Pro Gln Gly Leu Thr Arg Pro Ser Tyr Ala Ser Ala Arg Leu Gln
        260                 265                 270

Ala Met Asp Leu Asn Gly Asp Leu Glu His Gln Glu His Val Ile Lys
        275                 280                 285

Asn Thr Ala Ala Glu Val Asn Val Gly Gly Asp Thr Thr Val Ser
290                 295                 300

Ala Met Ser Ala Phe Ile Leu Ala Met Val Lys Tyr Pro Glu Val Gln
305                 310                 315                 320

Arg Lys Val Gln Ala Glu Leu Asp Ala Leu Thr Asn Asn Gly Gln Ile
            325                 330                 335

Pro Asp Tyr Asp Glu Glu Asp Ser Leu Pro Tyr Leu Thr Ala Cys
        340                 345                 350

Ile Lys Glu Leu Phe Arg Trp Asn Gln Ile Ala Pro Leu Ala Ile Pro
        355                 360                 365

His Lys Leu Met Lys Asp Asp Val Tyr Arg Gly Tyr Leu Ile Pro Lys
        370                 375                 380

Asn Thr Leu Val Phe Ala Asn Thr Trp Ala Val Leu Asn Asp Pro Glu
385                 390                 395                 400

Val Tyr Pro Asp Pro Ser Val Phe Arg Pro Glu Arg Tyr Leu Gly Pro
            405                 410                 415

Asp Gly Lys Pro Asp Asn Thr Val Arg Asp Pro Arg Lys Ala Ala Phe
        420                 425                 430

Gly Tyr Gly Arg Arg Asn Cys Pro Gly Ile His Leu Ala Gln Ser Thr
        435                 440                 445

Val Trp Ile Ala Gly Ala Thr Leu Leu Ser Ala Phe Asn Ile Glu Arg
450                 455                 460

Pro Val Asp Gln Asn Gly Lys Pro Ile Asp Ile Pro Ala Asp Phe Thr
465                 470                 475                 480

Thr Gly Phe Phe Arg His Pro Val Pro Phe Gln Cys Arg Phe Val Pro
            485                 490                 495

Arg Thr Glu Gln Val Ser Gln Ser Val Ser Gly Pro
        500                 505

<210> SEQ ID NO 33
<211> LENGTH: 507
<212> TYPE: PRT
<213> ORGANISM: Psilocybe cyanescens

<400> SEQUENCE: 33

Met Ile Val Leu Leu Val Ser Leu Val Leu Ala Gly Cys Ile Tyr Tyr

-continued

```
1               5                   10                  15
Ala Asn Ala Arg Arg Val Arg Arg Ser Arg Leu Pro Pro Gly Pro Pro
            20                  25                  30

Gly Ile Pro Leu Pro Phe Ile Gly Asn Met Phe Asp Met Pro Ser Glu
            35                  40                  45

Ser Pro Trp Leu Arg Phe Leu Gln Trp Gly Arg Asp Tyr His Thr Asp
        50                  55                  60

Ile Leu Tyr Leu Asn Ala Gly Gly Thr Glu Ile Ile Leu Asn Thr
65                  70                  75                  80

Leu Asp Ala Ile Thr Asp Leu Leu Glu Lys Arg Gly Ser Met Tyr Ser
                85                  90                  95

Gly Arg Leu Glu Ser Thr Met Val Asn Glu Leu Met Gly Trp Phe
            100                 105                 110

Asp Leu Gly Phe Ile Thr Tyr Gly Glu Arg Trp Arg Glu Arg Arg
            115                 120                 125

Met Phe Ala Lys Glu Phe Ser Glu Lys Asn Ile Arg Gln Phe Arg His
    130                 135                 140

Ala Gln Ile Lys Ala Ala Asn Gln Leu Val Arg Gln Leu Ile Lys Thr
145                 150                 155                 160

Pro Asp Arg Trp Ser Gln His Ile Arg His Gln Ile Ala Ala Met Ser
                165                 170                 175

Leu Asp Ile Gly Tyr Gly Ile Asp Leu Ala Glu Asp Pro Trp Ile
            180                 185                 190

Ala Ala Thr Gln Leu Ala Asn Glu Gly Leu Ala Glu Ala Ser Val Pro
        195                 200                 205

Gly Ser Phe Trp Val Asp Ser Phe Pro Ala Leu Lys Tyr Leu Pro Ser
    210                 215                 220

Trp Leu Pro Gly Ala Gly Phe Lys Arg Lys Ala Lys Val Trp Lys Glu
225                 230                 235                 240

Gly Ala Asp His Met Val Asn Met Pro Tyr Glu Thr Met Lys Lys Leu
                245                 250                 255

Thr Val Gln Gly Leu Ala Arg Pro Ser Tyr Ala Ser Ala Arg Leu Gln
            260                 265                 270

Ala Met Asp Pro Asp Gly Asp Leu Glu His Gln Glu His Val Ile Arg
        275                 280                 285

Asn Thr Ala Thr Glu Val Asn Val Gly Gly Asp Thr Thr Val Ser
    290                 295                 300

Ala Val Ser Ala Phe Ile Leu Ala Met Val Lys Tyr Pro Glu Val Gln
305                 310                 315                 320

Arg Gln Val Gln Ala Glu Leu Asp Ala Leu Thr Ser Lys Gly Val Val
                325                 330                 335

Pro Asn Tyr Asp Glu Glu Asp Ser Leu Pro Tyr Leu Thr Ala Cys
            340                 345                 350

Val Lys Glu Ile Phe Arg Trp Asn Gln Ile Ala Pro Leu Ala Ile Pro
        355                 360                 365

His Arg Leu Ile Lys Asp Asp Val Tyr Arg Gly Tyr Leu Ile Pro Lys
    370                 375                 380

Asn Ala Leu Val Tyr Ala Asn Ser Trp Ala Val Leu Asn Asp Pro Glu
385                 390                 395                 400

Glu Tyr Pro Asn Pro Ser Glu Phe Arg Pro Glu Arg Tyr Leu Ser Ser
                405                 410                 415

Asp Gly Lys Pro Asp Pro Thr Val Arg Asp Pro Arg Lys Ala Ala Phe
            420                 425                 430
```

```
Gly Tyr Gly Arg Arg Asn Cys Pro Gly Ile His Leu Ala Gln Ser Thr
            435                 440                 445

Val Trp Ile Ala Gly Ala Thr Leu Leu Ser Val Phe Asn Ile Glu Arg
        450                 455                 460

Pro Val Asp Gly Asn Gly Lys Pro Ile Asp Ile Pro Ala Thr Phe Thr
465                 470                 475                 480

Thr Gly Phe Phe Arg His Pro Glu Pro Phe Gln Cys Arg Phe Val Pro
                    485                 490                 495

Arg Thr Gln Glu Ile Leu Lys Ser Val Ser Gly
            500                 505

<210> SEQ ID NO 34
<211> LENGTH: 483
<212> TYPE: PRT
<213> ORGANISM: Psilocybe cyanescens

<400> SEQUENCE: 34

Met Ile Asn Leu Pro Leu Ser Leu Val Leu Val Gly Cys Val Tyr Tyr
1               5                   10                  15

Ile Val Ser Arg Arg Ile Arg Arg Ser Arg Leu Pro Pro Gly Pro Pro
            20                  25                  30

Gly Ile Pro Ile Pro Phe Val Gly Asn Met Tyr Asp Met Pro Ser Glu
        35                  40                  45

Ser Pro Trp Leu Thr Phe Leu Gln Trp Gly Arg Glu Tyr Asn Asp Arg
    50                  55                  60

Gly Leu Thr Thr Ile Phe Arg Val Glu Ser Thr Met Val Asn Lys Leu
65              70                  75                  80

Met Gly Trp Glu Phe Asp Leu Gly Phe Ile Thr Tyr Gly Asp Arg Trp
                85                  90                  95

Arg Glu Glu Arg Arg Met Phe Ser Lys Glu Phe Ser Glu Lys Ala Ile
            100                 105                 110

Lys Gln Phe Arg His Ser Gln Val Lys Ala Ala His Arg Phe Val Gln
        115                 120                 125

Gln Leu Ala Ala Asn Gly Glu Pro Ser Arg Leu Pro His Tyr Ile Arg
    130                 135                 140

His Gln Ile Ala Ala Met Ser Leu Asp Ile Gly Tyr Gly Val Asp Leu
145             150                 155                 160

Ala Gln Asp Asp Pro Trp Leu Glu Ala Ala His Leu Ala Asn Glu Gly
                165                 170                 175

Leu Ala Thr Ala Ser Val Pro Gly Thr Phe Trp Ile Asp Ser Phe Pro
            180                 185                 190

Ala Leu Lys Tyr Leu Pro Ser Trp Phe Pro Gly Ala Gly Phe Lys Arg
        195                 200                 205

Gln Ala Lys Ile Trp Lys Glu Ala Ala Asp His Met Val Asn Met Pro
    210                 215                 220

Tyr Glu Arg Met Lys Lys Leu Ala Pro Gln Gly Leu Ala Arg Pro Ser
225             230                 235                 240

Tyr Ala Ser Ala Arg Leu Gln Ala Met Asp Pro Asn Gly Asp Leu Glu
                245                 250                 255

Tyr Gln Glu Gln Val Ile Lys Asn Thr Ala Ser Gln Val Asn Val Gly
            260                 265                 270

Gly Gly Asp Thr Thr Val Ser Ala Val Ser Ala Phe Ile Leu Ala Met
        275                 280                 285

Val Ile Tyr Pro Glu Val Gln Arg Lys Val Gln Ala Glu Leu Asp Ala
```

```
                290                 295                 300
Val Leu Ser Asn Gly Arg Ile Pro Asp Tyr Asp Glu Glu Asn Asp Ser
305                 310                 315                 320

Met Pro Tyr Leu Thr Ala Cys Val Lys Glu Leu Phe Arg Trp Asn Gln
                325                 330                 335

Ile Ala Pro Leu Ala Ile Pro His Lys Leu Val Lys Asp Asp Ile Tyr
            340                 345                 350

Arg Gly Tyr Leu Ile Pro Lys Asn Thr Leu Val Phe Ala Asn Ser Trp
        355                 360                 365

Ala Val Leu Asn Asp Pro Glu Val Tyr Pro Asp Pro Ser Val Phe Arg
370                 375                 380

Pro Glu Arg Tyr Leu Gly Pro Asp Gly Lys Pro Asn Asp Thr Val Arg
385                 390                 395                 400

Asp Pro Arg Lys Ala Ala Phe Gly Tyr Gly Arg Arg Asn Cys Pro Gly
                405                 410                 415

Ile His Leu Ala Leu Ser Thr Val Trp Ile Thr Ala Ala Thr Leu Leu
            420                 425                 430

Ser Val Phe Asp Ile Glu Arg Pro Val Asp His Lys Gly Asn Pro Ile
        435                 440                 445

Asp Ile Pro Ala Ala Phe Thr Lys Gly Phe Phe Arg His Pro Glu Pro
    450                 455                 460

Phe Gln Cys Arg Phe Val Pro Arg Asn Glu Asp Ser Leu Lys Ser Leu
465                 470                 475                 480

Ser Gly Leu

<210> SEQ ID NO 35
<211> LENGTH: 563
<212> TYPE: PRT
<213> ORGANISM: Gymnopilus dilepis

<400> SEQUENCE: 35

Met Gln Gly Asn Pro Ala Val Leu Leu Leu Leu Thr Leu Thr Leu
1               5                   10                  15

Cys Val Tyr Tyr Ala His Ser Arg Arg Ala Arg Arg Ala Arg Leu Pro
                20                  25                  30

Pro Gly Pro Pro Gly Ile Pro Leu Pro Phe Val Gly Asn Leu Phe Asp
            35                  40                  45

Met Pro Ser Asn Ser Pro Trp Leu Thr Tyr Leu Gln Trp Gly Glu Thr
        50                  55                  60

Tyr Gln Thr Asp Ile Ile Tyr Leu Asn Ala Gly Gly Thr Glu Met Val
65                  70                  75                  80

Ile Leu Asn Thr Leu Glu Ala Ile Thr Asp Leu Leu Glu Lys Arg Gly
                85                  90                  95

Ser Ile Tyr Ser Gly Arg Phe Glu Ser Thr Met Val Asn Glu Leu Met
            100                 105                 110

Gly Trp Asp Phe Asp Leu Gly Phe Ile Thr Tyr Gly Glu Arg Trp Arg
        115                 120                 125

Glu Glu Arg Arg Met Phe Ser Lys Glu Phe Asn Glu Lys Asn Ile Lys
    130                 135                 140

Gln Phe Arg His Ala Gln Ile Arg Ala Ala Asn Leu Leu Val Gly Gln
145                 150                 155                 160

Leu Thr Lys Thr Pro Glu Arg Trp His Gln Leu Ile Arg His Gln Ile
                165                 170                 175

Ala Ala Met Ser Leu Asp Ile Gly Tyr Gly Ile Asp Leu Leu Glu Gly
```

```
            180                 185                 190
Asp Pro Trp Leu Glu Ala Thr Gln Leu Ala Asn Glu Gly Leu Ala Ile
        195                 200                 205
Ala Ser Val Pro Gly Ser Phe Trp Val Asp Ser Leu Pro Ile Leu Lys
    210                 215                 220
Tyr Met Pro Ser Trp Phe Pro Gly Ala Glu Phe Lys Arg Lys Ala Lys
225                 230                 235                 240
Val Trp Arg Glu Ser Thr Asp His Met Ile Asn Met Pro Tyr Glu Lys
                245                 250                 255
Met Lys Lys Leu Met Val Gln Asp Leu Val Arg Pro Ser Tyr Ala Ser
            260                 265                 270
Ala Arg Leu Gln Glu Met Asp Pro Asn Gly Asp Leu Gln His Gln Glu
        275                 280                 285
His Val Ile Arg Asn Thr Ala Met Glu Val Asn Val Gly Gly Ala Asp
    290                 295                 300
Thr Thr Val Ser Ala Val Ala Ala Phe Ile Leu Ala Met Val Lys Tyr
305                 310                 315                 320
Pro Asp Val Gln Arg Lys Val Gln Ala Glu Leu Asp Ala Val Gly Cys
                325                 330                 335
Arg Asp Glu Leu Pro Glu Phe Asp Glu Asp Asn Asp Ala Leu Pro Tyr
            340                 345                 350
Leu Thr Ala Cys Val Lys Glu Ile Phe Arg Trp Asn Gln Val Ala Pro
        355                 360                 365
Leu Ala Ile Pro His Arg Leu Asp Lys Asp Asp His Tyr Arg Gly Tyr
    370                 375                 380
Ile Ile Pro Lys Asn Ala Leu Val Phe Ala Asn Thr Trp Ala Val Leu
385                 390                 395                 400
Asn Asp Pro Ser Val Tyr Pro Asp Pro Ser Glu Phe Arg Pro Glu Arg
                405                 410                 415
Tyr Leu Gly Pro Asp Gly Lys Pro Asp Pro Arg Ile Arg Asp Pro Arg
            420                 425                 430
Lys Ala Ala Phe Gly Tyr Gly Arg Arg Ala Cys Pro Gly Ile His Leu
        435                 440                 445
Ala Gln Ser Thr Val Trp Ile Val Gly Ala Thr Leu Leu Ser Val Phe
    450                 455                 460
Asp Ile Glu Arg Pro Met Asp Ala Asn Gly Lys Pro Ile Asp Ile Pro
465                 470                 475                 480
Ala Ala Phe Thr Thr Gly Phe Phe Arg Tyr Ser Ile His Asp Cys Leu
                485                 490                 495
Val Val Glu Thr Met His Pro Ala Asn Thr Val Cys Val Asp Ile Pro
            500                 505                 510
Asn Pro Ser Asp Ala Asp Ser Phe Leu Val Pro Lys Arg Leu Ser Asn
        515                 520                 525
Pro His Pro Ile Ile Asp Leu Pro Ser Arg Asn Pro Ala Cys Gln Glu
    530                 535                 540
Asp Gly Val Val Ala Leu Ser Asn Ala Trp Arg Ser Thr Leu Pro Val
545                 550                 555                 560
Gln Asp Val

<210> SEQ ID NO 36
<211> LENGTH: 691
<212> TYPE: PRT
<213> ORGANISM: Saccharomyces cerevisiae
```

```
<400> SEQUENCE: 36

Met Pro Phe Gly Ile Asp Asn Thr Asp Phe Thr Val Leu Ala Gly Leu
1               5                   10                  15

Val Leu Ala Val Leu Leu Tyr Val Lys Arg Asn Ser Ile Lys Glu Leu
            20                  25                  30

Leu Met Ser Asp Asp Gly Asp Ile Thr Ala Val Ser Ser Gly Asn Arg
        35                  40                  45

Asp Ile Ala Gln Val Val Thr Glu Asn Lys Asn Tyr Leu Val Leu
    50                  55                  60

Tyr Ala Ser Gln Thr Gly Thr Ala Glu Asp Tyr Ala Lys Lys Phe Ser
65                  70                  75                  80

Lys Glu Leu Val Ala Lys Phe Asn Leu Asn Val Met Cys Ala Asp Val
                85                  90                  95

Glu Asn Tyr Asp Phe Glu Ser Leu Asn Asp Val Pro Val Ile Val Ser
            100                 105                 110

Ile Phe Ile Ser Thr Tyr Gly Glu Gly Asp Phe Pro Asp Gly Ala Val
        115                 120                 125

Asn Phe Glu Asp Phe Ile Cys Asn Ala Glu Ala Gly Ala Leu Ser Asn
    130                 135                 140

Leu Arg Tyr Asn Met Phe Gly Leu Gly Asn Ser Thr Tyr Glu Phe Phe
145                 150                 155                 160

Asn Gly Ala Ala Lys Lys Ala Glu Lys His Leu Ser Ala Ala Gly Ala
                165                 170                 175

Ile Arg Leu Gly Lys Leu Gly Glu Ala Asp Gly Ala Gly Thr Thr
        180                 185                 190

Asp Glu Asp Tyr Met Ala Trp Lys Asp Ser Ile Leu Glu Val Leu Lys
    195                 200                 205

Asp Glu Leu His Leu Asp Glu Gln Glu Ala Lys Phe Thr Ser Gln Phe
210                 215                 220

Gln Tyr Thr Val Leu Asn Glu Ile Thr Asp Ser Met Ser Leu Gly Glu
225                 230                 235                 240

Pro Ser Ala His Tyr Leu Pro Ser His Gln Leu Asn Arg Asn Ala Asp
                245                 250                 255

Gly Ile Gln Leu Gly Pro Phe Asp Leu Ser Gln Pro Tyr Ile Ala Pro
        260                 265                 270

Ile Val Lys Ser Arg Glu Leu Phe Ser Ser Asn Asp Arg Asn Cys Ile
    275                 280                 285

His Ser Glu Phe Asp Leu Ser Gly Ser Asn Ile Lys Tyr Ser Thr Gly
    290                 295                 300

Asp His Leu Ala Val Trp Pro Ser Asn Pro Leu Glu Lys Val Glu Gln
305                 310                 315                 320

Phe Leu Ser Ile Phe Asn Leu Asp Pro Glu Thr Ile Phe Asp Leu Lys
                325                 330                 335

Pro Leu Asp Pro Thr Val Lys Val Pro Phe Pro Thr Pro Thr Thr Ile
        340                 345                 350

Gly Ala Ala Ile Lys His Tyr Leu Glu Ile Thr Gly Pro Val Ser Arg
        355                 360                 365

Gln Leu Phe Ser Ser Leu Ile Gln Phe Ala Pro Asn Ala Asp Val Lys
370                 375                 380

Glu Lys Leu Thr Leu Leu Ser Lys Asp Lys Asp Gln Phe Ala Val Glu
385                 390                 395                 400

Ile Thr Ser Lys Tyr Phe Asn Ile Ala Asp Ala Leu Lys Tyr Leu Ser
                405                 410                 415
```

```
Asp Gly Ala Lys Trp Asp Thr Val Pro Met Gln Phe Leu Val Glu Ser
            420                 425                 430

Val Pro Gln Met Thr Pro Arg Tyr Tyr Ser Ile Ser Ser Ser Ser Leu
            435                 440                 445

Ser Glu Lys Gln Thr Val His Val Thr Ser Ile Val Glu Asn Phe Pro
            450                 455                 460

Asn Pro Glu Leu Pro Asp Ala Pro Pro Val Val Gly Val Thr Thr Asn
465                 470                 475                 480

Leu Leu Arg Asn Ile Gln Leu Ala Gln Asn Asn Val Asn Ile Ala Glu
                485                 490                 495

Thr Asn Leu Pro Val His Tyr Asp Leu Asn Gly Pro Arg Lys Leu Phe
            500                 505                 510

Ala Asn Tyr Lys Leu Pro Val His Val Arg Arg Ser Asn Phe Arg Leu
            515                 520                 525

Pro Ser Asn Pro Ser Thr Pro Val Ile Met Ile Gly Pro Gly Thr Gly
            530                 535                 540

Val Ala Pro Phe Arg Gly Phe Ile Arg Glu Arg Val Ala Phe Leu Glu
545                 550                 555                 560

Ser Gln Lys Lys Gly Gly Asn Asn Val Ser Leu Gly Lys His Ile Leu
                565                 570                 575

Phe Tyr Gly Ser Arg Asn Thr Asp Asp Phe Leu Tyr Gln Asp Glu Trp
            580                 585                 590

Pro Glu Tyr Ala Lys Lys Leu Asp Gly Ser Phe Glu Met Val Val Ala
            595                 600                 605

His Ser Arg Leu Pro Asn Thr Lys Lys Val Tyr Val Gln Asp Lys Leu
            610                 615                 620

Lys Asp Tyr Glu Asp Gln Val Phe Glu Met Ile Asn Asn Gly Ala Phe
625                 630                 635                 640

Ile Tyr Val Cys Gly Asp Ala Lys Gly Met Ala Lys Gly Val Ser Thr
                645                 650                 655

Ala Leu Val Gly Ile Leu Ser Arg Gly Lys Ser Ile Thr Thr Asp Glu
            660                 665                 670

Ala Thr Glu Leu Ile Lys Met Leu Lys Thr Ser Gly Arg Tyr Gln Glu
            675                 680                 685

Asp Val Trp
    690

<210> SEQ ID NO 37
<211> LENGTH: 695
<212> TYPE: PRT
<213> ORGANISM: Aspergillus niger

<400> SEQUENCE: 37

Met Ala Gln Leu Asp Thr Leu Asp Leu Val Val Leu Ala Val Leu Leu
1               5                   10                  15

Val Gly Ser Val Ala Tyr Phe Thr Lys Gly Thr Tyr Trp Ala Val Ala
            20                  25                  30

Lys Asp Pro Tyr Ala Ser Thr Gly Pro Ala Met Asn Gly Ala Ala Lys
            35                  40                  45

Ala Gly Lys Thr Arg Asn Ile Ile Glu Lys Met Glu Glu Thr Gly Lys
            50                  55                  60

Asn Cys Val Ile Phe Tyr Gly Ser Gln Thr Gly Thr Ala Glu Asp Tyr
65                  70                  75                  80

Ala Ser Arg Leu Ala Lys Glu Gly Ser Gln Arg Phe Gly Leu Lys Thr
```

-continued

```
                85                  90                  95
Met Val Ala Asp Leu Glu Glu Tyr Asp Tyr Glu Asn Leu Asp Gln Phe
                100                 105                 110
Pro Glu Asp Lys Val Ala Val Phe Val Leu Ala Thr Tyr Gly Glu Gly
                115                 120                 125
Glu Pro Thr Asp Asn Ala Val Glu Phe Tyr Gln Phe Phe Thr Gly Asp
            130                 135                 140
Asp Val Ala Phe Glu Ser Gly Ala Ser Ala Asp Glu Lys Pro Leu Ser
145                 150                 155                 160
Lys Leu Lys Tyr Val Ala Phe Gly Leu Gly Asn Asn Thr Tyr Glu His
                165                 170                 175
Tyr Asn Ala Met Val Arg Gln Val Asp Ala Ala Phe Gln Lys Leu Gly
            180                 185                 190
Ala Gln Arg Ile Gly Ser Ala Gly Glu Gly Asp Gly Ala Gly Thr
                195                 200                 205
Met Glu Glu Asp Phe Leu Ala Trp Lys Glu Pro Met Trp Ala Ala Leu
        210                 215                 220
Ser Glu Ser Met Asp Leu Gln Glu Arg Glu Ala Val Tyr Glu Pro Val
225                 230                 235                 240
Phe Cys Val Thr Glu Asn Glu Ser Leu Ser Pro Glu Asp Glu Ser Val
                245                 250                 255
Tyr Leu Gly Glu Pro Thr Gln Ser His Leu Gln Gly Thr Pro Lys Gly
            260                 265                 270
Pro Tyr Ser Ala His Asn Pro Phe Ile Ala Pro Ile Ala Glu Ser Arg
        275                 280                 285
Glu Leu Phe Thr Val Lys Asp Arg Asn Cys Leu His Met Glu Ile Ser
    290                 295                 300
Ile Ala Gly Ser Asn Leu Ser Tyr Gln Thr Gly Asp His Ile Ala Val
305                 310                 315                 320
Trp Pro Thr Asn Ala Gly Ala Glu Val Asp Arg Phe Leu Gln Val Phe
                325                 330                 335
Gly Leu Glu Gly Lys Arg Asp Ser Val Ile Asn Ile Lys Gly Ile Asp
            340                 345                 350
Val Thr Ala Lys Val Pro Ile Pro Thr Pro Thr Thr Tyr Asp Ala Ala
        355                 360                 365
Val Arg Tyr Tyr Met Glu Val Cys Ala Pro Val Ser Arg Gln Phe Val
    370                 375                 380
Ala Thr Leu Ala Ala Phe Ala Pro Asp Glu Glu Ser Lys Ala Glu Ile
385                 390                 395                 400
Val Arg Leu Gly Ser Asp Lys Asp Tyr Phe His Glu Lys Val Thr Asn
                405                 410                 415
Gln Cys Phe Asn Ile Ala Gln Ala Leu Gln Ser Ile Thr Ser Lys Pro
            420                 425                 430
Phe Ser Ala Val Pro Phe Ser Leu Leu Ile Glu Gly Ile Thr Lys Leu
        435                 440                 445
Gln Pro Arg Tyr Tyr Ser Ile Ser Ser Ser Ser Leu Val Gln Lys Asp
    450                 455                 460
Lys Ile Ser Ile Thr Ala Val Val Glu Ser Val Arg Leu Pro Gly Ala
465                 470                 475                 480
Ser His Met Val Lys Gly Val Thr Thr Asn Tyr Leu Leu Ala Leu Lys
                485                 490                 495
Gln Lys Gln Asn Gly Asp Pro Ser Pro Asp Pro His Gly Leu Thr Tyr
            500                 505                 510
```

```
Ser Ile Thr Gly Pro Arg Asn Lys Tyr Asp Gly Ile His Val Pro Val
            515                 520                 525

His Val Arg His Ser Asn Phe Lys Leu Pro Ser Asp Pro Ser Arg Pro
        530                 535                 540

Ile Ile Met Val Gly Pro Gly Thr Gly Val Ala Pro Phe Arg Gly Phe
545                 550                 555                 560

Ile Gln Glu Arg Ala Ala Leu Ala Ala Lys Gly Glu Lys Val Gly Pro
                565                 570                 575

Thr Val Leu Phe Phe Gly Cys Arg Lys Ser Asp Glu Asp Phe Leu Tyr
            580                 585                 590

Lys Asp Glu Trp Lys Thr Tyr Gln Asp Gln Leu Gly Asp Asn Leu Lys
        595                 600                 605

Ile Ile Thr Ala Phe Ser Arg Glu Gly Pro Gln Lys Val Tyr Val Gln
    610                 615                 620

His Arg Leu Arg Glu His Ser Glu Leu Val Ser Asp Leu Leu Lys Gln
625                 630                 635                 640

Lys Ala Thr Phe Tyr Val Cys Gly Asp Ala Ala Asn Met Ala Arg Glu
                645                 650                 655

Val Asn Leu Val Leu Gly Gln Ile Ile Ala Ala Gln Arg Gly Leu Pro
            660                 665                 670

Ala Glu Lys Gly Glu Glu Met Val Lys His Met Arg Ser Ser Gly Ser
        675                 680                 685

Tyr Gln Glu Asp Val Trp Ser
    690                 695

<210> SEQ ID NO 38
<211> LENGTH: 1351
<212> TYPE: PRT
<213> ORGANISM: Psilocybe cyanescens

<400> SEQUENCE: 38

Met Thr Asp Pro Asn Arg Thr Thr Phe Ser Ser Ala Leu His Pro Leu
1               5                   10                  15

Ala Val Val Ser Met Ala Ser Ser Ser Asp Val Phe Val Leu Gly
            20                  25                  30

Leu Gly Val Val Leu Ala Ala Leu Tyr Ile Phe Arg Asp Gln Leu Phe
        35                  40                  45

Ala Ala Ser Lys Pro Lys Val Ala Pro Val Ser Thr Thr Lys Pro Ala
    50                  55                  60

Asn Gly Ser Ala Asn Pro Arg Asp Phe Ile Ala Lys Met Lys Gln Gly
65                  70                  75                  80

Lys Lys Arg Ile Val Ile Phe Tyr Gly Ser Gln Thr Gly Thr Ala Glu
                85                  90                  95

Glu Tyr Ala Ile Arg Leu Ala Lys Glu Ala Lys Gln Lys Phe Gly Leu
                100                 105                 110

Ala Ser Leu Val Cys Asp Pro Glu Glu Tyr Asp Phe Glu Lys Leu Asp
            115                 120                 125

Gln Leu Pro Glu Asp Ser Ile Ala Phe Phe Val Val Ala Thr Tyr Gly
        130                 135                 140

Glu Gly Glu Pro Thr Asp Asn Ala Val Gln Leu Gln Asn Leu Gln
145                 150                 155                 160

Asp Asp Ser Phe Glu Phe Ser Asn Gly Glu Arg Lys Leu Ser Gly Leu
                165                 170                 175

Lys Tyr Val Val Phe Gly Leu Gly Asn Lys Thr Tyr Glu His Tyr Asn
```

```
                180                 185                 190
Leu Ile Gly Arg Thr Val Asp Ala Gln Leu Ala Lys Met Gly Ala Val
            195                 200                 205

Arg Val Gly Glu Arg Gly Gly Asp Asp Lys Ser Met Glu Glu
        210                 215                 220

Asp Tyr Leu Glu Trp Lys Asp Gly Met Trp Asp Ala Phe Ala Ala Ala
225                 230                 235                 240

Met Gly Val Glu Glu Gly Gln Gly Gly Asp Ser Ala Asp Phe Val Val
            245                 250                 255

Ser Glu Leu Glu Ser His Pro Pro Glu Lys Val Tyr Leu Gly Glu Tyr
            260                 265                 270

Ser Ala Arg Ala Leu Thr Lys Thr Lys Gly Ile His Asp Ala Lys Asn
            275                 280                 285

Pro Leu Ala Ala Pro Ile Thr Val Ala Arg Glu Leu Phe Gln Ser Val
            290                 295                 300

Val Asp Arg Asn Cys Val His Val Glu Phe Asn Ile Glu Gly Ser Gly
305                 310                 315                 320

Ile Thr Tyr Gln His Gly Asp His Val Gly Leu Trp Pro Leu Asn Pro
                325                 330                 335

Asp Val Glu Val Glu Arg Leu Leu Cys Val Leu Gly Leu Thr Glu Lys
            340                 345                 350

Arg Asp Ala Val Ile Ser Ile Glu Ser Leu Asp Pro Ala Leu Ala Lys
            355                 360                 365

Val Pro Phe Pro Val Pro Thr Thr Tyr Ala Ala Val Leu Arg His Tyr
            370                 375                 380

Ile Asp Val Ser Ala Val Ala Gly Arg Gln Ile Leu Gly Thr Leu Ser
385                 390                 395                 400

Lys Phe Ala Pro Thr Pro Glu Ala Glu Ala Phe Leu Lys Asn Leu Asn
                405                 410                 415

Thr Asn Lys Glu Glu Tyr His Asn Val Val Ala Asn Gly Cys Leu Lys
                420                 425                 430

Leu Gly Glu Ile Leu Gln Val Ala Thr Gly Asn Asp Ile Thr Val Ala
            435                 440                 445

Pro Thr Pro Gly Asn Thr Thr Lys Trp Pro Ile Pro Phe Asp Ile Ile
            450                 455                 460

Val Ser Ala Ile Pro Arg Leu Gln Pro Arg Tyr Tyr Ser Ile Ser Ser
465                 470                 475                 480

Ser Pro Lys Val His Pro Asn Thr Ile His Ala Thr Val Val Leu
                485                 490                 495

Lys Tyr Glu Asn Val Pro Thr Asp Pro Ile Pro Arg Lys Trp Val Tyr
            500                 505                 510

Gly Val Gly Ser Asn Phe Leu Leu Asn Leu Lys His Ala Ile Asn Lys
            515                 520                 525

Glu Pro Val Pro Phe Ile Thr Gln Asn Gly Glu Gln Arg Val Gly Val
            530                 535                 540

Pro Glu Tyr Leu Ile Ala Gly Pro Arg Gly Ser Tyr Lys Thr Glu Ser
545                 550                 555                 560

His Phe Lys Ala Pro Ile His Val Arg Arg Ser Thr Phe Arg Leu Pro
                565                 570                 575

Thr Asn Pro Lys Ser Pro Val Ile Met Ile Gly Pro Gly Thr Gly Val
            580                 585                 590

Ala Pro Phe Arg Gly Phe Val Gln Glu Arg Val Ala Leu Ala Arg Arg
            595                 600                 605
```

Ser Val Glu Lys Asn Gly Pro Glu Ser Leu Asn Asp Trp Gly Arg Ile
610             615                 620

Ser Leu Phe Tyr Gly Cys Arg Arg Ser Asp Glu Asp Phe Leu Tyr Lys
625             630              635                 640

Asp Glu Trp Pro Gln Tyr Gln Glu Leu Lys Gly Lys Phe Lys Leu
                645             650                 655

His Cys Ala Phe Ser Arg Glu Asn Tyr Lys Pro Asp Gly Ser Lys Ile
            660             665                 670

Tyr Val Gln Asp Leu Ile Trp Glu Asp Arg Glu His Ile Ala Asp Ala
        675             680              685

Ile Leu Asn Gly Lys Gly Tyr Val Tyr Ile Cys Gly Glu Ala Lys Ser
690             695                 700

Met Ser Lys Gln Val Glu Val Leu Ala Arg Ile Leu Gly Glu Ala
705             710             715                 720

Lys Gly Gly Ser Gly Ala Val Glu Gly Val Ala Glu Ile Lys Leu Leu
            725             730                 735

Lys Glu Arg Ser Arg Leu Met Leu Asp Tyr Glu Leu Ala Phe Arg Lys
            740             745                 750

Phe Ser Gln Leu Gln Phe Ala Arg Val Ala Thr Phe Ala Met Leu Arg
        755             760             765

Ser Ser Phe Ser Leu Gln Arg Leu Phe Ser Thr Ser Ala Leu Arg
770             775             780

Asn Val Gln Arg Pro Ile Arg Asp His Leu Gln Lys Gln Asp Ala Pro
785             790             795                 800

Trp Glu Pro Arg Val Ala Glu Ser Ala Gln Ser Val Ser Glu Glu Ile
            805             810                 815

Leu Lys Ala Gln Thr Pro Leu Gln Val Pro Thr Asn Ala Lys Ala Thr
            820             825                 830

Thr Ser Asp Ser Arg Thr Asp Ser Arg Glu Pro Leu Thr Ala Tyr Asp
            835             840             845

Leu Gln Leu Val Lys Lys Arg Val Arg Glu Trp Ser Glu Gln Ala Met
850             855             860

Ile Ala Leu Arg Asn Arg Ala Asp Asp Phe Thr Ala His Thr Lys Thr
865             870             875                 880

Thr Phe Ser Gln Leu Gly Leu Gln Leu Asn Arg Val Thr Gly Tyr Glu
            885             890             895

Glu Ile Glu Ala Leu Lys Arg Gly Val Val Glu Gln Glu Arg Ile
        900             905             910

Asn Val Ala Arg Gln Ala Ala Arg Lys Ala Lys Val Ala Tyr Glu Glu
            915             920             925

Ala Val Val Gln Arg Ser Asn Ser Gln Arg Glu Val Asn Asp Leu Leu
930             935             940

Gln Arg Lys Ser Ser Trp Met Asp Ser Asp Val Gly Arg Phe Thr Thr
945             950             955                 960

Leu Val Arg Gln Asp His Leu Tyr Glu Gln Glu Ala Arg Ala Lys
            965             970             975

Ala Ala Val Glu Glu Thr Glu Glu Ala Val Asp Arg Glu Phe Ser Lys
            980             985                 990

Leu Leu Arg Thr Ile Leu Ala Arg Tyr His Glu Glu Gln Val Trp Ser
        995             1000            1005

Asp Lys Ile Arg Ser Ala Ser Thr Tyr Gly Ser Leu Ala Ala Leu
    1010            1015            1020

Gly Leu Asn Met Leu Val Phe Ile Met Ala Ile Val Val Val Glu
1025                1030                1035

Pro Trp Lys Arg Arg Leu Ala Gln Thr Phe Glu Arg Lys Ile
    1040                1045                1050

Glu Glu Leu Ser Glu Glu Asn Gly Ile Lys Leu Asp Ala Thr Met
    1055                1060                1065

Leu Ser Ile Ala Gln Gln Ile Glu Gln Gln Val Asn Leu Ile Gly
    1070                1075                1080

Ser Leu Lys Asp Asp Ile Ser Arg Asn Ala Pro Val Ile Pro Glu
    1085                1090                1095

Pro Ala Gln Glu Val Arg Ala Glu Thr Glu Ile Glu Glu Glu Thr
    1100                1105                1110

Ser Pro Phe Val Ser Leu Glu Phe Leu Pro Leu Ser Arg Arg Gln
    1115                1120                1125

Leu Glu Val Ala Ala Val Gly Ala Gly Ala Phe Ala Ser Asn Leu
    1130                1135                1140

Trp Phe Gly Phe Gly Asp Asp Ala Leu Glu Leu Leu Met Leu Ser
    1145                1150                1155

Thr Arg Ala Asn Lys Val Pro Pro Arg Asn Leu Ser Arg Ile His
    1160                1165                1170

Met Thr Ser Phe Ile Ile Lys Ala His Glu Asp Arg Pro Thr Asn
    1175                1180                1185

Ser Thr Trp Lys Gln Asp Leu Glu Cys Ala Phe Cys Arg Ile Ile
    1190                1195                1200

Arg Gly Glu Leu Pro Ala Ser Lys Val Tyr Glu Asn Asp Lys Val
    1205                1210                1215

Ile Ala Ile Leu Asp Ile Met Pro Leu Arg Lys Gly His Thr Leu
    1220                1225                1230

Val Ile Pro Lys Ala His Ile Ser Arg Leu Ser Glu Leu Pro Ser
    1235                1240                1245

Glu Leu Ala Ser Ser Val Gly Glu Ala Val Cys Lys Val Ala His
    1250                1255                1260

Ala Leu Thr Gln Ala Leu Asp Asn Thr Gly Leu Asn Val Val Cys
    1265                1270                1275

Asn Gln Glu Tyr Ala Gln Ala Val Pro His Val His Tyr His Val
    1280                1285                1290

Ile Pro Ala Pro Lys Phe Gly Tyr Pro Gly His Gly Val Glu Ser
    1295                1300                1305

Thr Asn Gly Val Val Gly Gly Lys Ala Pro Leu Thr His Arg Glu
    1310                1315                1320

Met His Gln Lys Glu Phe Glu Ala Arg Glu Glu Leu Asp Asp Asp
    1325                1330                1335

Asp Ala Lys Val Leu Leu Lys Ser Ile Arg Ala Arg Leu
    1340                1345                1350

<210> SEQ ID NO 39
<211> LENGTH: 592
<212> TYPE: PRT
<213> ORGANISM: Psilocybe cyanescens

<400> SEQUENCE: 39

Met Ser Val Ser Glu Asp Asp His Arg Gly Leu Leu Ile Val Tyr Ala
1               5                   10                  15

Thr Glu Thr Gly Asn Ala Gln Asp Ala Ala Asp Tyr Ile Ala Arg Gln
            20                  25                  30

```
Cys Arg Arg Ile Ala Phe Gln Cys Arg Val Val Asn Ile Asp Ser Phe
     35                  40                  45

Leu Leu Pro Asp Leu Leu Ser Glu Thr Ile Val Ile Phe Val Val Ser
 50                  55                  60

Thr Thr Gly Ser Gly Val Glu Pro Arg Ser Met Thr Pro Leu Trp Thr
 65                  70                  75                  80

Ser Leu Leu Arg Gly Asp Leu Pro Thr Asp Thr Phe Glu Asp Leu Tyr
                 85                  90                  95

Phe Ser Val Phe Gly Leu Gly Asp Thr Ala Tyr Glu Lys Phe Cys Trp
            100                 105                 110

Ala Ala Lys Lys Leu Ser Arg Arg Leu Glu Ser Ile Gly Gly Ile Glu
            115                 120                 125

Phe Tyr Met Arg Gly Glu Gly Asp Glu Gln His Pro Leu Gly Ile Asp
            130                 135                 140

Gly Ala Leu Gln Pro Trp Thr Asp Gly Leu Ile Asn Lys Leu Leu Glu
145                 150                 155                 160

Val Ala Pro Leu Pro Pro Gly Glu Glu Ile Lys Pro Ile Asn Asp Val
                165                 170                 175

Pro Leu Pro Arg Val Leu Leu Lys Asp Thr Ser Lys Thr Ala Leu Asn
            180                 185                 190

His Ser Ala Asp Pro Leu Lys Ser Asp Leu Gln Tyr His Lys Ala Ile
            195                 200                 205

Val Lys Lys Asn Asp Arg Ile Thr Ala Ala Asp Trp Tyr Gln Asp Val
            210                 215                 220

Arg His Leu Val Phe Asp Phe Gln Asp Asn Ile Gln Tyr Ser Pro Gly
225                 230                 235                 240

Asp Val Ala Val Ile His Pro Val Ala Leu Glu His Asp Val Asp Ala
                245                 250                 255

Phe Leu Val Thr Met Ser Trp Gln Asn Ile Ala Asp Glu Pro Phe Glu
            260                 265                 270

Ile Glu Gln Ala Met Tyr Asp Gln Ser Leu Pro Asp His Leu Pro Pro
            275                 280                 285

Ile Thr Thr Leu Arg Thr Leu Phe Thr Arg Phe Leu Asp Phe Asn Ala
            290                 295                 300

Val Pro Arg Arg Ser Phe Phe Gln Tyr Leu Arg Tyr Phe Thr Ser Asp
305                 310                 315                 320

Glu Arg Glu Gln Glu Lys Leu Asp Gly Phe Leu Ser Ala Ala Gly Ala
                325                 330                 335

Asp Glu Leu Tyr Glu Tyr Cys Tyr Arg Val Arg Arg Thr Ile His Glu
            340                 345                 350

Val Leu Ser Glu Phe Arg His Val Lys Ile Pro Lys Gly Tyr Ile Phe
            355                 360                 365

Asp Val Phe Pro Pro Leu Arg Pro Arg Glu Phe Ser Ile Ala Ser Ser
            370                 375                 380

Ile Lys Thr His Leu His Gln Ile His Leu Cys Val Ala Ile Val Lys
385                 390                 395                 400

Tyr Arg Thr Lys Leu Lys Ile Pro Arg Lys Gly Val Cys Thr Tyr Tyr
                405                 410                 415

Leu Ser Ile Leu Lys Pro Gly Asp Thr Leu Leu Val Gly Ile Arg Arg
            420                 425                 430

Gly Leu Leu Arg Leu Pro Gly Lys Asn Asp Thr Pro Val Ile Phe Ile
            435                 440                 445
```

```
Gly Pro Gly Thr Gly Ile Ala Pro Met Arg Ser Ala Ile Glu Gln Arg
            450                 455                 460
Ile Ala Asn Gly Cys His Glu Asn Thr Leu Tyr Phe Gly Cys Arg Ser
465                 470                 475                 480
Ala Ser Lys Asp Gln His Tyr Gly Ser Glu Trp Gln Ala Tyr Ala Ala
            485                 490                 495
Asn Gln Glu Leu Lys Tyr Arg Ser Ala Phe Ser Arg Asp Gly Val Glu
            500                 505                 510
Gly Glu Ala Arg Val Tyr Val Gln Asp Leu Ile Arg Gln Asp Ser Glu
            515                 520                 525
Arg Ile Trp Asp Leu Val Gly His His Lys Ala Trp Val Leu Val Ser
530                 535                 540
Gly Ser Ser Asn Lys Met Pro Ala Ala Val Lys Asp Ala Val Ala Tyr
545                 550                 555                 560
Ala Val Glu Lys Tyr Gly Gly Leu Ser Ala Glu Ala Lys Glu Tyr
            565                 570                 575
Val His Leu Met Val Lys Glu Gly Arg Leu Ile Glu Glu Cys Trp Ser
            580                 585                 590

<210> SEQ ID NO 40
<211> LENGTH: 1063
<212> TYPE: PRT
<213> ORGANISM: Psilocybe cyanescens

<400> SEQUENCE: 40

Met Ser Leu Asn Gly Ser Gly Leu Leu Thr Pro Ser Ser Glu Val Thr
1               5                   10                  15
Leu Ser Ser Pro Ser Thr Pro Val Leu Ile Tyr Thr Phe Pro Gln Ser
            20                  25                  30
Asn Gly Thr Arg Pro Lys Ser Pro Val Tyr Ile His Ile Asp Asp Pro
        35                  40                  45
Gly Val Gln Val Ser Thr Leu Val Glu Tyr Ile Ser Ser Gln Pro Glu
    50                  55                  60
Asn Ser Ser Ser Val Tyr Ile Tyr Asp Val Ala Glu Gln Val Gly Phe
65                  70                  75                  80
Gly Thr Ser Thr Lys Gln Trp Ala Lys Gln Gly Leu Asp Ile Ser Pro
                85                  90                  95
Val Val Asp Leu Gln Thr Arg Ala Gly Ala Gly Leu Ser Leu Val Gly
            100                 105                 110
Arg Leu Ser Gln Gly Thr Ser Ile Asp Ala Val Lys Gly Thr Val Leu
        115                 120                 125
Thr Ala Tyr Thr Thr Pro Ser Gly Leu Ala Leu Met Ala Pro Ser Phe
    130                 135                 140
Ala Tyr Leu Pro Val Pro Ser Ser Thr Thr Arg Leu Ile Ile Gln Val
145                 150                 155                 160
Pro Thr Val Thr Pro Val Gly Glu Thr Leu Thr Leu Ser Pro Thr Leu
                165                 170                 175
Ser Pro Leu Ala Ser Val Trp Ser Ile Leu Pro Glu Asn Val Ala Val
            180                 185                 190
Leu Leu Ser Ser Ser Pro Gln Gln Thr Val Asp Phe Ala Thr Leu Ala
        195                 200                 205
Tyr Lys Val Ile Asp Ser His Ile Val His Leu Phe Asp His His Ser
    210                 215                 220
Ser Ala Arg Glu Ile Gly Arg Thr Phe Thr Pro Leu Thr Thr Ile Gly
225                 230                 235                 240
```

-continued

```
Lys Ser Gly Leu Thr Leu Gln Glu Ala Val Lys Gln Ala Gly Tyr Glu
            245                 250                 255
Pro Leu Glu Tyr His Gly Asp Pro Glu Ala Lys Thr Ile Val Val Leu
        260                 265                 270
Leu Asn Ser Ser Leu Ala Leu Ser Leu Lys Ala Ala Val Ser Val Gly
        275                 280                 285
Thr Ser Gly Leu Gly Val Val Val Asn Val Leu Arg Pro Trp Asp
290                 295                 300
Glu Ala Ala Ile Gln Thr Ile Ile Pro Ser Ser Ala Thr Ile Val His
305                 310                 315                 320
Val Leu Asp Asp Val Pro Asn Ala Val Thr Gln Gly Ser Leu Tyr Val
                325                 330                 335
Asp Val Phe Ser Ala Leu Trp Ser Thr Thr Pro Lys Arg Ser Val His
                340                 345                 350
Ser His Arg Ile Thr Pro Ser Gln Thr Gln Lys Phe Ile Ala Ala Gly
            355                 360                 365
Gly Glu Phe Leu Arg Phe Val Glu Val Thr His Ile Ala Val Ser
        370                 375                 380
Glu Pro Ser Val Ala Ser Ile Lys Lys Thr Leu Phe Ser Val Pro
385                 390                 395                 400
Asp Ser Pro Leu Ala Leu Leu Ser Arg Phe Val Gln Glu Leu Phe Leu
                405                 410                 415
Thr Lys Arg Thr Ile Ser Ser Arg His Leu Thr Asp Tyr Asp Val Tyr
                420                 425                 430
Ser Lys Pro Gly Gly Ile Ser Ala Gln Arg Leu Leu Ile Ser Arg Asp
            435                 440                 445
Lys Ser Thr Asp Asn Val Pro Val Gln Ala Ile Leu Pro Leu Asp Pro
450                 455                 460
Asn Ser Val Gly His Ser Asp Phe Leu Gly Val Leu Asp His Asn Leu
465                 470                 475                 480
Leu Lys Thr His Ser Leu Leu Lys His Ala Lys Lys Gly Ser Ile Val
                485                 490                 495
Val Val Ala Ser Pro Trp Thr Pro Asp Glu Phe Ser Ala Asn Ile Thr
            500                 505                 510
Tyr Glu Val Ala Glu Val Ile Thr Ser Arg Gln Leu Ser Val Tyr Thr
        515                 520                 525
Ile Asp Val Lys Ser Ile Ala Asn Asp Leu Glu Leu Phe Ile Gln Glu
530                 535                 540
Gln Lys Ile Glu Lys Gly Glu Ala Gln Val Leu Leu Phe Glu Phe Val
545                 550                 555                 560
Phe Leu Arg Phe Tyr Leu Gly Ala Ala Ala Thr Glu Gln Ala Ile Ile
                565                 570                 575
Gln Leu Met Ser Val Leu Phe Asp Asp Ile Asp Leu Thr Lys Phe Ser
            580                 585                 590
Ala Ala Ala Trp Leu Gly Leu Lys Pro Val Val Ala Leu Pro Glu
        595                 600                 605
Val Thr Pro Ser Asp Ser Pro Thr Leu Lys Glu Phe Glu Ala Asn Ala
        610                 615                 620
Ile Ala Val Glu Thr Ser Glu Gly Gln Thr Val Val Asn Gly Ala Arg
625                 630                 635                 640
Leu Ser Thr Trp His Asp Ala Ala Lys His Leu Leu Phe Pro Ser Ala
                645                 650                 655
```

```
Phe Ser Pro Pro Thr Asp Pro Asp Ser Leu Ser Asn Pro Ala Leu Arg
            660                 665                 670

Pro Glu Val Pro Asp Thr Thr Phe Leu Val Thr Cys Thr Val Asn Lys
        675                 680                 685

Arg Leu Thr Pro Leu Glu Tyr Asp Arg Asn Val Phe His Leu Glu Phe
    690                 695                 700

Asp Thr Ser Gly Thr Gly Leu Lys Tyr Ala Ile Gly Glu Ala Leu Gly
705                 710                 715                 720

Val His Gly Trp Asn Asp Glu Gln Glu Val Leu Asp Phe Cys Glu Trp
                725                 730                 735

Tyr Gly Val Asp Pro Asp Arg Leu Ile Thr Ile Pro Val Ile Gly Ser
            740                 745                 750

Asp Asp Gly Lys Met His Thr Arg Thr Val Leu Gln Ala Leu Gln Gln
        755                 760                 765

Gln Ile Asp Leu Phe Gly Arg Pro Pro Lys Ser Phe Tyr Thr Asp Leu
    770                 775                 780

Ala Glu Tyr Ala Thr Val Asp Val Asp Arg Tyr Ala Leu Arg Phe Ile
785                 790                 795                 800

Gly Ser Pro Glu Gly Val Ser Thr Phe Lys Lys Met Ser Glu Lys Asp
                805                 810                 815

Thr Val Ser Phe Gly Asp Val Leu Lys Lys Tyr Lys Ser Ala Arg Pro
            820                 825                 830

Gly Ile Glu Arg Leu Cys Glu Leu Ile Gly Asp Ile Lys Pro Arg His
        835                 840                 845

Tyr Ser Ile Ala Ser Ala Gln Ser Val Val Gly Asp Arg Val Asp Leu
    850                 855                 860

Leu Val Val Thr Val Asp Trp Leu Thr Pro Glu Gly Ser Pro Arg Tyr
865                 870                 875                 880

Gly Gln Cys Thr Arg Tyr Leu Ala Gly Leu Lys Ile Gly Gln Lys Val
                885                 890                 895

Thr Val Ser Ile Lys Pro Ser Val Met Lys Leu Pro Pro Asn Leu Lys
            900                 905                 910

Gln Pro Leu Ile Met Ala Gly Leu Gly Thr Gly Ala Ala Pro Phe Arg
        915                 920                 925

Ala Phe Leu Gln His Leu Ala Trp Leu Ala Ser Lys Gly Glu Glu Ile
930                 935                 940

Gly Pro Val Phe Tyr Tyr Phe Gly Ser Arg Tyr Gln Ala Ala Glu Tyr
945                 950                 955                 960

Leu Tyr Gly Glu Glu Ile Glu Ala Phe Ile Leu Gly Gly Val Ile Thr
                965                 970                 975

Arg Ala Gly Leu Ala Phe Ser Arg Asp Gly Pro Lys Lys Val Tyr Ile
            980                 985                 990

Gln His Lys Met Leu Glu Asp Ser  Glu Thr Leu Ala Lys  Met Leu His
        995                 1000                 1005

Asp Asp  Asp Gly Val Phe Tyr  Leu Cys Gly Pro Thr  Trp Pro Val
        1010                 1015                 1020

Pro Asp  Val Tyr Glu Ala Leu  Val Asn Ala Leu Val  Lys Tyr Lys
        1025                 1030                 1035

Gly Ser  Asp Pro Val Lys Ala  Gly Glu Tyr Leu Glu  Ser Leu Lys
        1040                 1045                 1050

Glu Glu  Glu Arg Tyr Val Leu  Glu Val Tyr
        1055                 1060
```

<210> SEQ ID NO 41
<211> LENGTH: 362
<212> TYPE: PRT
<213> ORGANISM: Psilocybe cubensis

<400> SEQUENCE: 41

| | | | | | | | | | | | | | | |
|---|---|---|---|---|---|---|---|---|---|---|---|---|---|---|
| Met | Ala | Phe | Asp | Leu | Lys | Thr | Glu | Asp | Gly | Leu | Ile | Thr | Tyr | Leu | Thr |
| 1 | | | | 5 | | | | | 10 | | | | | 15 |

Lys His Leu Ser Leu Asp Val Asp Thr Ser Gly Val Lys Arg Leu Ser
                20                  25                  30

Gly Gly Phe Val Asn Val Thr Trp Arg Ile Lys Leu Asn Ala Pro Tyr
            35                  40                  45

Gln Gly His Thr Ser Ile Ile Leu Lys His Ala Gln Pro His Met Ser
        50                  55                  60

Thr Asp Glu Asp Phe Lys Ile Gly Val Glu Arg Ser Val Tyr Glu Tyr
65                  70                  75                  80

Gln Ala Ile Lys Leu Met Met Ala Asn Arg Glu Val Leu Gly Gly Val
                85                  90                  95

Asp Gly Ile Val Ser Val Pro Glu Gly Leu Asn Tyr Asp Leu Glu Asn
            100                 105                 110

Asn Ala Leu Ile Met Gln Asp Val Gly Lys Met Lys Thr Leu Leu Asp
        115                 120                 125

Tyr Val Thr Ala Lys Pro Pro Leu Ala Thr Asp Ile Ala Arg Leu Val
130                 135                 140

Gly Thr Glu Ile Gly Gly Phe Val Ala Arg Leu His Asn Ile Gly Arg
145                 150                 155                 160

Glu Arg Arg Asp Asp Pro Glu Phe Lys Phe Phe Ser Gly Asn Ile Val
                165                 170                 175

Gly Arg Thr Thr Ser Asp Gln Leu Tyr Gln Thr Ile Ile Pro Asn Ala
            180                 185                 190

Ala Lys Tyr Gly Val Asp Asp Pro Leu Leu Pro Thr Val Val Lys Asp
        195                 200                 205

Leu Val Asp Asp Val Met His Ser Glu Glu Thr Leu Val Met Ala Asp
210                 215                 220

Leu Trp Ser Gly Asn Ile Leu Leu Gln Leu Glu Glu Gly Asn Pro Ser
225                 230                 235                 240

Lys Leu Gln Lys Ile Tyr Ile Leu Asp Trp Glu Leu Cys Lys Tyr Gly
                245                 250                 255

Pro Ala Ser Leu Asp Leu Gly Tyr Phe Leu Gly Asp Cys Tyr Leu Ile
            260                 265                 270

Ser Arg Phe Gln Asp Glu Gln Val Gly Thr Thr Met Arg Gln Ala Tyr
        275                 280                 285

Leu Gln Ser Tyr Ala Arg Thr Ser Lys His Ser Ile Asn Tyr Ala Lys
290                 295                 300

Val Thr Ala Gly Ile Ala Ala His Ile Val Met Trp Thr Asp Phe Met
305                 310                 315                 320

Gln Trp Gly Ser Glu Glu Arg Ile Asn Phe Val Lys Lys Gly Val
                325                 330                 335

Ala Ala Phe His Asp Ala Arg Gly Asn Asn Asp Asn Gly Glu Ile Thr
            340                 345                 350

Ser Thr Leu Leu Lys Glu Ser Ser Thr Ala
        355                 360

<210> SEQ ID NO 42
<211> LENGTH: 362

<212> TYPE: PRT
<213> ORGANISM: Psilocybe cyanescens

<400> SEQUENCE: 42

Met Ala Phe Asp Leu Lys Thr Pro Glu Gly Leu Leu Tyr Leu Thr
1               5                   10                  15

Arg His Leu Ser Leu Asp Val Asp Pro Ser Gly Val Lys Arg Leu Ser
            20                  25                  30

Gly Gly Phe Val Asn Val Thr Trp Arg Ile Arg Leu Asn Ala Pro Tyr
            35                  40                  45

Gln Gly His Thr Ser Ile Ile Leu Lys His Ala Gln Pro His Leu Ser
        50                  55                  60

Ser Asp Glu Asp Phe Lys Ile Gly Val Glu Arg Ser Ala Tyr Glu Tyr
65                  70                  75                  80

Gln Ala Leu Lys Val Met Ser Ala Asn Gln Glu Val Leu Gly Gly Asp
                85                  90                  95

Asp Ser Arg Val Ser Val Pro Glu Gly Leu His Tyr Asp Val Glu Asn
            100                 105                 110

Asn Ala Leu Ile Met Gln Asp Val Gly Thr Met Lys Thr Leu Leu Asp
        115                 120                 125

Tyr Ala Thr Ala Lys Pro Pro Leu Ser Thr Glu Ile Ala Ser Leu Val
130                 135                 140

Gly Thr Glu Ile Gly Ala Phe Ile Ala Arg Leu His Asn Leu Gly Arg
145                 150                 155                 160

Lys Arg Arg Asp Gln Pro Ala Phe Lys Phe Phe Ser Gly Asn Ile Val
                165                 170                 175

Gly Arg Thr Thr Ala Asp Gln Leu Tyr Gln Thr Ile Ile Pro Asn Ala
            180                 185                 190

Ala Lys Tyr Gly Ile Asn Asp Pro Leu Leu Pro Thr Val Val Lys Asp
        195                 200                 205

Leu Val Gly Glu Val Met Asn Ser Glu Glu Thr Leu Ile Met Ala Asp
210                 215                 220

Leu Trp Ser Gly Asn Ile Leu Leu Glu Phe Val Glu Gly Asn Pro Ser
225                 230                 235                 240

Glu Leu Lys Lys Ile Trp Leu Val Asp Trp Glu Leu Cys Lys Tyr Gly
                245                 250                 255

Pro Ala Ser Leu Asp Met Gly Tyr Phe Leu Gly Asp Cys Tyr Leu Ile
            260                 265                 270

Ala Arg Phe Gln Asp Glu Leu Val Gly Thr Thr Met Arg Lys Ala Tyr
        275                 280                 285

Leu Lys Gly Tyr Ala Arg Thr Ala Lys Gly Thr Ile Asn Tyr Ser Lys
290                 295                 300

Val Thr Ala Ser Ile Gly Ala His Leu Val Met Trp Thr Asp Phe Met
305                 310                 315                 320

Lys Trp Gly Asn Tyr Glu Glu Arg Glu Glu Phe Val Lys Lys Gly Val
                325                 330                 335

Glu Ala Leu His Asp Ala Trp Glu Asp Asn Asn Asp Gly Glu Ile Thr
            340                 345                 350

Ser Val Leu Val Asn Glu Ala Ser Ser Thr
        355                 360

<210> SEQ ID NO 43
<211> LENGTH: 362
<212> TYPE: PRT
<213> ORGANISM: Psilocybe cyanescens

<400> SEQUENCE: 43

Met Ala Phe Asp Leu Lys Thr Val Glu Gly Leu Ile Val Tyr Leu Thr
1               5                   10                  15

Lys Cys Leu Ser Leu Glu Val Asp Ser Ser Gly Val Lys Arg Leu Ser
            20                  25                  30

Gly Gly Phe Val Asn Val Thr Trp Arg Ile Arg Leu Asn Ala Pro Tyr
        35                  40                  45

Gln Gly His Thr Ser Ile Ile Leu Lys His Ala Gln Pro His Met Ser
    50                  55                  60

Thr Asp Lys Asp Phe Lys Ile Gly Val Glu Arg Ser Val Tyr Glu Tyr
65                  70                  75                  80

Gln Ala Leu Lys Val Ile Ser Ala Asn Arg Glu Ala Leu Gly Gly Ile
                85                  90                  95

Asp Ser Arg Val Ser Ala Pro Glu Gly Leu His Tyr Asp Val Glu Asn
            100                 105                 110

Asn Ala Leu Ile Met Gln Asp Val Gly Thr Leu Lys Thr Leu Met Asp
        115                 120                 125

Tyr Val Ile Glu Lys Pro Ala Ile Ser Thr Glu Met Ala Arg Leu Ile
    130                 135                 140

Gly Thr Glu Ile Gly Asp Phe Val Ala Arg Leu His Ser Ile Gly Arg
145                 150                 155                 160

Gln Lys Arg Asp Gln Pro Asp Phe Lys Phe Ser Gly Asn Ile Val
                165                 170                 175

Gly Arg Thr Thr Ala Asp Gln Leu Tyr Gln Thr Ile Leu Pro Asn Thr
            180                 185                 190

Ala Lys Tyr Gly Ile Asp Asp Pro Leu Leu Pro Thr Val Val Lys Asp
        195                 200                 205

Leu Val Asp Glu Ala Met Gln Ser Glu Glu Thr Leu Ile Met Ala Asp
    210                 215                 220

Leu Trp Thr Gly Asn Ile Leu Val Glu Phe Glu Gly Asn Leu Ser
225                 230                 235                 240

Val Leu Lys Lys Ile Trp Leu Val Asp Trp Glu Leu Cys Lys Tyr Gly
                245                 250                 255

Pro Val Arg Leu Asp Met Gly Tyr Phe Leu Gly Asp Cys Phe Leu Ile
            260                 265                 270

Ser Arg Phe Lys Asn Glu Gln Val Ala Lys Ala Met Arg Gln Ala Phe
        275                 280                 285

Leu Gln Arg Tyr Asn Arg Val Ser Asp Thr Pro Ile Asn Tyr Ser Val
    290                 295                 300

Ala Thr Thr Gly Ile Ala Ala His Ile Val Met Trp Thr Asp Phe Met
305                 310                 315                 320

Asn Trp Gly Thr Glu Glu Arg Lys Glu Tyr Val Lys Lys Gly Val
                325                 330                 335

Ala Gly Ile His Asp Gly Arg Asn His Asn Val Asp Gly Glu Ile Thr
            340                 345                 350

Ser Ile Leu Met Gln Glu Ala Ser Thr Ala
        355                 360

<210> SEQ ID NO 44
<211> LENGTH: 360
<212> TYPE: PRT
<213> ORGANISM: Gymnopilus dilepis

<400> SEQUENCE: 44

Met Thr Phe Asp Leu Lys Thr Glu Glu Gly Leu Leu Val Tyr Leu Thr
1               5                   10                  15

Gln His Leu Ser Leu Asp Val Asp Leu Asp Gly Leu Lys Arg Leu Ser
                20                  25                  30

Gly Gly Phe Val Asn Ile Thr Trp Arg Ile Arg Leu Asn Ala Pro Phe
            35                  40                  45

Lys Gly Tyr Thr Asn Ile Ile Leu Lys His Ala Gln Pro His Leu Ser
50                  55                  60

Ser Asp Glu Asn Phe Lys Ile Gly Val Glu Arg Ser Ala Tyr Glu Tyr
65                  70                  75                  80

Arg Ala Leu Lys Ile Val Ser Glu Ser Pro Ile Leu Ser Gly Asp Asp
                85                  90                  95

Asn Leu Val Phe Val Pro Gln Ser Leu His Tyr Asp Val Val His Asn
            100                 105                 110

Ala Leu Ile Val Gln Asp Val Gly Ser Leu Lys Thr Leu Met Asp Tyr
        115                 120                 125

Val Thr Ala Arg Pro Ser Leu Ser Ser Glu Met Ala Lys Leu Val Gly
    130                 135                 140

Gly Gln Ile Gly Ala Phe Ile Ala Arg Leu His Asn Ile Gly Arg Glu
145                 150                 155                 160

Asn Lys Asp His Pro Glu Phe Asn Phe Phe Ser Gly Asn Ile Val Gly
                165                 170                 175

Arg Thr Thr Ala Val Gln Leu Tyr Glu Thr Ile Val Pro Asn Ala Thr
            180                 185                 190

Lys Tyr Asp Ile Asp Asp Pro Ile Ile Pro Val Val Gln Glu Leu
        195                 200                 205

Ile Glu Glu Val Lys Gly Ser Asp Glu Thr Leu Ile Met Ala Asp Leu
    210                 215                 220

Trp Gly Gly Asn Ile Leu Leu Glu Phe Gly Lys Asp Ser Ser Asp Leu
225                 230                 235                 240

Gly Lys Ile Trp Val Val Asp Trp Glu Leu Cys Lys Tyr Gly Pro Pro
                245                 250                 255

Ser Leu Asp Met Gly Tyr Phe Leu Gly Asp Cys Phe Leu Leu Ala Gln
            260                 265                 270

Phe Gln Asp Glu Lys Val Ala Thr Ala Met Arg Arg Ala Tyr Leu Glu
        275                 280                 285

Asn Tyr Ala Lys Ile Ala Lys Val Pro Met Asp Tyr Asp Arg Ser Thr
    290                 295                 300

Thr Gly Ile Gly Ala His Leu Val Met Trp Thr Asp Phe Met Asn Trp
305                 310                 315                 320

Gly Ser Asp Glu Glu Arg Lys Thr Ser Val Glu Lys Gly Val Arg Ala
                325                 330                 335

Phe His Asp Ala Lys Arg Asp Asn Lys Glu Gly Glu Ile Pro Ser Ile
            340                 345                 350

Leu Leu Arg Glu Ser Ser Arg Thr
        355                 360

<210> SEQ ID NO 45
<211> LENGTH: 622
<212> TYPE: PRT
<213> ORGANISM: Saccharomyces cerevisiae

<400> SEQUENCE: 45

Met Leu Phe Tyr Ser Phe Val Trp Ser Val Leu Ala Ala Ser Val Ala

-continued

```
1               5                   10                  15
Leu Ala Lys Thr His Lys Leu Asn Tyr Thr Ala Ser Trp Val Thr Ala
                20                  25                  30
Asn Pro Asp Gly Leu His Glu Lys Arg Met Ile Gly Phe Asn Gly Glu
                35                  40                  45
Trp Pro Leu Pro Asp Ile His Val Glu Lys Gly Asp Arg Val Glu Leu
                50                  55                  60
Tyr Leu Thr Asn Gly Phe Gln Asp Asn Thr Ala Thr Ser Leu His Phe
65              70                  75                  80
His Gly Leu Phe Gln Asn Thr Ser Leu Gly Asn Gln Leu Gln Met Asp
                85                  90                  95
Gly Pro Ser Met Val Thr Gln Cys Pro Ile Val Pro Gly Gln Thr Tyr
                100                 105                 110
Leu Tyr Asn Phe Thr Val Pro Glu Gln Val Gly Thr Phe Trp Tyr His
                115                 120                 125
Ala His Met Gly Ala Gln Tyr Gly Asp Gly Met Arg Gly Ala Phe Ile
                130                 135                 140
Ile His Asp Pro Glu Glu Pro Phe Glu Tyr Asp His Glu Arg Val Ile
145             150                 155                 160
Thr Leu Ser Asp His Tyr His Glu Asn Tyr Lys Thr Val Thr Lys Glu
                165                 170                 175
Phe Leu Ser Arg Tyr Asn Pro Thr Gly Ala Glu Pro Ile Pro Gln Asn
                180                 185                 190
Ile Leu Phe Asn Asn Thr Met Asn Val Thr Leu Asp Phe Thr Pro Gly
                195                 200                 205
Glu Thr Tyr Leu Phe Arg Phe Leu Asn Val Gly Leu Phe Val Ser Gln
                210                 215                 220
Tyr Ile Ile Leu Glu Asp His Glu Met Ser Ile Val Glu Val Asp Gly
225             230                 235                 240
Val Tyr Val Lys Pro Asn Phe Thr Asp Ser Ile Tyr Leu Ser Ala Gly
                245                 250                 255
Gln Arg Met Ser Val Leu Ile Lys Ala Lys Asp Lys Met Pro Thr Arg
                260                 265                 270
Asn Tyr Ala Met Met Gln Ile Met Asp Glu Thr Met Leu Asp Val Val
                275                 280                 285
Pro Pro Glu Leu Gln Leu Asn Gln Thr Ile Gln Met Arg Tyr Gly His
                290                 295                 300
Ser Leu Pro Glu Ala Arg Ala Leu Asn Ile Glu Asp Cys Asp Leu Asp
305             310                 315                 320
Arg Ala Thr Asn Asp Phe Tyr Leu Glu Pro Leu Ile Glu Arg Asp Leu
                325                 330                 335
Leu Ala His Tyr Asp His Gln Ile Val Met Asp Val Arg Met Val Asn
                340                 345                 350
Leu Gly Asp Gly Val Lys Tyr Ala Phe Phe Asn Asn Ile Thr Tyr Val
                355                 360                 365
Thr Pro Lys Val Pro Thr Leu Thr Thr Leu Thr Ser Gly Lys Leu
                370                 375                 380
Ala Ser Asp Pro Arg Ile Tyr Gly Asp Asn Ile Asn Ala Gln Leu Leu
385             390                 395                 400
Lys His Asn Asp Ile Ile Glu Val Val Leu Asn Asn Tyr Asp Ser Gly
                405                 410                 415
Arg His Pro Phe His Leu His Gly His Asn Phe Gln Ile Val Gln Lys
                420                 425                 430
```

```
Ser Pro Gly Phe His Val Asp Glu Ala Tyr Asp Ser Glu Gln Asp
        435                 440                 445

Glu Met Thr Val Pro Tyr Asn Glu Ser Ala Pro Leu Gln Pro Phe Pro
450                 455                 460

Glu Arg Pro Met Val Arg Asp Thr Val Val Leu Glu Pro Ser Gly His
465                 470                 475                 480

Val Val Leu Arg Phe Arg Ala Asp Asn Pro Gly Val Trp Tyr Phe His
            485                 490                 495

Cys His Val Asp Trp His Leu Gln Gln Gly Leu Ala Ser Val Phe Ile
            500                 505                 510

Glu Ala Pro Val Leu Leu Gln Glu Arg Glu Lys Leu Asn Glu Asn Tyr
            515                 520                 525

Leu Asp Ile Cys Lys Ala Ala Asp Ile Pro Val Val Gly Asn Ala Ala
            530                 535                 540

Gly His Ser Asn Asp Trp Phe Asp Leu Lys Gly Leu Pro Arg Gln Pro
545                 550                 555                 560

Glu Pro Leu Pro Lys Gly Phe Thr Thr Glu Gly Tyr Leu Ala Leu Ile
                565                 570                 575

Ile Ser Thr Ile Ile Gly Val Trp Gly Leu Tyr Ser Ile Ala Gln Tyr
            580                 585                 590

Gly Ile Gly Glu Val Ile Pro Asn Asp Glu Lys Val Tyr His Thr Leu
            595                 600                 605

Arg Glu Ile Leu Ala Glu Asn Glu Ile Glu Val Ser Arg Gly
        610                 615                 620

<210> SEQ ID NO 46
<211> LENGTH: 207
<212> TYPE: PRT
<213> ORGANISM: Bos taurus

<400> SEQUENCE: 46

Met Ser Thr Pro Ser Ile His Cys Leu Lys Pro Ser Pro Leu His Leu
1               5                   10                  15

Pro Ser Gly Ile Pro Gly Ser Pro Gly Arg Gln Arg Arg His Thr Leu
            20                  25                  30

Pro Ala Asn Glu Phe Arg Cys Leu Thr Pro Lys Asp Ala Ala Gly Val
        35                  40                  45

Phe Glu Ile Glu Arg Glu Ala Phe Ile Ser Val Ser Gly Asn Cys Pro
50                  55                  60

Leu Asn Leu Asp Glu Val Arg His Phe Leu Thr Leu Cys Pro Glu Leu
65                  70                  75                  80

Ser Leu Gly Trp Phe Val Glu Gly Arg Leu Val Ala Phe Ile Ile Gly
                85                  90                  95

Ser Leu Trp Asp Glu Glu Arg Leu Thr Gln Glu Ser Leu Thr Leu His
            100                 105                 110

Arg Pro Gly Gly Arg Thr Ala His Leu His Ala Leu Ala Val His His
        115                 120                 125

Ser Phe Arg Gln Gln Gly Lys Gly Ser Val Leu Leu Trp Arg Tyr Leu
130                 135                 140

Gln His Ala Gly Gly Gln Pro Ala Val Arg Arg Ala Val Leu Met Cys
145                 150                 155                 160

Glu Asp Ala Leu Val Pro Phe Tyr Gln Arg Phe Gly Phe His Pro Ala
                165                 170                 175

Gly Pro Cys Ala Val Val Val Gly Ser Leu Thr Phe Thr Glu Met His
```

```
                180               185                 190
Cys Ser Leu Arg Gly His Ala Ala Leu Arg Arg Asn Ser Asp Arg
        195                 200                 205

<210> SEQ ID NO 47
<211> LENGTH: 499
<212> TYPE: PRT
<213> ORGANISM: Schistosoma mansoni

<400> SEQUENCE: 47

Met Ile Ser Thr Glu Ser Asp Leu Arg Arg Gln Leu Asp Glu Asn Val
1               5                   10                  15

Arg Ser Glu Ala Asp Glu Ser Thr Lys Glu Glu Cys Pro Tyr Ile Asn
            20                  25                  30

Ala Val Gln Ser His His Gln Asn Val Gln Glu Met Ser Ile Ile Ile
        35                  40                  45

Ser Leu Val Lys Asn Met Asn Asp Met Lys Ser Ile Ile Ser Ile Phe
    50                  55                  60

Thr Asp Arg Asn Ile Asn Ile Leu His Ile Glu Ser Arg Leu Gly Arg
65                  70                  75                  80

Leu Asn Met Lys Lys His Thr Glu Lys Ser Glu Phe Glu Pro Leu Glu
                85                  90                  95

Leu Leu Val His Val Glu Val Pro Cys Ile Glu Val Glu Arg Leu Leu
            100                 105                 110

Glu Glu Leu Lys Ser Phe Ser Ser Tyr Arg Ile Val Gln Asn Pro Leu
        115                 120                 125

Met Asn Leu Pro Glu Ala Lys Asn Pro Thr Leu Asp Asp Lys Val Pro
    130                 135                 140

Trp Phe Pro Arg His Ile Ser Asp Leu Asp Lys Val Ser Asn Ser Val
145                 150                 155                 160

Leu Met Tyr Gly Lys Glu Leu Asp Ala Asp His Pro Gly Phe Lys Asp
                165                 170                 175

Lys Glu Tyr Arg Lys Arg Arg Met Met Phe Ala Asp Ile Ala Leu Asn
            180                 185                 190

Tyr Lys Trp Gly Gln Gln Ile Pro Ile Val Glu Tyr Thr Glu Ile Glu
        195                 200                 205

Lys Thr Thr Trp Gly Arg Ile Tyr Arg Glu Leu Thr Arg Leu Tyr Lys
    210                 215                 220

Thr Ser Ala Cys His Glu Phe Gln Lys Asn Leu Gly Leu Leu Gln Asp
225                 230                 235                 240

Lys Ala Gly Tyr Asn Glu Phe Asp Leu Pro Gln Leu Gln Val Val Ser
                245                 250                 255

Asp Phe Leu Lys Ala Arg Thr Gly Phe Cys Leu Arg Pro Val Ala Gly
            260                 265                 270

Tyr Leu Ser Ala Arg Asp Phe Leu Ser Gly Leu Ala Phe Arg Val Phe
        275                 280                 285

Tyr Cys Thr Gln Tyr Ile Arg His Gln Ala Asp Pro Phe Tyr Thr Pro
    290                 295                 300

Glu Pro Asp Cys Cys His Glu Leu Leu Gly His Val Pro Met Leu Ala
305                 310                 315                 320

Asp Pro Lys Phe Ala Arg Phe Ser Gln Glu Ile Gly Leu Ala Ser Leu
                325                 330                 335

Gly Thr Ser Asp Glu Glu Ile Lys Lys Leu Ala Thr Cys Tyr Phe Phe
            340                 345                 350
```

```
Thr Ile Glu Phe Gly Leu Cys Arg Gln Asp Asn Gln Leu Lys Ala Tyr
            355                 360                 365

Gly Ala Gly Leu Leu Ser Ser Val Ala Glu Leu Gln His Ala Leu Ser
        370                 375                 380

Asp Lys Ala Val Ile Lys Pro Phe Ile Pro Met Lys Val Ile Asn Glu
385                 390                 395                 400

Glu Cys Leu Val Thr Thr Phe Gln Asn Gly Tyr Phe Glu Thr Ser Ser
                405                 410                 415

Phe Glu Asp Ala Thr Arg Gln Met Arg Glu Phe Val Arg Thr Ile Lys
            420                 425                 430

Arg Pro Phe Asp Val His Tyr Asn Pro Tyr Thr Gln Ser Ile Glu Ile
        435                 440                 445

Ile Lys Thr Pro Lys Ser Val Ala Lys Leu Val Gln Asp Leu Gln Phe
450                 455                 460

Glu Leu Thr Ala Ile Asn Glu Ser Leu Leu Lys Met Asn Lys Glu Ile
465                 470                 475                 480

Arg Ser Gln Gln Phe Thr Thr Asn Lys Ile Val Thr Glu Asn Arg Ser
                485                 490                 495

Ser Gly Ser

<210> SEQ ID NO 48
<211> LENGTH: 345
<212> TYPE: PRT
<213> ORGANISM: Homo sapiens

<400> SEQUENCE: 48

Met Gly Ser Ser Glu Asp Gln Ala Tyr Arg Leu Leu Asn Asp Tyr Ala
1               5                   10                  15

Asn Gly Phe Met Val Ser Gln Val Leu Phe Ala Ala Cys Glu Leu Gly
            20                  25                  30

Val Phe Asp Leu Leu Ala Glu Ala Pro Gly Pro Leu Asp Val Ala Ala
        35                  40                  45

Val Ala Ala Gly Val Arg Ala Ser Ala His Gly Thr Glu Leu Leu Leu
    50                  55                  60

Asp Ile Cys Val Ser Leu Lys Leu Leu Lys Val Glu Thr Arg Gly Gly
65                  70                  75                  80

Lys Ala Phe Tyr Arg Asn Thr Glu Leu Ser Ser Asp Tyr Leu Thr Thr
                85                  90                  95

Val Ser Pro Thr Ser Gln Cys Ser Met Leu Lys Tyr Met Gly Arg Thr
            100                 105                 110

Ser Tyr Arg Cys Trp Gly His Leu Ala Asp Ala Val Arg Glu Gly Arg
        115                 120                 125

Asn Gln Tyr Leu Glu Thr Phe Gly Val Pro Ala Glu Glu Leu Phe Thr
    130                 135                 140

Ala Ile Tyr Arg Ser Glu Gly Glu Arg Leu Gln Phe Met Gln Ala Leu
145                 150                 155                 160

Gln Glu Val Trp Ser Val Asn Gly Arg Ser Val Leu Thr Ala Phe Asp
                165                 170                 175

Leu Ser Val Phe Pro Leu Met Cys Asp Leu Gly Gly Gly Ala Gly Ala
            180                 185                 190

Leu Ala Lys Glu Cys Met Ser Leu Tyr Pro Gly Cys Lys Ile Thr Val
        195                 200                 205

Phe Asp Ile Pro Glu Val Val Trp Thr Ala Lys Gln His Phe Ser Phe
    210                 215                 220
```

```
Gln Glu Glu Gln Ile Asp Phe Gln Gly Asp Phe Phe Lys Asp
225                 230                 235                 240

Pro Leu Pro Glu Ala Asp Leu Tyr Ile Leu Ala Arg Val Leu His Asp
                245                 250                 255

Trp Ala Asp Gly Lys Cys Ser His Leu Leu Glu Arg Ile Tyr His Thr
                260                 265                 270

Cys Lys Pro Gly Gly Gly Ile Leu Val Ile Glu Ser Leu Leu Asp Glu
                275                 280                 285

Asp Arg Arg Gly Pro Leu Leu Thr Gln Leu Tyr Ser Leu Asn Met Leu
        290                 295                 300

Val Gln Thr Glu Gly Gln Glu Arg Thr Pro Thr His Tyr His Met Leu
305                 310                 315                 320

Leu Ser Ser Ala Gly Phe Arg Asp Phe Gln Phe Lys Lys Thr Gly Ala
                325                 330                 335

Ile Tyr Asp Ala Ile Leu Ala Arg Lys
        340                 345

<210> SEQ ID NO 49
<211> LENGTH: 356
<212> TYPE: PRT
<213> ORGANISM: Tabernanthe iboga

<400> SEQUENCE: 49

Asp Ala Met Lys Ser Ala Glu Leu Phe Lys Ala Gln Ala His Ile Phe
1               5                   10                  15

Lys Gln Val Phe Cys Phe Thr Asn Gly Ala Ser Leu Lys Cys Ala Val
                20                  25                  30

Gln Leu Gly Ile Pro Asp Ala Ile Asp Asn His Gly Lys Ala Met Thr
            35                  40                  45

Leu Ser Glu Leu Thr Asp Ala Leu Pro Ile Asn Pro Ser Lys Ala Pro
    50                  55                  60

His Ile His Arg Leu Met Arg Ile Leu Val Thr Ala Gly Phe Phe Val
65                  70                  75                  80

Glu Glu Arg Leu Gly Asn Gly Lys Glu Lys Ala Asn Gly Tyr Ala
                85                  90                  95

Leu Thr Pro Ser Ser Arg Leu Leu Leu Lys Asn Lys Pro Leu Ser Leu
                100                 105                 110

Arg Ala Ser Ala Leu Thr Met Leu Asp Pro Val Thr Val Lys Thr Trp
            115                 120                 125

Asn Ala Leu Ser Glu Trp Phe Gln Asn Glu Asp Gln Thr Ala Phe Glu
    130                 135                 140

Thr Ala His Gly Lys Asn Met Trp Asp Phe Phe Ala Glu Asp Pro Gly
145                 150                 155                 160

Leu Ser Lys Lys Phe Asn Glu Ser Met Ala Ser Asp Ser Gln Leu Val
                165                 170                 175

Thr Glu Val Leu Val Thr Lys Cys Lys Phe Val Phe Glu Gly Leu Thr
            180                 185                 190

Ser Met Val Asp Val Gly Gly Gly Thr Gly Thr Val Ala Gly Ala Ile
    195                 200                 205

Ala Lys Thr Phe Pro Ser Leu Arg Cys Thr Val Phe Asp Leu Pro His
210                 215                 220

Val Val Ala Asn Leu Glu Pro Thr Glu Asn Leu Asp Phe Val Ala Gly
225                 230                 235                 240

Asp Met Phe Gly Lys Ile Pro Pro Ala Asn Ala Ile Phe Leu Lys Trp
                245                 250                 255
```

```
Val Leu His Asp Trp Asn Asp Glu Asp Cys Val Lys Ile Leu Lys Asn
            260             265                 270
Cys Lys Arg Ala Ile Pro Gly Lys Glu Lys Gly Gly Lys Val Ile Ile
        275             280             285
Val Asp Ile Ile Met Glu Thr Glu Lys His Asp Ile Asp Glu Phe Asp
    290             295             300
Tyr Ala Lys Met Cys Met Asp Met Glu Met Leu Val Leu Cys Asn Ser
305             310             315                 320
Lys Glu Arg Thr Glu Lys Glu Leu Ala Met Leu Val Ser Glu Ala Gly
            325             330             335
Phe Ser Gly Tyr Lys Ile Phe Pro Val Leu Gly Ile Arg Ser Leu Ile
            340             345             350
Glu Val Tyr Pro
            355
```

PROCESSES FOR THE PRODUCTION OF TRYPTAMINES

CROSS-REFERENCE

This application is a continuation application of U.S. patent application Ser. No. 17/012,737, filed Sep. 4, 2020, which is a continuation application of International Patent Application No. PCT/US2019/021489, filed Mar. 8, 2019, which claims the benefit of U.S. Provisional Patent Application No. 62/640,443, filed Mar. 8, 2018, which applications are each incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 4, 2021, is named 54033-701_302_SL.txt and is 201,197 bytes in size.

BACKGROUND

Tryptamine is a monoamine alkaloid. It contains an indole ring structure, and is structurally similar to the amino acid tryptophan, from which the name derives. Tryptamine is found in trace amounts in the brains of mammals and is hypothesized to play a role as a neuromodulator or a neurotransmitter. Tryptamine is the common functional group in a set of compounds, termed collectively, substituted tryptamines. This set includes many biologically active compounds, including neurotransmitters and psychotropic drugs.

SUMMARY

In one aspect, a microbial cell that produces a tryptamine is provided, the microbial cell containing therein one or more heterologous nucleic acid sequences encoding one or more enzymes involved in a biosynthesis pathway that converts an anthranilate to a tryptamine.

In another aspect, a microbial cell that produces a tryptamine is provided, the microbial cell containing therein one or more heterologous nucleic acid sequences encoding one or more enzymes involved in a biosynthesis pathway that converts an indole to a tryptamine.

In another aspect, a microbial cell that produces a tryptamine is provided, the microbial cell containing therein one or more heterologous nucleic acid sequences encoding one or more enzymes involved in a biosynthesis pathway that converts tryptophan to a tryptamine.

In some cases, the anthranilate is a substituted anthranilate. In some cases, the anthranilate is:

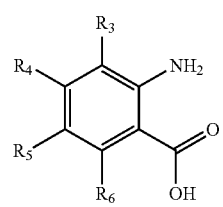

where:
each R is independently a hydrogen, a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the indole is a substituted indole. In some cases, the indole is:

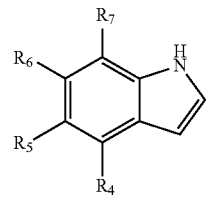

where:
each R is independently a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the tryptamine is a substituted tryptamine. In some cases, the tryptamine is:

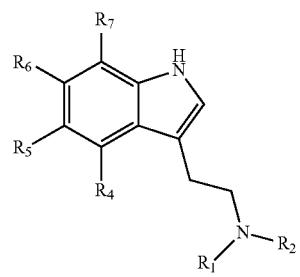

where:
each R is independently a hydrogen, a halogen, —OH, $C_1$-$C_5$ alkyl, $C_1$-$C_5$ alkoxy, $NO_2$, NH, COOH, CN, sulfur, $SO_3$, $SO_4$, or $PO_4$.

In some cases, the one or more enzymes comprise one or more of: trpD, trpB, trpC, and trpA. In some cases, the one or more heterologous nucleic acid sequences comprises a multicistronic operon encoding at least two of trpD, trpB, trpC, and trpA. In some cases, the multicistronic operon has a nucleic acid sequence having at least 80% sequence identity to any one of SEQ ID NOs: 1-4. In some cases, the trpD comprises an amino acid sequence having at least 80% sequence identity to any one of SEQ ID NOs: 5-7. In some cases, the trpC comprises an amino acid sequence having at least 80% sequence identity to any one of SEQ ID NOs: 8 and 9. In some cases, the trpB comprises an amino acid sequence having at least 80% sequence identity to any one of SEQ ID NOs: 10 and 11. In some cases, the trpA comprises an amino acid sequence having at least 80% sequence identity to any one of SEQ ID NOs: 12 and 13. In some cases, the one or more enzymes comprise a decarboxylase. In some cases, the decarboxylase is a tryptophan decarboxylase. In some cases, the tryptophan decarboxylase comprises an amino acid sequence having at least 50%, at least 60%, at least 70%, at least 80%, at least 90%, or at least 95% sequence identity to any one of SEQ ID NOs: 14-20. In some cases, the one or more enzymes comprise a transferase. In some cases, the transferase is selected from the group consisting of: tryptamine N-methyltransferase, tryptamine benzoyl transferase, serotonin N-acetyltransferase, dopamine N-acetyltransferase, arylalkylamine N-acetyltransferase, and tryptamine hydroxycinnamoyltransferase. In some cases, the transferase comprises an amino acid sequence having at least 50% sequence identity to any one of SEQ ID NOs: 21-31 or 46. In some cases, the one or more enzymes comprise tryptamine 4-hydroxylase. In some cases, the tryptamine 4-hydroxylase comprises an amino acid sequence having at least 50%, at least 60%, at least 70%, at least 80%, at least 90%, or at least 95% sequence identity to any one of SEQ ID NOs: 32-35. In some cases, the one or more enzymes comprises a P450 reductase. In some cases, the P450 reductase comprises an amino acid sequence having at least 50%, at least 60%, at least 70%, at least 80, at least 90%, or at least 95% sequence identity to any one of SEQ ID NOs: 36-40. In some cases, the one or more enzymes comprises a kinase. In some cases, the kinase comprises an amino acid sequence having at least 50%, at least 60%, at least 70%, at least 80%, at least 90%, or at least 95% sequence identity to any one of SEQ ID NOs: 41-44. In some cases, the anthranilate is biosynthetically produced by the microbial cell. In some cases, the anthranilate is fed to the engineered microbial cell. In some cases, the anthranilate is 5-bromoanthranilate, 6-hydroxyanthranilate, 5-hydroxyanthranilate, 6-chloroanthranilate, or 5-chloroanthranilate. In some cases, the indole is biosynthetically produced by the microbial cell. In some cases, the indole is fed to the engineered microbial cell. In some cases, the indole is selected from the group consisting of: 5-hydroxyindole, 4-hydroxyindole, 7-hydroxyindole, and 4-chloroindole, 5-bromoindole, or 4-fluoroindole. In some cases, the microbial cell secretes the tryptamine in culture broth. In some cases, the tryptamine is selected from any tryptamine described in FIG. 4, FIG. 6, or FIG. 8. In some cases, the tryptamine is selected from the group consisting of: tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, 4-hydroxy-N-acetyl-tryptamine. In some cases, the microbial cell is a eukaryotic cell. In some cases, the microbial cell is a yeast cell. In some cases, the yeast cell is of the species *Saccharomyces cerevisiae*. In some cases, the yeast cell does not express one or more of aromatic aminotransferase I (aro8) and phenylpyruvate decarboxylase (aro10). In some cases, the yeast cell overexpresses one or more of phosphoribosylanthranilate isomerase (TRP1), anthranilate synthase (TRP2), indole-3-glycerolphosphate synthase (TRP3), anthranilate phosphoribosyl transferase (TRP4), and tryptophan synthase (TRP5). In some cases, the yeast cell overexpresses a mutant of one or more of phosphoribosylanthranilate isomerase (TRP1), anthranilate synthase (TRP2), indole-3-glycerolphosphate synthase (TRP3), anthranilate phosphoribosyl transferase (TRP4), and tryptophan synthase (TRP5). In some cases, the yeast cell has two or more copies of the one or more heterologous nucleic acid sequences and they act synergistically. In some cases, the microbial cell is a prokaryote. In some cases, the microbial cell is a bacterial cell. In some cases, the bacterial cell is of the species *Escherichia coli* or *Corynebacterium glutamicum*. In some cases, the bacterial cell does not express one or more of tryptophanase (tna), tryptophan repressor element (trpR), or anthranilate synthase (trpE) genes. In some cases, at least one copy of the one or more heterologous nucleic acid sequences is stably integrated into the genome of the microbial cell. In some cases, two or more copies of the one or more heterologous nucleic acid sequences are stably integrated into the genome of the microbial cell. In some cases, the two or more copies of the one or more heterologous nucleic acid sequences are from a same sequence. In some cases, the two or more copies of the one or more heterologous nucleic acid sequences are from a distinct sequence.

In another aspect, a method for synthesizing a tryptamine is provided, the method comprising: culturing a microbial cell according to any of the preceding in a presence of anthranilate, thereby synthesizing the tryptamine. In some cases, the method further comprises feeding the anthranilate to the microbial cell. In some cases, the anthranilate is produced biosynthetically by the microbial cell. In some cases, the anthranilate is a substituted anthranilate.

In another aspect, a method for synthesizing a tryptamine is provided, the method comprising: culturing a microbial cell according to any of the preceding in a presence of indole, thereby synthesizing the tryptamine. In some cases, the method further comprises feeding the indole to the microbial cell. In some cases, the indole is produced biosynthetically by the microbial cell. In some cases, the indole is a substituted indole.

In another aspect, a method for synthesizing a tryptamine is provided, the method comprising: culturing a microbial cell of any of the preceding in a presence of tryptophan, thereby synthesizing the tryptamine. In some cases, the method further comprises feeding the tryptophan to the microbial cell. In some cases, the tryptophan is produced biosynthetically by the microbial cell.

In some cases, any method of the preceding further comprises purifying the tryptamine from the culture.

In another aspect, a microbial cell is provided containing therein one or more heterologous nucleic acid sequences encoding one or more enzymes involved in a biosynthesis pathway to convert a tryptamine to a tryptamine derivative. In some cases, the one or more enzymes comprise a tryptamine 4-hydroxylase. In some cases, tryptamine 4-hydroxylase comprises an amino acid sequence having at least 50%, at least 60%, at least 70%, at least 80%, at least 90%, or at least 95% sequence identity to any one of SEQ ID NOs:32-35. In some cases, the one or more enzymes comprise a tryptamine 5-hydroxylase. In some cases, the tryptamine 5-hydroxylase comprises an amino acid sequence having at least 50%, at least 60%, at least 70%, at least 80%, at least 90%, or at least 95% sequence identity to SEQ ID NO:47. In some cases, the one or more enzymes comprise a 4-hydroxytryptamine kinase. In some cases, the 4-hydroxytryptamine kinase comprises has an amino acid sequence having at least 50%, at least 60%, at least 70%, at least 80%, at least 90%, or at least 95% sequence identity according to any one of SEQ ID NOs:41-44. In some cases, the tryptamine is a substituted tryptamine. In some cases, the tryptamine is selected from the group consisting of: 5-methoxy-N,N-dimethyl-tryptamine, N,N-diisopropyl-tryptamine, N-methyl-N-isopropyltryptamine, N,N-dimethyltryptamine, N,N-tetramethylenetryptamine, N,N-dipropyltryptamine, 4-hydroxy-N,N-dimethyltryptamine, tryptamine, 4-hydroxytryptamine, 5-hydroxytryptamine, ibogamine, 4-hydroxyibogamine, and 5-hydroxyibogamine. In some cases, the tryptamine derivative is any tryptamine derivative described in FIG. 16. In some cases, the tryptamine derivative is selected from the group consisting of: 5-hydroxy-N,N-diisopropyl-tryptamine, 5-hydroxy-N-methyl-N-isopropyltryptamine, 5-hydroxy-N,N-dimethyltryptamine, 5-hydroxy-N,N-tetramethylenetryptamine, 5-hydroxy-N,N-dipropyltryptamine, 4,5-methoxy-N,N-dimethyl-tryptamine, 4-hydroxy-N,N-diisopropyl-tryptamine, 4-hydroxy-N-methyl-N-isopropyltryptamine, 4-hydroxy-N,N-dimethyltryptamine, 4-hydroxy-N,N-tetramethylenetryptamine, 4-hydroxy-N,N-dipropyltryptamine, 4-phosphoryloxy-N,N-dipropyltryptamine, 4-hydroxytryptamine, 5-hydroxytryptamine, 4-methoxytryptamine, 5-methoxytryptamine, 4-phosphoryloxytryptamine, 5-phosphoryloxytryptamine, 4-hydroxyibogamine, 5-hydroxyibogamine, 4-phosphoryloxyibogamine, and 5-phosphoryloxyibogamine.

In another aspect, a method of synthesizing a tryptamine derivate from a tryptamine is provided, the method comprising: culturing a microbial cell according to any of the preceding in a presence of a tryptamine, thereby synthesizing the tryptamine derivative. In some cases, the method further comprises purifying the tryptamine derivative from the culture.

In yet another aspect, a vector is provided comprising one or more heterologous nucleic acid sequences encoding one or more enzymes comprising an amino acid sequence having at least 50%, at least 60%, at least 70%, at least 80%, at least 90%, or at least 95% sequence identity to any one of SEQ ID NOs: 5-49.

In yet another aspect, a microbial cell is provided containing therein one or more heterologous nucleic acid sequences encoding an enzyme from a tryptamine synthesis pathway or a functional fragment thereof comprising an amino acid sequence having at least 50%, at least 60%, at least 70%, at least 80%, at least 90%, or at least 95% sequence identity to any one of SEQ ID NOs: 5-49.

In another aspect, a method is provided for screening for the levels of 4-hydroxytryptamine within any microbial cell of the preceding, the method comprising: detecting a color or a fluorescence product of the 4-hydroxytryptamine within the microbial cell. In some cases, the 4-hydroxytryptamine is oxidized within the microbial cell, thereby producing an oxidized 4-hydroxytryptamine. In some cases, the oxidized 4-hydroxytryptamine is directly proportional to a level of 4-hydroxytryptamine synthesized within the microbial cell. In some cases, an oxidation of the oxidized 4-hydroxytryptamine is catalyzed by iron sulphate. In some cases, an oxidation of the oxidized 4-hydroxytryptamine is catalyzed by an enzyme expressed by the microbial cell. In some cases, the enzyme comprises an amino acid sequence having at least 50%, at least 60%, at least 70%, at least 80%, at least 90%, or at least 95% sequence identity to SEQ ID NO: 45.

In another aspect, a method of converting an anthranilate to a tryptamine is provided, the method comprising incubating the anthranilate in a presence of one or more enzymes involved in a biosynthesis pathway that converts an anthranilate to a tryptamine.

In yet another aspect, a method of converting an indole to a tryptamine is provided, the method comprising incubating the indole in a presence of one or more enzymes involved in a biosynthesis pathway that converts an indole to a tryptamine.

In yet another aspect, a method of converting tryptophan to a tryptamine is provided, the method comprising incubating the tryptophan in a presence of one or more enzymes involved in a biosynthesis pathway that converts tryptophan to a tryptamine.

In yet another aspect, a method of converting a tryptamine to a derivatized tryptamine is provided, the method comprising incubating the tryptamine in a presence of one or more enzymes involved in a biosynthetic pathway that converts tryptamine to a derivatized tryptamine.

In some cases, a method of the preceding is performed in the absence of a biological cell. In some cases, a method of the preceding is performed under in vitro conditions. In some cases, a method of the preceding is performed under cell-free conditions. In some cases, a method of the preceding is performed in a cell lysate.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Some novel features of the invention are set forth in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
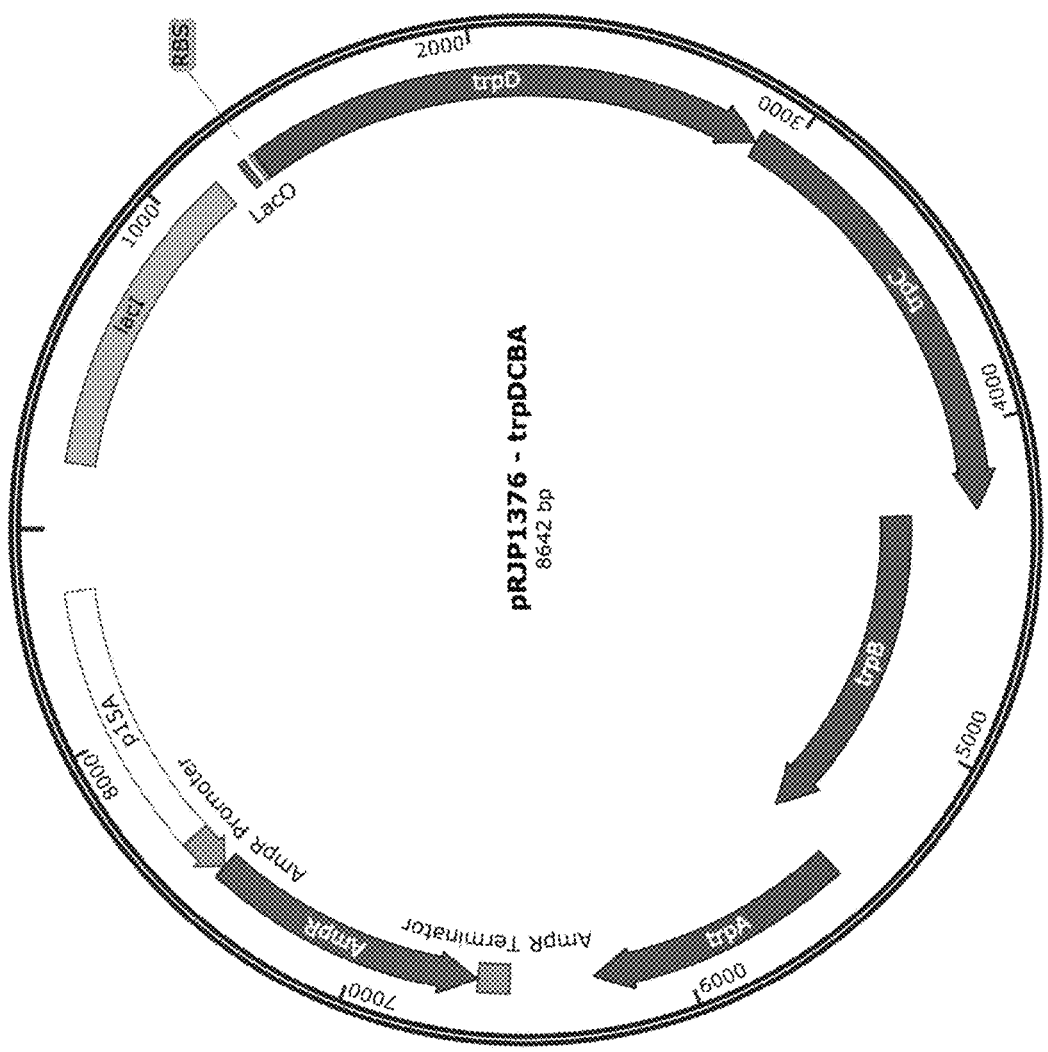
FIG. 1 depicts a non-limiting example of a plasmid map suitable for overexpression of the bacterial tryptophan operon in bacteria in accordance with embodiments of the disclosure. Plasmid is medium copy (p15a) and contains ampicillin resistance. TrpD, trpC, trpB and trpA are expressed in a multicistronic operon (e.g., SEQ ID NO: 1).

The present disclosure relates to microorganisms containing heterologous DNA useful in the production of tryptamines with 4-, 5-, 6-, or 7-indole substitutions, and/or R1 or R2 amine substitutions. Furthermore, this disclosure relates to processes for optimizing production, executing production, and recovering such substituted tryptamines. The disclosure provided herein provides processes for the production of various compounds, such as tryptamines. The disclosure further provides prokaryotic and eukaryotic microbes, including bacteria (e.g., *Escherichia coli*) and yeast (e.g., *Saccharomyces cerevisiae*), that may be genetically altered to contain heterologous sequences that encode biological molecules that can provide a biosynthetic pathway for the synthesis of tryptamine and/or substituted tryptamines in vivo. In some aspects, the disclosure provides microbes that may be engineered to contain plasmids and stable gene integrations containing sufficient genetic information for conversion of anthranilate or substituted anthranilates, and/or indole or substituted indoles, to a respective tryptamine or substituted tryptamine. The fermentative production of substituted tryptamines in a whole-cell biocatalyst may be useful for cost effective production of these compounds for therapeutic use.

Tryptamines are naturally occurring monoamine alkaloids derived from tryptophan, from which the name is derived. Analogs within the tryptamine family contain substitutions at the indole ring structure and the amine group. This family of compounds contains psychotropically active members, including N,—N-dimethyltryptophan (DMT), 5-methoxy-N,N-dimethyltryptamine (5-MeO-DMT), 4-hydroxy dimethyl-tryptophan (psilocin) and its 4-O-phosphate ester, psilocybin (Hofmann et al. 1959). Psilocin may act as a partial agonist on 5HT1a, 5HT2a, and 5HT2c receptors (Hasler et al. 2004). Several basidiomycete fungi of the genus Psilocybe and other genera produce substituted tryptamines biosynthetically, including psilocybin, psilocin, norpsilocin, baeocystin, norbaeocystin and aeruginascin (Lenz, Wick, and Hoffmeister 2017). The compound N,N-dimethyltryptamine is ubiquitous in nature and is produced by many plants and animals (Carbonaro and Gatch 2016). Substituted tryptamines can also be synthetically derived, including the tryptans (e.g., Zolmitriptan and Sumatriptan), which are chemically synthesized and used as medications used to treat migraines and cluster headaches (Derry, Derry, and Moore 2014).

Tryptamines, such as psilocin, can cause profound changes in perception and mood in human subjects. Administration of high-dose psilocybin has been found to reliably induce mystical experiences leading to significant and enduring improvements in quality of life (Griffiths et al. 2006). Psilocybin administration has been concluded to be safe and well tolerated on 9 patients with severe, refractory obsessive-compulsive disorder and may be associated with "robust acute reductions" in core symptoms (Moreno et al. 2006).

Due to their complex structure, tryptamines and their respective substituted analogs are difficult to obtain commercially at economically feasible prices, if at all in large scale. Several organic chemistry methods exist for production of substituted tryptamines, including psilocybin. Dr. Albert Hoffmann originally published on the organics synthesis of psilocybin in 1958 (Hofmann et al. 1958). However, a dangerous reagent was used to phosphorylate the phosphate at the −4 position of the indole ring and later improvements were made for the synthesis (Hofmann, A. & Troxler, F. 1963. Esters of Indoles (U.S. Pat. No. 3,075,992), Basel, Switzerland: Sandoz Ltd.). This production method was adopted by Dr. David E Nichols for early clinical trials, but at a high cost for production (Nichols 2014).

Extraction of tryptamines from basidiomycete fungal tissue naturally producing the compounds is not suitable for large scale up production. The reported concentrations of psilocybin in mushrooms Psilocybe cubensis are less than 1% of the dry cell weight (J. Gartz 1994), causing a challenge for extraction and purification. Furthermore, the cultivation of such fungal tissue requires month-long time scales and would cause supply challenges (Jochen Gartz, Allen, and Merlin 1994). Furthermore, use of natural tissue precludes the ability to produce novel and unnatural tryptamine compounds with therapeutic properties.

The instant disclosure provides methods and materials to produce substituted tryptamines in high yield from inexpensive media components. The methods of the disclosure provide for production of tryptamine derivatives not naturally found in nature or tryptamine derivatives that are not accessible by synthetic chemistry. In some instances, the disclosed tryptamine derivatives may have favorable pharmacological effects (e.g., half-life, indications, etc). Additional advantages of the methods described herein include the use of a single biocatalyst for production of several substituted tryptamine analogues and a whole cell catalyst that is robust in fermentation and can regenerate itself for ease of use during production runs.

Accordingly, the objective of the present invention is to provide novel processes for the biosynthetic production of 4-, 5-, 6- or 7-indole substituted and/or R1 or R2 amine substituted tryptamines.

In some cases of the present disclosure, 4-, 5-, 6- or 7-indole substituted and/or R1 or R2 amine substituted tryptamines may be biosynthetically produced from corresponding substituted anthranilates and indoles by engineered microbial cells. Substituted anthranilates and indoles are widely available, vast in variety, and inexpensive compared to their respective substituted tryptamines.

In other aspects of the disclosure, a method of converting an anthranilate to a tryptamine is provided, the method comprising incubating the anthranilate in the presence of one or more enzymes involved in a biosynthesis pathway that converts an anthranilate to a tryptamine. In other aspects of the disclosure, a method of converting an indole to a tryptamine is provided, the method comprising incubating the indole in the presence of one or more enzymes involved in a biosynthesis pathway that converts an indole to a tryptamine. In other aspects of the disclosure, a method of converting tryptophan to a tryptamine is provided, the method comprising incubating the tryptophan in the presence of one or more enzymes involved in a biosynthesis pathway that converts tryptophan to a tryptamine. In other aspects of the disclosure, a method of converting a tryptamine to a derivatized tryptamine is provided, the method comprising incubating the tryptamine in the presence of one or more enzymes involved in a biosynthetic pathway that converts tryptamine to a derivatized tryptamine. In some cases, the methods may be performed within a biological cell (e.g., by an engineered microbial cell as described herein). In other cases, the methods may be performed in the absence of a biological cell. In some cases, the methods may be performed under in vitro conditions. In some cases, the methods may be performed under cell-free conditions. In some cases, the methods may be performed in a cell lysate.

Synthesis of a Substituted Tryptamine from a Substituted Anthranilate in Engineered Microbial Cells.

In an aspect of the disclosure, the processes described herein provide for the production of 4-, 5-, 6- or 7-indole substituted tryptamines with R1 or R2 substitutions at the amine. In some cases, anthranilate or an anthranilate substituted at 3-, 4-, 5-, or 6- can be used to make 4-, 5-, 6- or 7-indole substituted tryptamines with R1 or R2 substitutions. In some cases, the process may be carried out in a whole-cell microbial fermentation. In some cases, an engineered microbial cell may be cultured in the presence of anthranilate or a substituted anthranilate (e.g., anthranilate or substituted anthranilate may be fed to or otherwise incubated with the microbial cell). In other cases, the anthranilate or substituted anthranilate may be produced biosynthetically by the microbial cell. For example, a microbial cell may produce anthranilate or a substituted anthranilate naturally (e.g., as part of central carbon metabolism). In other cases, the microbial cell may be engineered to produce anthranilate or a substituted anthranilate (e.g., by overexpressing enzymes for the production of substituted anthranilates).

Scheme 1 below depicts a non-limiting example of synthesis of a substituted tryptamine from anthranilate or a substituted anthranilate in an engineered microbial cell.

Scheme 1

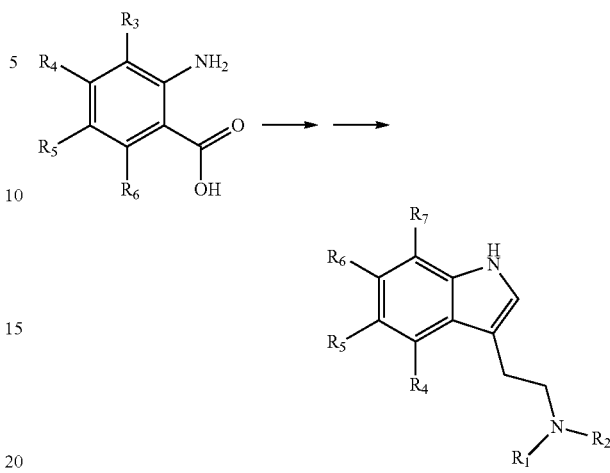

In some aspects, the disclosure provides a method for the production of substituted tryptamines by cultivating engineered microbes in the presence of anthranilate or a substituted anthranilate,

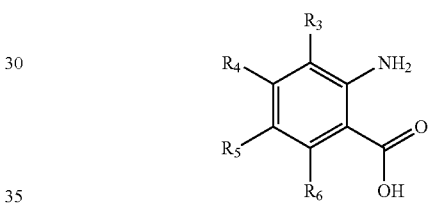

where —R is, but is not limited to, a halogen (—Br, —F, —Cl, —I, etc), —OH, $C_1$-$C_5$ alkyl, $C_1$-$C_5$ alkoxy, $NO_2$, $NH$, COOH, CN, sulfur, $SO_3$, $SO_4$, or $PO_4$. The resulting substituted tryptamine,

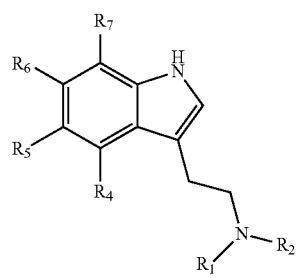

may be recovered from the culture broth. In some cases, the resulting tryptamine may be used in further downstream chemistry, taking advantage of chemical leaving groups or protecting groups incorporated into the tryptamine scaffold during the fermentative biosynthetic process.

In another aspect of the disclosure, indole or indole substituted at 4-, 5-, 6-, or 7-can be used to make 4-, 5-, 6-, or 7-indole substituted tryptamines with R1 or R2 substitutions. In some cases, the process may be carried out in a whole-cell microbial fermentation. In some cases, an engineered microbial cell may be cultured in the presence of indole or a substituted indole (e.g., indole or substituted indole may be fed to or otherwise incubated with the microbial cell). In other cases, the indole or substituted indole may be produced biosynthetically by the microbial cell. For example, a microbial cell may produce indole or a substituted indole naturally. In other cases, the microbial cell may be engineered to produce indole or a substituted indole (e.g., by overexpressing enzymes for the production of substituted indoles).

Synthesis of a Substituted Tryptamine from Indole or a Substituted Indole in Engineered Microbial Cells.

Scheme 2 depicts a non-limiting example of synthesis of a substituted tryptamine from indole or a substituted indole in an engineered microbial cell.

Scheme 2

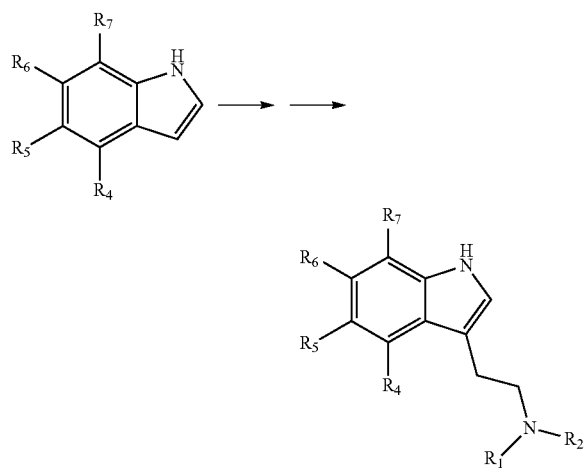

In some aspects, the disclosure provides a method for the production of substituted tryptamines by cultivating engineered microbes in the presence of indole or a substituted indole,

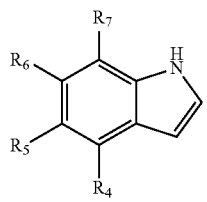

where —R is, but is not limited to, a halogen (—Br, —F, —Cl, —I, etc), —OH, $C_1$-$C_5$ alkyl, $C_1$-$C_5$ alkoxy, $NO_2$, NH, COOH, CN, sulfur, $SO_3$, $SO_4$, or $PO_4$. The resulting substituted tryptamine,

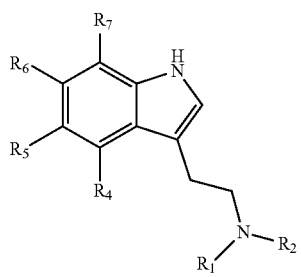

may be recovered from the culture broth. In some cases, the resulting tryptamine may be used in further downstream chemistry, taking advantage of chemical leaving groups or protecting groups incorporated into the tryptamine scaffold during the fermentative biosynthetic process.

Synthesis of a Substituted Tryptamine from Anthranilate or a Substituted Anthranilate in Engineered Microbial Cells.

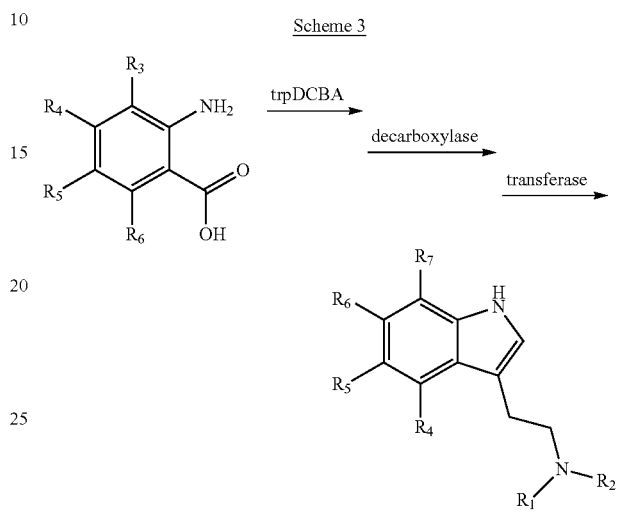

Scheme 3

In some aspects, the processes described herein may involve the use of engineered microbes for the production of substituted tryptamines from anthranilate or substituted anthranilate. Scheme 3 depicts a non-limiting example of production of a substituted tryptamine from a substituted anthranilate in an engineered microbial cell. In some cases, the engineered microbial cell may be a bacterial cell. In some cases, the bacteria may be *Escherichia coli* or *Corynebacterium glutamicum*. In some cases, the bacteria may comprise modified host genetics, including knockout of tna (tryptophanase), trpR (tryptophan repressor element), and trpE (anthranilate synthase). In some cases, the engineered microbial cell may be a yeast cell. In some cases, the yeast cell may be of the species *Saccharomyces cerevisiae*. In some cases, the microbial cell may be further modified to express or overexpress one or more genes. In some cases, the microbial cell may be engineered to contain extra DNA copies by plasmid or genomic integration of an endogenous or heterologous trpDCBA operon. In some cases, the trpDCBA operon may comprise any one of SEQ ID NOs: 1-4. In some cases, the trpDCBA operon may comprise a nucleic acid sequence having at least 40%, at least 50%, at least 60%, at least 70%, at least 80%, at least 90%, or at least 95% sequence identity to any one of SEQ ID NOs: 1-4. In some cases, the engineered microbial cell may produce one or more enzymes having an amino acid sequence according to any one of SEQ ID NOs: 5-13, or an amino acid sequence having at least 40%, at least 50%, at least 60%, at least 70%, at least 80%, at least 90%, or at least 95% sequence identity to any one of SEQ ID NOs: 5-13. In some cases, the engineered microbial cell may produce one or more of trpD, trpB, trpC, or trpA, wherein the enzyme has been modified or mutated to exhibit higher levels of activity.

In some cases, the microbial cell may be further engineered to express or overexpress one or more additional genes. In some aspects, such microbial cell may further express a tryptamine decarboxylase (see Scheme 3, "decarboxylase"). In some cases, the tryptamine decarboxylase may be expressed by genomic integration of DNA or expression of a plasmid in the microbial cell. Tryptamine decarboxylases may be pyridoxal phosphate (PLP)-independent or may be PLP-dependent. In some cases, a tryptamine decarboxylase may comprise any one of the amino acid sequences according to SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a tryptamine decarboxylase that has been modified or mutated to exhibit higher activity levels.

In some cases, the R1 and R2 amino positions of the tryptamine or substituted tryptamines derived from fermentation can be modified by a transferase to yield, by non-limiting example, N-methyl, N,N-dimethyl, N-acetyl, or N-hydroxycinnamoyl functional groups. Thus, in some cases, an engineered microbial cell may further express or overexpress a transferase (see Scheme 3). In some cases, a transferase may comprise any one of the amino acid sequences shown in SEQ ID NOs: 21-31 (see Table 2), or an amino acid sequence having at least 40%, at least 50%, at least 60%, at least 70%, at least 80%, at least 90%, or at least 95% sequence identity to an amino acid sequence of any one of SEQ ID NOs: 21-31. In some cases, an engineered microbial cell may express a transferase that has been modified or mutated to exhibit higher activity levels.

In some cases, an additional transferase can be expressed, such as, but not limited to, a phosphotransferase (kinase), acetyl transferase, glucosyl transferase, or sulfotransferase, to further modify hydroxyls on the indole ring of the tryptamine. For example, such as when engineered cells are cultivated in the presence of 6-hydroxyanthranilate or 4-hydroxy indole to yield 4-hydroxy-N,N-dimethyltryptamine, a kinase can be expressed yielding the phosphate ester of 4-hydroxy-N,N-dimethyltryptamine, psilocybin. Suitable kinases may include, but are not limited to, an amino acid sequence shown in any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence of any one of SEQ ID NOs: 41-44.

In some cases, the substituted anthranilate may be any one of 5-bromoanthranilate, 6-hydroxyanthranilate, 5-hydroxyanthranilate, 6-chloroanthranilate, and 5-chloroanthranilate. In some cases, the tryptamine may be any one of tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, and 4-hydroxy-N-acetyl-tryptamine.

Synthesis of a Substituted Tryptamine from Indole or a Substituted Indole in Engineered Microbial Cells.

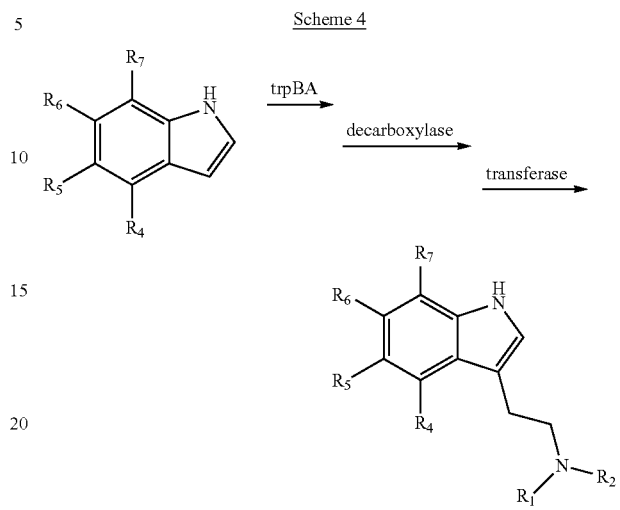

In some aspects, the processes described herein may involve the use of engineered microbes for the production of substituted tryptamines from indole or substituted indole. Scheme 4 depicts a non-limiting example of production of a substituted tryptamine from a substituted indole in an engineered microbial cell. In some cases, the engineered microbial may be a bacterial cell. In some cases, the bacterial cell may be of the species Escherichia coli or Corynebacterium glutamicum. In some cases, the bacterial cell may comprise modified host genetics, including knockout of tna (tryptophanase), trpR (tryptophan repressor element), and trpE (anthranilate synthase). In some cases, the microbial cell may be a yeast cell. In some cases, the yeast cell may be of the species Saccharomyces cerevisiae.

In some cases, the microbial cell may be further modified to express or overexpress one or more genes. In some cases, the microbial cell may be engineered to contain extra DNA copies by plasmid or genomic integration of endogenous or heterologous trpB and trpA (see, e.g., Scheme 4). In some cases, trpB and trpA may comprise amino acid sequences according to any one of SEQ ID NOs; 5-13 (see Table 2), or an amino acid sequence having at least 40%, at least 50%, at least 60%, at least 70%, at least 80%, at least 90%, or at least 95% sequence identity to any amino acid sequence shown in SEQ ID NOs: 5-13. In some cases, an engineered microbial cell may express trpB and/or trpA that has been modified or mutated to exhibit higher activity levels.

In some cases, the microbial cell may be further engineered to express or overexpress one or more additional genes. In some aspects, such microbial cell may further express a tryptamine decarboxylase (see, e.g., Scheme 4, "decarboxylase"). In some cases, the tryptamine decarboxylase may be expressed by genomic integration of DNA or expression of a plasmid in the microbial cell. Tryptamine decarboxylases may be pyridoxal phosphate (PLP)-independent or may be PLP-dependent. In some cases, a tryptamine decarboxylase may comprise any one of the amino acid sequences according to SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a tryptamine decarboxylase that has been modified or mutated to exhibit higher activity levels.

In some cases, the R1 and R2 amino positions of the tryptamine or substituted tryptamines derived from fermentation can be modified by a transferase to yield, by non-limiting example, N-methyl, N,N-dimethyl, N-acetyl, or N-hydroxycinnamoyl functional groups. Thus, in some cases, an engineered microbial cell may further express or overexpress a transferase (see, e.g., Scheme 4). In some cases, a transferase may comprise any one of the amino acid sequences shown in SEQ ID NOs: 21-31 (see Table 2), or an amino acid sequence having at least 40%, at least 50%, at least 60%, at least 70%, at least 80%, at least 90%, or at least 95% sequence identity to an amino acid sequence of any one of SEQ ID NOs: 21-31. In some cases, an engineered microbial cell may express a transferase that has been modified or mutated to exhibit higher activity levels. In some cases, an additional transferase can be expressed, such as, but not limited to, a phosphotransferase (kinase), acetyl transferase, glucosyl transferase, or sulfotransferase, to further modify hydroxyls on the indole ring of the tryptamine. For example, such as when engineered cells are cultivated in the presence of 6-hydroxyanthranilate or 4-hydroxy indole to yield 4-hydroxy-N,N-dimethyltryptamine, a kinase can be expressed yielding the phosphate ester of 4-hydroxy-N,N-dimethyltryptamine, psilocybin. Suitable kinases may include, but are not limited to, an amino acid sequence shown in any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence of any one of SEQ ID NOs: 41-44.

In some cases, the substituted indole may be any one of 5-hydroxyindole, 4-hydroxyindole, 7-hydroxyindole, and 4-chloroindole, 5-bromoindole, and 4-fluoroindole. In some cases, the tryptamine may be any one of tryptamine, 5-hydroxytryptamine, 5-hydroxymethyltryptamine, 5-hydroxy-N,N-dimethyltryptamine, 5-phosphoryloxymethyltryptamine, 5-phosphoryloxy-N,N-dimethyltryptamine, 4-hydroxytryptamine, 4-hydroxy-N,N-dimethyltryptamine, 4-phosphoryloxytryptamine, 4-phosphoryloxy-N,N-tryptamine, 7-hydroxytryptamine, 7-phosphoryloxymethyltryptamine, 7-phosphoryloxy-N,N-dimethyltryptamine, 4-chloro-tryptamine, 4-chloro-N,N-dimethyltryptamine, 5-bromotryptamine, 5-bromo-methyltryptamine, 5-bromo-N-methyltryptamine, 5-bromo-N,N-dimethyltryptamine, N-acetyl-tryptamine, and 4-hydroxy-N-acetyl-tryptamine.

Synthesis of 4-Hydroxyl Substituted and/or R1 or R2 Amine Substituted Tryptamines from Tryptophan by Engineered Microbial Cells Scheme 5

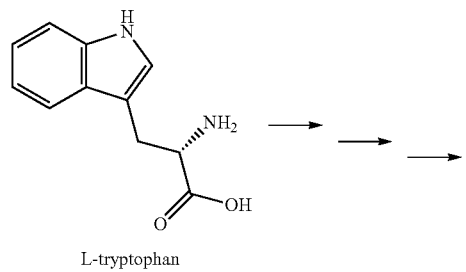

L-tryptophan

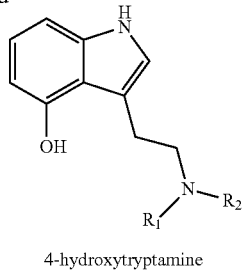

4-hydroxytryptamine

In another aspect, 4-hydroxyl substituted and/or R1 or R2 amine substituted tryptamines may be biosynthetically produced from tryptophan by engineered microbial cells, in accordance with Scheme 5.

In some cases, a microbial cell, may contain heterologous DNA on a plasmid or by integration into the genome that expresses enzymes that convert L-tryptophan to tryptamine (e.g., a decarboxylase) and/or that convert tryptamine to 4-hydroxytryptamine (e.g., a tryptophan 4-hydroxylase). Decarboxylases may be pyridoxal phosphate (PLP)-independent or PLP-dependent.

In some cases, the microbial cell may be engineered to express or overexpress a decarboxylase. In some cases, the decarboxylase may have an amino acid sequence of any one of SEQ ID NOs: 14-20 (see Table 2), or an amino acid sequence having at least 40%, at least 50%, at least 60%, at least 70%, at least 80%, at least 90%, or at least 95% sequence identity to an amino acid sequence of any one of SEQ ID NOs: 14-20. In some cases, an engineered microbial cell may express a decarboxylase that has been modified or mutated to exhibit higher activity levels.

In some cases, the microbial cell may be engineered to express or overexpress a tryptamine 4-hydroxylase. Tryptamine 4-hydroxylases are P450 enzymes that require a P450 reductase pair to provide reducing power via transfer of electrons from NADPH. In some cases, the tryptamine 4-hydroxylase may have an amino acid sequence according to any one of SEQ ID NOs: 32-35 (see Table 2), or an amino acid sequence having at least 40%, at least 50%, at least 60%, at least 70%, at least 80%, at least 90%, or at least 95% sequence identity to an amino acid sequence of any one of SEQ ID NOs: 32-35. In some cases, an engineered microbial cell may express a tryptamine 4-hydroxylase that has been modified or mutated to exhibit higher activity levels.

In some cases, the microbial cell may be engineered to express or overexpress a P450 reductase. In some cases, the P450 reductase may have an amino acid sequence according to any one of SEQ ID NOs: 36-40 (see Table 2), or an amino acid sequence having at least 40%, at least 50%, at least 60%, at least 70%, at least 80%, at least 90%, or at least 95% sequence identity to any one of SEQ ID NOs: 36-40. In some cases, an engineered microbial cell may express a P450 reductase that has been modified or mutated to exhibit higher activity levels.

In some cases, an additional transferase can be expressed, such as, but not limited to, a phosphotransferase (kinase), acetyl transferase, glucosyl transferase, or sulfotransferase to further modify hydroxyls on the indole ring of the tryptamine. When the production compound of interest is 4-hydroxy-N,N-dimethyltryptamine, a kinase can be expressed yielding the phosphate ester of 4-hydroxy-N,N-dimethyltryptamine, psilocybin. In some cases, the microbial cell may be further engineered to express or overexpress a kinase. In some cases, the kinase may have an amino acid sequence according to any one of SEQ ID NOs: 41-44 (see Table 2), or an amino acid sequence having at least 40%, at least 50%, at least 60%, at least 70%, at least 80%, at least 90%, or at least 95% sequence identity to any one of SEQ ID NOs: 41-44. In some cases, an engineered microbial cell may express a kinase that has been modified or mutated to exhibit higher activity levels.

Synthesis of Tryptamine Derivatives from Substitute Tryptamines in Engineered Microbial Cells In another aspect, derivatives of tryptamine may be biosynthetically produced from substituted tryptamines by engineered microbial cells.

In some cases, a microbial cell, may contain heterologous DNA on a plasmid or by integration into the genome that expresses enzymes that convert a substitute tryptamine to a tryptamine derivative. In some cases, the microbial cell may be engineered to express or overexpress a tryptamine 4-hydroxylase. In some cases, the tryptamine 4-hydroxylase may have an amino acid sequence of any one of SEQ ID NOs: 32-35 (see Table 2), or an amino acid sequence having at least 40%, at least 50%, at least 60%, at least 70%, at least 80%, at least 90%, or at least 95% sequence identity to an amino acid sequence of any one of SEQ ID NOs: 32-35. In some cases, an engineered microbial cell may express a tryptamine 4-hydroxylase that has been modified or mutated to exhibit higher activity levels. In some cases, the microbial cell may be engineered to express or overexpress a tryptamine 5-hydroxylase. In some cases, the tryptamine 5-hydroxylase may have an amino acid sequence according to SEQ ID NO: 47 (see Table 2), or an amino acid sequence having at least 40%, at least 50%, at least 60%, at least 70%, at least 80%, at least 90%, or at least 95% sequence identity to an amino acid sequence according to SEQ ID NO: 47. In some cases, an engineered microbial cell may express a tryptamine 5-hydroxylase that has been modified or mutated to exhibit higher activity levels. In some cases, the microbial cell may be engineered to express or overexpress a 4-hydroxytryptamine kinase. In some cases, the 4-hydroxytryptamine kinase may have an amino acid sequence according to any one of SEQ ID NOs: 41-44 (see Table 2), or an amino acid sequence having at least 40%, at least 50%, at least 60%, at least 70%, at least 80%, at least 90%, or at least 95% sequence identity to an amino acid sequence according to any one of SEQ ID NOs: 41-44. In some cases, an engineered microbial cell may express a 4-hydroxytryptamine kinase that has been modified or mutated to exhibit higher activity levels.

Figure 18A:
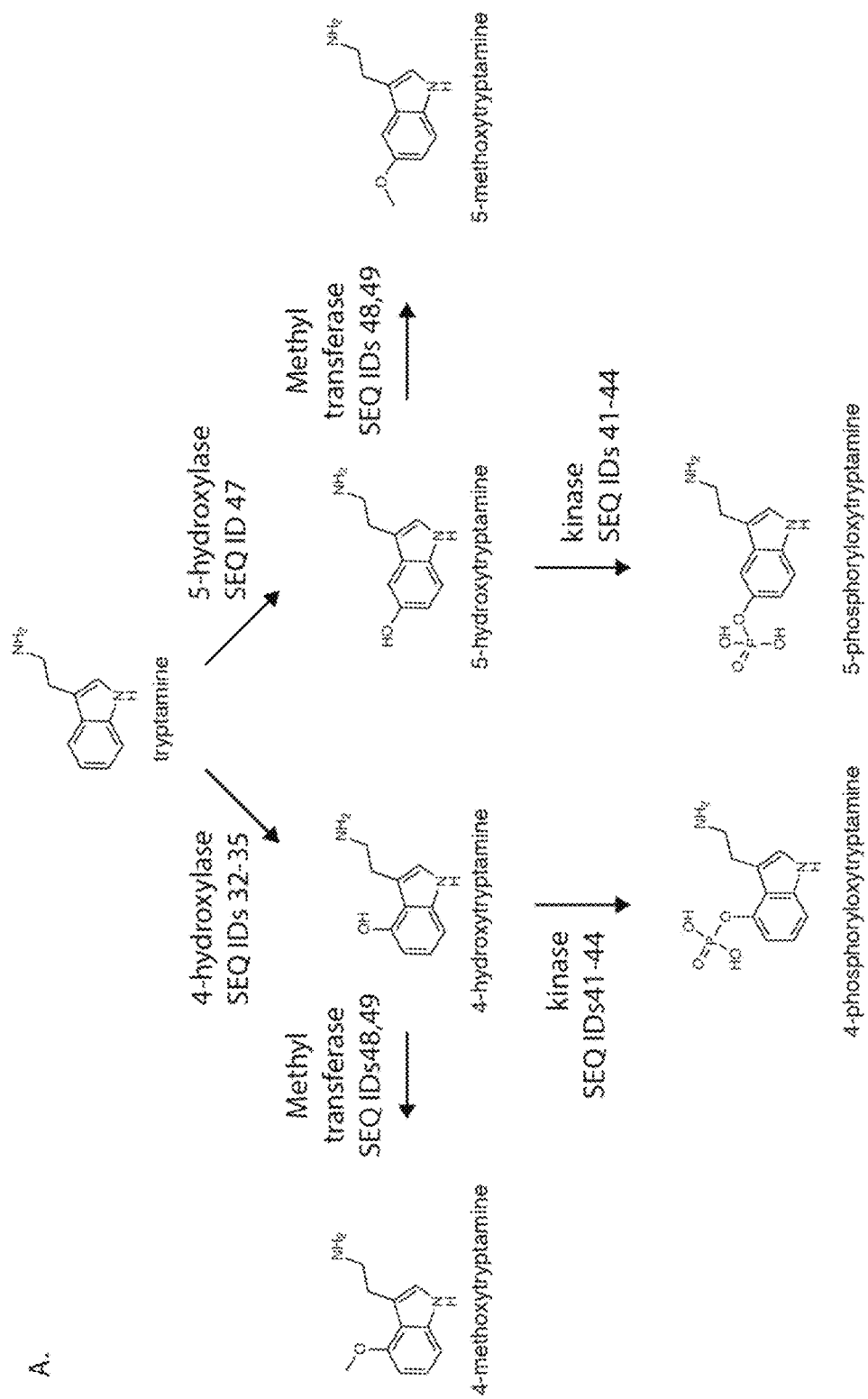
FIG. 18A depicts a non-limiting example of a biosynthetic pathway converting tryptamine to tryptamine derivatives.

FIG. 18A depicts a non-limiting example of a biosynthetic pathway for converting tryptamine to tryptamine derivatives. For example, tryptamine may be converted to 4-hydroxytryptamine by 4-hydroxylase (e.g., SEQ ID NOs:32-35). 4-hydroxytryptamine may be converted to 4-methoxytryptamine by a methyl transferase (e.g., SEQ ID NOs:48 or 49), or 4-phosphoryloxytryptamine by a kinase (e.g., SEQ ID NOs:41-44). In another example, tryptamine may be converted to 5-hydroxytryptamine by 5-hydroxylase (e.g., SEQ ID NO:47). 5-hydroxytryptamine may be converted to 5-methoxytryptamine by a methyl transferase (e.g., SEQ ID NOs:48 or 49), or to 5-phosphoryloxytryptamine by a kinase (e.g., SEQ ID NOs:41-44).

Figure 18B:
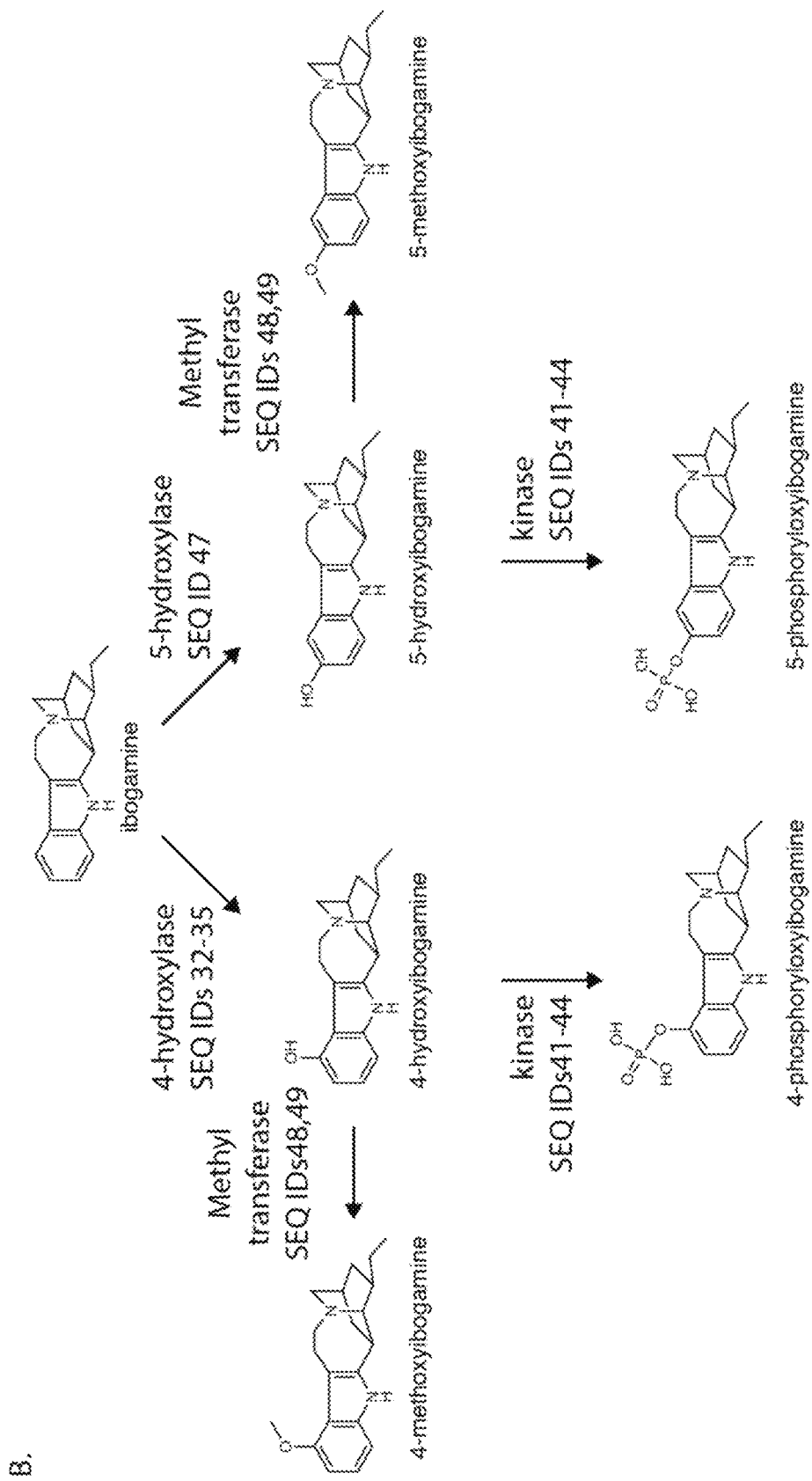
FIG. 18B depicts a non-limiting example of a biosynthetic pathway converting ibogamine to derivatives of ibogamine.

FIG. 18B depicts a non-limiting example of a biosynthetic pathway converting ibogamine to derivatives of ibogamine. For example, ibogamine may be converted to 4-hydroxyibogamine by 4-hydroxylase (e.g., SEQ ID NOs:32-35). 4-hydroxyibogamine may be converted to 4-methoxyibogamine by a methyl transferase (e.g., SEQ ID NOs:48 or 49), or to 4-phosphoryloxyibogamine by a kinase (e.g., SEQ ID NOs:41-44). In another example, ibogamine may be converted to 5-hydroxyibogamine by 5-hydroxylase (e.g., SEQ ID NO:47). 5-hydroxyibogamine may be converted to 5-methoxyibogamine by a methyl transferase (e.g., SEQ ID NO:48 or 49), or to 5-phosphoryloxyibogamine by a kinase (e.g., SEQ ID NOs:41-44).

In some cases, the engineered microbial cell may be cultured in the presence of one or more tryptamines. In some cases, the tryptamine is selected from the group consisting of: 5-methoxy-N,N-dimethyl-tryptamine, N,N-diisopropyl-tryptamine, N-methyl-N-isopropyltryptamine, N,N-dimethyltryptamine, N,N-tetramethylenetryptamine, N,N-dipropyltryptamine, ibogamine, and 12-methoxyibogamine, tryptamine, 4-hydroxytryptamine, 5-hydroxytryptamine, ibogamine, 4-hydroxyibogamine, and 5-hydroxyibogamine.

In some cases, the engineered microbial cell may convert a tryptamine to a tryptamine derivative. In some cases, the tryptamine derivative is any tryptamine derivative described in FIG. 16. In some cases, the tryptamine derivative is selected from the group consisting of: 5-hydroxy-N,N-diisopropyl-tryptamine, 5-hydroxy-N-methyl-N-isopropyl-tryptamine, 5-hydroxy-N,N-dimethyltryptamine, 5-hydroxy-N,N-tetramethylenetryptamine, 5-hydroxy-N,N-dipropyltryptamine, 4,5-methoxy-N,N-dimethyl-tryptamine, 4-hydroxy-N,N-diisopropyl-tryptamine, 4-hydroxy-N-methyl-N-isopropyltryptamine, 4-hydroxy-N,N-dimethyltryptamine, 4-hydroxy-N,N-tetramethylenetryptamine, 4-hydroxy-N,N-dipropyltryptamine, 4-phosphoryloxy-N,N-dipropyltryptamine, ibogamine, 12-methoxyibogamine, 4-hydroxytryptamine, 5-hydroxytryptamine, 4-methoxytryptamine, 5-methoxytryptamine, 4-phosphoryloxytryptamine, 5-phosphoryloxytryptamine, 4-hydroxyibogamine, 5-hydroxyibogamine, 4-phosphoryloxyibogamine, and 5-phosphoryloxyibogamine.

Assay for Detecting Levels of 4-Hydroxytryptamine in a Host Cell

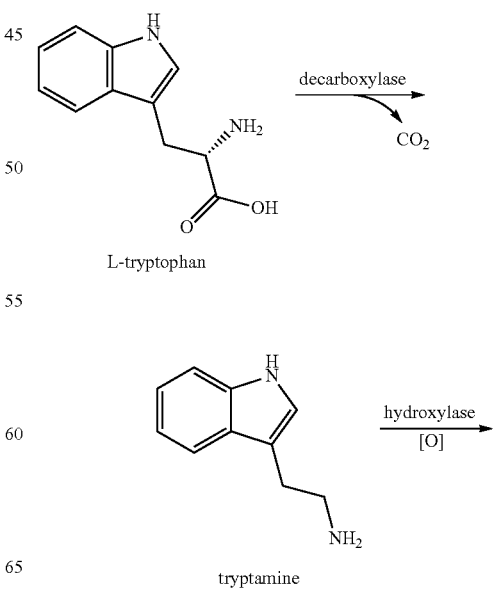

Scheme 6

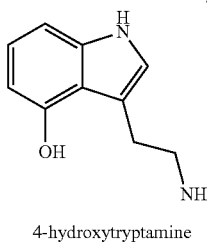

4-hydroxytryptamine → Oxidation → Blue Product

In another aspect, the disclosure provides a method for detecting levels of 4-hydroxytryptamine in a host cell. In some cases, the method comprises detecting, in a host cell genetically modified to produce a 4-hydroxytryptamine, a colored or fluorescent product of 4-hydroxytryptamine. In some cases, the colored or fluorescent product of 4-hydroxytryptamine may be produced by the action of an oxidizing mechanism produced in the cell. In some cases, the level of 4-hydroxytryptamine produced in the cell may be directly proportional to the level of 4-hydroxytryptamine or a colored product of 4-hydroxytryptamine produced in the cell (see, e.g., Scheme 6). Such in vivo screening methods may be used to rapidly screen for tryptamine 4-hydroxylase mutants having high activity in the engineered production host cell (DeLoache et al. 2015).

The oxidizing mechanism can be catalyzed by iron sulphate or by an enzyme expressed by a host cell, including, but not limited to, the enzyme multicopper oxidase (Blaschko and Levine 1960). A non-limiting example of a suitable oxidase is shown in SEQ ID NO: 45 (see Table 2). In some cases, a genetically modified cell comprising a nucleic acid sequence encoding a variant tryptophan 4-hydroxylase may produce a level of 4-hydroxytryptamine, or a colored or fluorescent product thereof, that is higher than a level of 4-hydroxytryptamine, or a colored or fluorescent product thereof, in a control cell not comprising a nucleic acid sequence encoding the variant tryptamine 4-hydroxylase. This may indicate that the variant enzyme increases flux through the biosynthetic pathway, thereby creating higher titers and rates of 4-hydroxytryptamine production. The genetically modified host cell containing higher 4-hydroxytryptamine production can contain enzymes, such as methyl-, sulphono-, glucosyl- and/or phospho transferases for the 4-hydroxyindole position or amino position, as described herein.

In some cases, the modified host cell may be modified to increase flux through tryptophan and to increase tryptophan production. This can be achieved by knockout of aro8 and aro10 and overexpression of TRP1, TRP2, TRP3, TRP4 and TRP5. Additionally, inclusion of TRP2 feedback resistant mutant allele can be employed.

In a non-limiting example (see Example 1), 1-tryptophan may be converted, in a modified microbial host cell expressing a decarboxylase, hydroxylase, P450 reductase, methyltransferase and kinase, to O-phosphoryl-4-hydroxy-N,N-dimethyltryptamine.

Culture Conditions and Product Production

In some cases, the genetically modified host cell may be cultured under aerobic conditions. In some cases, the genetically modified host cell may be cultured under anaerobic conditions.

In some cases, the culture media may be a minimal media, including, but not limited to, M9, MOPS, YNB, ammonia salts, or a complex media containing, for example, yeast extract, casamino acids, peptone, or tryptone. In some cases, the culture media may be buffered, for example, by phosphate salts, HEPES, or Tris. In some cases, the culture media may contain a reducing agent, for example, L-ascorbic acid, dithiothreitol, or mercaptoethanol. In some cases, the culture media may be supplemented with additional amino acids, such as L-methionine, Histidine, Arginine, Alanine, Isoleucine, Cysteine, Aspartic acid, Leucine, Glutamine, Asparagine, Lysine, Glycine, Glutamic acid, Proline, Serine, Phenylalanine, Tyrosine, Selenocysteine, Threonine, Pyrrolysine, Tryptophan, or Valine. In some cases, additional vitamins and cofactors may be added, for example, L-ascorbic acid, thiamine, pyridoxal phosphate, niacin, pyridoxine, biotin, folic acid, tetrahydrofolic acid, riboflavin, pantothenic acid, copper salts, magnesium salts, manganese salts, molybdenum salts, iron salts, zinc salts, nickel salts, glutathione, heme, or D-aminolevulinic acid.

In some cases, the genetically modified host cell may be fed a substituted anthranilate by single addition, batch feeding, or constant dilution in culture. In some cases, the genetically modified host cell may be fed a substituted indole by single addition, batch feeding, or constant dilution in culture.

In some cases, a downstream product may be produced. In some cases, the downstream product may be purified, e.g., isolated and purified from the culture medium, from a cell lysate, or both. In some cases, the downstream product may be at least, or about, 25%, 30%, 40%, 50%, 60%, 70%, 75%, 80%, 90%, 95%, or 99%, by weight, pure. Purification can be carried out by any known method or combination of methods, which methods include, e.g., column chromatography, phase separation, precipitation, crystallization, decantation, gas stripping, membrane enhanced separation, fractionation, adsorption/desorption, pervaporation, thermal or vacuum desorption from a solid phase, extraction of the product that is immobilized or absorbed to a solid phase with a solvent, etc. Purity can be assessed by any appropriate method, e.g., by column chromatography, high performance liquid chromatography (HPLC) analysis, or gas chromatography-mass spectrometry (GC-MS) analysis.

In some cases, the cells in culture may convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the fed precursor in the cell culture medium into the desired product. In some cases, the cells in culture may produce at least 2 g/L, at least 3 g/L, at least 4 g/L, at least 5 g/L, at least 7 g/L, at least 10 g/L, or more than 50 g/L of the desired product in liquid culture medium.

In some cases, the cells in culture may convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into the desired product. In some cases, the cells in culture may produce at least 2 g/L, at least 3 g/L, at least 4 g/L, at least 5 g/L, at least 7 g/L, at least 10 g/L, or more than 50 g/L of the desired product in liquid culture medium.

Host Cells

Suitable host cells include cells that can be cultured in media, e.g., as unicellular organisms. Suitable host cells include yeast cells, fungal cells, insect cells, mammalian cells, algal cells, and bacterial cells. Suitable host cells may further include filamentous fungal cells; suitable filamentous fungal cells include, e.g., *Aspergillus, Neurospora*, and the like.

The host cell can be a prokaryotic cell. Suitable prokaryotic cells include, but are not limited to, any of a variety of laboratory strains of *Escherichia coli*, *Corynebacterium glutamicum*, *Lactobacillus* sp., *Salmonella* sp., *Shigella* sp., *Citrobacter*, *Enterobacter*, *Clostridium*, *Klebsiella*, *Aerobacter*, and the like. See, e.g., Carrier et al. (1992) J. Immunol. 148:1176-1181; U.S. Pat. No. 6,447,784; and Sizemore et al. (1995) Science 270:299-302. Examples of *Salmonella* strains which can be employed in the present invention include, but are not limited to, *Salmonella typhi* and *S. typhimurium*. Suitable *Shigella* strains include, but are not limited to, *Shigella flexneri*, *Shigella sonnei*, and *Shigella disenteriae*. Typically, the laboratory strain is one that is non-pathogenic. Non-limiting examples of other suitable bacteria include, but are not limited to, *Bacillus subtilis*, *Pseudomonas pudita*, *Pseudomonas aeruginosa*, *Pseudomonas mevalonii*, *Rhodobacter sphaeroides*, *Rhodobacter capsulatus*, *Rhodospirillum rubrum*, *Rhodococcus* sp., and the like. In some cases, the host cell is *Escherichia coli*.

Non-limiting examples of suitable yeast host cells are strains selected from a cell of a species of *Candida*, *Kluyveromyces*, *Saccharomyces*, *Schizosaccharomyces*, *Pichia*, *Hansenula*, and *Yarrowia*. In some cases, the yeast host cell may be selected from the group consisting of: *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, *Schizosaccharomyces pombe*, *Saccharomyces uvarum*, *Pichia kluyveri*, *Yarrowia lipolytica*, *Candida utilis*, *Candida cacaoi*, and *Geotrichum fermentans*. Other useful yeast host cells are *Kluyveromyces lactis*, *Kluyveromyces fragilis*, *Hansenula polymorpha*, *Pichia pastoris*, *Yarrowia lipolytica*, *Schizosaccharomyces pombe*, *Ustilgo maylis*, *Candida maltose*, *Pichia guillermondii* and *Pichia methanoliol*. Suitable yeast host cells may include, but are not limited to, *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, and the like. In some cases, a yeast host cell may be *Saccharomyces cerevisiae*; e.g., a genetically modified cell of the present disclosure may be a genetically modified *Saccharomyces cerevisiae* cell.

The filamentous fungi may be characterized by a mycelial wall composed of chitin, cellulose, glucan, chitosan, mannan, and other complex polysaccharides. Vegetative growth may be by hyphal elongation and carbon catabolism may be obligately aerobic. Suitable filamentous fungal strains include, but are not limited to, strains of *Acremonium*, *Agaricus*, *Aspergillus*, *Aureobasidium*, *Chrysosporium*, *Coprinus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Phanerochaete*, *Pleurotus*, *Schizophyllum*, *Talaromyces*, *Thermoascus*, *Thielavia*, *Tolypocladium*, and *Trichoderma*. Non-limiting examples of suitable filamentous fungal cells include, e.g., *Aspergillus niger*, *Aspergillus awamori*, *Aspergillus foetidus*, *Aspergillus sojae*, *Aspergillus fumigatus*, and *Aspergillus oryzae*. Another example of a suitable fungal cell is a *Neurospora crassa* cell.

Heterologous Protein Expression in Modified Host Cells

In some cases, a nucleotide sequence encoding a heterologous polypeptide may be operably linked to a transcriptional control element.

Suitable promoters for expression in bacteria may include, but are not limited to, pT7, ptac, pLac, pLacUV5, pTet, pBAD, and the constitutive BBa series of promoters of the Anderson promoter library (Kelly et al, "Measuring the activity of BioBrick promoters using an in vivo reference standard" Journal of Biological Engineering 2009 3:4). Suitable promoters for expression in yeast may include, but are not limited to, TDH3, CCW12, CYC1, HIS3, GAL1, GAL10, ADH1, PGK, PHO5, GAPDH, ADC1, TRP1, URA3, LEU2, ENO, and TP1; and, AOX1 (e.g., for use in *Pichia*).

The expression vector may also contain a ribosome binding site for translation initiation and a transcription terminator. The expression vector may also include appropriate sequences for amplifying expression.

In some cases, the expression of the amino acid sequence may be codon optimized or biased to increase expression of protein in vivo. This may be achieved by several algorithms (Hanson and Coller, Nature Reviews Molecular Cell Biology volume 19, pages 20-30 (2018)), (Quax, et al Molecular Cell Review volume 59, Jul. 16, 2015). In some cases, the native amino acid sequence may be used for coding an amino acid sequence in vivo.

In some cases, a genetically modified microbial cell of the disclosure may comprise one or more nucleic acid sequences according to any one of SEQ ID NOs: 1-4 (see Table 1), or a nucleic acid sequence having at least 40%, at least 50%, at least 60%, at least 70%, at least 80%, at least 90%, or at least 95% sequence identity to any one of SEQ ID NOs: 1-4.

In some cases, a genetically modified microbial cell of the disclosure may express or overexpress one or more enzymes having an amino acid sequence according to any one of SEQ ID NOs: 5-49, or an amino acid sequence having at least 40%, at least 50%, at least 60%, at least 70%, at least 80%, at least 90%, or at least 95% sequence identity to any one of SEQ ID NOs: 5-49.

TABLE 1

DNA Sequences

| Operonic sequences | Host/ Sequence origin | Sequence |
| --- | --- | --- |
| trpDCBA | Prokaryotic/ *E. coli* | atggctgacattctgctgctcgataatatcgactcllllacgtacaacctggcagatcagttgcgca gcaatgggcataacgtggtgatttaccgcaaccatattccggcgcaaaccttaattgaacgcctg gcgaccatgagcaatccggtgctgatgctttctcctggcccggtgtgccgagcgaagccggtt gtatgccggaactcctcacccgcttgcgtggcaagctgcccattattggcatttgcctcggacatc aggcgattgtcgaagcttacgggggctatgtcggtcaggcgggcgaaattctccacggtaaagc ctccagcattgaacatgacggtcaggcgatgtagccggattaacaaacccgctgccggtggcg cgttatcactcgctggttggcagtaacattccggccggittaaccatcaacgcccallitaatggca tggtgatggcagtacgtcacgatgcggatcgcgtttgtggattccagttccatccggaatccattct caccacccagggcgctcgcctgctggaacaaacgctggcctgggcgcagcagaaactagagc cagccaacacgctgcaaccgattctggaaaaactgtatcaggcgcagacgcttagccaacaag |

TABLE 1-continued

DNA Sequences

| Operonic sequences | Host/ Sequence origin | Sequence |
|---|---|---|
| | | aaagccaccagctgliticagcggtggtgcgtggcgagctgaagccggaacaactggcggcg<br>gcgctggtgagcatgaaaattcgcggtgagcacccgaacgagatcgccggggcagcaaccgc<br>gctactggaaaacgcagcgccgttcccgcgccggattatctgtttgctgatatcgtcggtactgg<br>cggtgacggcagcaacagtatcaatatttctaccgccagtgcgtttgtcgccgcggcctgtgggc<br>tgaaagtggcgaaacacggcaaccgtagcgtctccagtaaatctggttcgtccgatctgctggcg<br>gcgttcggtattaatcttgatatgaacgccgataaatcgcgccaggcgctggatgagttaggtgta<br>tgtttcctctctttgcgccgaagtatcacaccggattccgccacgcgatgccggttcgccagcaactg<br>aaaacccgcaccctgttcaatgtgctggggccattgattaacccggcgcatccgccgctggcgtt<br>aattggtgtttatagtccggaactggtgctgccgattgccgaaaccttgcgcgtgctggggtatca<br>acgcgcggcggtggtgcacagcggcgggatggatgaagtacattacacgcgccgacaatcgt<br>tgccgaactgcatgacggcgaaattaaaagctatcagctcaccgcagaagactttgccctgaca<br>ccctaccaccaggagcaactggcaggcggaacaccggaagaaaaccgtgacallitaacacgt<br>tgttacaaggtaaaggcgacgccgcccatgaagcagccgtcgctgcgaacgtcgccatgttaa<br>tgcgcctgcatggccatgaagatctgcaagccaatgcgcaaaccgttcttgaggtactgcgcagt<br>ggttccgcttacgacagagtcaccgcactggcggccacgagggtaaatgatgcaaaccgttttag<br>cgaaaatcgtcgcagacaaggcgatttgggtagaagcccgcaaacagcagcaaccgctggcc<br>agttttcagaatgaggttcagccgagcacgcgacallittatgatgcgctacagggtgcgcgcac<br>ggcgtttattctggagtgcaagaaagcgtcgccgtcaaaaggcgtgatccgtgatgatttcgatcc<br>agcacgcattgccgccatttataaacattacgcttcggcaatttcggtgctgactgatgagaaatat<br>tttcaggggagctttaatttcctccccatcgtcagccaaatcgccccgcagccgattttatgtaaag<br>acttcattatcgaccctaccagatctatctggcgcgctattaccaggccgatgcctgcttattaatg<br>ctttcagtactggatgacgaccaatatcgccagcttgccgccgtcgctcacagtctggagatggg<br>ggtgctgaccgaagtcagtaatgaagaggaacaggagcgcgccattgcattgggagcaaaggt<br>cgttggcatcaacaaccgcgatctgcgtgatttgtcgattgatctcaaccgtacccgcgagcttgc<br>gccgaaactggggcacaacgtgacggtaatcagcgaatccggcatcaatacttacgctcaggtg<br>cgcgagttaagccacttcgctaacggliticctgattggttcggcgttgatggcccatgacgatttgc<br>acgccgccgtgcgccgggtgttgctgggtgagaataaagtatgtggcctgacgcgtgggcaag<br>atgctaaagcagcttatgacgcgggcgcgatttacggtgggttgattllitgttgcgacatcaccgc<br>gttgcgtcaacgttgaacaggcgcaggaagtgatggctgcggcaccgttgcagtatgttggcgt<br>gttccgcaatcacgatattgccgatgtggtggacaaaagctaaggtgttatcgctggcggcagtgc<br>aactgcatggtaatgaagaacagctgtatatcgatacgctgcgtgaagctctgccagcacatgttg<br>ccatctggaaagcattaagcgtcggtgaaacctgcccgcccgcgagtacagcacgttgataaa<br>tatgttttagacaacggccagggtggaagcgggcaacgttttgactggtcactattaaatggtcaa<br>tcgcttggcaacgttctgctggcggggggcttaggcgcagataactgcgtggaagcggcacaa<br>accggctgcgccggacttgattttaattctgctgtagagtcgcaaccgggcatcaaagacgcacg<br>tcttttggcctcgglittccagacgctgcgcgacaatattacggaaaaggaacaatgacaacattactta<br>accccctattliggtgagtaggcggcatgtacgtgccacaaatcctgatgcctgctctgcgccagct<br>ggaagaagcttttgtcagtgcgcaaaaagatcctgaatttcaggctcagttcaacgacctgctgaa<br>aaactatgccgggcgtccaaccgcgctgaccaaatgccagaacattacagccgggacgaaca<br>ccacgctgtatctcaagcgtgaagatttgctgcacggcggcgcgcataaaactaaccaggtgct<br>ggggcaggcgttgctggcgaagcggatgggtaaaaccgaaatcatcgccgaaaccggtgccg<br>gtcagcatggcgtggcgtcggcccttgccagcgccctgctcggcctgaaatgccgtatttatatg<br>ggtgccaaagacgttgaacgccagtcgcctaacgttttttcgtatgcgcttaatgggtgcggaagt<br>gatcccggtgcatagcggttccgcgacgctgaaagtgcctgtaacgaggcgctgcgcgactg<br>gtccggtagttacgaaaccgcgcactatatgctgggcaccgcagctggcccgcatccttatccg<br>accattgtgcgtgagtttcagcggatgattggcgaagaaaccaaagcgcagattctggaaagag<br>aaggtcgcctgccggatgccgttatcgcctgtgttggcggcggttcgaatgccatcggcatgtttg<br>ctgatttcatcaatgaaaccaacgtcggcctgattgtgtggagccaggtggtcacggtatcgaa<br>actggcgagcacggcgcaccgctaaaacatggtcgcgtgggtatctatttcggtatgaaagcgc<br>cgatgatgcaaaccgaagacgggcagattgaagaatcttactccatctccgccggactggatttc<br>ccgtctgtcggcccacaacacgcgtatcttaacagcactggacgcgctgattacgtgtctattacc<br>gatgatgaagcccttgaagccttcaaaacgctgtgcctgcacgaagggatcatcccggcgctgg<br>aatcctcccacgccctggccatgcgttgaaaatgatgcgcgaaaaaccggataaagagcagct<br>actggtggttaaccttccggtcgcggcgataaagacatcttcaccgttcacgatattligaaagca<br>cgaggggaaatctgatggaacgctacgaatctctgtttgcccagttgaaggagcgcaaagaagg<br>cgcattcgttcattcgtcacgctcggtgatccgggcattgagcagtcattgaaaattatcgatacg<br>ctaattgaagccggtgctgacgcgctggagttaggtatcccctctccgacccactggcggatgg<br>cccgacgattcaaaacgccactctgcgcgcctttgcggcaggtgtgactccggcacaatgllllg<br>aaatgctggcactgattcgccagaaacacccgaccattcccattggcctgttgatgtatgccaatc<br>tggtgtttaacaaaggcattgatgagttttatgcccagtgcgaaaaagtcggcgtcgattcggtgct<br>ggttgccgatgtgccagttgaagagtccggccgcttccgccaggccgcgttgcgtcataatgtcg<br>cacctatcttcatctgcccgccaaatgccgatgacgacctgctgcgccagatagcctcttacggtc<br>gtggttacacctatttgctgtcacgagcaggcgtgaccggcgcagaaaccgccgcgttacc<br>cctcaatcatctggttgcgaagctgaaagagtacaacgctgcacctccattgcagggatttggtat<br>ttccgccccggatcaggtaaaagcagcgattgcaggagctgcgggcgcgatttctggttcg<br>gccattgttaaaatcatcgagcaacatattaatgagcagagaaaatgctggcggcactgaaagt<br>ttttgtacaaccgatgaaagcggcgacgcgcagttaa (SEQ ID NO: 1) |
| trpDCBA | Prokaryotic/ B. subtilis | atgaacagatttctacaattgtgcgttgacggaaaaaacccttactgccggtgaggctgaaacgctg<br>atgaatatgatgatggcagcggaaatgactccttctgaaatgggggggatattgtcaattcttgctc<br>atcggggggagacgccagaagagcttgcgggittlgtgaaggcaatgcgggcacacgctctta<br>cagtcgatggacttcctgatattgttgatacatgcggaacaggggggagacggtatttccactittaa<br>tatctcaacggcctcggcaattgttgcctcggcagctggtgcgaaaatcgctaagcatggcaatc<br>gctctgtctcttctaaaagcggaagcgctgatgglittagaggagctagaggtttctattcaaaccact |

TABLE 1-continued

DNA Sequences

| Operonic sequences | Host/ Sequence origin | Sequence |
|---|---|---|
| | | cccgaaaaggtcaaaagcagcattgaaacaaacaacatgggatttclattgcgccgctttaccatt<br>cgtctatgaaacatgtagcaggtactagaaaagagctaggtttcagaacggtatttaatctgcttgg<br>gccgctcagcaatcctttacaggcgaagcgtcaggtgattggggtctattctgttgaaaaagctgg<br>actgatggcaagcgcactggagacgtttcagccgaagcacgttatgtagtatcaagccgtgacg<br>gtttagatgagcificaattacagcaccgaccgacgtgattgaattaaaggacggagagcgccgg<br>gagtataccgtttcacccgaagatttcggtacacaaatggcagacttgaagatttacaggtgcagt<br>ctccgaaagagagcgcttatctcattcagaatattttgaaaataaaagcagcagttccgctttatct<br>attacgggclittaatgcgggtgctgcgatttacacggcgggaattaccgcctcactgaaggaagg<br>aacggagctggcgttagagacgattacaagcggaggcgctgccgcgcagcttaacgactaa<br>agcagaaagaggaagagatctatgcttgaaaaaatcatcaaacaaaagaaagaagaagtgaaa<br>acactggttctgccggtagagcagccctttcgagaaacgttcatttaaggaggcgctggcaagccc<br>gaatcggtttatcgggttgattgccgaagtgaagaaagcatcgccgtcaaaagggcttattaaag<br>aggattttgtacctgtgcagattgcaaaagactatgaggctgcgaaggcagatgcgatttccgtttt<br>aacagacaccccgttlittcaaggggaaaacagctatttatcagacgtaaagcgtgctgtttcgatt<br>cctgtacttagaaaagatillattgattctcttcaagtagaggaatcaagaagaatcggagcggatg<br>ccatattgttaatcggcgaggtgcttgatccctacaccttcatgaattatatcttgaagcaggtgaa<br>aaggggatggacgtgttagtggaggttcatgatgcatcaacgctagaacaaatattgaaagtgttc<br>acacccgacattctcggcgtaaataatcgaaacctaaaaacgtttgaaacatctgtaaagcagac<br>agaacaaatcgcatctctcgttccgaaagaatccttgcttgtcagcgaaagcggaatcggttctta<br>gaacatttaacatttgtcaatgaacatggggcgcgagctgtacttatcggtgaatcattgatgagac<br>aaacttctcagcgtaaagcaatccatgctttgtttagggagtgaggttgtgaagaaaccggcatta<br>aaatattgcggtattcggtcactaaaggatttgcagcttgcggcggaatcacaggctgattaccta<br>ggatttallittgctgaaagcaaacgaaaagtatctccggaagatgtgaaaaaatggctgaaccaa<br>gttcgtgtcgaaaaacaggttgcaggtgttttttgttaatgaatcaatagagacgatgtcacgtattgc<br>caagagcttgaagctcgacgtcattcagcttcacggtgatgaaaaaccggcggatgctgctgctc<br>ttcgcaagctgacaggctgtgaaatatgaaggcgcttcaccatcaagataacacaactcaaga<br>aatagcccgctttaaagataatgttgacggctttgtgattgattcatctgtaaaagggtctagaggc<br>ggaactggtgttgcattttcttgggaatgtgtgccggaatatcagcaggcggctattggtaaacgc<br>tgctttatcgctggcggcgtgaatccggatagcatcacacgcctattgaaatggcagccagaagg<br>aattgaccttgccagcggaattgaaaaaaacggacaaaaagatcagaatctgatgaggcttttag<br>aagaaaggatgaaccgatatgtatccatatccgaatgaaataggcagatacggtgattaggcgg<br>aaagtttgttccggaaacactcatgcagccgttagatgaaatacaaacagcatttaaacaaatcaa<br>ggatgatcccgcttttcgtgaagagtattataagctgttaaaggactattccggacgcccgactgc<br>attaacatacgctgatcgagtcactgaatacttaggcggcgcgaaaatctatttgaaacgagaag<br>atttaaaccatacaggttctcataaaatcaataatgcgctaggtcaagcgctgcttgctaaaaaaat<br>gggcaaaacgaaaatcattgctgaaaccggtgccggccagcatggtgttgccgctgcaacagtt<br>gcagccaaattcggclittcctgtactgtgttttatgggtgaagaggatgttgcccgccagtctctga<br>acglittccgcatgaagcttcttggagcggaggtagtgcctgtaacaagcggaaacggaacattg<br>aaggatgccacaaatgaggcgatccggtactgggttcagcattgtgaggatcactillatatgatt<br>ggatcagttgtcggcccgcatccttatccgcaagtggtccgtgaatttcaaaaaatgatcggaga<br>ggaagcgaaggatcagttgaaacgtattgaaggcactatgcctgataaagtagtggcatglgtag<br>gcggaggaagcaatgcgatgggtatgtttcaggcatttttaaatgaagatgttgaactgatcggcg<br>ctgaagcagcaggaaaaggaattgatacacctcttcatgccgccactatttcgaaaggaaccgta<br>ggggttattcacggttcattgacttatctcattcaggactgagttcgggcaaattattgagccctactct<br>atttcagccggtctcgactatcctggaatcggtccggagcatgcatatttgcataaaagcggccgt<br>gtcacttatgacagtataaccgatgaagaagcggtggatgcattaaagctilllgtcagaaaaagag<br>gggattttgccggcaatcgaatctgcccatgcgttagcgaaagcattcaaactcgccaaaggaat<br>ggatcgcggtcaactcattctcgtctgtttatcaggccggggagacaaggatgtcaacacattaat<br>gaatgtattggaagaagaggtgaaagcccatgtttaaattggatcttcaaccatcagaaaaattgtt<br>tatcccgtttattacggcgggcgatccagttcctgaggtttcgattgaactggcgaagtcactccaa<br>aaagcaggcgccacagcattggagcttggtgttgcatactctgacccgcttgcagacggtccgg<br>tgatccagcgggcttcaaagcgggcgcttgatcaaggaatgaatatcgtaaaggcaatcgaatta<br>ggcggagaaatgaaaaaaaacggagtgaattattccgattatcctctttacgtattataatcctgtgtt<br>acaattgaacaaagaatacttttttcgctttactgcgggaaaatcatattgacggtctgcttgttccgg<br>atctgccattagaagaaagcaacagccttcaagaggaatgtaaaagccatgaggtgacgtatatt<br>tctttagttgcgccgacaagcgaaagccgtttgaaaaccattattgaacaagccgagggttcgtc<br>tactgtgtatcttctctgggtgtgaccggtgtccgcaatgagttcaattcatccgtgtacccgttcatt<br>cgtactgtgaagaatctcagcactgttccggttgctgtagggttcggtatatcaaaccgtgaacag<br>gtcataaagatgaatgaaattagtgacggtgtcgtagtgggaagtgcgctcgtcagaaaaataga<br>agaattaaaggaccggctcatcagcgctgaaacgagaaatcaggcgctgcaggagtttgagga<br>ttatgcaatggcgtttagcggcttgtacagtttaaaatga (SEQ ID NO: 2) |
| trpDCBA | Prokaryotic/<br>L. lactis | atgaaaacaaggagtcatcaaatgaaaaatgaacttgaaaagtgatgtcaggtcgtgacatgac<br>cgaaaatgaaatgaatatgcttgctaattcaattatccaaggtgaattaagcgaggtccaaattgcc<br>agctilltagtagcattaaaaatgaaaggtgaagcagcaagcgaatttgactggtttggctcgagctt<br>tacaaaaagcagcgattcccattccaacaaatttgacaaatgcgatggacaattgtggaacagga<br>ggcgaccgctcattcagttttaatatttcaaccacagccgclatgattagcagctggtggagtcaa<br>tatggcaaaacacggaaatcgctccattaccagtaaatctggctcggcagacgttcttgaggcctt<br>aggaatcaatctttatttaccagcagaaaagttagctcaaglattgacaaagttggtttagtttttcdtt<br>ttgctcaaaatctccacccagcgatgaaatacttcacgccagtccgcagacaactcgaaattcca<br>acaattatgaacttgactgggccactaatcaatccaattccacttgatacgcaacttcttggtacctc<br>acgtccagatttacttgaattaacagcaaatglittgaaaggctttgggcgtaagcgagcattagtc<br>atcacaggtgaaggcggaatggacgaagcaactcccctttggacttaatcattacgcactittagaa<br>aatgacaaagtgactttgcatgaatttagagcctcagaagttggtatttcagaagttcaactcaatg |

TABLE 1-continued

DNA Sequences

| Operonic sequences | Host/ Sequence origin | Sequence |
|---|---|---|
| | | atattcgtggaggtgaagccccagaaaatgctgaaattttaaaaaatgtccttgaaaatcaaccgt
cagccattlagaaacgaccgttttaaatgccggacttggatttatgccaatggaaaagttgattcc
atcaaatccggagttgaccttgcaagagaagtaattagtacaggagcagctcttaccaagttgcat
gaattacaagcagaacaaattggttaaaaatcttgatggcaaattttgaaatagcagaaaatgaga
gaaaaatatgaacataaaaaaaggaaaatttctagaaacaatcctagcagaaaaacgacttgaaa
ttgctaaaatgccagaagaacaagtaggaaaagttcgtcaaacatacaattttttatgattacttaaaa
gaacattccgaccagcttcaagtgattgccgaagtcaaaaaagcttcgcccagtctaggtgatatt
aacttagaagtggatatcgttgaccaagccaaaaattacgaacaagccggtgccgctatgatttcc
gtcttaactgaccctgtattttttaaaggaaatattgaatatctctgtgaaatttcagaaaatgtccaaa
tcccccaccttgaacaaggatttatcatcgataaaaaacaaatcaatcgggcagtaatgcgggag
caacagttatttactcattgtcgcaglittgaaaatcaatacccaaactccaaaacctctacaact
acgcactttcactaggacttgaagttcttgttgaaacacataataaagcagaacttgagattgctcat
cagcttggagctaaaattattggagttaataatcgtaatttaaaaacctagaagtgatcttacaaat
tcagtagatttgacacccttacttttaaagaagacagtatctacataccgaatcaggcallittagcgc
aaacgaagcccaaaaagttttccgatactttcaatggaatattggttggaacagcactcatgcaatc
agaaaatctagaaaaatctttgaaagatttaaaagtcaaggagaaaacgaatgaaaattaaaatct
gtggcttatctacaaaagaagctgttgatacagctgtagaatctggtgtcacacatctcggttttatt
cttagtccctcaaaacgccaagttgcaccagaaaaaattcttcaaatcacaaacgatgtcccaaaa
acagtcaaaaaagtaggagtilligttgatgaacctattgattligtaaaaaaagccattcaagttgct
caactcgatctggttcagcttcacggaaatgaagatatgaattacattaatcaactagatatttcggt
tattaaagcaataagaccagaccaagaatttaaagaatacgaagatgtaattttattatttgatagtc
cacaagctggaagtggtcaagcatttgattgggactcttggtgaccagcggtctgaaaaataaat
ttttcatcgctggtggacttaatccagaaaatgtagcagctgctattcaacattttccaaatgcctac
ggtgtggatgtttcttctggagtagaaactgacggaattaaaaaccttacaaaaataaaaaactttg
ttcaaaatgcaagccttgcctcatcaaagcaattatttatagaattttaagaatcacaaaaaagcta
aatgaaaataagattatcccttatttaatgggaagtttagcagttgagcaaataatcaattttccaaca
aatcctgatgacattgatattcaactcaaaacgtctgattttgaaaattttgagcaattaacaagtttaa
tggaaaaattaggttatcagcttattgacttacatgagcagaaatttgaaaaagctagtattcatgttg
gctttgcaagtgtggagacccttaaaaactatgccggggttgactatttgaccattcaacaagaaa
gaatggaaaatggcgaaaaatatcatcttccaaatgttgaacaatcccttaaaatctatgaggcag
caaaacgagatgagtggcgaggagggaagcaaaaagattcctttatttcgatgagttaataaag
gaacagaagaggaatgacaatgaatgataatcttattgaagagggtgtagagattcgaaatggtc
tcattattaagtcaattcaaaaagaagatatattagagctttggcaaattagttatggacctaaatctg
atttacattggatgtcttcaacgctccctattttgaggagccaatcctgagttgggaagaattttcaa
gaaaaatatctcttaaaataaattaaccaaatgttgcacttattatctttcaaaatcgaatcattggaat
gctgtcagcttattgggaagacggtaaattacaaaaatggcttgagtttggtatagtgatttatgata
gtaaattgtggggacgtgaaattggacaggatgccttatclattggttgaagcacclattgaaactt
atccgaagattcagcacataggatttacaacttggtcaggaaatcaaggaatgatgagactagga
gaaaaaagtggtctaaaacttgaagggcaaatcagaaaagttagatattggcaagaaacttggta
tgattcaataaaatatggaatitttaagaagaactaaaaaaaataaataaaaaaaatcaaaggagc
aacaacatgacctacaaccaacctaacaacaaaggattttacggccaattcgggggccaattcgt
acctgagacactaatgacagcagtaaaacaattagaagaagcctacgtagatagtaaaaaagac
cctctctacaagcagaacttaaagaattacttaaagactatgttggacgagaaaacccactctatta
tgcaaaacgcttaacagaatatgcgggcggagcaaaaatttatctttaaaagagaagacctaaacc
atacaggagcacacaaaattaacaatgccctcggacaagtcctccttgccaaaaaaatgggaaa
aaataaagtcattgctgaaacaggtgcaggccaacacggtgtcgcaagcgcaaccgcggctgc
cctctaggcatggaatgtacgatttatatgggtgaagaagacgttaaaagacaatctctcaatgtct
ttcgcatggaattactcggggcaaaagttcattcagtaactgatggttcacgcgtacttaaagatgc
ggttaatgcagcacttagagcatgggttgctcaagttgaagtacgcattatgtaatggctcagtt
cttggaccacatccatttccacaaattgtgcgtgattatcaagctgttattggacaggaagcgcgtg
cccaattlitagaaaagaaaataaactccagatgctttagtagcttgtgtcggtggaggttcaaat
tctatgggacttttttatcccttcgttaatgatgaatcagttgccatgtatggtgttgaagccgctggc
cttgggattgatacaccacatcatgcggcaacaattactaaaggccgccccggtgttcttcacgg
aacactcatggatgtccttcaagatgaaaatggtcaaatgttagaagccttagtatttttcagccggtt
tagactatccaggaatcggaccagaacactctttatttcaatgctgaggacgagcaaaatatgttga
tattacagatgaagaagcacttgaagglittaaaatcttatctagaactgaaggaattatcccagca
ctagaaagttctcatgctatcgcctatgcagtcaaattagcaaaagaattaggagcagatatctca
atgattgtttgtctttcaggacgtggagataaggatgtggttcaagttaaagaacgacttgaagcag
aaaaagaggtgaaaaaatgaaaactttacaaatgactttaagcaataaaaaaaaataattttattcctt
atatcatggctggcgaccatgaaaaaggcttagaaggtcttaaagaaaccattcaactgcttgag
caagctgggagttccgctattgaaattggcgttccattlicagatccggttgctgatggtccagtcat
cgaacaagcaggtttgcgtgcgttagcaagaaatgtatcactttcaagtattcttgaaacctttaaaa
acaattgatacaaaagttcctctagtaattatgacctatttcaatcccgtttatcagtttggaattgaaa
agtttgttgcagctcttgaaaaaacaccagttaaaggccttatcattcctgatttgcctaaagaacat
gaggactatatcaaaccatttatcaatgataaagatatctgttttagttcctctggtctcattaaccacg
ccactttctcggcaaaaagaacttgtagccgatgctgaaggatttatctatgccgttgcaataaatg
gagtaactgggaaagaaatgcttatagtaaccagcttgaccaacatttaaaagcgttatcttcatt
aacggatgttcctgtlIttgacaggatttggaatttctacattatctgatgtggaccglittaataaagtg
tcctcaggagttattgttggttcaaaaattgttcgtgatttacatgaaggtaaagaaaacgaagttatt
aaatttattgaaaacgcaatcaatttttaa (SEQ ID NO: 3) |

TABLE 1-continued

DNA Sequences

| Operonic sequences | Host/ Sequence origin | Sequence |
|---|---|---|
| trpDCBA | Prokaryotic/ C. glutamicum | atgacttctccagcaacactgaaagttctcaacgcctacttggataacccccactccaaccctggag gaggcaattgaggtgttcaccccgctgaccgtgggtgaatacgatgacgtgcacatcgcagcgc tgcttgccaccatccgtactcgcggtgagcagttcgctgatattgccggcgctgccaaggcgttc ctcgcggcgggctcgtccgttcccgattactggcgcaggtagctagattccgctggtactggtggc gacggtgccaacaccatcaacatcaccaccggcgcatccctgatcgcagcatccggtggagtg aagctggttaagcacggcaaccgttcggtgagctccaagtccggctccgccgatgtgctggaag cgctgaatattccttttgggccttgatgtggatcgtgctgtgaagtggttcgaagcgtccaacttcac cttcctgttcgcacctgcgtacaaccctgcgattgcgcatgtgcagccggttcgccaggcgctga aattccccaccatcttcaacacgcttggaccattgctgtccccggcgcgcccggagcgtcagatc atgggcgtggccaatgccaatcatggacagctcatcgccgaggtcttccgcgagttgggccgta cacgcgcgcttgttgtgcatggcgcaggcaccgatgagatcgcagtccacggcaccaccttggt gtgggagcttaaagaagacggcaccatcgagcattacaccatcgagcctgaggaccttggcctt ggccgctacacccttgaggatctcgtaggtggcctcggcactgagaacgccgaagctatgcgc gctactttcgcgggcaccggccctgatgcacaccgtgatgcgttggctgcgtccgcaggtgcga tgttctacctcaacggcgatgtcgactccttgaaagatggtgcacaaaaggcgctttccttgcttgc cgacggcaccaccaggcatggttggccaagcacgaagagatcgattactcagaaaaggagt cttccaatgactagtaataatctgcccacagtgttggaaagcatcgtcgagggtcgtcgcggaca cctggaggaaattcgcgctcgcatcgctcaagtggatgtggatgcgcttccaaaatccacccgtt ctctgtttgattccctcaaccagggtaggggagggcgcgtttcatcatggagtgcaagtccgca tcgccttctttgggaatgattcgtgagcactaccagccgggtgaaatcgctcgcgtgtactctcgct acgccagcggcatttccgtgctgtgcgagccggatcgttaggtggcgattacgatcacctcgcta ccgttgccgctacctctcatcttccggtgctgtgcaaagacttcatcattgatcctgtccaggtacac gcggcgcgttactttggtgctgatgccatcctgctcatgctctctgtgcttgatgatgaagagtacg cagcactcgctgccgaggctgcgcglittgatctggatatcctcaccgaggttattgatgaggag gaagtcgcccgcgccatcaagctgggtgcgaagatctttggcgtcaaccaccgcaacctgcatg atctgtccattgatttggatcgttcacgtcgcctgtccaagctcattccagcagatgccgtgctcgtg tctgagtctggcgtgcgcgataccgaaaccgtccgccagctaggtgggcactccaatgcattcct cgttggctcccagctgaccagccaggaaaacgtcgatctggcagcccgcgaattagtctacggc cccaacaaagtctgcggactcacctcaccaagtgcagcacaaaccgctcgcgcagcgggtgc gglictacgcgggctcatcttcgaagaggcatcgccacgcaatgtttcacgtgaaacattgcaaa aaatcatcgccgcagagcccaacctgcgctacgtcggtcagccgtcgcacctccgggtaca aggatttgcttgtcgacggcatcttcgccgtacaaatccacgccccactgcaggacagcgtcgaa gcagaaaaggcattgatcgccgcc gttcgtgaagaggttggaccgcaggtccaggictggcgc gcgatctcgatgtccagcccttgggggctgaagtggcagctgcggtggagggtgacgtcgat aagctaattcttgatgccatgaaggtggcagcggggaagtattcgactgggctacggtgccgg ccgctgtgaaggcaaagtctcttgctcgcgggaggcatctctccggacaacgctgcgcaggcact cgctgtgggctgcgcaggittggacatcaactctggcgtggaataccccgccggtgcaggcac gtgggctggggcgaaagacgccggcgcgctgctgaaaattacgcgaccatctccacattccatt actaaaggittaaataggatcatgactgaaaaagaaaacttgggcggctccacgctgctgcctgc atacttcggtgaattcggcggccagttcgtcgcgggaatccctcctgcctgctctcgaccagctgg agaaggccttcgttgacgcgaccaacagcccagagttccgcgaagaactcggcggctacctcc gcgattacctcggccgcccaaccccgctgaccgaatgctccaacctgccactcgcaggcgaag gcaaaggctttgcgcggatcttcctcaagcgcgaagacctcgtccacggcggtgcacacaaaa ctaaccaggtgatcggccaggtgctgcttgccaagcgcatgggcaaaacccgcatcatcgcag agaccggcgcaggccagcacggcaccgccaccgctctcgcatgtgcgctcatgggcctcgag tgcgttgtctacatgggcgccaaggacgttgcccgccagcagcccaacgtctaccgcatgcagc tgcacggcgcgaaggtcatccccgtggaatctggttccggcaccctgaaggagcgcgtgaatg aagcgctgcgcgattggaccgcaaccttccacgagtcccactacttctcggcaccgccgccg gcccgcacccattcccaaccatcgtcgtgaattccacaaggtgatctctgaggaagcaaggc acagatgctagagcgcaccggcaagcttcccgacgttgtggtcgcctgtgtcggtggtggctcc aacgccatcggcatgttcgcagacttcattgacgatgaaggtgtagagctcgtcggcgctgagc cagccggtgaaggcctcgactccggcaagcacggcgcaaccatcaccaacgctcagatcggc atcctgcacggcacccgttcctacctgatgcgcaactccgacggccaagtggaagagtcctact ccatctccgccggacttgattaccaggcgtcggcccacagcacgcacacctgcacgccaccg gccgcgccacctacgttggtatcaccgacgccgaagccctccaagcattccagtacctcgcccg ctacgaaggcatcatccccgcactggaatcctcacacgcgttcgcctacgcactcaagcgcgcc aagaccgccgaagaggaaggccagaacttaaccatcctcgtctccctatccggccgtggcgac aaggacgttgaccacgtgcgccgcacccctcgaagaaaatccagaactgatcctgaaggacaac cgatgagccgttacgacgatctttttgcacgcctcgacacggcaggggagggcgcctagttccc ttcatcatgctgagcgacccttcaccagaggaggcMccagatcatctccacagcaatcgaagct ggcgcagatgcactggaacttggcgtaccttttctccgacccccagttgccgatggccccaccgtcg cggaatccacctccgcgcactcgacggcggcgccaccgtagacagcgcactcgagcagatc aagcgcgtgcgcgcagcctacccagaggttcccatcggaatgctcatctacggcaacgttcctttt cacccgtggcttggatcgcttctaccaagagttcgctgaagctggcgcagactccatcctcctgc cagacgtcccagtccgcgaaggcgcaccgliticlgcagcagctgcagcagccggaattgatcc catttacatcgctccggcaaacgccagcgagaaaaccctcgagggtgtctccgccgcatcaaag ggctacatctacgccatctcccgcgacgcgtcaccggcaccgaacgtgaatcatccaccgac ggcctgtccgcagtggtggacaacatcaagaaatttgatggcgcaccatctcttgggcttcgg catctcatccctcagcacgtggcagacgcgattgcagcgggtgcttccggtgcgatcacgggtt tccgcgatcaccaagatcattgcttcccactgcgaaggtgagcacccgaacccgtccaccattcg agatatggacggtttgaagaaggatctcactgagttcatctctgcgatgaaggcagcgaccaaga aggtttag (SEQ ID NO: 4) |

TABLE 2

| Enzyme/ Source Organism | genbank/uniprot number | Sequence |
|---|---|---|
| trpD/ E. coli | P00904 | MADILLLDNIDSFTYNLADQLRSNGHNVVIYRNHIPAQTLIER LATMSNPVLMLSPGPGVPSEAGCMPELLTRLRGKLPIIGICLG HQAIVEAYGGYVGQAGEILHGKASSIEHDGQAMFAGLTNPLP VARYHSLVGSNIPAGLTINAHFNGMVMAVRHDADRVCGFQF HPESILTTQGARLLEQTLAWAQQKLEPANTLQPILEKLYQAQT LSQQESHQLFSAVVRGELKPEQLAAALVSMKIRGEHPNEIAG AATALLENAAPFPRPDYLFADIVGTGGDGSNSINISTASAFVA AACGLKVAKHGNRSVSSKSGSSDLLAAFGINLDMNADKSRQ ALDELGVCFLFAPKYHTGFRHAMPVRQQLKTRTLFNVLGPLI NPAHPPLALIGVYSPELVLPIAETLRVLGYQRAAVVHSGGMD EVSLHAPTIVAELHDGEIKSYQLTAEDFGLTPYHQEQLAGGTP EENRDILTRLLQGKGDAAHEAAVAANVAMLRLHGHEDLQ ANAQTVLEVLRSGSAYDRVTALAARG (SEQ ID NO: 5) |
| trpD/ C. glutamicum | P06559 | MTSPATLKVLNAYLDNPTPTLEEAIEVFTPLTVGEYDDVHIAA LLATIRTRGEQFADIAGAAKAFLAAARPFPITGAGLLLDSAGTG GDGANTINITTGASLIAASGGVKLVKHGNRSVSSKSGSADVLE ALNIPLGLDVDRAVKWFEASNFTFLFAPAYNPAIAHVQPVRQ ALKFPTIFNTLGPLLSPARPERQIMGVANANHGQLIAEVFREL GRTRALVVHGAGTDEIAVHGTTLVWELKEDGTIEHYTIEPED LGLGRYTLEDLVGGLGTENAEAMRATFAGTGPDAHRDALAA SAGAMFYLNGDVDSLKDGAQKALSLLADGTTQAWLAKHEEI DYSEKESSND (SEQ ID NO: 6) |
| trpD* feedback resistant (S149F, A161E)/ C. glutamicum | P06559* | MTSPATLKVLNAYLDNPTPTLEEAIEVFTPLTVGEYDDVHIAA LLATIRTRGEQFADIAGAAKAFLAAARPFPITGAGLLLDSAGTG GDGANTINITTGASLIAASGGVKLVKHGNRSVSSKSGSADVLE ALNIPLGLDVDRAVKWFEAFNFTFLFAPAYNPEIAHVQPVRQ ALKFPTIFNTLGPLLSPARPERQIMGVANANHGQLIAEVFREL GRTRALVVHGAGTDEIAVHGTTLVWELKEDGTIEHYTIEPED LGLGRYTLEDLVGGLGTENAEAMRATFAGTGPDAHRDALAA SAGAMFYLNGDVDSLKDGAQKALSLLADGTTQAWLAKHEEI DYSEKESSND (SEQ ID NO: 7) |
| trpC/ E. coli | P00909 | MQTVLAKIVADKAIWVETRKEQQPLASFQNEVQPSTRHFYDA LQGARTAFILECKKASPSKGVIRDDFDPARIAAIYKHYASAISV LTDEKYFQGSFDFLPIVSQIAPQPILCKDFIIDPYQIYLARYYQA DACLLMLSVLDDEQYRQLAAVAHSLEMGVLTEVSNEEELER AIALGAKVVGINNRDLRDLSIDLNRTRELAPKLGHNVTVISES GINTYAQVRELSHFANGFLIGSALMAHDDLNAAVRRVLLGEN KVCGLTRGQDAKAAYDAGAIYGGLIFVATSPRCVNVEQAQE VMAAAPLQYVGVFRNHDIADVADKAKVLSLAAVQLHGNED QLYIDNLREALPAHVAIWKALSVGETLPARDFQHIDKYVFDN GQGGSGQRFDWSLLNGQTLGNVLLAGGLGADNVCEAAQTG CAGLDFNSAVESQPGIKDARLLASVFQTLRAY (SEQ ID NO: 8) |
| trpC/ C. glutamicum | P06560 | MTSNNLPTVLESIVEGRRGHLEEIRARIAHVDVDALPKSTRSL FDSLNQGRGGARFIMECKSASPSLGMIREHYQPGEIARVYSRY ASGISVLCEPDRFGGDYDHLATVAATSHLPVLCKDFIIDPVQV HAARYFGADAILLMLSVLDDEEYAALAAEEAARFDLDILTEVI DEEEVARAIKLGAKIFGVNHRNLHDLSIDLDRSRRLSKLIPAD AVLVSESGVRDTETVRQLGGHSNAFLVGSQLTSQENVDLAAR ELVYGPNKVCGLTSPSAAQTARAAGAVYGGLIFEEASPRNVS RETLQKIIAAEPNLRYVAVSRRTSGYKDLLVDGIFAVQIHAPL QDSVEAEKALIAAVREEVGPQVQVWRAISMSSPLGAEVAAA VEGDVDKLILDAHEGGSGEVFDWATVPAAVKAKSLLAGGISP DNAAQALAVGCAGLDINSGVEYPAGAGTWAGAKDAGALLK IFATISTPHY (SEQ ID NO: 9) |
| trpB/ E. coli | P0A879 | MTTLLNPYFGEFGGMYVPQILMPALRQLEEAFVSAQKDPEFQ AQFNDLLKNYAGRPTALTKCQNITAGTNTTLYLKREDLLHGG AHKTNQVLGQALLAKRMGKTEIIAAETGAGQHGVASALASAL LGLKCRIYMGAKDVERQSPNVFRMRLMGAEVIPVHSGSATL KDACNEALRDWSGSYETAHYMLGTAAGPHPYPTIVREFQRM IGEETKAQILEREGRLPDAVIACVGGGSNAIGMFADFINETNV GLIGVEPGGHGIETGEHGAPLKHGRVGIYFGMKAPMMQTED GQIEESYSISAGLDFPSVGPQHAYLNSTGRADYVSITDDEALE AFKTLCLHEGIIPALESSHALAHALKMMRENPDKEQLLVVNL SGRGDKDIFTVHDILKARGEI (SEQ ID NO: 10) |

TABLE 2-continued

Enzymes

| Enzyme/ Source Organism | genbank/uniprot number | Sequence |
|---|---|---|
| trpB/ C. glutamicum | P06561 | MTEKENLGGSTLLPAYFGEFGGQFVAESLLPALDQLEKAFVD ATNSPEFREELGGYLRDYLGRPTPLTECSNLPLAGEGKGFARI FLKREDLVHGGAHKTNQVIGQVLLAKRMGKTRIIAETGAGQ HGTATALACALMGLECVVYMGAKDVARQQPNVYRMQLHG AKVIPVESGSGTLKDAVNEALRDWTATFHESHYLLGTAAGPH PFPTIVREFHKVISEEAKAQMLERTGKLPDVVVACVGGGSNAI GMFADFIDDEGVELVGAEPAGEGLDSGKHGATITNGQIGILH GTRSYLMRNSDGQVEESYSISAGLDYPGVGPQHAHLHATGR ATYVGITDAEALQAFQYLARYEGIIPALESSHAFAYALKRAKT AEEEGQNLTILVSLSGRGDKDVDHVRRTLEENPELILKDNR (SEQ ID NO: 11) |
| trpA/ E. coli | P00895 | MQTQKPTLELLTCEGAYRDNPTALFHQLCGDRPATLLLESAD IDSKDDLKSLLLVDSALRITALGDTVTIQALSGNGEALLALLD NALPAGVESEQSPNCRVLRFPPVSPLLDEDARLCSLSVFDAFR LLQNLLNVPKEEREAMFFGGLFSYDLVAGFEDLPQLSAENNC PDFCFYLAETLMVIDHQKKSTRIQASLFAPNEEEKQRLTARLN ELRQQLTEAAPPLPVVSVPHMRCECNQSDEEFGGVVRLLQKA IRAGEIFQVVPSRRFSLPCPSPLAAYYVLKKSNPSPYMFFMQD NDFTLFGASPESSLKYDATSRQIEIYPIAGTRPRGRRADGSLDR DLDSRIELEMRTDHKELSEHLMLVDLARNDLARICTPGSRYV ADLTKVDRYSVMHLVSRVVGELRHDLDALHAYRACMNM GTLSGAPKVRAMQLIAEAEGRRRGSYGGAVGYFTAHGDLDT CIVIRSALVENGIATVQAGAGVVLDSVPQSEADETRNKARAV LRAIATAHHAQETF (SEQ ID NO: 12) |
| trpA/ C. glutamicum | P06562 | MSRYDDLFARLDTAGEGAFVPFIMLSDPSPEEAFQIISTAIEAG ADALELGVPFSDPVADGPTVAESHLRALDGGATVDSALEQIK RVRAAYPEVPIGMLIYGNVPFTRGLDRFYQEFAEAGADSILLP DVPVREGAPFSAAAAAGIDPIYIAPANASEKTLEGVSAASKG YIYAISRDGVTGTERESSTDGLSAVVDNIKKFDGAPILLGFGIS SPQHVADAIAAGASGAITGSAITKIIASHCEGEHPNPSTIRDMD GLKKDLTEFISAMKAATKKV (SEQ ID NO: 13) |
| Tryptophan Decarboxylase/ P. cubensis | P0DPA6 | MQVIPACNSAAIRSLCPTPESFRNMGWLSVSDAVYSEFIGELA TRASNRNYSNEFGLMQPIQEFKAFIESDPVVHQEFIDMFEGIQ DSPRNYQELCNMFNDIFRKAPVYGDLGPPVYMIMAKLMNTR AGFSAFTRQRLNLHFKKLFDTWGLFLSSKDSRNVLVADQFDD RHCGWLNERALSAMVKHYNGRAFDEVFLCDKNAPYYGFNS YDDFFNRRFRNRDIDRPVVGGVNNTTLISAACESLSYNVSYD VQSLDTLVFKGETYSLKHLLNNDPFTPQFEHGSILQGFLNVTA YHRWHAPVNGTIVKIINVPGTYFAQAPSTIGDPIPDNDYDPPP YLKSLVYFSNIAARQIMFIEADNKEIGLIFLVFIGMTEISTCEAT VSEGQHVNRGDDLGMFHFGGSSFALGLRKDCRAEIVEKFTEP GTVIRINEVVAALKA (SEQ ID NO: 14) |
| Tryptophan Decarboxylase/ P. cyanescens | A0A4P8WEG8 | MQVLPACQSSALKTLCPSPEAFRKLGWLPTSDEVYNEFIDDLT GRTCNEKYSSQVTLLKPIQDFKTFIENDPIVYQEFISMFEGIEQS PTNYHELCNMFNDIFRKAPLYGDLGPPVYMIMARIMNTQAGF SAFTKESLNFHFKKLFDTWGLFLSSKNSRNVLVADQFDDKHY GWFSERAKTAMMINYPGRTFEKVFICDEHVPYHGFTSYDDFF NRRFRDKDTDRPVVGGVTDTTLIGAACESLSYNVSHNVQSLD TLVIKGEAYSLKHLLHNDPFTPQFEHGSIIQGFLNVTAYHRWH SPVNGTIVKIVNVPGTYFAQAPYTIGSPIPDNDRDPPPYLKSLV YFSNIAARQIMFIEADNKDIGLIFLVFIGMTEISTCEATVCEGQH VNRGDDLGMFHFGGSSFALGLRKDSKAKILEKFAKPGTVIRIN ELVASVRK (SEQ ID NO: 15) |
| Tryptophan Decarboxylase/ P. cyanescens | PPQ80975 | MQVLTACYTSTLKSLLPSFDAFRSMGWLPVSDKTYNEWIGDL RSRASDKNYTSQVGLIQPIKDFKAFIESDPVVHQEFITMFEGIE ESPRNYEELCHMFNDIFRKAPVYGDLGPPVYMVMARIMNTQ AGFSAFTKQSLNSHFKRLFDTWGVFLSSKESRYVLVTDQFDD NHYGWLSDRAKSAMVKHYYGRTFEQVFICDEHAPYHGFQSY DDFFNRRFRDRDIDRPVVGGIENTTLISAACESLSYNVCHDLQ SLDTLVFKGESYSLKHLLNDDPFARQFEHGSILQGFLNVTAYH RWHAPVNGTILKIINVPGTYFAQAPHTIGDSLDSDHPPYLKSL AYFSNIAARQIMFIEADNKDIGLIFLVFIGMTEISTCEATVSEGQ HVNRGDDLGMFHFGGSSFALGLRKDCKAEIFERFAEQGTVIKI NEVVAAVKD (SEQ ID NO: 16) |

TABLE 2-continued

Enzymes

| Enzyme/ Source Organism | genbank/uniprot number | Sequence |
|---|---|---|
| Tryptophan Decarboxylase/ G. dilepis | PPQ70875 | MAKTLRPTAQAFRELGWLPASDGVYNKFMKDLTNRASNEN HLCHVALLQPIQDFKTFIENDPVVYQEFVCMFEGIEESPRNYH ELCNMFNEIFRRAPYYGDLGPPVYMAMAKIMNTRAGFSAFTR ESLNFHFKRLFDTWGLFLSSPASRDVLVADKFDSKHYGWFSE PAKAAMMAQYDGRTFEQVFICDETAPYHGFKSYDDFFNRKF RAMDIDRPVVGGIANTTLIGSPCEALSYNVSDDVHSLETLYFK GEGYSLRHLLHDDPSTEQFEHGSIIQGFLNITGYHRWHAPVSG TIMKIVDVPGTYFAQAPSTIGDPFPVNDYDPQAPYLRSLAYFS NIAARQIIFIQADNEDIGLIYLILIGMTEVSTCEALVCPGQHVER GDDLGMFHFGGSSFALGLRKNSKAAILEELKTQGTVIKVNDV IAAVQA (SEQ ID NO: 17) |
| Tryptophan Decarboxylase/ H. sapiens | P20711 | MNASEFRRRGKEMVDYMANYMEGIEGRQVYPDVEPGYLRP LIPAAAPQEPDTFEDIINDVEKIIMPGVTHWHSPYFFAYFPTAS SYPAMLADMLCGAIGCIGFSWAASPACTELETVMMDWLGK MLELPKAFLNEKAGEGGGVIQGSASEATLVALLAARTKVIHR LQAASPELTQAAIMEKLVAYSSDQAHSSVERAGLIGGVKLKA IPSDGNFAMRASALQEALERDKAAGLIPFFMVATLGTTTCCSF DNLLEVGPICNKEDIWLHVDAAYAGSAFICPEFRHLLNGVEFA DSFNFNPHKWLLVNFDCSAMWVKKRTDLTGAFRLDPTYLKH SHQDSGLITDYRHWQIPLGRRFRSLKMWFVFRMYGVKGLQA YIRKHVQLSHEFESLVRQDPRFEICVEVILGLVCFRLKGSNKV NEALLQRINSAKKIHLVPCHLRDKFVLRFAICSRTVESAHVQR AWEHIKELAADVLRAERE (SEQ ID NO: 18) |
| Tryptophan Decarboxylase/ B. atrophaeus | I0DFJ0 | MSENLQLSAEEMRQLGYQAVDLIIDHMNHLKSKPVSETIDSDI LRNKLTESIPENGSDPKELLHFLNRNVFNQITHVDHPHFLAFV PGPNNYVGVVADFLASGFNVFPTAWIAGAGAEQIELTTINWL KSMLGFPDSAEGLFVSGGSMANLTALTVARQAKLNNDIENA VVYFSDQTHFSVDRALKVLGFKHHQICRIETDEHLRISVSALK KQIKEDRTKGKKPFCVIANAGTTNCGAVDSLNELADLCNDED VWLHADGSYGAPAILSEKGSAMLQGIHRADSLTLDPHKWLF QPYDVGCVLIRNSQYLSKTFRMMPEYIKDSETNVEGEINFGEC GIELSRRFRALKVWLSFKVFGVAAFRQAIDHGIMLAEQVEAF LGKAKDWEVVTPAQLGIVTFRYIPSELASTDTINEINKKLVKEI THRGFAMLSTTELKEKVVIRLCSINPRTTTEEMLQIMMKIKAL AEEVSISYPCVAE (SEQ ID NO: 19) |
| Tryptophan Decarboxylase/ C. roseus | P17770 | MGSIDSTNVAMSNSPVGEFKPLEAEEFRKQAHRMVDFIADYY KNVETYPVLSEVEPGYLRKRIPETAPYLPEPLDDIMKDIQKDII PGMTNWMSPNFYAFFPATVSSAAFLGEMLSTALNSVGFTWV SSPAATELEMIVMDWLAQILKLPKSFMFSGTGGGVIQNTTSES ILCTIIAARERALEKLGPDSIGKLVCYGSDQTHTMFPKTCKLA GIYPNNIRLIPTTVETDFGISPQVLRKMVEDDVAAGYVPLFLC ATLGTTSTTATDPVDSLSEIANEFGIWIHVDAAYAGSACICPEF RHYLDGIERVDSLSLSPHKWLLAYLDCTCLWVKQPHLLLRAL TTNPEYLKNKQSDLDKVVDFKNWQIATGRKFRSLKLWLILRS YGVVNLQSHIRSDVAMGKMFEEWVRSDSRFEIVVPRNFSLVC FRLKPDVSSLHVEEVNKKLLDMLNSTGRVYMTHTIVGGIYML RLAVGSSLTEEHHVRRVWDLIQKLTDDLLKEA (SEQ ID NO: 20) |
| Tryptamine n-methyl-transferase/ P. cubensis | ASU62238.1 | MHIRNPYRTPIDYQALSEAFPPLKPFVSVNADGTSSVDLTIPEA QRAFTAALLHRDFGLTMTIPEDRLCPTVPNRLNYVLWIEDIFN YTNKTLGLSDDRPIKGVDIGTGASAIYPMLACARFKAWSMVG TEVERKCIDTARLNVVANNLQDRLSILETSIDGPILVPIFEATEE YEYEFTMCNPPFYDGAADMQTSDAAKGFGFGVGAPHSGTVI EMSTEGGESAFVAQMVRESLKLRTRCRWYTSNLGKLKSLKEI VGLLKELEISNYAINEYVQGSTRRYAVAWSFTDIQLPEELSRP SNPELSSLF (SEQ ID NO: 21) |
| Tryptamine n-methyl-transferase/ P. cyanescens | PPQ83230.1 | MHIRNPYRSPIDYQALVEAFPPLRPYVTVNQDNTTSIDLTVPE VQRLYTAALLHRDFGLVIDLPEDRLCPTLLTRTPRLNYVLWV EDILKVTNTALGLSEDRPVKGIDIGTGAAAIYPMLACARFKTW SMIGTEIDRKCIDTARVNVLTNNLQDRLSIIETSIDGPILVPIFEA TTDYEYDFTMCNPPFYDGAADMQTSDAAKGFGFGVNAPHSG TVIEMSTEGGESAFVAQMVRESLDHRTCRWFTSNLGKLKSL HEIVGLLREHQISNYAINEYVQGTTRRYAIAWSFTNIRLPEDLT RPSNPELSSLF (SEQ ID NO: 22) |

TABLE 2-continued

Enzymes

| Enzyme/ Source Organism | genbank/uniprot number | Sequence |
|---|---|---|
| Tryptamine n-methyl-transferase/ P. cyanescens | PPQ80976.1 | MHNRNPYRDVIDYQALAEAYPPLKPHVTVNADNTASIDLTIP EVQRQYTAALLHRDFGLTITLPEDRLCPTVPNRLNYVLWIEDI FQCTNKALGLSDDRPVKGVDIGTGASAIYPMLACARFKQWS MIATEVERKCIDTARLNVLANNLQDRLSILEVSVDGPILVPIFD TFERATSDYEFEFTMCNPPFYDGAADMQTSDAAKGFGFGVN APHSGTVIEMATEGGEAAFVAQMVRESMKLQTRCRWFTSNL GKLKSLHEIVALLRESQITNYAINEYVQGTTRRYALAWSFTDI KLTEELYRPSNPELGPLCSTFV (SEQ ID NO: 23) |
| Tryptamine n-methyl-transferase/ G. dilepis | PPQ70884.1 | MHIRNPYLTPPDYEALAEAFPALKPYVTVNPDKTTTIDFAIPE AQRLYTAALLYRDFGLTITLPPDRLCPTVPNRLNYVLWIQDIL QITSAALGLPEARQVKGVDIGTGAAAIYPILGCSLAKNWSMV GTEVEQKCIDIARQNVISNGLQDRITITANTIDAPILLPLFEGDS NFEWEFTMCNPPFYDGAADMETSQDAKGFGFGVNAPHTGTV VEMATDGGEAAFVSQMVRESLHLKTRCRWFTSNLGKLKSLH EIVGLLREHQITNYAINEYVQGTTRRYAIAWSFTDLRLSDHLP RPPNPDLSALF (SEQ ID NO: 24) |
| Tryptamine n-methyl-transferase/ H. sapiens | O95050 | MKGGFTGGDEYQKHFLPRDYLATYYSFDGSPSPEAEMLKFNL ECLHKTFGPGGLQGDTLIDIGSGPTIYQVLAACDSFQDITLSDF TDRNREELEKWLKKEPGAYDWTPAVKFACELEGNSGRWEEK EEKLRAAVKRVLKCDVHLGNPLAPAVLPLADCVLTLLAMEC ACCSLDAYRAALCNLASLLKPGGHLVTTVTLRLPSYMVGKR EFSCVALEKEEVEQAVLDAGFDIEQLLHSPQSYSVTNAANNG VCFIVARKKPGP (SEQ ID NO: 25) |
| Tryptamine n-methyl-transferase/ A. sp. ANC 4654 | WP_086164675.1 | MIYKFYQQHIFPHLLNQVMQTPSLMDQRRQLLLPIAGDVLEIG FGTGVNLPFYQNVETLYALEPNADLYQLAAKRIHESTIHVQHI QAYAEKLPFADASLDHIVSTWTLCSIENLAQALIEMYRVLKPN GTLHLVEHVQYQDNAKLQHLQNLLTPIQKRLADGCHLNRNIE QALRDAHFDFTEQHYFAAQGIPKLAQRMFFARAQKQPE (SEQ ID NO: 26) |
| Tryptamine benzoyl transferase/ O. sativa subsp. japonica | A0A1L2EH62 | MEITS SAMLKTTTTPPHPLAGEKVPLSAFDRAAFDVFVPLVFA YRAPAPS SEAVKEGLRVAVAAYPLVSGRIAVDGQGRRRRRR VLHVNNEGVLVLDATVEVDLDAVLAANVATDLYPALPEHSF GAALLQVQLTRFGCGGLVVGLIGHHHVFDGHSMSTFCATWA RAVRDSEAFIVPSPSLDRAITGVPRSPPAPVFDHRSIEFKVGNK SSDSSGAAAAAAVEKIANIGVRFTAKFVAELKARVGGRCSTF ECVLAHAWKKITAARGLKPEEFTRVRVAVNCRRRANPPAPA DLFGNMVLWAFPRLQVRRLLSSSYRDVVGAIRAAVARVDAE YIQSFVDYVEVADARGEELAATAAEPGETLCPDLEVDSWLGF RFHEMDLGTGPPAAVLSPDLPIEGLMILVPVGGDGGGVDLFV ALADDHAQAFEQICYSLEEHAMIHSHL (SEQ ID NO: 27) |
| Serotonin N-acetyl-transferase/ H. sapiens | Q16613 | MSTQSTHPLKPEAPRLPPGIPESPSCQRRHTLPASEFRCLTPED AVSAFEIEREAFISVLGVCPLYLDEIRHFLTLCPELSLGWFEEG CLVAFIIGSLWDKERLMQESLTLHRSGGHIAHLHVLAVHRAF RQQGRGPILLWRYLHHLGSQPAVRRAALMCEDALVPFYERFS FHAVGPCAITVGSLTFMELHCSLRGHPFLRRNSGC (SEQ ID NO: 28) |
| Dopamine N-acetyl-transferase/ D. melanogaster | Q94521 | MEVQKLPDQSLISSMMLDSRCGLNDLYPIARLTQKMEDALTV SGKPAACPVDQDCPYTIELIQPEDGEAVIAMLKTFFFKDEPLN TFLDLGECKELEKYSLKPLPDNCSYKAVNKKGEIIGVFLNGL MRRPSPDDVPEKAADSCEHPKFKKILSLMDHVEEQFNITFVYP DEELILDGKILSVDTNYRGLGIAGRLTERAYEYMRENGINVYH VLCSSHYSARVMEKLGFHEVFRMQFADYKPQGEVVFKPAAP HVGIQVMAKEVGPAKAAQTKL (SEQ ID NO: 29) |
| Arylalkylamine N-acetyl-transferase/ D. rerio | Q9PVD7 | MMAPQVVSSPFLKPFFLKTPISVSSPRRQRRHTLPASEFRNLTP QDAISVFEIEREAFISVSGECPLTLDEVLVFLGQCPELSMGWFE EGQLVAFIIGSGWDKEKLEQEAMSTHVPDSPTVHIHVLSVHR HCRQQGKGSILLWRYLQYLRCLPGLRRALLVCEEFLVPFYQK AGFKEKGPSAISVAALTFTEMEYQLGGLAYARRNSGC (SEQ ID NO: 30) |
| Tryptamine hydroxycinnamoyltrans-ferase/ O. sativa | Q338X7 | MAAVTVEITRSEVLRPSPASAGGGEMVPLTVFDRAATDGYIP TMFAWDAAAAAALSNDAIKDGLAAVLSRFPHLAGRFAVDER GRKCFRLNNAGARVLEASAAGDLADALAHDVAAHVNQLYP QADKDRVDEPLLQVQLTRYTCGGLVIGAVSHHQVADGQSMS VFFTEWAAAVRTAGAALPTPFLDRSAVAAPRIPPAPAFDHRN VEFRGEGSRSHSYGALPLERMRNLAVHPPPEFVAGLKARVGG |

TABLE 2-continued

Enzymes

| Enzyme/<br>Source<br>Organism | genbank/un<br>iprot<br>number | Sequence |
|---|---|---|
| | | ARCSTFQCLLAHAWKKITAARDLSPKEYTQVRVAVNCRGRA<br>GPAVPTDYFGNMVLWAFPRMQVRDLLSASYAAVVGVIRDA<br>VARVDERYIQSFVDFGEVAAGDELAPTAAEPGTAFCPDLEVD<br>SWIGFRFHDLDFGGGPPCAFLPPDVPIDGLLIFVPSCAAKGGVE<br>MFMALDDQHVEALRQICYSMD (SEQ ID NO: 31) |
| Tryptamine 4-<br>hydroxylase/<br>P. cubensis | P0DPA7.1 | MIAVLFSFVIAGCIYYIVSRRVRRSRLPPGPPGIPIPFIGNMFDM<br>PEESPWLTFLQWGRDYNTDILYVDAGGTEMVILNTLETITDLL<br>EKRGSIYSGRLESTMVNELMGWEFDLGFITYGDRWREERRMF<br>AKEFSEKGIKQFRHAQVKAAHQLVQQLTKTPDRWAQHIRHQI<br>AAMSLDIGYGIDLAEDDPWLEATHLANEGLAIASVPGKFWVD<br>SFPSLKYLPAWFPGAVFKRKAKVWREAADHMVDMPYETMR<br>KLAPQGLTRPSYASARLQAMDLNGDLEHQEHVIKNTAAEVN<br>VGGGDTTVSAMSAFILAMVKYPEVQRKVQAELDALTNNGQI<br>PDYDEEDDSLPYLTACIKELFRWNQIAPLAIPHKLMKDDVYR<br>GYLIPKNTLVFANTWAVLNDPEVYPDPSVFRPERYLGPDGKP<br>DNTVRDPRKAAFGYGRRNCPGIHLAQSTVWIAGATLLSAFNI<br>ERPVDQNGKPIDIPADFTTGFFRHPVPFQCRFVPRTEQVSQSVS<br>GP (SEQ ID NO: 32) |
| Tryptamine 4-<br>hydroxylase/<br>P. cyanescens | A5U62250.1 | MIVLLVSLVLAGCIYYANARRVRRSRLPPGPPGIPLPFIGNMFD<br>MPSESPWLRFLQWGRDYHTDILYLNAGGTEIIILNTLDAITDLL<br>EKRGSMYSGRLESTMVNELMGWEFDLGFITYGERWREERRM<br>FAKEFSEKNIRQFRHAQIKAANQLVRQLIKTPDRWSQHIRHQI<br>AAMSLDIGYGIDLAEDDPWIAATQLANEGLAEASVPGSFWVD<br>SFPALKYLPSWLPGAGFKRKAKVWKEGADHMVNMPYETMK<br>KLTVQGLARPSYASARLQAMDPDGDLEHQEHVIRNTATEVN<br>VGGGDTTVSAVSAFILAMVKYPEVQRQVQAELDALTSKGVV<br>PNYDEEDDSLPYLTACVKEIFRWNQIAPLAIPHRLIKDDVYRG<br>YLIPKNALVYANSWAVLNDPEEYPNPSEFRPERYLSSDGKPDP<br>TVRDPRKAAFGYGRRNCPGIHLAQSTVWIAGATLLSVFNIERP<br>VDGNGKPIDIPATFTTGFFRHPEPFQCRFVPRTQEILKSVSG<br>(SEQ ID NO: 33) |
| Tryptamine 4-<br>hydroxylase/<br>P. cyanescens | PPQ98746.1 | MINLPLSLVLVGCVYYIVSRRIRRSRLPPGPPGIPIPFVGNMYD<br>MPSESPWLTFLQWGREYNDRGLTTIFRVESTMVNKLMGWEF<br>DLGFITYGDRWREERRMFSKEFSEKAIKQFRHSQVKAAHRFV<br>QQLAANGEPSRLPHYIRHQIAAMSLDIGYGVDLAQDDPWLEA<br>AHLANEGLATASVPGTFWIDSFPALKYLPSWFPGAGFKRQAK<br>IWKEAADHMVNMPYERMKKLAPQGLARPSYASARLQAMDP<br>NGDLEYQEQVIKNTASQVNVGGGDTTVSAVSAFILAMVIYPE<br>VQRKVQAELDAVLSNGRIPDYDEENDSMPYLTACVKELFRW<br>NQIAPLAIPHKLVKDDIYRGYLIPKNTLVFANSWAVLNDPEVY<br>PDPSVFRPERYLGPDGKPNDTVRDPRKAAFGYGRRNCPGIHL<br>ALSTVWITAATLLSVFDIERPVDHKGNPIDIPAAFTKGFFRHPE<br>PFQCRFVPRNEDSLKSLSGL (SEQ ID NO: 34) |
| Tryptamine 4-<br>hydroxylase/<br>G. dilepis | PPQ70878.1 | MQGNPAVLLLLLTLTLCVYYAHSRRARRARLPPGPPGIPLPFV<br>GNLFDMPSNSPWLTYLQWGETYQTDIIYLNAGGTEMVILNTL<br>EAITDLLEKRGSIYSGRFESTMVNELMGWDFDLGFITYGERW<br>REERRMFSKEFNEKNIKQFRHAQIRAANLLVGQLTKTPERWH<br>QLIRHQIAAMSLDIGYGIDLLEGDPWLEATQLANEGLAIASVP<br>GSFWVDSLPILKYMPSWFPGAEFKRKAKVWRESTDHMINMP<br>YEKMKKLMVQDLVRPSYASARLQEMDPNGDLQHQEHVIRN<br>TAMEVNVGGADTTVSAVAAFILAMVKYPDVQRKVQAELDA<br>VGCRDELPEFDEDNDALPYLTACVKEIFRWNQVAPLAIPHRL<br>DKDDHYRGYIIPKNALVFANTWAVLNDPSVYPDPSEFRPERY<br>LGPDGKPDPRIRDPRKAAFGYGRRACPGIHLAQSTVWIVGAT<br>LLSVFDIERPMDANGKPIDIPAAFTTGFFRYSIHDCLVVETMHP<br>ANTVCVDIPNPSDADSFLVPKRLSNPHPIIDLPSRNPACQEDGV<br>VALSNAWRSTLPVQDV (SEQ ID NO: 35) |
| P450<br>reductase/S.<br>cerevisiae | NP_011908.1 | MPFGIDNTDFTVLAGLVLAVLLYVKRNSIKELLMSDDGDITA<br>VSSGNRDIAQVVTENNKNYLVLYASQTGTAEDYAKKFSKEL<br>VAKFNLNVMCADVENYDFESLNDVPVIVSIFISTYGEGDFPDG<br>AVNFEDFICNAEAGALSNLRYNMFGLGNSTYEFFNGAAKKAE<br>KHLSAAGAIRLGKLGEADDGAGTTDEDYMAWKDSILEVLKD<br>ELHLDEQEAKFTSQFQYTVLNEITDSMSLGEPSAHYLPSHQLN<br>RNADGIQLGPFDLSQPYIAPIVKSRELFSSNDRNCIHSEFDLSGS<br>NIKYSTGDHLAVWPSNPLEKVEQFLSIFNLDPETIFDLKPLDPT<br>VKVPFPTPTTIGAAIKHYLEITGPVSRQLFSSLIQFAPNADVKE<br>KLTLLSKDKDQFAVEITSKYFNIADALKYLSDGAKWDTVPMQ<br>FLVESVPQMTPRYYSISSSSLSEKQTVHVTSIVENFPNPELPDA<br>PPVGVTTNLLRNIQLAQNNVNIAETNLPVHYDLNGPRKLFA<br>NYKLPVHVRRSNFRLPSNPSTPVIMIGPGTGVAPFRGFIRERVA |

TABLE 2-continued

Enzymes

| Enzyme/ Source Organism | genbank/un iprot number | Sequence |
|---|---|---|
| | | FLESQKKGGNNVSLGKHILFYGSRNTDDFLYQDEWPEYAKKL DGSFEMVVAHSRLPNTKKVYVQDKLKDYEDQVFEMINNGAF IYVCGDAKGMAKGVSTALVGILSRGKSITTDEATELIKMLKTS GRYQEDVW (SEQ ID NO: 36) |
| P450 reductase/A. niger | GAQ41948.1 | MAQLDTLDLVVLAVLLVGSVAYFTKGTYWAVAKDPYASTG PAMNGAAKAGKTRNIIEKMEETGKNCVIFYGSQTGTAEDYAS RLAKEGSQRFGLKTMVADLEEYDYENLDQFPEDKVAVFVLA TYGEGEPTDNAVEFYQFFTGDDVAFESGASADEKPLSKLKYV AFGLGNNTYEHYNAMVRQVDAAFQKLGAQRIGSAGEGDDG AGTMEEDFLAWKEPMWAALSESMDLQEREAVYEPVFCVTE NESLSPEDESVYLGEPTQSHLQGTPKGPYSAHNPFIAPIAESRE LFTVKDRNCLHMEISIAGSNLSYQTGDHIAVWPTNAGAEVDR FLQVFGLEGKRDSVINIKGIDVTAKVPIPTPTTYDAAVRYYME VCAPVSRQFVATLAAFAPDEESKAEIVRLGSDKDYFHEKVTN QCFNIAQALQSITSKPFSAVPFSLLIEGITKLQPRYYSISSSSLVQ KDKISITAVVESVRLPGASHMVKGVTTNYLLALKQKQNGDPS PDDPHGLTYSITGPRNKYDGIHVPVHVRHSNFKLPSDPSRPIIMV GPGTGVAPFRGFIQERAALAAKGEKVGPTVLFFGCRKSDEDF LYKDEWKTYQDQLGDNLKIITAFSREGPQKVYVQHRLREHSE LVSDLLKQKATFYVCGDAANMAREVNLVLGQIIAAQRGLPA EKGEEMVKHMRSSGSYQEDVWS (SEQ ID NO: 37) |
| P450 reductase/P. cyanescens | PPQ81263.1 | MTDPNRTTFSSALHPLAVVSMASSSSDVFVLGLGVVLAALYIF RDQLFAASKPKVAPVSTTKPANGSANPRDFIAKMKQGKKRIV IFYGSQTGTAEEYAIRLAKEAKQKFGLASLVCDPEEYDFEKLD QLPEDSIAFFVVATYGEGEPTDNAVQLLQNLQDDSFEFSNGER KLSGLKYVVFGLGNKTYEHYNLIGRTVDAQLAKMGAVRVGE RGEGDDDKSMEEDYLEWKDGMWDAFAAAMGVEEGQGGDS ADFVVSELESHPPEKVYLGEYSARALTKTKGIHDAKNPLAAPI TVARELFQSVVDRNCVHVEFNIEGSGITYQHGDHVGLWPLNP DVEVERLLCVLGLTEKRDAVISIESLDPALAKVPFPVPTTYAA VLRHYIDVSAVAGRQILGTLSKFAPTPEAEAFLKNLNTNKEEY HNVVANGCLKLGEILQVATGNDITVAPTPGNTTKWPIPFDIIV SAIPRLQPRYYSISSSPKVHPNTIHATVVVLKYENVPTDPIPRK WVYGVGSNFLLNLKHAINKEPVPFITQNGEQRVGVPEYLIAG PRGSYKTESHFKAPIHVRRSTFRLPTNPKSPVIMIGPGTGVAPF RGFVQERVALARRSVEKNGPESLNDWGRISLFYGCRRSDEDF LYKDEWPQYQEELKGKFKLHCAFSRENYKPDGSKIYVQDLI WEDREHIADAILNGKGYVYICGEAKSMSKQVEEVLARILGEA KGGSGAVEGVAEIKLLKERSRLMLDYELAFRKFSQLQFARVA TFAMLRSSFSLQRLFSTSSALRNVQRPIRDHLQKQDAPWEPRV AESAQSVSEEILKAQTPLQVPTNAKATTSDSRTDSREPLTAYD LQLVKKRVREWSEQAMIALRNRADDFTAHTKTTFSQLGLQL NRVTGYEEIEALKRGVVEQEERINVARQAARKAKVAYEEAV VQRNSQREVNDLLQRKSSWMDSDVGRFTTLVRQDHLYEQE EARAKAAVEETEEAVDREFSKLLRTILARYHEEQVWSDKIRS ASTYGSLAALGLNMLVFIMAIVVVEPWKRRRLAQTFERKIEE LSEENGIKLDATMLSIAQQIEQQVNLIGSLKDDISRNAPVIPEP AQEVRAETEIEEETSPFVSLEFLPLSRRQLEVAAVGAGAFASN LWFGFGDDALELLMLSTRANKVPPRNLSRIHMTSFIIKAHEDR PTNSTWKQDLECAFCRIIRGELPASKVYENDKVIAILDIMPLRK GHTLVIPKAHISRLSELPSELASSVGEAVCKVAHALTQALDNT GLNVVCNQEYAQAVPHVHYHVIPAPKFGYPGHGVESTNGVV GGKAPLTHREMHQKEFEAREELDDDDAKVLLKSIRARL (SEQ ID NO: 38) |
| P450 reductase/P. cyanescens | PPQ83917.1 | MSVSEDDHRGLLIVYATETGNAQDAADYIARQCRRIAFQCRV VNIDSFLLPDLLSETIVIFVVSTTGSGVEPRSMTPLWTSLLRGD LPTDTFEDLYFSVFGLGDTAYEKFCWAAKKLSRRLESIGGIEF YMRGEGDEQHPLGIDGALQPWTDGLINKLLEVAPLPPGEEIKP INDVPLPRVLLKDTSKTALNHSADPLKSDLQYHKAIVKKNDRI TAADWYQDVRHLVFDFQDNIQYSPGDVAVIHPVALEHDVDA FLVTMSWQNIADEPPFEIEQAMYDQSLPDHLPPITTLRTLFTRFL DFNAVPRRSFFQYLRYFTSDEREQEKLDEFLSAAGADELYEY CYRVRRTIHEVLSEFRHVKIPKGYIFDVFPPLRPREFSIASSIKT HLHQIHLCVAIVKYRTKLKIPRKGVCTYYLSILKPGDTLLVGIR RGLLRLPGKNDTPVIFIGPGTGIAPMRSAIEQRIANGCHENTLY FGCRSASKDQHYGSEWQAYAANQELKYRSAFSRDGVEGEAR VYVQDLIRQDSERIWDLVGHHKAWVLVSGSSNKMPAAVKD AVAYAVEKYGGLSAEEAKEYVHLMVKEGRLIEECWS (SEQ ID NO: 39) |

TABLE 2-continued

Enzymes

| Enzyme/<br>Source<br>Organism | genbank/un<br>iprot<br>number | Sequence |
|---|---|---|
| P450<br>reductase/*P.*<br>*cyanescens* | PPQ77370.1 | MSLNGSGLLTPSSEVTLSSPSTPVLIYTFPQSNGTRPKSPVYIHI<br>DDPGVQVSTLVEYISSQPENSSSVYIYDVAEQVGFGTSTKQW<br>AKQGLDISPVVDLQTRAGAGLSLVGRLSQGTSIDAVKGTVLT<br>AYTTPSGLALMAPSFAYLPVPSSTTRLIIQVPTVTPVGETLTLS<br>PTLSPLASVWSILPENVAVLLSSSPQQTVDFATLAYKVIDSHIV<br>HLFDHHSSAREIGRTFTPLTTIGKSGLTLQEAVKQAGYEPLEY<br>HGDPEAKTIVVLLNSSLALSLKAAVSVGTSGLGVVVVNVLRP<br>WDEAAIQTIIPSSATIVHVLDDVPNAVTQGSLYVDVFSALWST<br>TPKRSVHSHRITPSQTQKFIAAGGEFLRFVEEVTHIAVSEPSVA<br>SIKKTLFFSVPDSPLALLSRFVQELFLTKRTISSRHLTDYDVYS<br>KPGGISAQRLLISRDKSTDNVPVQAILPLDPNSVGHSDFLGVL<br>DHNLLKTHSLLKHAKKGSIVVVASPWTPDEFSANITYEVAEVI<br>TSRQLSVYTIDVKSIANDLELFIQEQKIEKGEAQVLLFEFVFLR<br>FYLGAAATEQAIIQLMSVLFDDIDLTKFSAAAWLGLKPVVVA<br>LPEVTPSDSPTLKEFEANAIAVETSEGQTVVNGARLSTWHDA<br>AKHLLFPSAFSPPTDPDSLSNPALRPEVPDTTFLVTCTVNKRLT<br>PLEYDRNVFHLEFDTSGTGLKYAIGEALGVHGWNDEQEVLDF<br>CEWYGVDPDRLITIPVIGSDDGKMHTRTVLQALQQQIDLFGRP<br>PKSFYTDLAEYATVDVDRYALRFIGSPEGVSTFKKMSEKDTV<br>SFGDVLKKYKSARPGIERLCELIGDIKPRHYSIASAQSVVGDR<br>VDLLVVTVDWLTPEGSPRYGQCTRYLAGLKIGQKVTVSIKPS<br>VMKLPPNLKQPLIMAGLGTGAAPFRAFLQHLAWLASKGEEIG<br>PVFYYFGSRYQAAEYLYGEEIEAFILGGVITRAGLAFSRDGPK<br>KVYIQHKMLEDSETLAKMLHDDDGVFYLCGPTWPVPDVYEA<br>LVNALVKYKGSDPVKAGEYLESLKEEERYVLEVY (SEQ ID<br>NO: 40) |
| 4-<br>hydroxytrypt-<br>amine kinase/<br>*P. cubensis* | P0DPA8 | MAFDLKTEDGLITYLTKHLSLDVDTSGVKRLSGGFVNVTWRI<br>KLNAPYQGHTSIILKHAQPHMSTDEDFKIGVERSVYEYQAIKL<br>MMANREVLGGVDGIVSVPEGLNYDLENNALIMQDVGKMKT<br>LLDYVTAKPPLATDIARLVGTEIGGFVARLHNIGRERRDDPEF<br>KFFSGNIVGRTTSDQLYQTIIPNAAKYGVDDPLLPTVVKDLVD<br>DVMHSEETLVMADLWSGNILLQLEEGNPSKLQKIYILDWELC<br>KYGPASLDLGYFLGDCYLISRFQDEQVGTTMRQAYLQSYART<br>SKHSINYAKVTAGIAAHIVMWTDFMQWGSEEERINFVKKGV<br>AAFHDARGNNDNGEITSTLLKESSTA (SEQ ID NO: 41) |
| 4-<br>hydroxytrypt-<br>amine kinase/<br>*P. cyanescens* | PPQ83229.1 | MAFDLKTPEGLLLYLTRHLSLDVDPSGVKRLSGGFVNVTWRI<br>RLNAPYQGHTSIILKHAQPHMSSDEDFKIGVERSAYEYQALKV<br>MSANQEVLGGDDSRVSVPEGLHYDVENNALIMQDVGTMKT<br>LLDYATAKPPLSTEIASLVGTEIGAFIARLHNLGRKRRDQPAF<br>KFFSGNIVGRTTADQLYQTIIPNAAKYGINDPLLPTVVKDLVG<br>EVMNSEETLIMADLWSGNILLEFVEGNPSELKKIWLVDWELC<br>KYGPASLDMGYFLGDCYLIARFQDELVGTTMRKAYLKGYAR<br>TAKGTINYSKVTASIGAHLVMWTDFMKWGNYEEREEFVKKG<br>VEALHDAWEDNNDGEITSVLVNEASST (SEQ ID NO: 42) |
| 4-<br>hydroxytrypt-<br>amine kinase/<br>*P. cyanescens* | PPQ98758.1 | MAFDLKTVEGLIVYLTKCLSLEVDSSGVKRLSGGFVNVTWRI<br>RLNAPYQGHTSIILKHAQPHMSTDKDFKIGVERSVYEYQALK<br>VISANREALGGIDSRVSAPEGLHYDVENNALIMQDVGTLKTL<br>MDYVIEKPAISTEMARLIGTEIGDFVARLHSIGRQKRDQPDFK<br>FFSGNIVGRTTADQLYQTILPNTAKYGIDDPLLPTVVKDLVDE<br>AMQSEETLIMADLWTGNILVEFEEGNLSVLKKIWLVDWELCK<br>YGPVRLDMGYFLGDCFLISRFKNEQVAKAMRQAFLQRYNRV<br>SDTPINYSVATTGIAAHIVMWTDFMNWGTEEERKEYVKKGV<br>AGIHDGRNHNVDGEITSILMQEASTA (SEQ ID NO: 43) |
| 4-<br>hydroxytrypt-<br>amine kinase/<br>*G. dilepis* | PPQ70874.1 | MTFDLKTEEGLLVYLTQHLSLDVDLDGLKRLSGGFVNITWRI<br>RLNAPFKGYTNIILKHAQPHLSSDENFKIGVERSAYEYRALKI<br>VSESESPILSGDDNLVFVPQSLHYDVVHNALIVQDVGSLKTLMD<br>YVTARPSLSSEMAKLVGGQIGAFIARLHNIGRENKDHPEFNFF<br>SGNIVGRTTAVQLYETIVPNATKYDIDDPIIPVVVQELIEEVKG<br>SDETLIMADLWGGNILLEFGKDSSDLGKIWVVDWELCKYGPP<br>SLDMGYFLGDCFLLAQFQDEKVATAMRRAYLENYAKIAKVP<br>MDYDRSTTGIGAHLVMWTDFMNWGSDEERKTSVEKGVRAF<br>HDAKRDNKEGEIPSILLRESSRT (SEQ ID NO: 44) |
| Multicopper<br>oxidase/*S.*<br>*cerevisiae* | NP_116612.1 | MLFYSFVWSVLAASVALAKTHKLNYTASWVTANPDGLHEK<br>RMIGFNGEWPLPDIHVEKGDRVELYLTNGFQDNTATSLHFHG<br>LFQNTSLGNQLQMDGPSMVTQCPIVPGQTYLYNFTVPEQVGT<br>FWYHAHMGAQYGDGMRGAFIIHDPEEPFEYDHERVITLSDHY<br>HENYKTVTKEFLSRYNPTGAEPIPQNILFNNTMNVTLDFTPGE<br>TYLFRFLNVGLFVSQYIILEDHEMSIVEVDGVYVKPNFTDSIYL |

TABLE 2-continued

Enzymes

| Enzyme/ Source Organism | genbank/ uniprot number | Sequence |
|---|---|---|
| | | SAGQRMSVLIKAKDKMPTRNYAMMQIMDETMLDVVPPELQ<br>LNQTIQMRYGHSLPEARALNIEDCDLDRATNDFYLEPLIERDL<br>LAHYDHQIVMDVRMVNLGDGVKYAFFNNITYVTPKVPTLTT<br>LLTSGKLASDPRIYGDNINAQLLKHNDIIEVVLNNYDSGRHPF<br>HLHGHNFQIVQKSPGFHVDEAYDESEQDEMTVPYNESAPLQP<br>FPERPMVRDTVVLEPSGHVVLRFRADNPGVWYFHCHVDWHL<br>QQGLASVFIEAPVLLQEREKLNENYLDICKAADIPVVGNAAG<br>HSNDWFDLKGLPRQPEPLPKGFTTEGYLALIISTIIGVWGLYS<br>AQYGIGEVIPNDEKVYHTLREILAENEIEVSRG* (SEQ ID NO: 45) |
| aralkylamine N-acetyl-transferase/ Bos taurus | O02785 | MSTPSIHCLKPSPLHLPSGIPGSPGRQRRHTLPANEFRCLTPKD<br>AAGVFEIEREAFISVSGNCPLNLDEVRHFLTLCPELSLGWFVE<br>GRLVAFIIGSLWDEERLTQESLTLHRPGGRTAHLHALAVHHSF<br>RQQGKGSVLLWRYLQHAGGQPAVRRAVLMCEDALVPFYQR<br>FGFHPAGPCAVVVGSLTFTEMHCSLRGHAALRRNSDR (SEQ ID NO: 46) |
| Tryptamine 5-hydroxylase/ Schistosoma mansoni | O96370 | MISTESDLRRQLDENVRSEADESTKEECPYINAVQSHHQNVQ<br>EMSIIISLVKNMNDMKSIISIFTDRNINILHIESRLGRLNMKKHT<br>EKSEFEPLELLVHVEVPCIEVERLLEELKSFSSYRIVQNPLMNL<br>PEAKNPTLDDKVPWFPRHISDLDKVSNSVLMYGKELDADHP<br>GFKDKEYRKRRMMFADIALNYKWGQQIPIVEYTEIEKTTWGR<br>IYRELTRLYKTSACHEFQKNLGLLQDKAGYNEFDLPQLQVVS<br>DFLKARTGFCLRPVAGYLSARDFLSGLAFRVFYCTQYIRHQA<br>DPFYTPEPDCCHELLGHVPMLADPKFARFSQEIGLASLGTSDE<br>EIKKLATCYFFTIEFGLCRQDNQLKAYGAGLLSSVAELQHALS<br>DKAVIKPFIPMKVINEECLVTTFQNGYFETSSFEDATRQMREF<br>VRTIKRPFDVHYNPYTQSIEIIKTPKSVAKLVQDLQFELTAINE<br>SLLKMNKEIRSQQFTTNKIVTENRSSGS* (SEQ ID NO: 47) |
| Acetylserotonin O-methyl-transferase/ Homo sapiens | P46597 | MGSSEDQAYRLLNDYANGFMVSQVLFAACELGVFDLLAEAP<br>GPLDVAAVAAGVRASAHGTELLLDICVSLKLLKVETRGGKAF<br>YRNTELSSDYLTTVSPTSQCSMLKYMGRTSYRCWGHLADAV<br>REGRNQYLETFGVPAEELFTAIYRSEGERLQFMQALQEVWSV<br>NGRSVLTAFDLSVFPLMCDLGGGAGALAKECMSLYPGCKITV<br>FDIPEVVWTAKQHFSFQEEEQIDFQEGDFFKDPLPEADLYILA<br>RVLHDWADGKCSHLLERIYHTCKPGGGILVIESLLDEDRRGPL<br>LTQLYSLNMLVQTEGQERTPTHYHMLLSSAGFRDFQFKKTGA<br>IYDAILARK (SEQ ID NO: 48) |
| Noribogaine 10-O-methyl-transferase/ Tabernanthe iboga | A0A2Z5P0W7 | DAMKSAELFKAQAHIFKQVFCFTNGASLKCAVQLGIPDAIDN<br>HGKAMTLSELTDALPINPSKAPHIHRLMRILVTAGFFVEERLG<br>NGKEEKANGYALTPSSRLLLKNKPLSLRASALTMLDPVTVKT<br>WNALSEWFQNEDQTAFETAHGKNMWDFFAEDPGLSKKFNES<br>MASDSQLVTEVLVTKCKFVFEGLTSMVDVGGGTGTVAGAIA<br>KTFPSLRCTVFDLPHVVANLEPTENLDFVAGDMFGKIPPANAI<br>FLKWVLHDWNDEDCVKILKNCKRAIPGKEKGGKVIIVDIIME<br>TEKHDIDEFDYAKMCMDMEMLVLCNSKERTEKELAMLVSEA<br>GFSGYKIFPVLGIRSLIEVYP (SEQ ID NO: 49) |

EXAMPLES

These examples are provided for illustrative purposes only and not to limit the scope of the claims provided herein.

Example 1: Detection of 4-Hydroxytryptamine in Engineered Cells

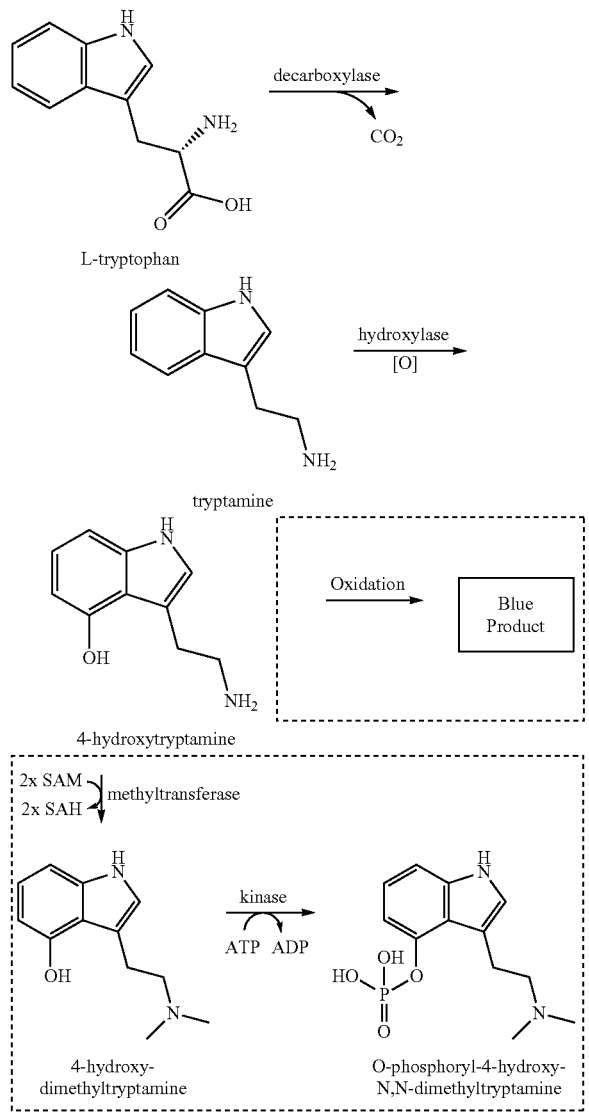

4-hydroxytryptamine can be oxidized to a blue product to screen for high biosynthetic flux through the upstream pathway (blue box). Alternatively, 4-hydroxytryptamine can be employed for conversion to O-phosphoryl-4-hydroxy-N, N-dimethyltryptamine, or psilocybin, by expression of the methyltransferase or kinase.

Example 2. Yeast and Bacterial Strains and Growth Conditions

Single gene expression plasmids were transformed into chemically competent TG1 *E. coli* and multigene plasmids were transformed into TransforMax™ EPI300™ (Epicentre) electrocompetent *E. coli*. Strains were constructed using chemical or electro-competency. Selections were performed on LB containing ampicillin (25 mg/L) and kanamycin (25 mg/L) as indicated. The background strain MG1655 with lambda DE3 (a phage construct that expresses T7 RNA polymerase under the control of a lacUV5 promoter) was used as a host strain and propagated at 37° C. *S. cerevisiae* strain BY4741 (MATa his3Δ1 leu2Δ0 met15Δ0 ura3Δ0) was used for experiments in this study and propagated at 30° C.

*E. coli* cultures were propagated in LB broth (1-liter medium contained 10 grams of tryptone, 5 grams of yeast extract, and 10 grams of sodium chloride). Yeast cultures were grown in YPD (10 g/L Bacto Yeast Extract; 20 g/L Bacto Peptone; 20 g/L D-glucose). Lithium acetate transformation method was used to transform yeast with plasmids containing the respective auxotrophic markers. Selection was performed on synthetic dropout media (6.7 g/L Difco yeast nitrogen base without amino acids; 2 g/L synthetic defined amino acid mix minus the respective autotrophy, without yeast nitrogen base (US Biological); 20 g/L D-glucose or the respective carbon source; 20 g/L BD Difco agar was used for plates). pH was adjusted when appropriate with NaOH or HCl.

Plasmids and Cloning

A hierarchical Golden Gate cloning scheme was used for assembling coding sequence part plasmids, yeast protein expression cassettes and multigene plasmids. All protein coding sequences were synthesized or PCR amplified to omit internal BsaI and BsmBI sites for use in golden gate cloning. The protein coding sequences for fungal pathway enzymes were codon optimized for *E. coli* or *S. cerevisiae* and synthesized by Integrated DNA Technologies (Coralville, Iowa).

Example 3. Production of Substituted Tryptamines by Fed Substituted Indoles and Anthranilates The background strain MG1655 with lambda DE3 is a phage construct that expresses T7 RNA polymerase under the control of a lacUV5 promoter and was used as a host strain. The strain was modified to have the tryptophan biosynthetic pathway (e.g., trpE, trpD, trpC, trpB, and trpA) and tryptophan deaminase (tnaA) knocked out. This genetic material was removed by modified λ red system as described by Datsenko and Wanner (2000). The resulting strain was named bNAB001.

Figure 2:
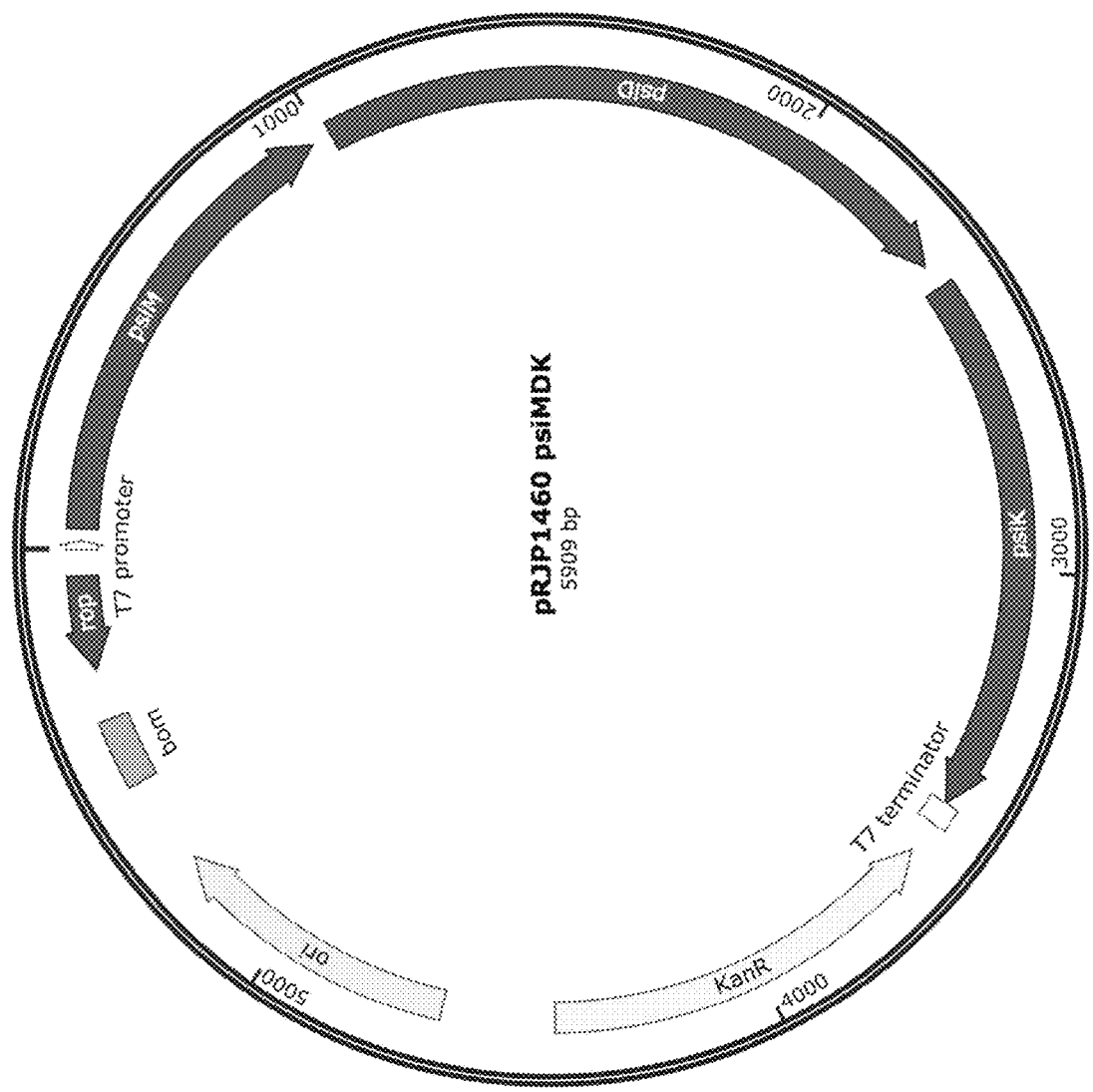
FIG. 2 depicts a non-limiting example of a plasmid map suitable for overexpression of psilocybin synthase (e.g., SEQ ID NO: 21), tryptophan decarboxylase (e.g., SEQ ID NO: 14) and 4-hydroxytryptamine kinase (e.g., SEQ ID NO: 41) in bacteria in accordance with embodiments of the disclosure.
Figure 3:
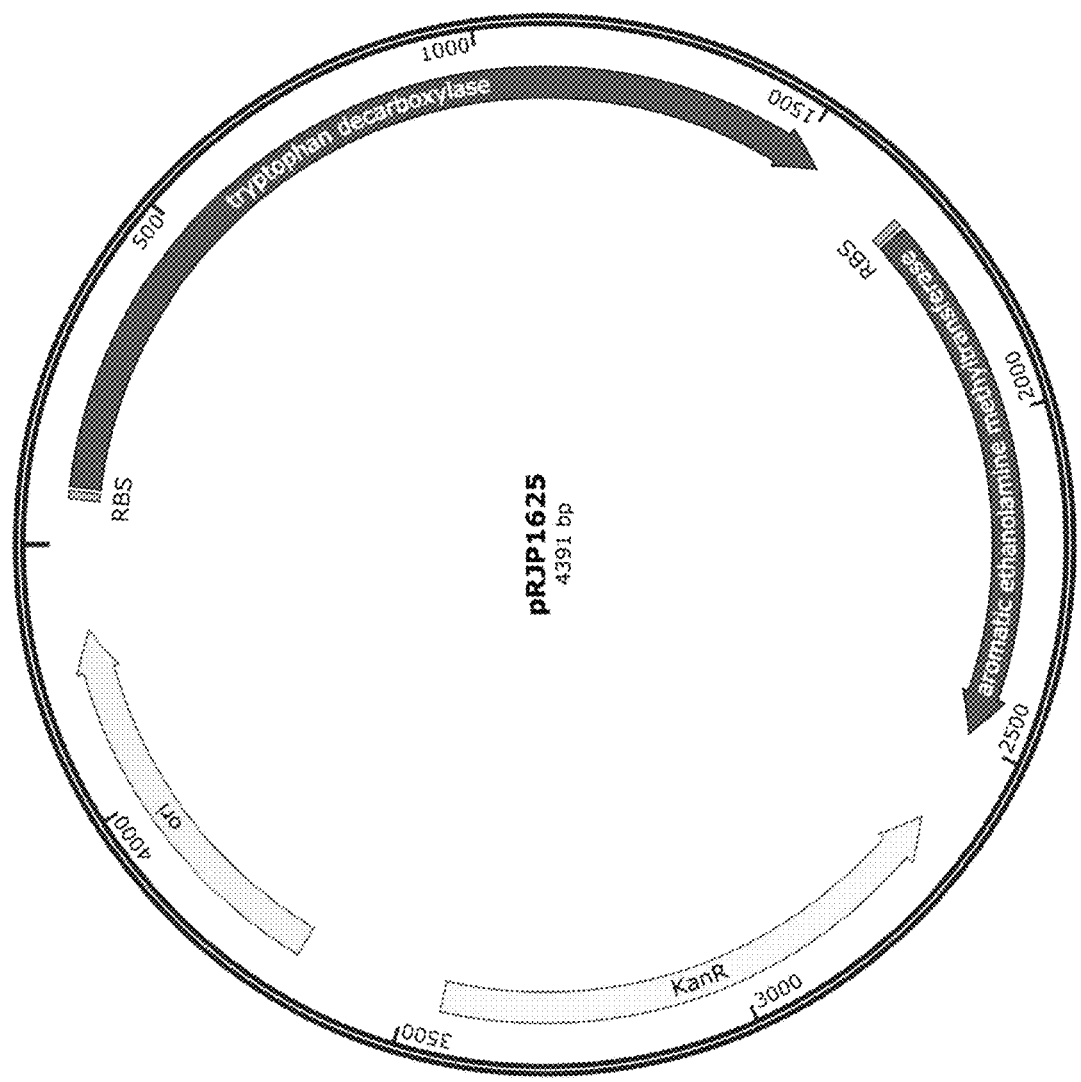
FIG. 3 depicts a non-limiting example of a plasmid map suitable for the production of N-methyl derivatives in bacteria by overexpression of tryptophan decarboxylase (e.g., SEQ ID NO: 19) and ethanolamine methyltransferase (e.g., SEQ ID NO: 25) in accordance with embodiments of the disclosure.

The tryptophan biosynthetic pathway, trpDCBA (SEQ ID NO: 1), was cloned under LacI operon control in an ampicillin resistance plasmid with p15a origin and was named pRJP1376 (FIG. 1). This plasmid was introduced into bNAB001 and resulted in strain bNAB002. Accordingly, the bNAB002 strain, upon isopropyl β-D-1-thiogalactopyranoside (IPTG) induction, allows for expression of trpDCBA operon for substituted tryptophan biosynthesis upon addition of substituted anthranilate and substituted indole addition. To further convert resulting substituted tryptophan compounds into downstream tryptamines, two plasmids were cloned. Coding sequences for tryptophan decarboxylase from *P. cubensis* (psiD, SEQ ID NO: 14) for converting substituted tryptophans to tryptamines; 4-hydroxytryptamine kinase from *P. cubensis* (psiK, SEQ ID NO: 41); and tryptamine N-methyltransferase from *P. cubensis* (psiM, SEQ ID NO: 21) were cloned into a plasmid containing a kanamycin resistance gene and BR322 origin of replication and was named pRJP1460 (FIG. 2). Coding sequences were oriented in a multi-cistronic operon downstream of a T7 promoter sequence. This plasmid was transformed into bNAB002 and the resulting strain was named bNAB003. Coding sequences for tryptophan decarboxylase from *B. atrophaeus* (SEQ ID NO: 19) and aromatic ethanolamine methyltransferase from *H. sapiens* (SEQ ID NO: 25) were cloned downstream of promoter and ribosome binding sequences with a kanamycin resistance gene and BR322 origin of replication sequences to form plasmid pRJP1625 (FIG. 3). The pRJP1625 plasmid was transformed into bNAB002 and the resulting strain was named bNAB004.

Figure 4:
FIG. 4 depicts non-limiting examples of substituted tryptamines produced by engineered bacterial cells fed with substituted anthranilate or indole compounds in accordance with embodiments of the disclosure.

An overnight bNAB003 culture was used to inoculate 1 L of LB (plus kanamycin and ampicillin) culture at 0.1 $OD_{600}$. The culture was grown to $OD_{600}$ of 0.5 and cooled to 18° C. on ice before induction with 0.5 mM of IPTG for expression of trpDCBA pathway proteins and psiMDK pathway proteins. The culture was transferred to a shaker at 18° C. with 200 RPM shaking for 16 hours. The cells were harvested, washed with sterile water, and resuspended in M9 media (0.2% glucose, 40 mM $Na_2HPO_4$, 20 mM $KH_2PO_4$, 1 mM $MgSO_4$, 0.1 mM $CaCl_2$, 0.5 mM IPTG, with added 100 mg/L of L-serine, 2 g/L sodium citrate, and 2 g/L yeast extract). The culture was split into 10 mL cultures in sterile culture tubes. 4 mM of 5-hydroxyindole, 4-hydroxyindole, 7-hydroxyindole, and 4-chloroindole were added to separate tubes. After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min. flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample. In the 5-hydroxyindole fed culture, 5-hydroxytryptamine was detected. In the 4-hydroxyindole culture, 4-hydroxytryptamine, 4-phosphoryloxytryptamine, and 4-phosphoryloxy-N,N-dimethyltryptamine were detected. In the 7-hydroxyindole fed culture, 7-hydroxytryptamine, 7-phosphoryloxytryptamine, and 7-phosphoryloxy-N,N-dimethyltryptamine were detected. In the 4-chloroindole fed culture, 4-chloro-N,N-dimethyltryptamine was detected (see FIG. 4).

An overnight bNAB004 culture was used to inoculate 1 L of LB (plus kanamycin and ampicillin) culture at 0.1 $OD_{600}$. The culture was grown to $OD_{600}$ of 0.5 and cooled to 18° C. on ice before induction with 0.5 mM of IPTG for expression of trpDCBA pathway proteins and psiMDK pathway proteins. The culture was transferred to a shaker at 18° C. with 200 RPM shaking for 16 hours. The cells were harvested, washed with sterile water, and resuspended in M9 media (0.2% glucose, 40 mM $Na_2HPO_4$, 20 mM $KH_2PO_4$, 1 mM $MgSO_4$, 0.1 mM $CaCl_2$, 0.5 mM IPTG, with added 100 mg/L of L-serine, 2 g/L sodium citrate, and 2 g/L yeast extract). The culture was split into 10 mL cultures in sterile culture tubes. 4 mM of 5-hydroxyindole, 4-chloroindole, and 5-bromoanthranilate were added to separate tubes. After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample. In the 5-hydroxyindole fed culture, 5-hydroxytryptamine, 5-hydroxymethyltryptamine, and 5-hydroxy-N,N-dimethyltryptamine were detected. In the 4-chloroindole fed culture, 4-chlorotryptamine and 4-chloro-N,N-dimethyltryptamine were detected. In the 5-bromoanthranilate fed culture, 5-bromotryptamine, 5-bromo-N-methyltryptamine, and 5-bromo-N,N-dimethyltryptamine were detected (see FIG. 4).

Example 4. Production of Substituted Tryptamines by Engineered Yeast

Figure 5:
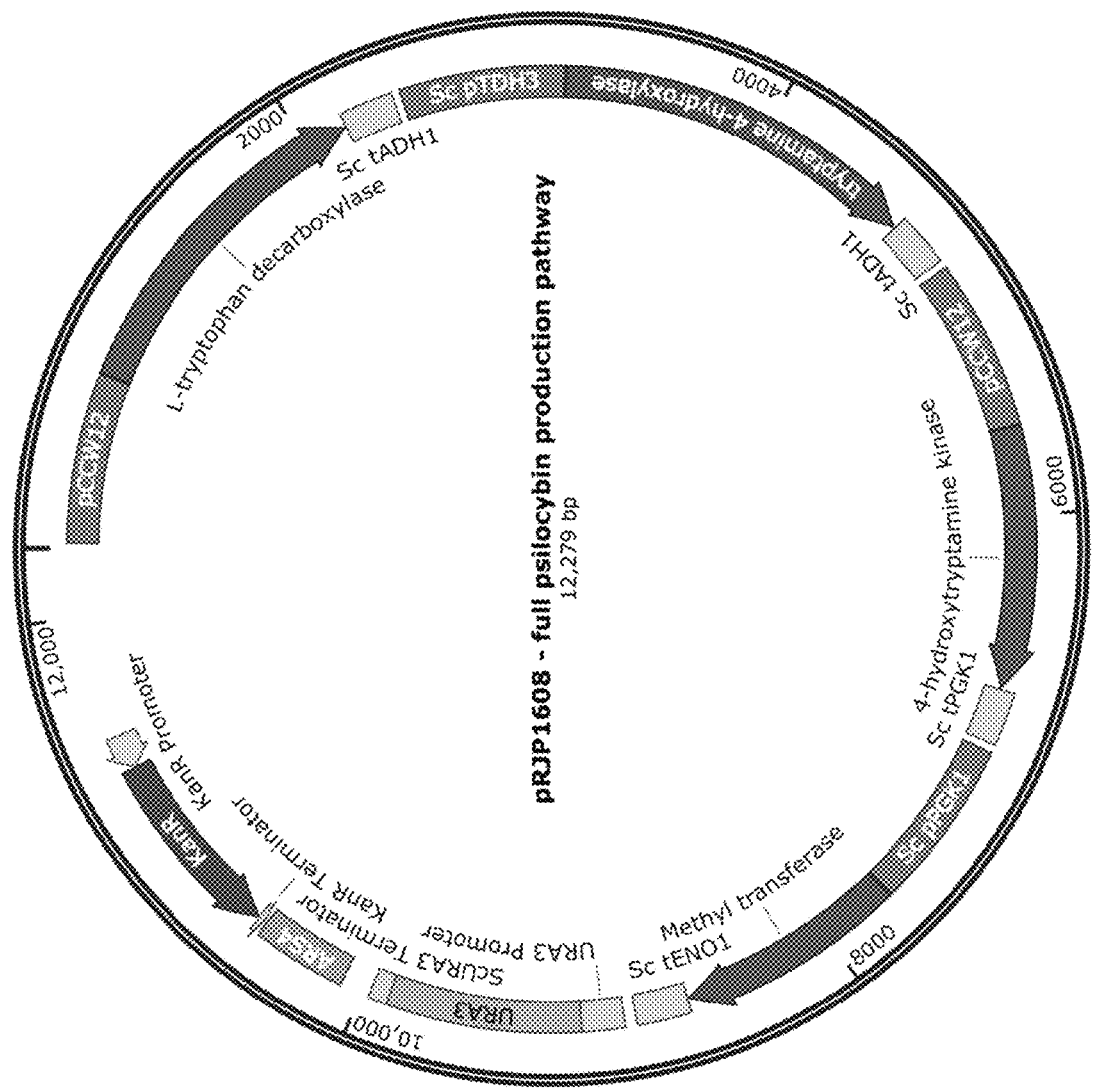
FIG. 5 depicts a non-limiting example of a plasmid map suitable for the production of N-methyl tryptamine derivatives in yeast by overexpression of tryptophan decarboxylase (e.g., SEQ ID NO: 19), 4-hydroxytryptamine kinase (e.g., SEQ ID NO: 41), psilocybin synthase (e.g., SEQ ID NO: 21) and tryptamine 4-hydroxylase (e.g., SEQ ID NO: 33) in accordance with embodiments of the disclosure.
Figure 6:
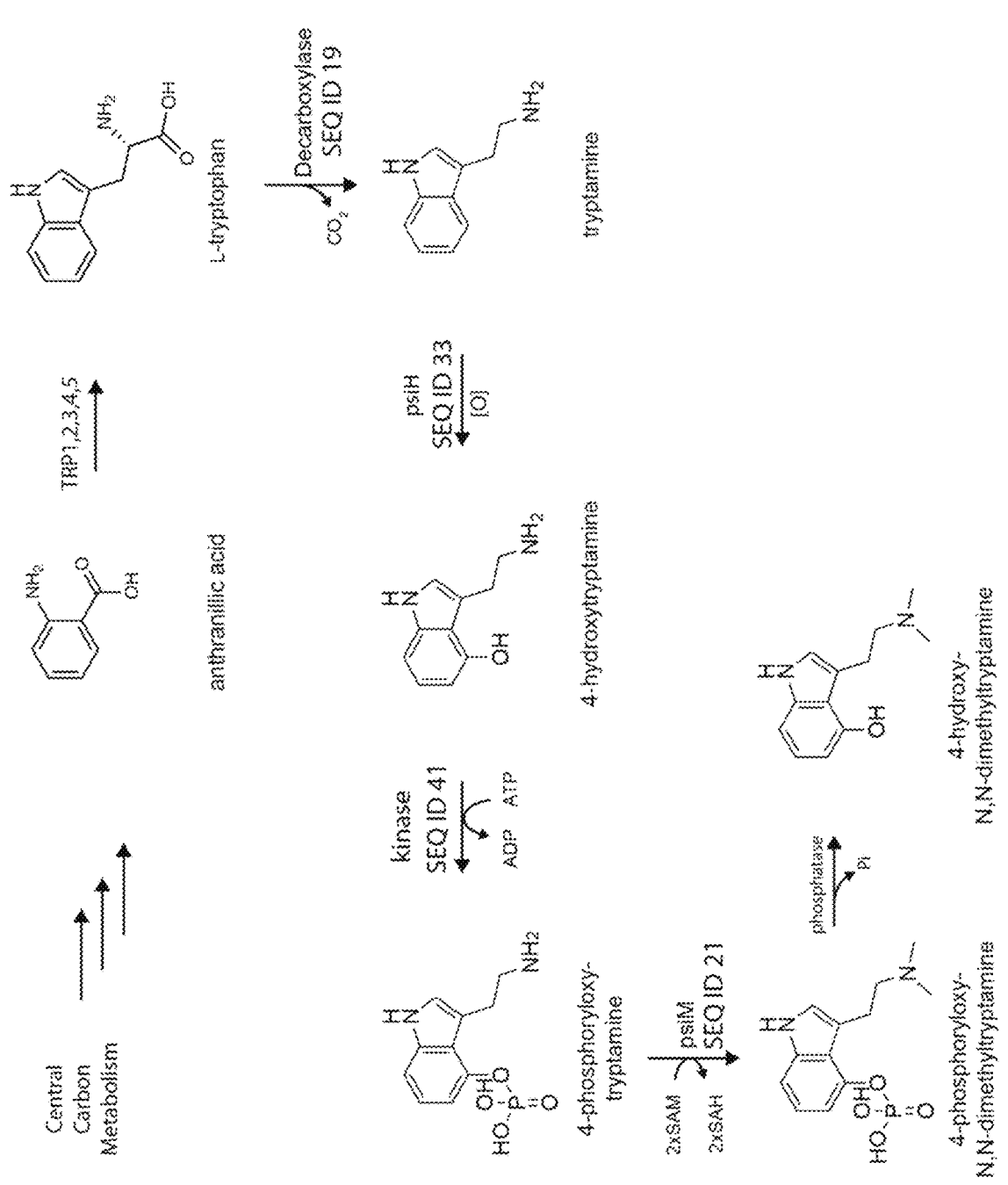
FIG. 6 depicts a non-limiting example of a biosynthetic pathway converting anthranilic acid present in yeast metabolism to tryptamines by enzymes encoded in pRJP1608 in accordance with embodiments of the disclosure.
Figure 7:
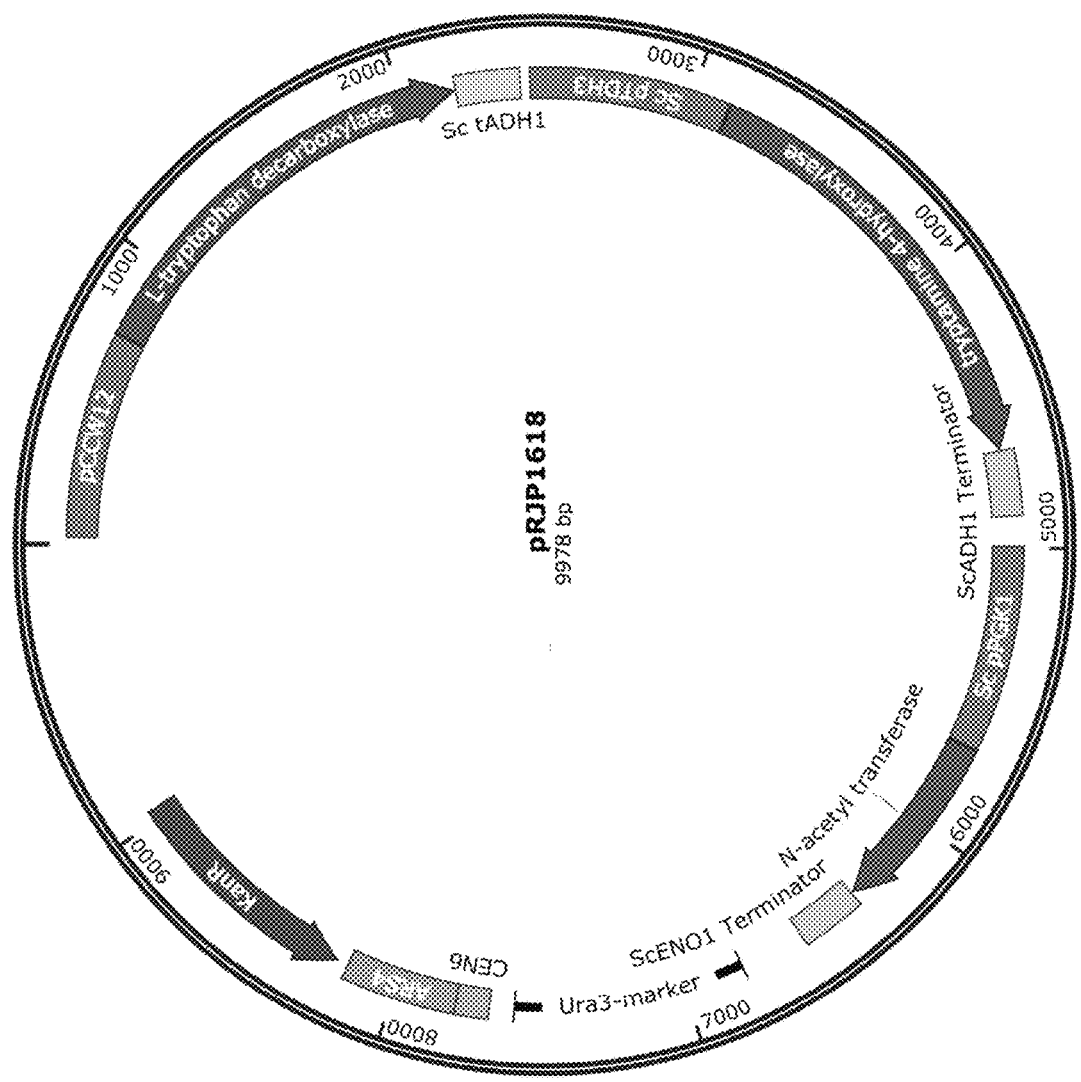
FIG. 7 depicts a non-limiting example of a plasmid map for the production of N-acetyl tryptamine derivatives in yeast by overexpression of tryptophan decarboxylase (e.g., SEQ ID NO: 19), tryptamine 4-hydroxylase (e.g., SEQ ID NO: 33) and N-acetyltransferase (e.g., SEQ ID NO: 28) in accordance with embodiments of the disclosure.

Anthranilate biosynthetically produced from central carbon metabolism (i.e., hydrogen substituted anthranilate) can be metabolized to form substituted tryptamines with genetic modification. Substitutions of the amine position of tryptamine and indole ring were investigated. A multigene plasmid with CEN6/ARS4 replication sequences, URA3 expression cassette and kanamycin resistance was cloned to contain coding sequences for tryptophan decarboxylase from *B. atrophaeus* (SEQ ID NO: 19), tryptophan 4-hydroxylase from *P. cyanescens* (SEQ ID NO: 33), 4-hydroxytryptamine kinase from *P. cubensis* (psiK, SEQ ID NO: 41), and tryptamine N-methyltransferase from *P. cubensis* (psiM, SEQ ID NO: 21) under control of high activity yeast promoter and terminator pairs (e.g., promoters pCCW12, pTDH3, and pPGK1, or terminators tADH1, tPGK1, and tENO1) and was named plasmid pRJP1608 (FIG. 5). The biosynthetic pathway converting anthranilic acid present in the yeast metabolism to tryptamines by enzymes encoded in pRJP1608 is outlined in FIG. 6. A second multigene plasmid with CEN6/ARS4 replication sequences, URA3 expression cassette, and kanamycin resistance was cloned to contain coding sequences for tryptophan decarboxylase from *B. atrophaeus* (SEQ ID NO: 19), tryptophan 4-hydroxylase from *P. cyanescens* (SEQ ID NO: 33), and aralkylamine N-acetyltransferase from *B. taurus* (SEQ ID NO: 46) under control of high activity yeast promoter and terminator pairs (e.g., promoters pCCW12, pTDH3, and pPGK1, or terminators tADH1, tPGK1, and tENO1) and was named plasmid pRJP1618 (FIG. 7). The biosynthetic pathway converting anthranilic acid present in the yeast metabolism to tryptamines by enzymes encoded in pRJP1618 is outlined in FIG. 8.

*S. cerevisiae* strain BY4741 (MATa his3Δ1 leu2Δ0 met15Δ0 ura3Δ0) was used for experiments in this study and propagated at 30° C. The pRJP1608 plasmid was transformed into BY4741 by lithium acetate protocol and selected for on synthetic complete medium lacking uracil. The resulting strain, yNAB001, was isolated and genotyped. The pRJP1618 plasmid was transformed into BY4741 by lithium acetate protocol and selected for on synthetic complete medium lacking uracil. The resulting strain, yNAB002, was isolated and genotyped.

Colonies of yNAB001 and yNAB002 were used to inoculate 5 mL cultures of synthetic complete medium and were grown at 30° C. in a rotary shaker at 225 rpm. Media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min. flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z).

Figure 8:
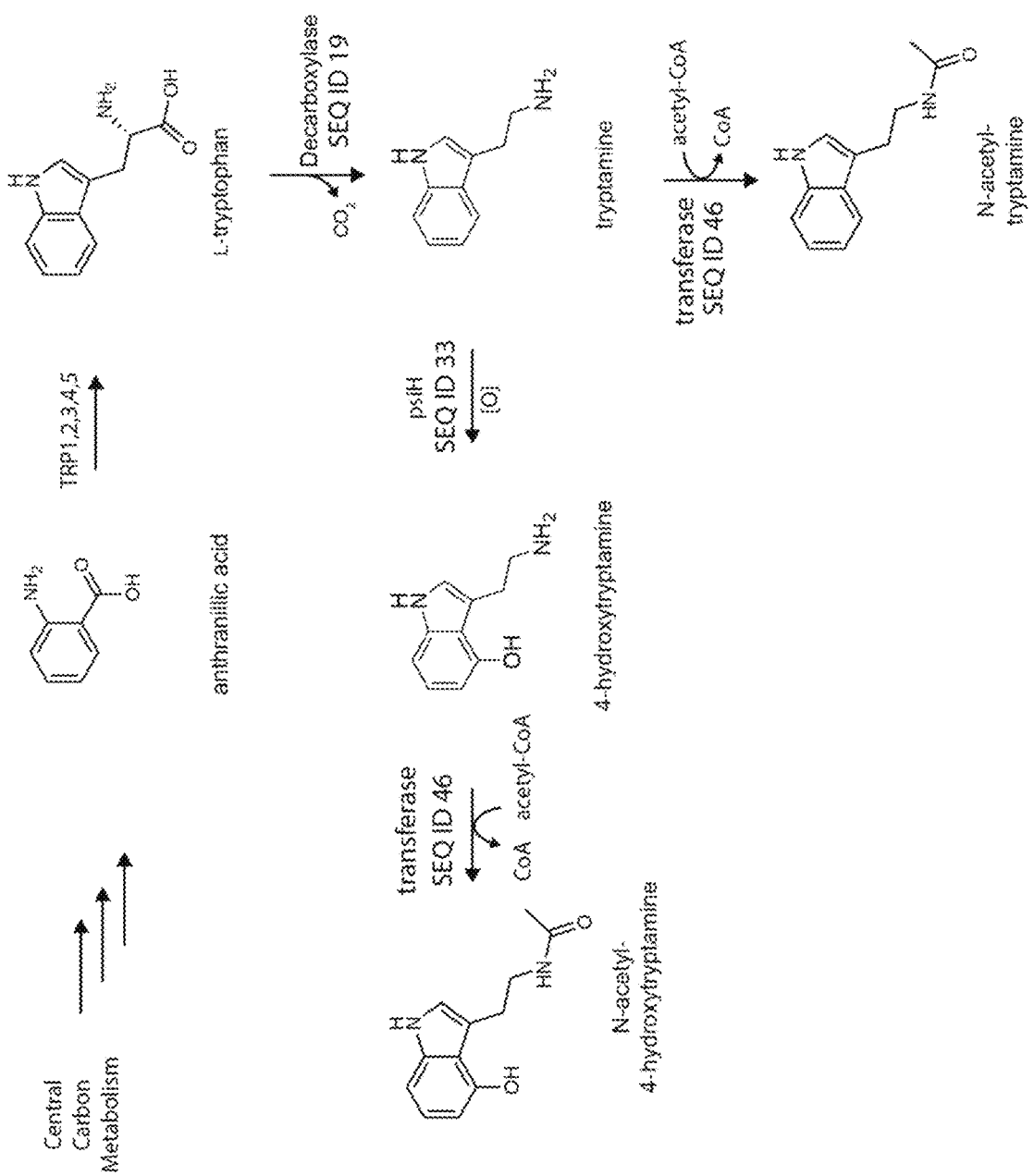
FIG. 8 depicts a non-limiting example of a biosynthetic pathway converting anthranilic acid present in yeast metabolism to tryptamines by enzymes encoded in pRJP1618 is in accordance with embodiments of the disclosure.
Figure 9:
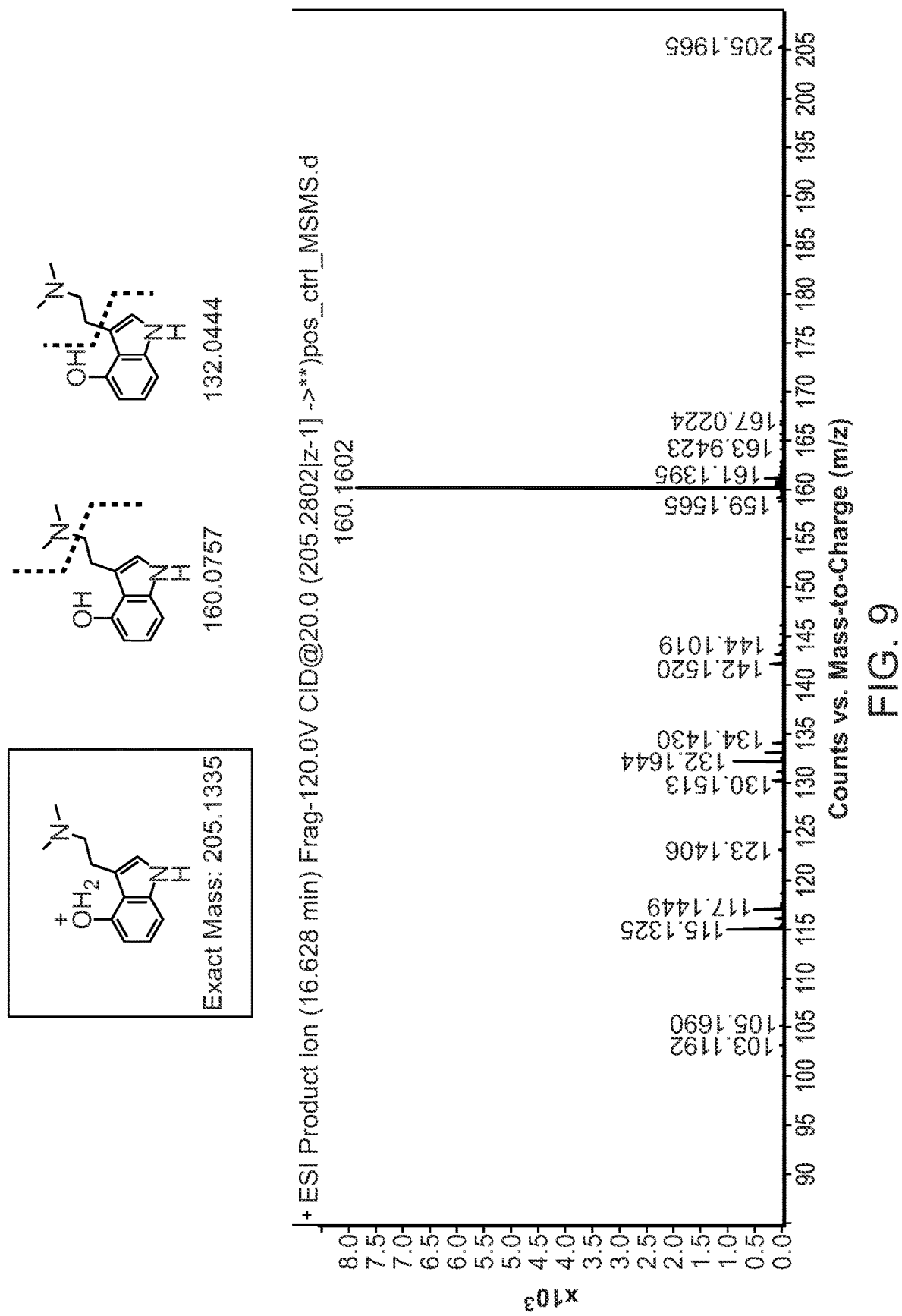
FIG. 9 depicts a non-limiting example of tandem mass spectrometry (MS/MS) of 4-hydroxy-N,N-dimethyl-tryptamine derived from engineered yeast cells in accordance with embodiments of the disclosure.
Figure 10:
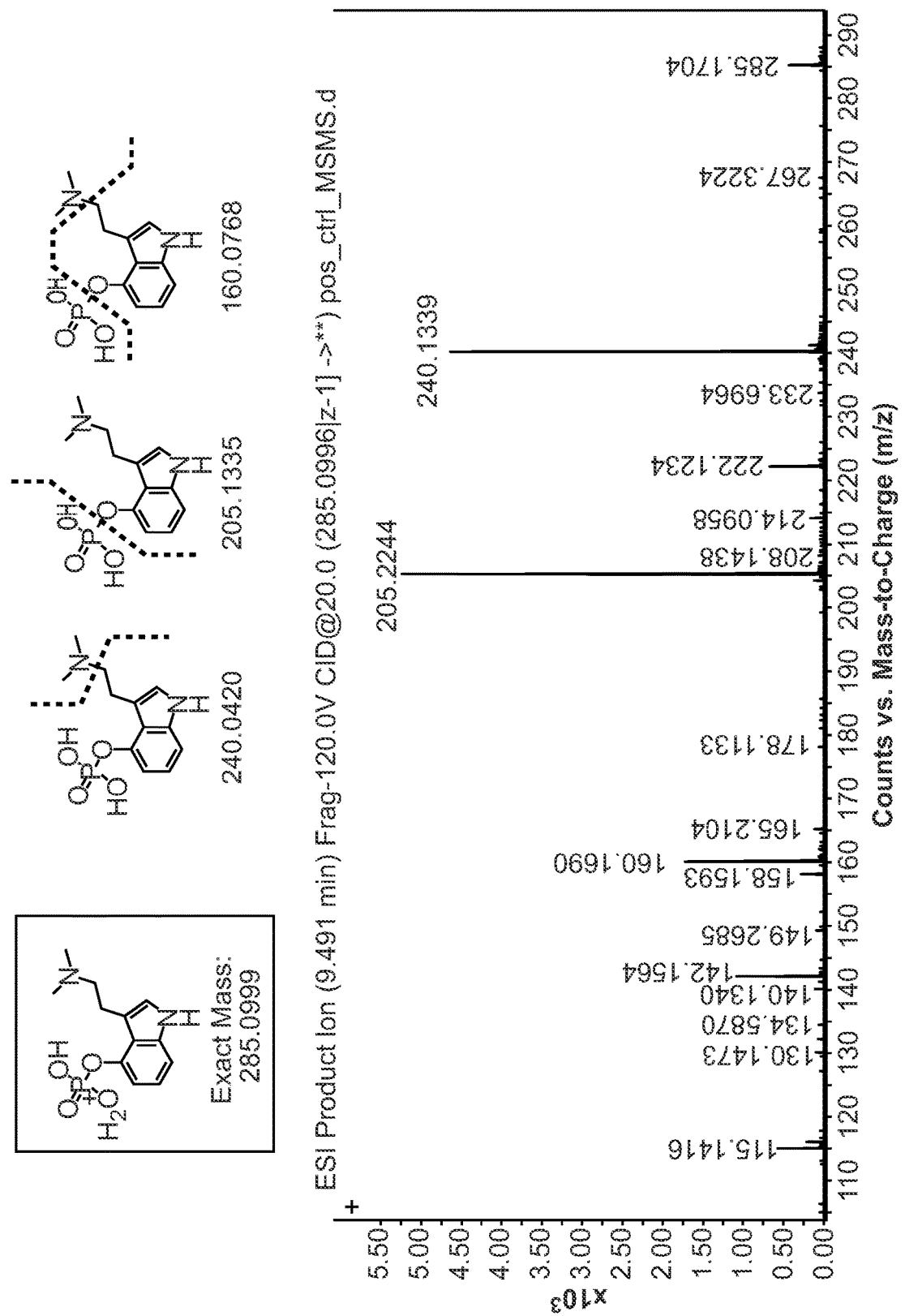
FIG. 10 depicts a non-limiting example of tandem mass spectrometry (MS/MS) of psilocybin derived from engineered yeast cells in accordance with embodiments of the disclosure.
Figure 11:
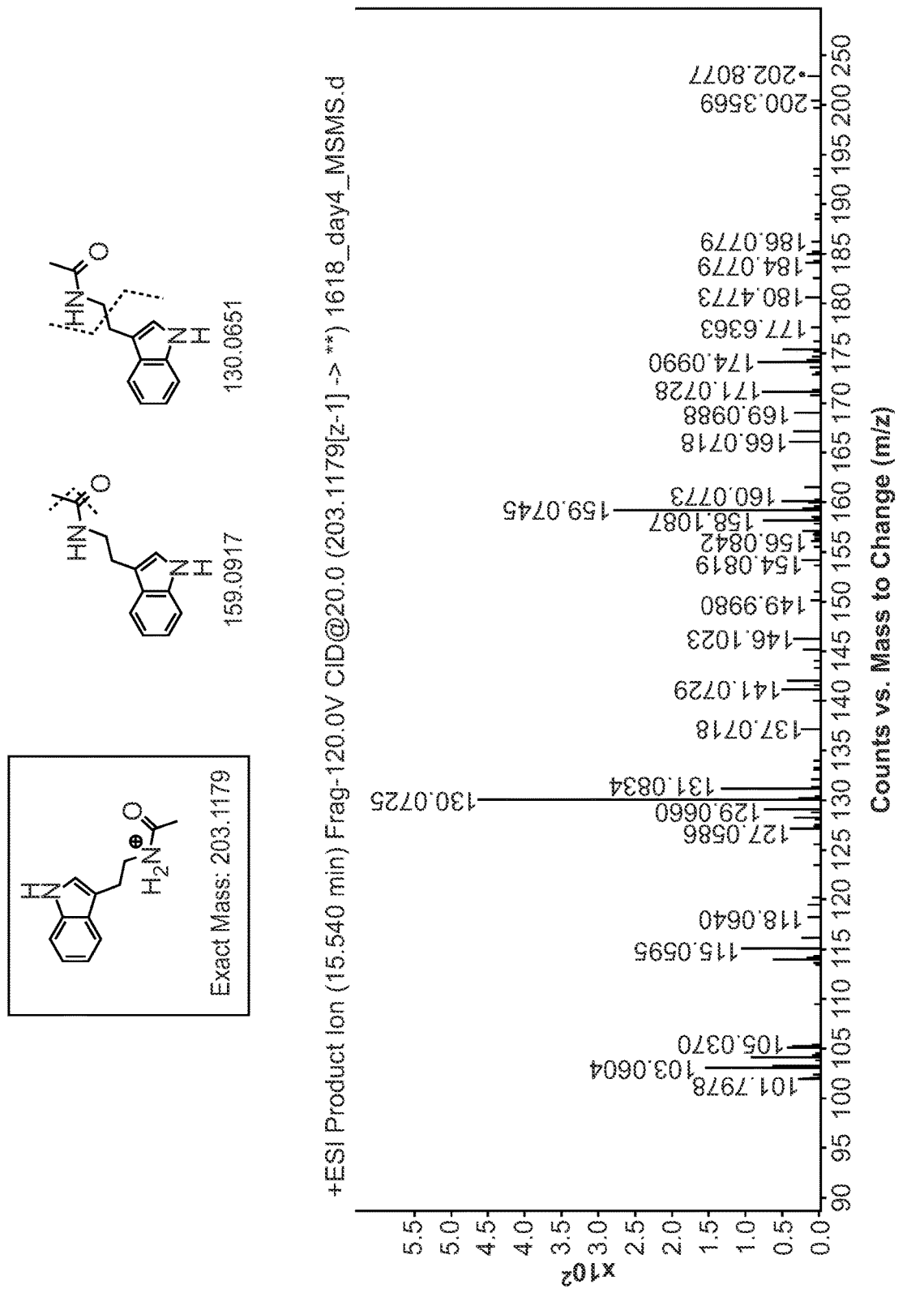
FIG. 11 depicts a non-limiting example of tandem mass spectrometry (MS/MS) of N-acetyltryptamine derived from engineered yeast cells in accordance with embodiments of the disclosure.
Figure 12:
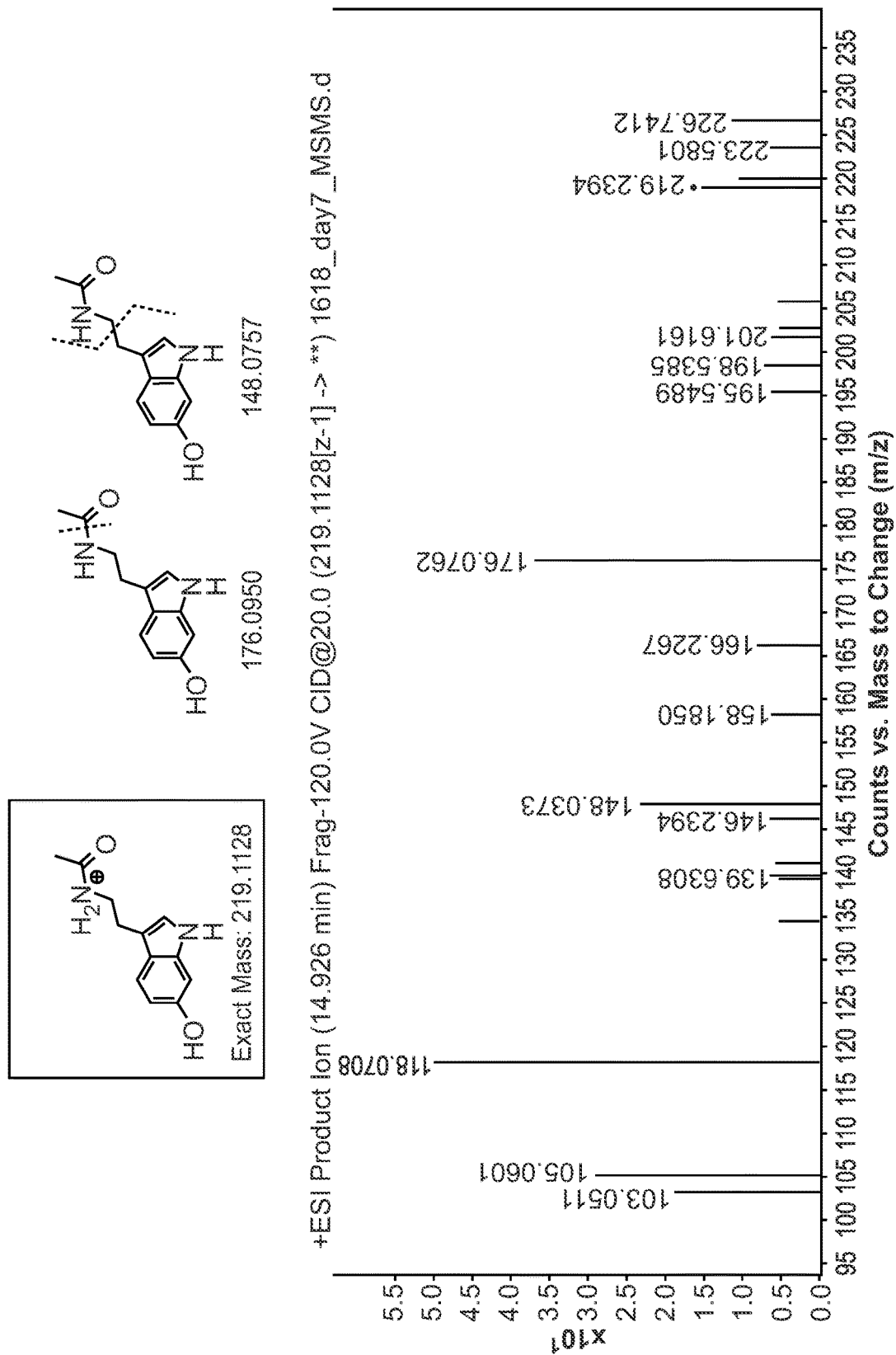
FIG. 12 depicts a non-limiting example of tandem mass spectrometry (MS/MS) of 4-hydroxy-N-acetyltryptamine derived from engineered yeast cells in accordance with embodiments of the disclosure.

Detection of tryptamines was conducted by extraction of ion masses of corresponding tryptamine not found in the unfed control sample. Additionally, tandem MS/MS was conducted. In the culture of yNAB001, ion masses for tryptamine, 4-hydroxytryptamine, 4-phosphoryloxytryptamine, 4-hydroxy-N,N-dimethyltryptamine, and 4-phosphoryloxy-N,N-dimethyltryptamine were detected (FIG. 6). Tandem MS/MS fragmentation data was collected for 4-hydroxy-N,N-dimethyltryptamine at a positive ion mass of 205.1335 m/z (FIG. 9) and 4-phosphoryloxy-N,N-dimethyltryptamine at a positive ion mass of 285.0999 m/z (FIG. 10). In the culture of yNAB002, ion masses for tryptamine, 4-hydroxytryptamine, N-acetyl-tryptamine, and 4-hydroxy-N-acetyl-tryptamine were detected (FIG. 8). Tandem MS/MS fragmentation data was collected for N-acetyl-tryptamine at a positive ion mass of 203.1179 m/z (FIG. 11) and 4-hydroxy-N-acetyl-tryptamine at a positive ion mass of 219.1128 (FIG. 12). Media from an untransformed strain of BY4741 detected only trace levels of tryptamine and no other aforementioned tryptamines from yNAB001 and yNAB002 media.

Figure 13:
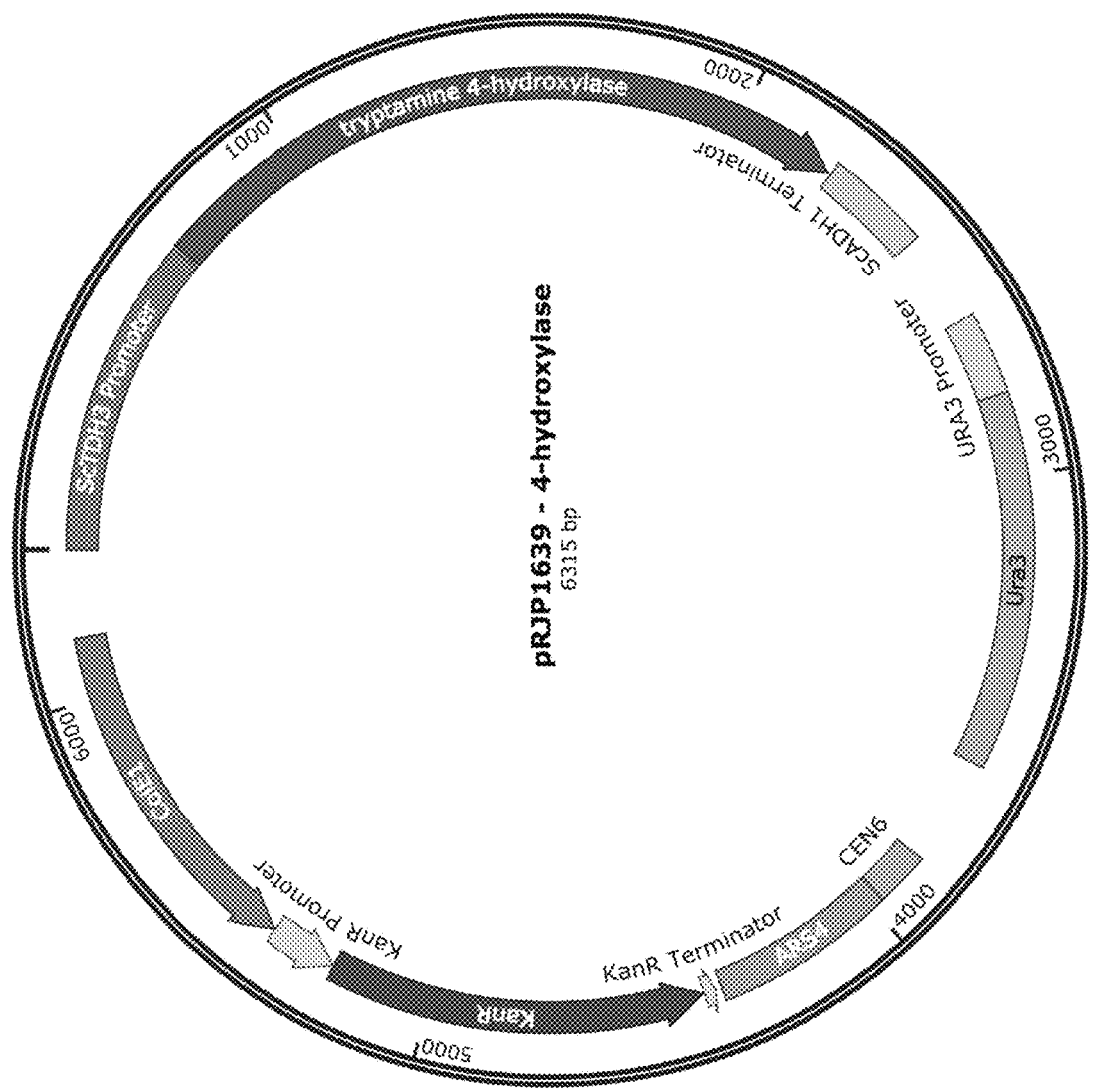
FIG. 13 depicts a non-limiting example of a plasmid map for the overexpression tryptamine 4-hydroxylase (e.g., SEQ ID NO: 33) in yeast in accordance with embodiments of the disclosure.
Figure 14:
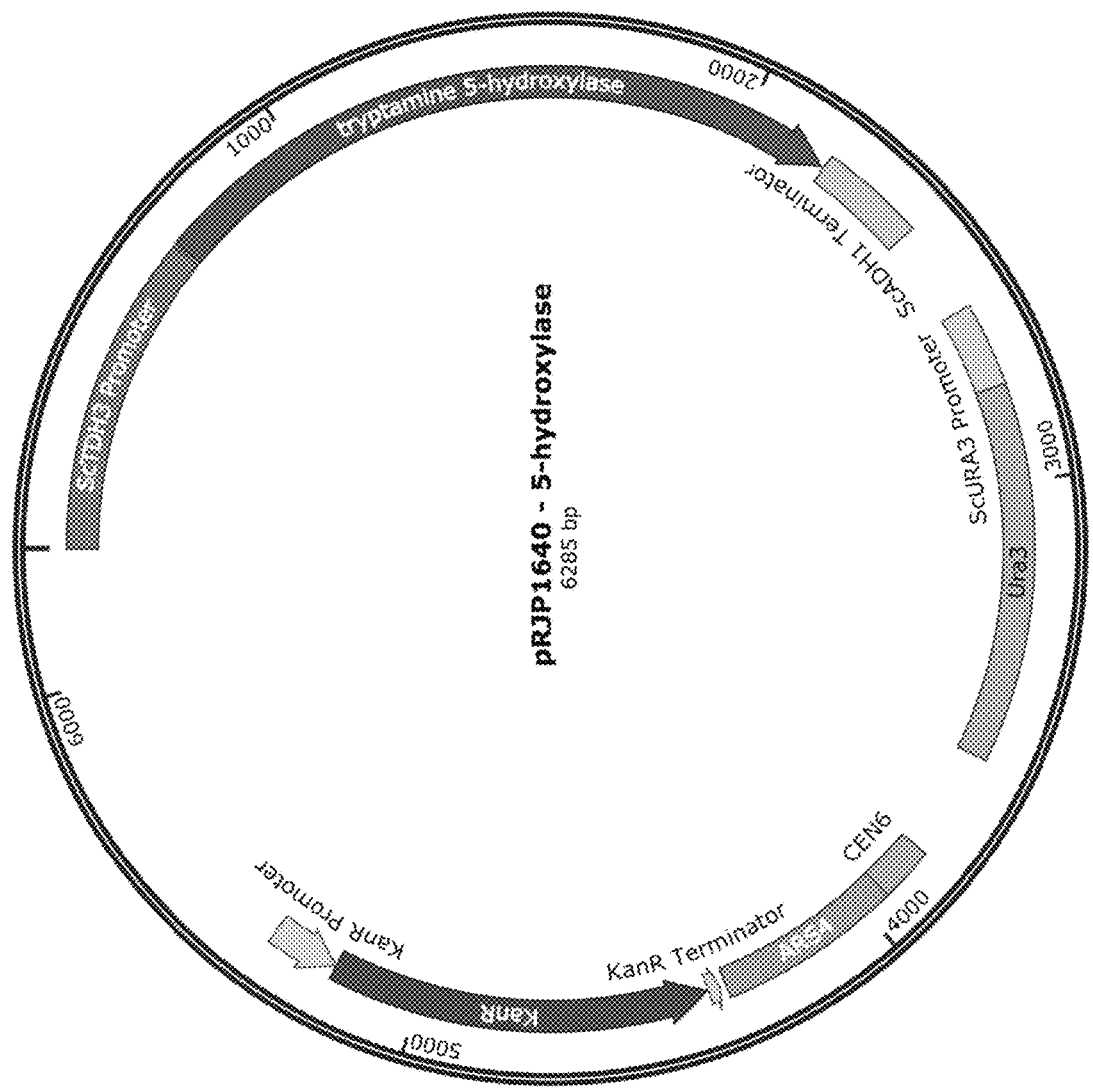
FIG. 14 depicts a non-limiting example of a plasmid map for the overexpression of tryptamine 5-hydroxylase (e.g., SEQ ID NO: 47) in yeast in accordance with embodiments of the disclosure.
Figure 15:
FIG. 15 depicts a non-limiting example of a plasmid map for the overexpression of 4-hydroxytryptamine kinase (e.g., SEQ ID NO: 41) in yeast in accordance with embodiments of the disclosure.

Example 5. Production of Tryptamine Derivatives from Fed Tryptamines Using Engineered Cells Microbes can be genetically modified to express metabolic enzymes capable of derivatizing tryptamines. Hydroxyl and phosphoryloxy substitutions to indole positions of tryptamines was investigated by expressing heterologous enzymes in yeast and feeding tryptamines with various amine substitutions. A single gene expression plasmid with CEN6/ARS4 replication sequences, URA3 expression cassette, and kanamycin resistance was cloned to contain a coding sequence for tryptamine 4-hydroxylase from P. cyanescens (SEQ ID NO: 33) and was named pRJP1639 (FIG. 13). A single gene expression plasmid with CEN6/ARS4 replication sequences, URA3 expression cassette, and kanamycin resistance was cloned to contain a coding sequence for tryptamine 5-hydroxylase from S. mansoni (SEQ ID NO: 47) and was named pRJP1640 (FIG. 14). A single gene expression plasmid with CEN6/ARS4 replication sequences, LEU2 expression cassette, and kanamycin resistance was cloned to contain a coding sequence for 4-hydroxytryptamine kinase from P. cubensis (SEQ ID NO: 41) and was named pRJP1641 (FIG. 15).

S. cerevisiae strain BY4741 (MATa his3Δ1 leu2Δ0 met15Δ0 ura3Δ0) was used for experiments in this study and was propagated at 30° C. The pRJP1639 plasmid was transformed into BY4741 by lithium acetate protocol and selected for on synthetic complete medium lacking uracil. The resulting strain, yNAB003, was isolated and genotyped. The pRJP1640 plasmid was transformed into BY4741 by lithium acetate protocol and selected for on synthetic complete medium lacking uracil. The resulting strain, yNAB004, was isolated and genotyped. The plasmid pRJP1641 was linearized by NotI digestion and transformed into strain yNAB003 by lithium acetate protocol and selected for on synthetic complete medium lacking leucine. The resulting strain, yNAB005, was isolated and genotyped.

Figure 16:
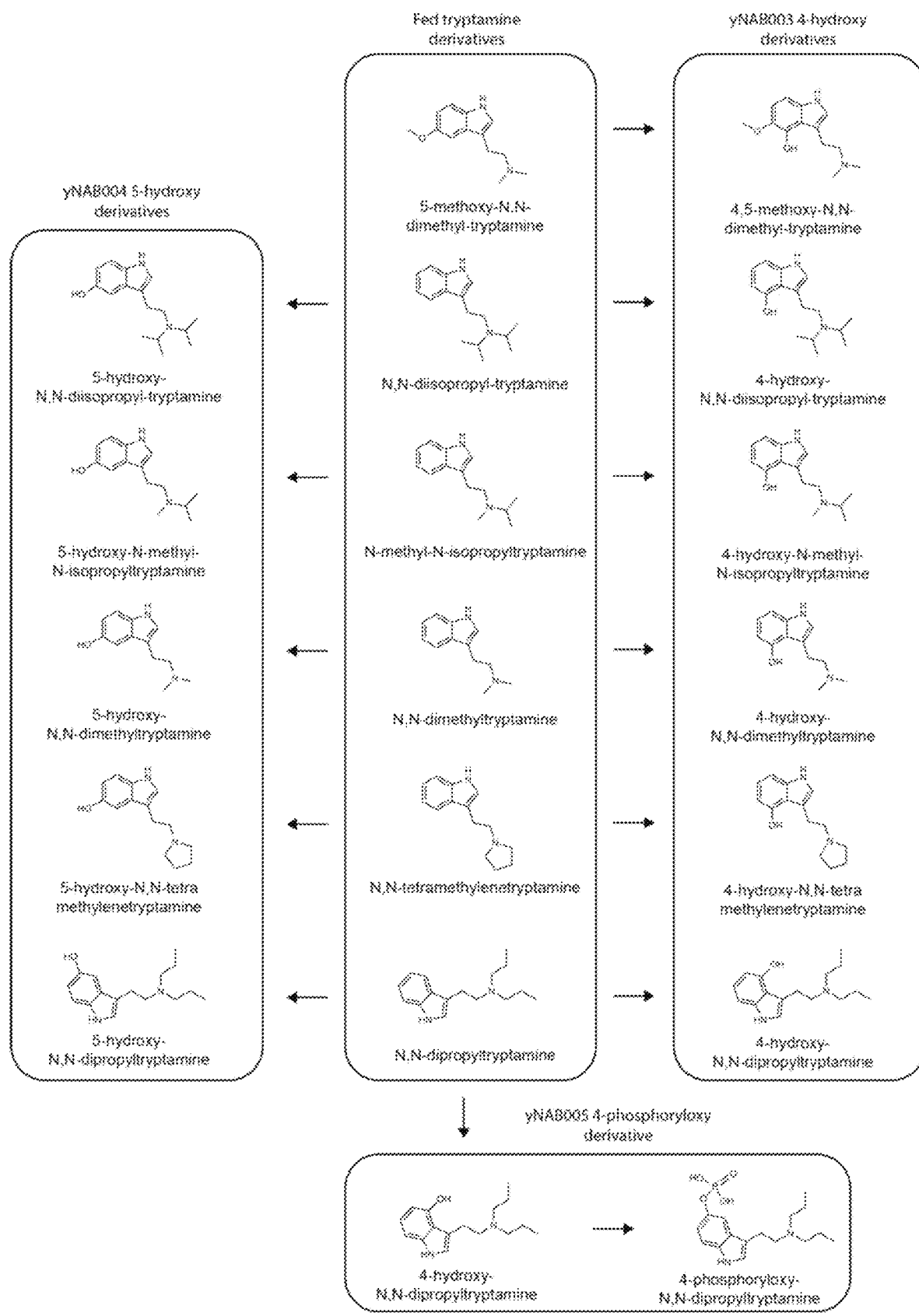
FIG. 16 depicts a non-limiting example of the production of substituted tryptamines from fed tryptamines using engineered yeast in accordance with embodiments of the disclosure.

Overnight grown cultures of yNAB003, yNAB004, and yNAB005 were used to inoculate 250 mL cultures of synthetic complete medium and were grown at 30° C. in a rotary shaker at 225 rpm. Cultures were concentrated into 25 mL of synthetic complete medium lacking uracil and transferred to 5 mL culture tubes. 5 mM of various tryptamines (including 5-methoxy-N,N-dimethyltryptamine, N,N-diisopropyltryptamine, N-methyl-N-isopropyltryptamine, N,N-dimethyltryptamine, N,N-tetramethylenetryptamine, and N,N-dipropyltryptamine) were added to separate tubes (FIG. 16). After 3 days of incubation at 30° C., media from cultures were sampled by centrifuging 1 mL of culture at 18000 rpm and transferring clarified media to sample vials. Analysis was performed by chromatography/mass spectrometry (LCMS) with a 1260 Infinity LC System connected to a 6120 Quadrupole Mass Spectrometer (Agilent Technologies). Zorbax Eclipse Plus C18 guard column (4.6 cm×12.5 cm, 5 μm packing, Agilent Technologies) was connected to a Zorbax Eclipse Plus C18 column (4.6 mm×100 mm, 3.5 μm packing, Agilent Technologies) at 20° C. using a 0.5 mL/min flow rate. Water and acetonitrile mobile phases contained 0.1% formic acid as the pH modifier. The elution gradient (water:acetonitrile volume ratio) was as follows: 98:2 (0-2 min), linear ramp from 98:2 to 5:95 (2-17 min), 5:95 (17-22 min), linear ramp from 5:95 to 98:2 (22-23 min), and 98:2 (23-28 min). Absorbance was measured using a diode array detector for UV-Vis analysis. MS was conducted in atmospheric pressure ionization-positive electrospray (API-ES positive) mode at 100-V fragmentor voltage with ion detection set to both full scanning mode (50-1200 m/z). Detection of tryptamines was conducted by extraction of ion masses of corresponding tryptamine not found in the unfed control sample or the original tryptamine chemical stock. 4-hydroxy derivatives of fed tryptamines were identified for the yNAB003 culture. 5-hydroxy derivatives of fed tryptamines were identified for the yNAB004 culture. Ion masses for 4-hydroxy-N,N-dipropyltryptamine and 4-phosphoryloxy-N,N-dipropyltryptamine were identified in the yNAB005 culture media fed with N,N-dipropyltryptamine (see FIG. 16).

Example 6. Colorimetric Screening for High Hydroxylation Activity

Figure 17:
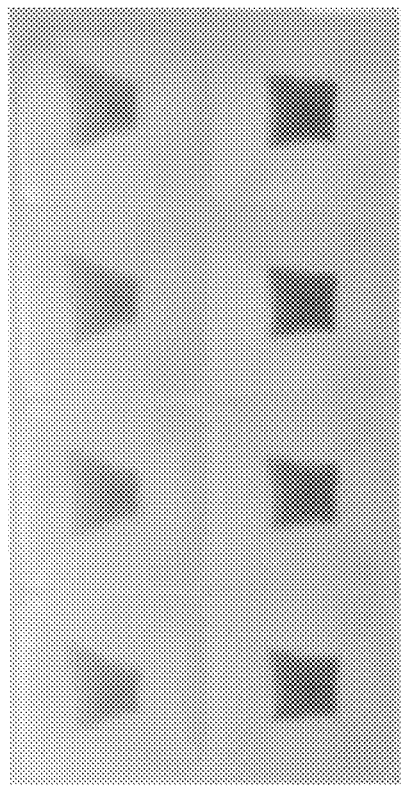
FIG. 17 depicts a non-limiting example of a colorimetric screening assay as an indicator of hydroxylase activity in yeast in accordance with embodiments of the disclosure.
Figure 17:
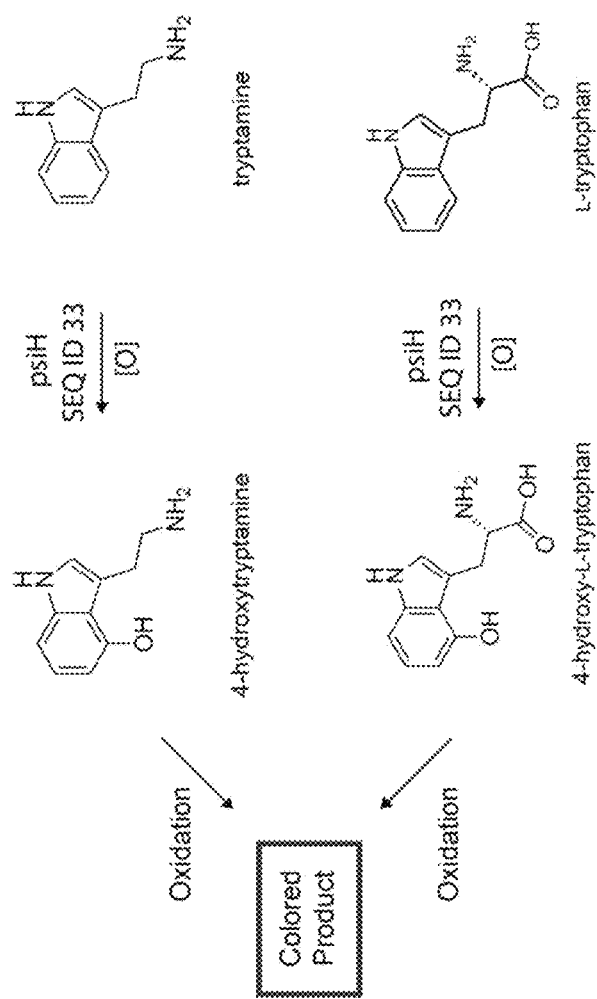

Without addition of a protecting group at the hydroxyl position of 4-hydroxy-tryptamine and 4-hydroxytryptophan, the compounds will oxidize to a colored compound. Accordingly, subsequent hydroxylase and oxidation activity on tryptamine and tryptophan can be used as an indicator of hydroxylase activity. To demonstrate this activity, color formation of the strain yNAB003 with high tryptamine 4-hydroxylase from *P. cyanescens* (SEQ ID NO: 33) was compared to activity of WT BY4741. Four separate 3 mL cultures were started for WT BY4741 and yNAB003 for 3 days at 30° C. in synthetic complete media with 4 mM added tryptamine at 750 rpm of high frequency shaking. After culturing, these cultures were centrifuged to pellet the cells for observation of pigment formation. The formation of blue product was observed in the yNAB003 cultures as an indication of tryptamine 4-hydroxylase activity and was not observed in the WT BY4741 cultures (FIG. 17).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A compound of Formula (I):

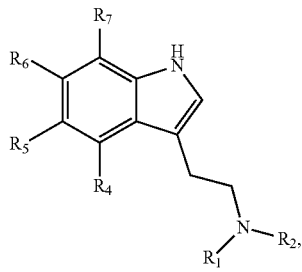

Formula (I)

or a pharmaceutically acceptable salt thereof, wherein, $R_1$ is selected from H and optionally substituted $C_{1-5}$alkyl;

$R_2$ is selected from optionally substituted linear $C_{3-5}$alkyl; and $R_4$, $R_5$, $R_6$, and $R_7$ are independently selected from H and —O(P=O)(OH)$_2$, wherein at least one of $R_4$, $R_5$, $R_6$, and $R_7$ is —O(P=O)(OH)$_2$.

2. The compound or pharmaceutically acceptable salt of claim 1, wherein $R_1$ is H.

3. The compound or pharmaceutically acceptable salt of claim 1, wherein $R_1$ is $C_{1-5}$alkyl.

4. The compound or pharmaceutically acceptable salt of claim 1, wherein $R_1$ is $C_3$ alkyl.

5. The compound or pharmaceutically acceptable salt of claim 1, wherein $R_4$ is —O(P=O)(OH)$_2$ and $R_5$, $R_6$, and $R_7$ are H.

6. The compound or pharmaceutically acceptable salt of claim 1, wherein $R_5$ is —O(P=O)(OH)$_2$ and $R_4$, $R_6$, and $R_7$ are H.

7. The compound or pharmaceutically acceptable salt of claim 1, wherein $R_6$ is —O(P=O)(OH)$_2$ and $R_4$, $R_5$, and $R_7$ are H.

8. The compound or pharmaceutically acceptable salt of claim 1, wherein $R_7$ is —O(P=O)(OH)$_2$ and $R_4$, $R_5$, and $R_6$ are H.

9. A compound selected from the group consisting of:

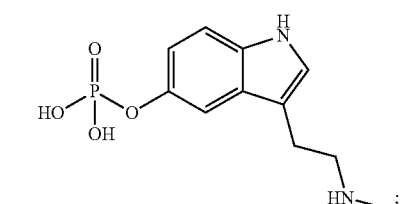

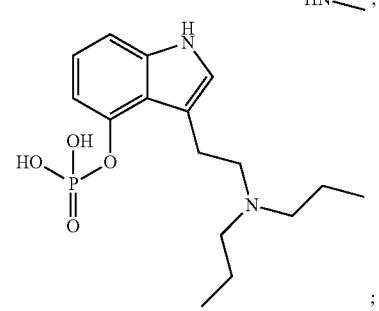

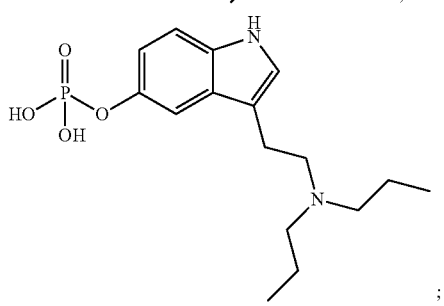

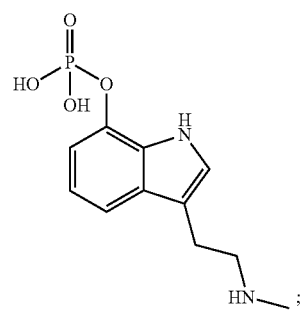

-continued

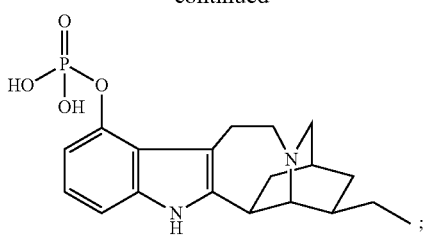

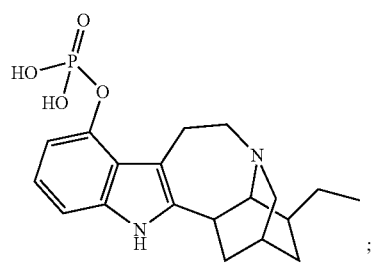

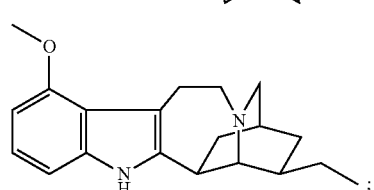

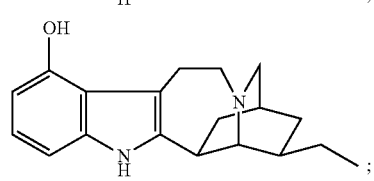

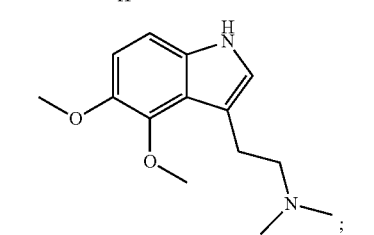

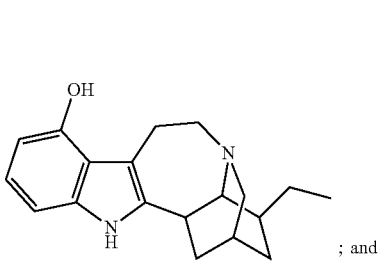

; and

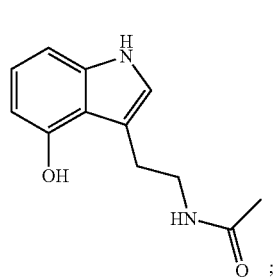

or a pharmaceutically acceptable salt of any one thereof.

10. The compound of claim 9, wherein the compound is:

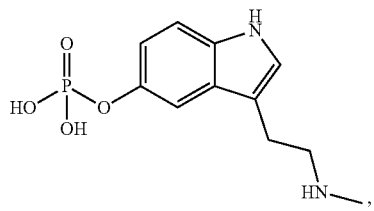 [SMILES: CNCCc1c[nH]c2ccc(OP(=O)(O)O)cc12]

or a pharmaceutically acceptable salt thereof.

11. The compound of claim 9, wherein the compound is:

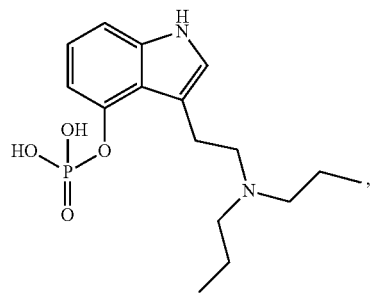 [SMILES: CCCN(CCC)CCc1c[nH]c2cccc(OP(=O)(O)O)c12]

or a pharmaceutically acceptable salt thereof.

12. The compound of claim 9, wherein the compound is:

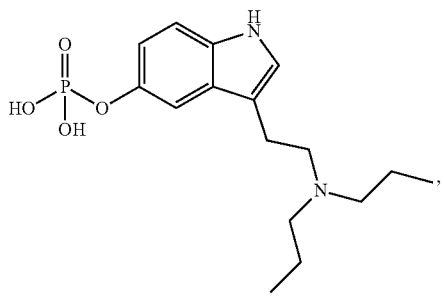 [SMILES: CCCN(CCC)CCc1c[nH]c2ccc(OP(=O)(O)O)cc12]

or a pharmaceutically acceptable salt thereof.

13. The compound of claim 9, wherein the compound is:

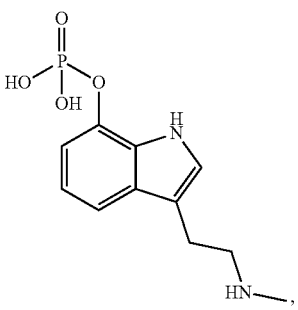 [SMILES: CNCCc1c[nH]c2c(OP(=O)(O)O)cccc12]

or a pharmaceutically acceptable salt thereof.

14. The compound of claim 9, wherein the compound is:

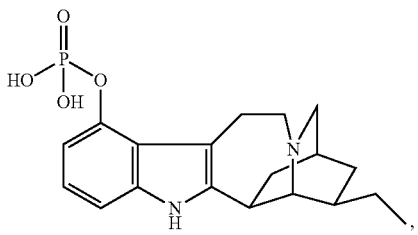 [SMILES: CCC1CC2CC3c4[nH]c5cccc(OP(=O)(O)O)c5c4CCN(C2)C13]

or a pharmaceutically acceptable salt thereof.

15. The compound of claim 9, wherein the compound is:

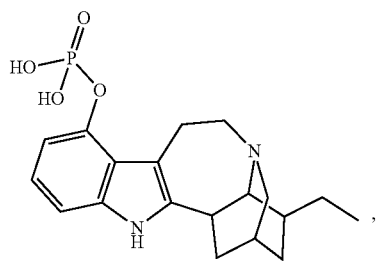 [SMILES: CCC1CC2CC3c4[nH]c5cccc(OP(=O)(O)O)c5c4CCN(C2)C13]

or a pharmaceutically acceptable salt thereof.

16. The compound of claim 9, wherein the compound is:

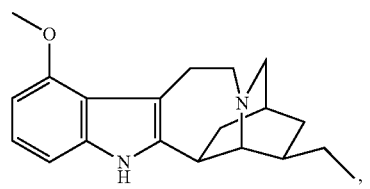 [SMILES: CCC1CC2CC3c4[nH]c5cccc(OC)c5c4CCN(C2)C13]

or a pharmaceutically acceptable salt thereof.

17. The compound of claim 9, wherein the compound is:

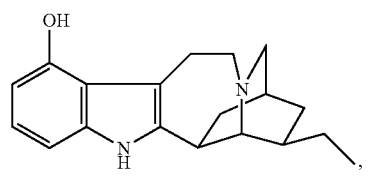 [SMILES: CCC1CC2CC3c4[nH]c5cccc(O)c5c4CCN(C2)C13]

or a pharmaceutically acceptable salt thereof.

18. The compound of claim 9, wherein the compound is:

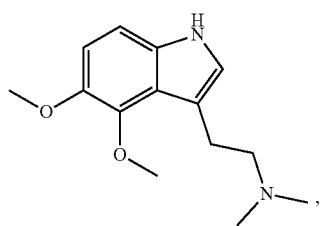

or a pharmaceutically acceptable salt thereof.

19. The compound of claim 9, wherein the compound is:

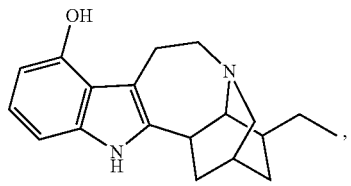 [SMILES: CCC1CC2CC3c4[nH]c5cccc(O)c5c4CCN(C2)C13]

or a pharmaceutically acceptable salt thereof.

20. The compound of claim 9, wherein the compound is:

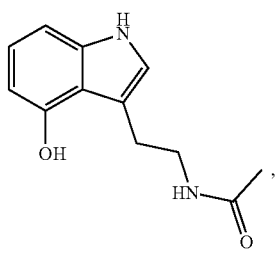 [SMILES: CC(=O)NCCc1c[nH]c2cccc(O)c12]

or a pharmaceutically acceptable salt thereof.

21. A pharmaceutical composition, comprising a compound of Formula (I):

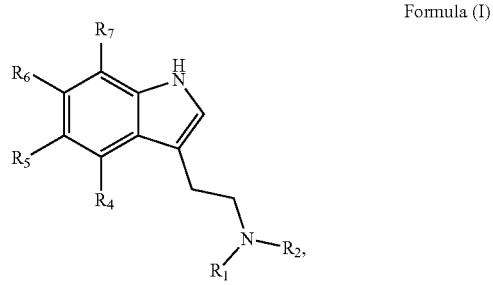

Formula (I)

or a pharmaceutically acceptable salt thereof, wherein, $R_1$ is selected from H and $C_{1-5}$alkyl;

$R_2$ is $C_{3-5}$alkyl; and $R_4$, $R_5$, $R_6$, and $R_7$ are independently selected from H and —O(P═O)(OH)$_2$, wherein at least one of $R_4$, $R_5$, $R_6$, and $R_7$ is —O(P═O)(OH)$_2$.

22. The pharmaceutical composition of claim 21, wherein one of $R_5$, $R_6$, and $R_7$ is —O(P═O)(OH)$_2$.

23. The pharmaceutical composition of claim 21, wherein $R_1$ is H or $C_3$ alkyl.

24. The pharmaceutical composition of claim 21, wherein $R_2$ is $C_3$ alkyl.

25. A method of improving perception and mood in a human subject in need thereof, comprising administering to the human subject in need thereof a compound of Formula (I):

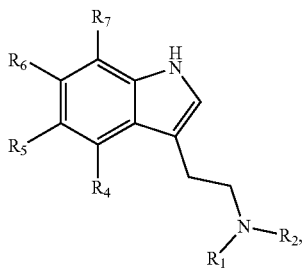
Formula (I)
or a pharmaceutically acceptable salt thereof, wherein,
$R_1$ is selected from H and $C_{1-5}$alkyl;
$R_2$ is $C_{3-5}$alkyl; and
$R_4$, $R_5$, $R_6$, and $R_7$ are independently selected from H and —O(P=O)(OH)$_2$, wherein at least one of $R_4$, $R_5$, $R_6$, and $R_7$ is —O(P=O)(OH)$_2$.
* * * * *